United States Patent
Balog et al.

(10) Patent No.: US 12,145,927 B2
(45) Date of Patent: Nov. 19, 2024

(54) INHIBITORS OF INDOLEAMINE 2,3-DIOXYGENASE AND METHODS OF THEIR USE

(71) Applicant: BRISTOL-MYERS SQUIBB COMPANY, Princeton, NJ (US)

(72) Inventors: James Aaron Balog, Princeton, NJ (US); Steven P. Seitz, Princeton, NJ (US); Jay A. Markwalder, Princeton, NJ (US); David K. Williams, Princeton, NJ (US); Weifang Shan, Princeton, NJ (US); Susheel Jethanand Nara, Bangalore (IN); Saumya Roy, Bangalore (IN); Srinivas Cheruku, Bangalore (IN); Nagalakshmi Pulicharla, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 930 days.

(21) Appl. No.: 17/261,968

(22) PCT Filed: Jul. 22, 2019

(86) PCT No.: PCT/US2019/042773
§ 371 (c)(1),
(2) Date: Jan. 21, 2021

(87) PCT Pub. No.: WO2020/023356
PCT Pub. Date: Jan. 30, 2020

(65) Prior Publication Data
US 2021/0355113 A1 Nov. 18, 2021

Related U.S. Application Data

(60) Provisional application No. 62/701,895, filed on Jul. 23, 2018.

(51) Int. Cl.
| | |
|---|---|
| C07D 405/14 | (2006.01) |
| C07D 307/79 | (2006.01) |
| C07D 313/08 | (2006.01) |
| C07D 405/10 | (2006.01) |
| C07D 413/10 | (2006.01) |
| C07D 413/14 | (2006.01) |
| C07D 417/14 | (2006.01) |
| C07K 16/28 | (2006.01) |

(52) U.S. Cl.
CPC ......... *C07D 405/14* (2013.01); *C07D 307/79* (2013.01); *C07D 313/08* (2013.01); *C07D 405/10* (2013.01); *C07D 413/10* (2013.01); *C07D 413/14* (2013.01); *C07D 417/14* (2013.01); *C07K 16/2818* (2013.01)

(58) Field of Classification Search
CPC .. C07D 405/14; C07D 307/78; C07D 313/08; C07D 405/10; C07D 413/10; C07D 413/14; C07D 417/14
See application file for complete search history.

(56) References Cited

U.S. PATENT DOCUMENTS

| | | | |
|---|---|---|---|
| 4,785,004 | A | 11/1988 | Von Sprecher et al. |
| 2010/0233166 | A1 | 9/2010 | Prendergast et al. |

FOREIGN PATENT DOCUMENTS

| | | |
|---|---|---|
| WO | 99/02310 A2 | 1/1999 |
| WO | 99/29310 A2 | 6/1999 |
| WO | 2004/094409 A1 | 11/2004 |
| WO | 2006/029879 | 3/2006 |
| WO | 2006/105021 A2 | 10/2006 |
| WO | 2006/122150 A1 | 11/2006 |
| WO | 2007/005874 A2 | 1/2007 |
| WO | 2007/075598 A2 | 7/2007 |
| WO | 2008/036642 A2 | 3/2008 |
| WO | 2008/036653 A2 | 3/2008 |
| WO | 2008/132601 A1 | 11/2008 |
| WO | 2009/009116 A2 | 1/2009 |
| WO | 2009/044273 A2 | 4/2009 |
| WO | 2009/073620 A2 | 6/2009 |
| WO | 2009/115652 A2 | 9/2009 |
| WO | 2010/019570 A2 | 2/2010 |
| WO | 2010/077634 A1 | 7/2010 |
| WO | 2011/028683 | 3/2011 |
| WO | 2011/056652 A1 | 5/2011 |

(Continued)

OTHER PUBLICATIONS

Cancer and Metastasis Reviews (1998), 17(1), 91-106.*
Science (1999), vol. 286, 531-537.*
Ball, H.J. et al., Characerization of an indoleamine 2,3-dioxygenase-like protein found in humans and mice [published correction appears in Gene. Oct. 1, 2010;465(1-2):66]. Gene. Jul. 1, 2007;396(1):203-213.
Brandacher, G. et al., Prognostic value of indoleamine 2,3-dioxygenase expression in colorectal cancer: effect on tumor-infiltrating T cells. Clin Cancer Res. Feb. 15, 2006; 12(4):1144-1151.
Bundgaard, H., Prodrugs as a mean to improve the delivery of peptide drugs. Adv. Drug Del. Rev. 8:1-38 (1992).

(Continued)

*Primary Examiner* — Rebecca L Anderson
(74) *Attorney, Agent, or Firm* — BakerHostetler

(57) ABSTRACT

The present invention provides compounds of formula (I) wherein all of the variables are as defined herein. These compounds are inhibitors of indoleamine 2,3-dioxygenase (IDO), which may be used as medicaments for the treatment of proliferative disorders, such as cancer, viral infections and/or autoimmune diseases.

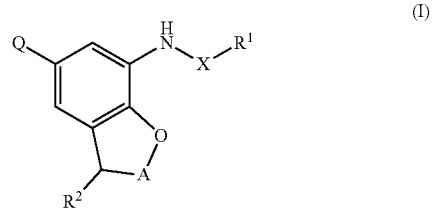

11 Claims, No Drawings

(56) References Cited

FOREIGN PATENT DOCUMENTS

| WO | 2011/070024 A1 | 6/2011 |
| WO | 2011/107533 A1 | 9/2011 |
| WO | 2011/131407 A1 | 10/2011 |
| WO | 2011/140249 A2 | 11/2011 |
| WO | 2012/032433 A1 | 3/2012 |
| WO | 2012/142237 A1 | 10/2012 |
| WO | 2013/079174 A1 | 6/2013 |
| WO | 2013/087699 A1 | 6/2013 |
| WO | 2013/119716 A1 | 8/2013 |
| WO | 2013/132044 A1 | 9/2013 |
| WO | 2013/169264 A1 | 11/2013 |
| WO | 2014/008218 A1 | 1/2014 |
| WO | 2014/036357 A1 | 3/2014 |
| WO | 2014/109400 A1 | 7/2014 |
| WO | 2014/150646 A1 | 9/2014 |
| WO | 2015/002918 A1 | 1/2015 |
| WO | 2016/073738 A2 | 5/2016 |
| WO | 2016/073770 A1 | 5/2016 |
| WO | 2016/073774 A2 | 5/2016 |

OTHER PUBLICATIONS

Goldstein et al., J. Biological efficacy of a chimeric antibody to the epidermal growth factor receptor in a human tumor xenograft model. Clin Cancer Res. 1995;1(11):1311-1318.

Kakeya, N. et al., Studies on Prodrugs of Cephalosporins. I. Synthesis and Biological Properties of Glycyloxybenzoyloxymethyl and Glycylaminobenzoyloxymethyl Esters of 7ß-[2-(2-Aminothiazol-4-yl)-(Z)-2-methoxyiminoacetamido]-3-methyl-3-cephem-4-carboxylic Acid, Chem. Pharm. Bull., 32:692 (1984).

Kohl et al., Inhibition of farnesyltransferase induces regression of mammary and salivary carcinomas in ras transgenic mice, Nat. Med., 1, 792-797 (1995).

Littlejohn, T.K. et al., Expression and Purification of Recombinant Human Indoleamine 2,3-Dioxygenase, Protein Expression Purification, 19:22-29 (Jun. 2000).

Nielsen, N.M. et al., Glycolamide esters as biolabile prodrugs of carboxylic acid agents: synthesis, stability, bioconversion, and physicochemical properties. J Pharm Sci. 1988;77(4):285-298.

Sarkar SA, Wong R, Hackl SI, et al. Induction of indoleamine 2,3-dioxygenase by interferon-gamma in human islets. Diabetes 2007;56:72-79.

Scheller et al., Paclitaxel Balloon Coating, a Novel Method for Prevention and Therapy of Restenosis, Circulation, 110:810-814 (2004).

Sekulic et al., A Direct Linkage Between the Phosphoinositide 3-Kinase-AKT Signaling Pathway and the Mammalian Target of Rapamycin in Mitogen-stimulated and Transformed Cells, J. Cancer Research, 60, 3504-3513, Jul. 1, 2000.

Serafini P, et al., Myeloid suppressor cells in cancer: Recruitment, phenotype, properties, and mechanisms of immune suppression, Seminars in Cancer Biology, 16(I):53-65 (Feb. 2006).

Vlahos et al, A Specif Inhibitor of Phosphatidylinositol 3-Kinase, 2-(4-Morpholinyl)-8-phenyl-4H-1-benzopyran-4-one (LY294002), J. Biol. Chem., 269:5241-5248 (1994).

* cited by examiner

INHIBITORS OF INDOLEAMINE 2,3-DIOXYGENASE AND METHODS OF THEIR USE

CROSS-REFERENCE TO RELATED APPLICATIONS

This application is the National Stage Application of International Patent Application No. PCT/US2019/01042773 filed Jul. 22, 2019, which claims the priority benefit of U.S. Provisional Application No. 62/701,895, filed Jul. 23, 2018; the contents of which are herein incorporated by reference in their entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini P, et al., *Semin. Cancer Biol.*, 16(1):53-65 (February 2006) and Ball, H. J. et al., *Gene*, 396(1):203-213 (July 2007)).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g, rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in, for example, WO 2004/094409, WO2014/150646, WO2016/073770, WO2016/073738, and WO2016/073774.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

SUMMARY OF THE INVENTION

The invention is directed to compounds of formula (I):

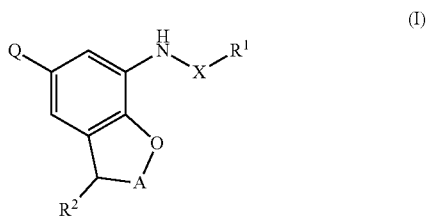

wherein all of the variables are as defined herein below.

Also within the scope of the invention are pharmaceutically acceptable salts, stereoisomers, tautomers, and solvates of the compounds of formula (I).

The invention is also directed to pharmaceutical compositions comprising one or more compounds of the invention. The invention is also directed to methods of treating cancer using one or more compounds of the invention.

The invention also provides processes and intermediates for making the compounds of formula (I) or pharmaceutically acceptable salts, stereoisomers, tautomers, and solvates thereof.

The compounds of the invention may be used in therapy. The compounds of the invention may be used for the manufacture of a medicament for the treatment of cancer.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

Compounds of the Invention

In a first aspect, the present invention provides, inter alia, a compound of formula (I):

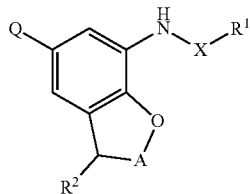
(I)

wherein:

A is —CR$^7$R$^8$—, —CR$^9$R$^{10}$CR$^{11}$R$^{12}$—, —CR$^{13}$R$^{14}$CR$^{15}$R$^{16}$CHR$^{17}$—, or —CR$^{14}$=CR$^{16}$CHR$^{17}$—;

Q is (C$_2$-C$_6$ alkyl substituted with (C(O)OH and R$^3$), (C$_3$-C$_6$ cycloalkyl substituted with W) or (phenyl substituted with W and R$^3$);

X is a bond, C(O), —C(O)CR$^4$R$^5$— or —C(O)NR$^6$—;

W is selected from: C(O)OR$^a$, C(O)NH$_2$, —S(O)$_2$NHR$^b$,

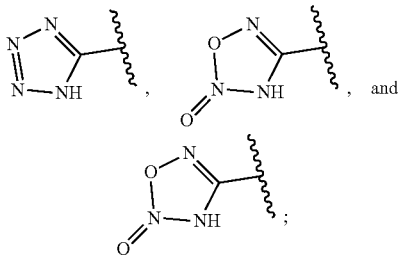

R$^1$ is selected from: C$_1$-C$_6$ alkyl, C$_3$-C$_6$ cycloalkyl, tetrahydro-2H-pyranyl, morpholinyl, phenyl, naphthalenyl, thiophenyl, thiazolyl, isoxazolyl, 1H-imidazolyl, pyrazolyl, 1,2,4-oxadiazolyl, 1,3,4-thiadiazolyl, 1H-tetrazolyl, pyridinyl, pyrimidinyl, pyridazinyl, pyrazinyl, benzo[b]thiophenyl, benzo[d]thiazolyl, benzo[d]oxazolyl, benzo[d]imidazolyl, pyrazolo[1,5-a]pyrimidinyl, [1,2,4]triazolo[4,3-b]pyridazinyl, 7H-pyrrolo[2,3-d]pyrimidinyl, and quinolin-2-yl; wherein each moiety is substituted with 0 to 2 R$^c$;

R$^2$ is selected from: C$_1$-C$_6$ alkyl, C$_1$-C$_6$ haloalkyl, C$_3$-C$_6$ cycloalkyl, and (phenyl substituted with 0 to 2 R$^d$);

R$^3$ is independently H, halo, C$_1$-C$_4$ alkyl, C$_1$-C$_4$ halolkyl, C$_1$-C$_4$ alkoxy or C$_1$-C$_4$ halolkoxy;

R$^4$ and R$^5$ are independently H, halo, or C$_1$-C$_4$ alkyl;

R$^6$ is H or C$_1$-C$_4$ alkyl;

R$^7$ is H, halo, C$_1$-C$_4$ alkyl, C$_2$-C$_4$ alkenyl, or cyclopropyl;

R$^8$ is H, halo, or C$_1$-C$_4$ alkyl;

R$^9$, R$^{10}$, R$^{11}$ and R$^{12}$ are H, halo, or C$_1$-C$_4$ alkyl;

R$^{13}$ and R$^{15}$ are independently H, OH, halo or C$_1$-C$_4$ alkyl;

R$^{14}$, R$^{16}$ and R$^{17}$ are independently H, halo or C$_1$-C$_4$ alkyl;

R$^a$ is H or C$_1$-C$_6$ alkyl;

R$^b$ is H, C(O)(C$_1$-C$_4$ alkyl), or C(O)Ph;

R$^c$ is independently selected from: halo, CN, C$_1$-C$_6$ alkyl, C$_1$-C$_6$ halolkyl, C$_1$-C$_6$ alkoxy, C$_1$-C$_6$ halolkoxy, CH$_2$OH, C(O)OH, C(O)NH$_2$, —S(O)$_2$(C$_1$-C$_4$ alkyl), C$_3$-C$_6$ cycloalkyl, and (phenyl substituted with 0 to 2 R$^e$); and R$^d$ and R$^e$ are independently selected from halo, C$_1$-C$_4$ alkyl, C$_1$-C$_4$ halolkyl, C$_1$-C$_4$ alkoxy and C$_1$-C$_4$ halolkoxy;

or a pharmaceutically acceptable salt, a stereoisomer, a tautomer, or a solvate thereof.

In a second aspect, the present invention provides a compound of formula (I), within the scope of the first aspect, wherein:

Q is C$_3$-C$_6$ alkyl substituted with (C(O)OH and R$^3$; and

R$^3$ is independently H, halo, C$_1$-C$_4$ alkyl, or C$_1$-C$_4$ alkoxy.

In a third aspect, the present invention provides a compound of formula (I), within the scope of the first aspect, wherein:

Q is

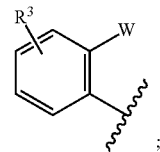

wherein:

W is selected from: C(O)OR$^a$, —S(O)$_2$NHR$^b$,

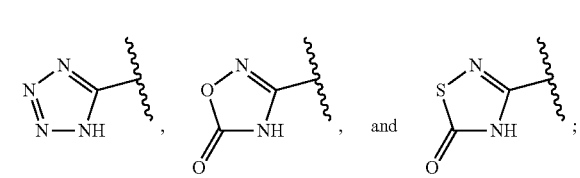 [SMILES: *c1nnn[nH]1 ; *c1noc(=O)[nH]1 ; *c1nsc(=O)[nH]1]

R$^a$ is H or C$_1$-C$_4$alkyl.

In a fourth aspect, the present invention provides a compound of formula (I), within the scope of the first or third aspect, wherein:

Q is

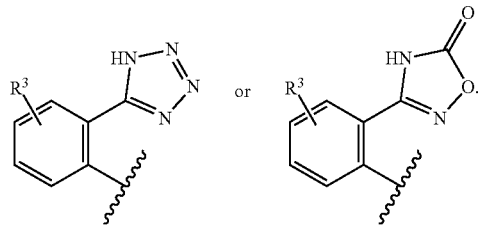

In a fifth aspect, the present invention provides a compound of formula (I), within the scope of the first to fourth aspects, wherein:

X is a bond, —C(O)CHR$^4$—, or —C(O)NR$^6$—.

In a sixth aspect, within the scope of the first, third to fifth aspects, the present invention provides a compound of formula (II),

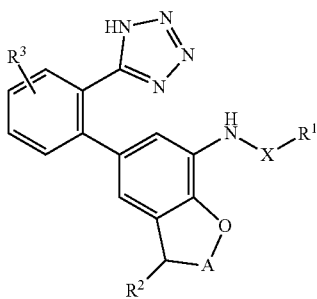

(II)

A is —CR⁷R⁸—, —CR⁹R¹⁰CR¹¹R¹²—, —CR¹³R¹⁴CR¹⁵R¹⁶CHR¹⁷—, or —CR¹³=CR¹⁵CHR¹⁷—;

X is a bond, —C(O)CH$_2$—, or —C(O)NH—;

R$^1$ is selected from: C$_3$-C$_6$ cycloalkyl, phenyl, thiazolyl, isoxazolyl, 1,2,4-oxadiazolyl, 1,3,4-thiadiazolyl, pyridinyl, pyrimidinyl, benzo[d]oxazolyl, benzo[d]thiazolyl, benzo[d]imidazolyl, pyrazolo[1,5-a]pyrimidinyl, and quinolinyl; wherein each moiety is substituted with 0 to 2 R$^c$;

R$^2$ is selected from: C$_1$-C$_6$ alkyl, C$_1$-C$_6$haloalkyl, C$_3$-C$_6$ cycloalkyl, and (phenyl substituted with 0 to 1 halo);

R$^3$ is H, halo, or C$_1$-C$_4$ alkyl;

R$^7$ is H, halo, C$_1$-C$_4$ alkyl, C$_2$-C$_4$ alkenyl, or cyclopropyl;

R$^8$ is H, halo, or C$_1$-C$_4$ alkyl;

R$^9$, R$^{10}$, R$^{11}$ and R$^{12}$ are H, halo, or C$_1$-C$_4$ alkyl;

R$^{13}$ and R$^{15}$ are independently H, OH, halo or C$_1$-C$_4$ alkyl;

R$^{14}$, R$^{16}$, and R$^{17}$ are independently H, halo or C$_1$-C$_4$ alkyl; and R$^c$ is independently selected from: halo, CN, C$_1$-C$_4$ alkyl, C$_1$-C$_4$ halolkyl, C$_1$-C$_4$ alkoxy, C$_1$-C$_4$haloalkoxy, cyclopropyl, and (phenyl is substituted with 0 to 1 C$_1$-C$_4$ alkyl);

or a pharmaceutically acceptable salt, a stereoisomer, a tautomer, or a solvate thereof.

In a seventh aspect, within the scope of the first, third to sixth aspects, the present invention provides a compound of formula (II), wherein:

A is —CR¹³R¹⁴CR¹⁵R¹⁶CHR¹⁷— or —CR¹³=CR¹⁵CHR¹⁷—;

R$^1$ is selected from: cyclopropyl, phenyl, thiazolyl, isoxazolyl, 1,2,4-oxadiazolyl, 1,3,4-thiadiazolyl, pyridinyl, pyrimidinyl, benzo[d]oxazolyl, benzo[d]thiazolyl, benzo[d]imidazolyl, pyrazolo[1,5-a]pyrimidinyl, and quinolinyl; wherein each moiety is substituted with 0 to 2 R$^c$;

R$^2$ is selected from: C$_1$-C$_6$ alkyl, C$_1$-C$_6$haloalkyl, cyclopropyl, and (phenyl substituted with 0 to 1 F);

R$^3$ is H, F, or CH$_3$;

R$^{13}$ and R$^{15}$ are independently H, OH, F, Cl or C$_1$-C$_4$ alkyl;

R$^{14}$, R$^{16}$ and R$^{17}$ are independently H, F, Cl and C$_1$-C$_4$ alkyl; and R$^c$ is independently selected from: halo, CN, C$_1$-C$_4$ alkyl, C$_1$-C$_4$ halolkyl, C$_1$-C$_4$ alkoxy, C$_1$-C$_4$haloalkoxy, cyclopropyl, and (phenyl is substituted with 0 to 1 C$_1$-C$_4$ alkyl).

In another aspect, within the scope of the first, third to seventh aspects, the present invention provides a compound of formula (II), wherein:

A is —CR¹³R¹⁴CR¹⁵R¹⁶CHR¹⁷—.

In another aspect, within the scope of the first, third to seventh aspects, the present invention provides a compound of formula (II), wherein:

A is —CR¹³=CR¹⁵CHR¹⁷—.

In an eighth aspect, within the scope of the first, third to sixth aspects, the present invention provides a compound of formula (II), wherein:

A is —CR⁷R⁸—;

R$^1$ is selected from: cyclopropyl, phenyl, thiazolyl, isoxazolyl, 1,2,4-oxadiazolyl, 1,3,4-thiadiazolyl, pyridinyl, pyrimidinyl, benzo[d]oxazolyl, benzo[d]thiazolyl, benzo[d]imidazolyl, pyrazolo[1,5-a]pyrimidinyl, and quinolinyl; wherein each moiety is substituted with 0 to 2 R$^c$;

R$^2$ is selected from: C$_1$-C$_6$ alkyl, C$_1$-C$_6$haloalkyl, cyclopropyl, and (phenyl substituted with 0 to 1 F);

R$^3$ is H, F, or CH$_3$;

R$^7$ is H, F, Cl, C$_1$-C$_4$ alkyl, C$_2$-C$_4$ alkenyl, or cyclopropyl;

R$^8$ is H, F, Cl, or C$_1$-C$_4$ alkyl; and

R$^c$ is independently selected from: halo, CN, C$_1$-C$_4$ alkyl, C$_1$-C$_4$ halolkyl, C$_1$-C$_4$ alkoxy, C$_1$-C$_4$ haloalkoxy, cyclopropyl, and (phenyl is substituted with 0 to 1 C$_1$-C$_4$ alkyl).

In a ninth aspect, the invention provides a compound selected from the exemplified examples or a pharmaceutically acceptable salt, a stereoisomer, a tautomer, or a solvate thereof.

In another aspect, the invention provides a compound selected from the exemplified examples or a pharmaceutically acceptable salt thereof.

In another aspect, the present invention provides a compound selected from any subset list of compounds or a single compound from the exemplified examples within the scope of any of the above aspects.

In some aspects, A is —CR⁷R⁸—. In other aspects, A is —CR⁹R¹⁰CR¹¹R¹²—. In other aspects, A is —CR¹³R¹⁴CR¹⁵R¹⁶CHR¹⁷—, or —CR¹³=CR¹⁵CHR¹⁷—. In other aspects, A is —CR¹³R¹⁴CR¹⁵R¹⁶CHR¹⁷—. In other aspects, A is —CR¹³=CR¹⁵CHR¹⁷—.

In some aspects, Q is C$_3$-C$_6$ alkyl substituted with (C(O)OH and R$^3$; and R$^3$ is independently H, halo, C$_1$-C$_4$ alkyl, or C$_1$-C$_4$ alkoxy. In other aspects, C$_3$-C$_6$ cycloalkyl substituted with W. In other aspects, Q is phenyl substituted with W and R$^4$. In other aspects, Q is

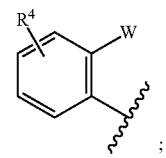

wherein: W is C(O)OR$^a$, C(O)NH$_2$, —S(O)$_2$NHR$^b$,

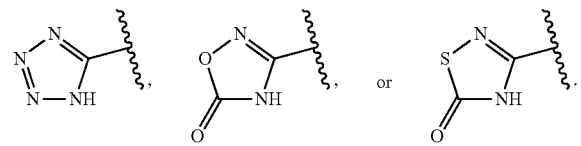 [SMILES: *c1nnn[nH]1 ; *c1noc(=O)[nH]1 ; *c1nsc(=O)[nH]1]

In other aspects, W is C(O)OR$^a$, —S(O)$_2$NHR$^b$,

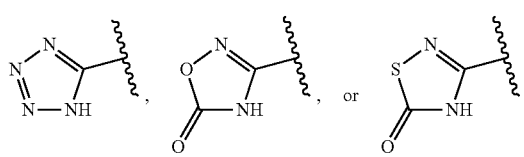

In other aspects, Q is

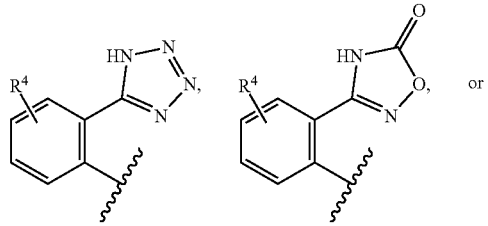

or

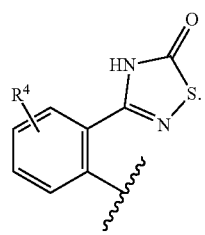

In other aspects, Q is

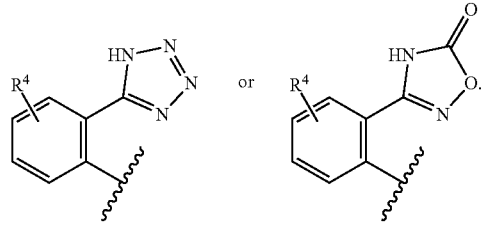

In some aspects, X is a bond, —C(O)CHR⁵—, or —C(O)NR⁷—. In other aspects, X is a bond, —C(O)CH₂—, or —C(O)NH—. In other aspects, X is a bond. In other aspects, X is C(O), —C(O)CHR⁵— or —C(O)NR⁷—. In other aspects, X is —C(O)CHR⁵—. In other aspects, X is —C(O)NR⁷—. In other aspects, X is —C(O)CH₂—. In other aspects, X is —C(O)NH—.

In some aspects, W is C(O)ORᵃ, —S(O)₂NHRᵇ,

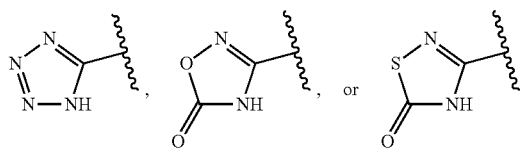

In other aspects, W is C(O)ORᵃ. In other aspects, W is —S(O)₂NHRᵇ. In other aspects, W is

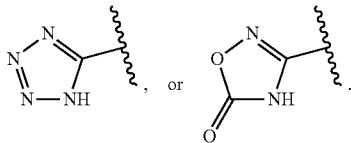 [SMILES: *c1nnn[nH]1 ; *c1noc(=O)[nH]1]

In other aspects, W is

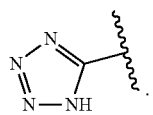

In other aspects, W is

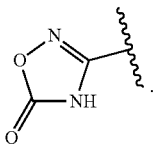 [SMILES: *c1noc(=O)[nH]1]

In other aspects, W is

In some aspects, R¹ is selected from: C₃-C₆ cycloalkyl, phenyl, thiazolyl, isoxazolyl, 1,2,4-oxadiazolyl, 1,3,4-thiadiazolyl, pyridinyl, pyrimidinyl, benzo[d]oxazolyl, benzo[d]thiazolyl, benzo[d]imidazolyl, pyrazolo[1,5-a]pyrimidinyl, and quinolinyl; wherein each moiety is substituted with 0 to 2 Rᶜ.

In some aspects, R² is selected from: C₁-C₆ alkyl, C₁-C₆ haloalkyl, C₃-C₆ cycloalkyl, and (phenyl substituted with 0 to 1 halo). In other aspects, R² is selected from: C₁-C₆ alkyl, C₁-C₆ haloalkyl, cyclopropyl, and (phenyl substituted with 0 to 1 F).

In some aspects, R³ is H, halo, or C₁-C₄ alkyl. In other aspects, R³ is H, F, or CH₃.

In some aspects, R⁴ and R⁵ are independently H, F, Cl, or C₁-C₄ alkyl. In other aspects, R⁴ and R⁵ are independently H or C₁-C₄ alkyl. In other aspects, R⁴ and R⁵ are H.

In some aspects, R⁶ is H. In other aspects, R⁶ is C₁-C₄ alkyl.

In another embodiment, the compounds of the invention have human IDO IC₅₀ values >50 nM but ≤1 μM. In another embodiment, the compounds of the invention have human IDO IC₅₀ values ≤50 nM. In another embodiment, the compounds of the invention have human IDO IC₅₀ values <5 nM.

OTHER EMBODIMENTS OF THE INVENTION

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another embodiment, the additional therapeutic agent(s) are YERVOY, OPDIVO, or KEYTRUDA, or a combination thereof.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid, arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb Rom the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.,* 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.,* 1(8):792-797 (1995)); (iv) inhibitors of Akt family kinases or the Akt pathway, such as, for example, rapamycin (see, for example, Sekulic et al., *Cancer Res.,* 60:3504-3513 (2000)); (v) cell cycle kinase inhibitors such as, for example, flavopiridol and UCN-O1 (see, for example, Sausville, *Curr. Med. Chem. Anti-Canc. Agents,* 3:47-56 (2003)); and (vi) phosphatidyl inositol kinase inhibitors such as, for example, LY294002 (see, for example, Vlahos et al, *J. Biol. Chem.,* 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas (I) and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g, malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see, e.g, Scheller et al., *Circulation,* 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfmavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of the present invention is administered with one or more immuno-oncology agents. The immuno-oncology agents used herein, also known as cancer immunotherapies, are effective to enhance, stimulate, and/or upregulate immune responses in a subject.

In one aspect, the Compound of the present invention is sequentially administered prior to administration of the immuno-oncology agent. In another aspect, the Compound of the present invention is administered concurrently with the immunology-oncology agent. In yet another aspect, the Compound of the present invention is sequentially administered after administration of the immuno-oncology agent.

In another aspect, the Compound of the present invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of the Compound of the present invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD 137), 4-1BBL, ICOS, ICOS-L, OX40, OX40L, GITR, GITRL, CD70, CD27, CD40, DR3 and CD28H.

Other agents that can be combined with the Compound of the present invention for the treatment of cancer include antagonists of inhibitory receptors on NK cells or agonists of activating receptors on NK cells. For example, the Compound of the present invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of the present invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MEDI4736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD 137 (4-1BB) agonist, such as an agonistic CD 137 antibody. Suitable CD 137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of the present invention, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington; The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —OCH$_3$ is attached through the oxygen atom.

Additionally, for purposes of clarity, when there is no substituent shown at the end of a solid line, this indicates that there is a methyl (CH$_3$) group connected to the bond.

As used herein, the terms "alkyl" and "alkylene" (also referred to as "alk") are intended to include both branched and straight-chain saturated aliphatic hydrocarbon groups having the specified number of carbon atoms. For example, "C$_1$-C$_6$ alkyl" or "C$_{1-6}$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). "C$_1$-C$_6$ alkylene" denotes alkylene having 1 to 6 carbon atoms. Example alkylene groups include, but are not limited to, methylene (—CH$_2$—), ethylene (—CH$_2$CH$_2$—), and the like.

As used herein, the terms "alkenyl" and "alkenylene" are intended to include both branched and straight-chain saturated aliphatic hydrocarbon groups having the specified number of carbon atoms and one or more, preferably one to two, carbon-carbon double bonds that may occur in any stable point along the chain. For example, "C$_2$-C$_6$ alkenyl" or "C$_{2-6}$ alkenyl" denotes alkyl having 2 to 6 carbon atoms. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl. "C$_2$-C$_6$ alkenylene" denotes alkenylene having 2 to 6 carbon atoms.

The term "alkoxy" or "alkyloxy" refers to an —O-alkyl group. For example, "C$_1$ to C$_6$ alkoxy" or "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy.

As used herein, "aryl" refers to an aromatic ring system which includes, but not limited to phenyl, biphenyl, indanyl, 1-naphthyl, 2-naphthyl and terahydronaphthyl.

"Halo" or "halogen" includes fluoro, chloro, bromo, and iodo.

"Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, and pentafluorothoxy.

The term "cycloalkyl" refers to hydrocarbon rings having the indicated number of ring atoms (e.g., C$_{3-10}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, adamantane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized.

The cycloheteroalkyl may be a monocyclic, a bicyclic or a polycyclic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A cycloheteroalkyl group can be attached to the remainder of the molecule through a ring carbon or a heteroatom.

As used herein, "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, 1,2,4-thiadiazolyl, isothiazolyl, purinyl, carbazolyl, indazolyl, quinolyl, isoquinolyl, benzimidazolyl, imidazopyridinyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

As referred to herein, the term "substituted" means that at least one hydrogen atom is replaced with a non-hydrogen group, provided that normal valencies are maintained and that the substitution results in a stable compound.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. Y., ed., *Remington; The Science and Practice of Pharmacy*, 22nd Edition, Pharmaceutical Press, London, UK (2012).

In addition, compounds of the present invention may have prodrug forms. Any compound that will be converted in vivo to provide the bioactive agent (i.e., a compound of formula (I)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991);

c) Bundgaard, H., *Adv. Drug Deliv. Rev.*, 8:1-38 (1992);

d) Nielsen, N. M. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery* (*Methods and Principles in Medicinal Chemistry*), Vol. 47, Wiley-VCH (2011).

Compounds containing a carboxy group can form physiologically hydrolyzable esters that serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry; Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, CA (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s).

Compounds of the invention may be prepared according to the following schemes utilizing chemical transformations familiar to anyone of ordinary proficiency in the art of organic/medicinal chemistry. References to many of these transformations can be found in March's Advanced Organic Chemistry Reactions, Mechanisms, and Structure, Fifth Edition by Michael B. Smith and Jerry March, Wiley-Interscience, New York, 2001, or other standard texts on the topic of synthetic organic chemistry. Functional groups such as carboxylic acids, amines, alcohols, or heterocycles may need to be carried through sequences in protected form to prevent their interfering with desired reactions. The use of such protecting groups is a topic familiar to those skilled in the art of organic/medicinal chemistry and has been thoroughly reviewed in books (see "Protecting Groups in Organic Synthesis" by Theodora W. Greene, Wiley Interscience) and in the chemical literature.

Compounds of formula (IIa) or formula (IIb) where Y is Cl, Br, or I and Z is a halogen are commercially available or can be prepared utilizing standard transformations known to those of ordinary proficiency in the art of organic/medicinal chemistry. Treatment of an allylic alcohol and a base of suitable strength to deprotonate it, ideally in a solvent such as THF, DMF, or NMP followed by a 2-halonitrobenzene IIb, affords adducts (III). Depending upon the degree of nucleophilicity of the alkoxide, heating may be required. Suitable bases for alcohols include, but are not be limited to, sodium hydride and organometallics such as Grignard or alkyllithium reagents. Alternatively, a 2-nitrophenol (IIa) can be O-allcylated with an allylic halide using a suitable base such as cesium or potassium carbonate in a solvent such as DMF or NMP. Depending upon the degree of nucleophilicity of the phenoxide, heating may be required. Nitrophenols IIa also react with allylic alcohols in solvents such as THF under Mitsunobu conditions (dialkylazodicarboxylate, $Ph_3P$) to afford ethers III. Upon heating, generally at a temperature between 150° C. and 190° C., ethers III undergo Claisen rearrangement to afford phenols IV. Typical solvents for this reaction include high-boiling ethers such as diglyme, diethyleneglycol diethyl ether, and eutectic liquids such as DOWTHERM. Phenols IV can be re-alkylated to give ethers V under the conditions for the conversion of IIa to III. Upon warming in dilute solution in the presence of a catalytic amount of an RCM catalyst such as (1,3-Bis-(2,4,6-trimethylphenyl)-2-imidazolidinylidene) dichloro(o-isopropoxyphenylmethylene)ruthenium, dichloro[1,3-bis(2,4,6-trimethylphenyl)-2-imidazolidinylidene](2-isopropoxyphenylmethylene)ruthenium(II) (Hoveyda-Grubbs Catalyst™, $2^{nd}$ Generation), dienes V undergo ring-closing metathesis reaction to afford 7-membered cyclic ethers VI. Generally this reaction is performed at a temperature between 50 and 60° C. in a non-coordinating solvent such as 1,2-dichloroethane at sufficient dilution to suppress intermolecular reactions. Selective reduction of the nitro group in VI affords anilines VIIa while leaving the olefin and aromatic halide functionalities unchanged. This transformation can be accomplished with finely-divided zinc and a proton source such as ammonium chloride in solvent systems such as ethanol-water or THF-ethanol-water. Anilines VIIa undergo reactions with isocyanates to afford ureas VIIb. Alternatively, these ureas can be prepared by activation with phosgene or an attenuated equivalent such as CDI and treatment with a second amine. Anilines VIIa can also be transformed into amides VIIc by various peptide couplings with carboxylic acids $RfCH_2CO_2H$. The use of peptide coupling reagents has been reviewed by Han, S-Y and Kim, Y-A: *Tetrahedron*, 60:2447-2467 (2004). Further compounds of interest are aryl/heteroaryl-substituted anilines VIId which can be prepared from VIIa and an aryl/heteroaryl halide thermally or under conditions of acid or Pd catalysis (Buchwald reaction). Conditions for these transformations are known to those of ordinary skills in the art of organic/medicinal chemistry and can be found in the literature with more specific conditions given in the experimental section. Reduction of the olefin to provide VIII is generally accomplished by treatment with a catalyst, preferably Pd on carbon, in a solvent (initially under an inert atmosphere to minimize the risk of fire) and then stirring under an atmosphere of hydrogen. Ethyl acetate is often chosen as solvent to minimize reduction of the aryl halide. Finally, VIII can be transformed into compounds of the invention (Ia) using Suzuki or related couplings followed by removal of any protecting groups still present. Racemic compounds of the invention (as well as intermediates) may also be resolved into their enantiomeric components by chiral SFC or other chiral chromatographic methods.

Scheme 1

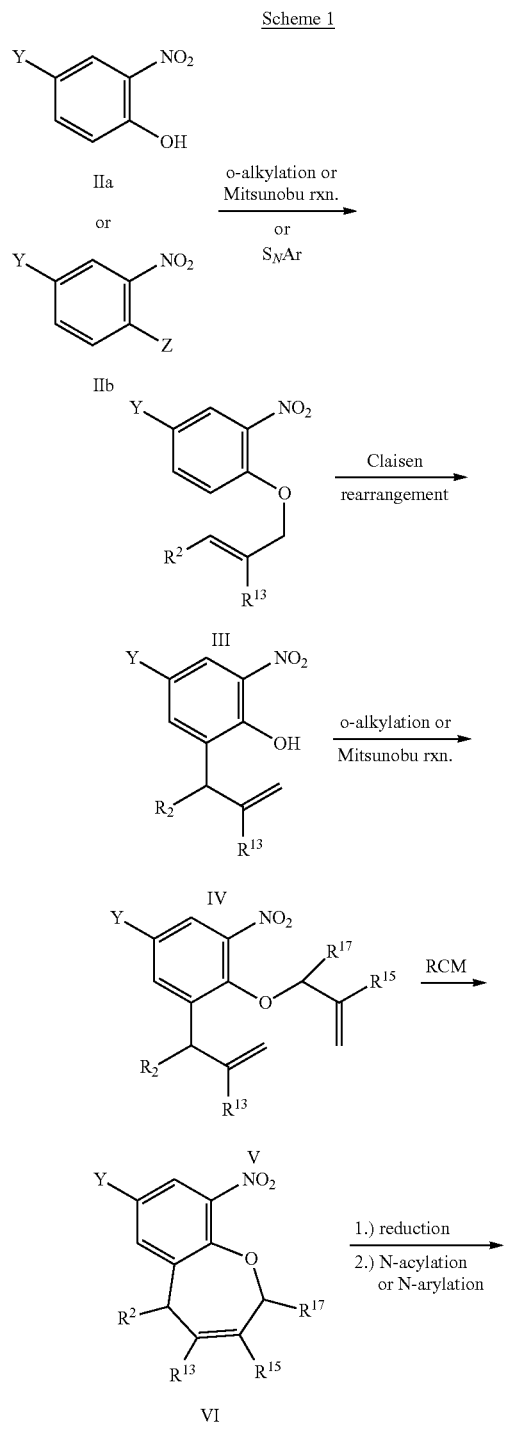

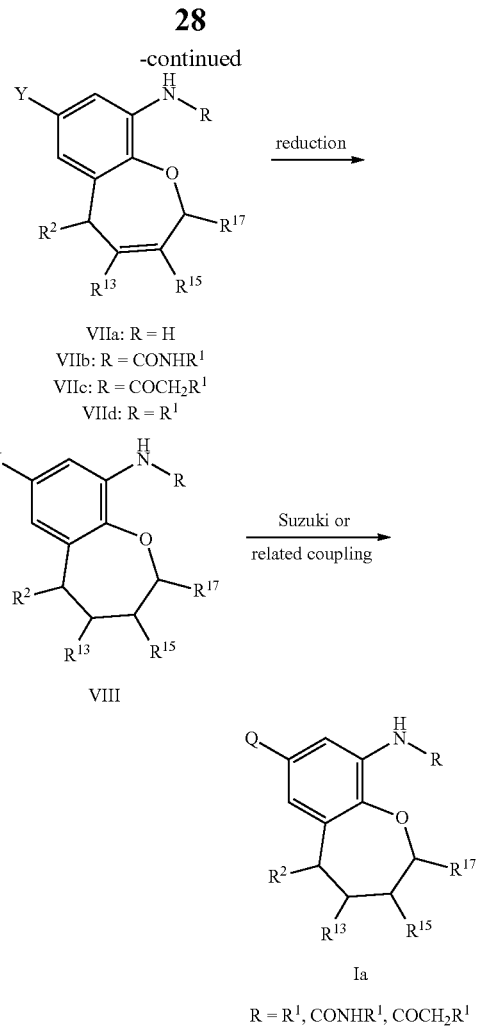

Scheme 2 describes a preparation of compounds of the invention (Ia) similar to that of Scheme 1 but with the transformations performed in a different order. Protection of the aniline functional group in VIIa affords IXa. Acceptable protecting groups include but are not limited to carbamates such as the Boc group. This substrate is a convenient intermediate for resolution by chiral chromatography to afford homochiral materials IXb. Reduction of the olefin now affords X, and the Rg group is installed by Suzuki or related coupling to give XI. Treatment of XI with protic or Lewis acids affords anilines XII, and incorporation of the Re group as in Scheme 1 affords compounds of the invention (Ia).

Scheme 2

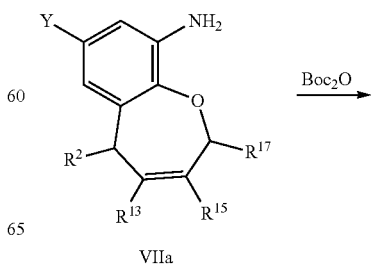

-continued

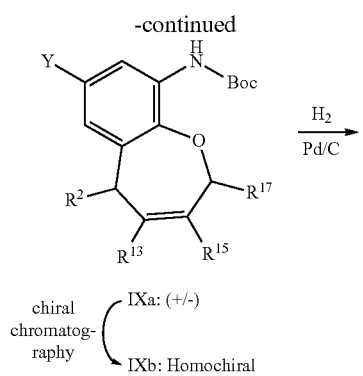

chiral chromatography
- IXa: (+/-)
- IXb: Homochiral

In Scheme 3 removal of the Boc group from intermediate X (either as a racemate or pure enantiomer) affords bromoanilines XIII. In practice, this aniline is a convenient intermediate for chiral resolution. The presence of both aryl halide and aniline functional groups in XIII makes it a poor choice of substrates for Buchwald reactions, but it may be converted to N-acylated or N-arylated derivatives XIV by many of the other methods described above and more specifically in the experimental section. Finally, XIV can be transformed into compounds of the invention (Ia) using Suzuki or related couplings followed by removal of any protecting groups still present.

Scheme 3

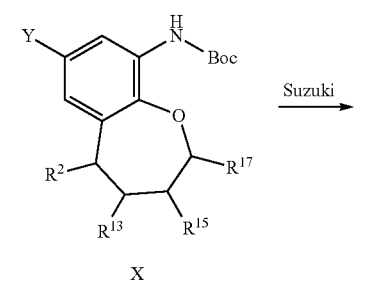

X

Suzuki →

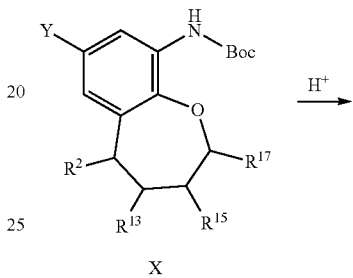

X

H+ →

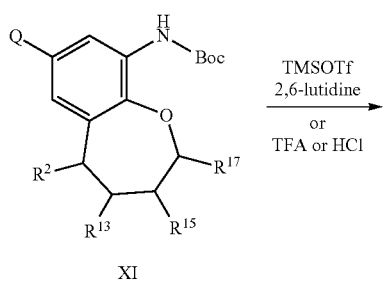

XI

TMSOTf
2,6-lutidine
or
TFA or HCl
→

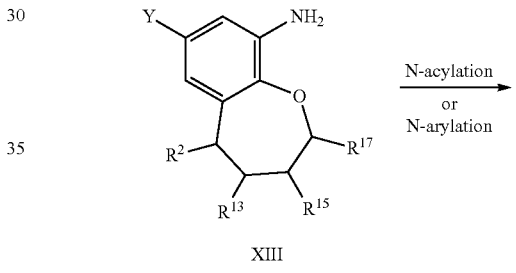

XIII

N-acylation
or
N-arylation
→

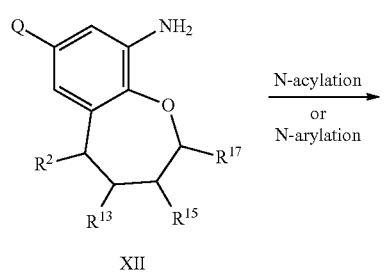

XII

N-acylation
or
N-arylation
→

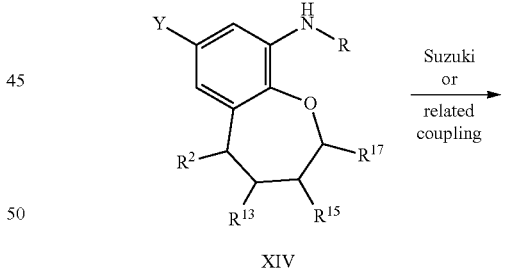

XIV

Suzuki
or
related
coupling
→

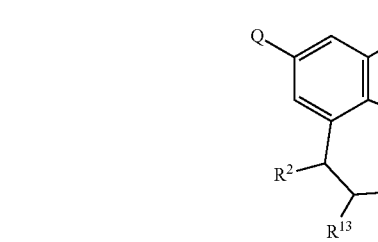

Ia

R = R¹, CONHR¹, COCH₂R¹

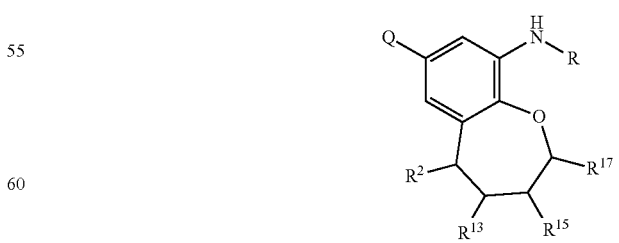

Ia

R = R¹, CONHR¹, COCH₂R¹

Scheme 4

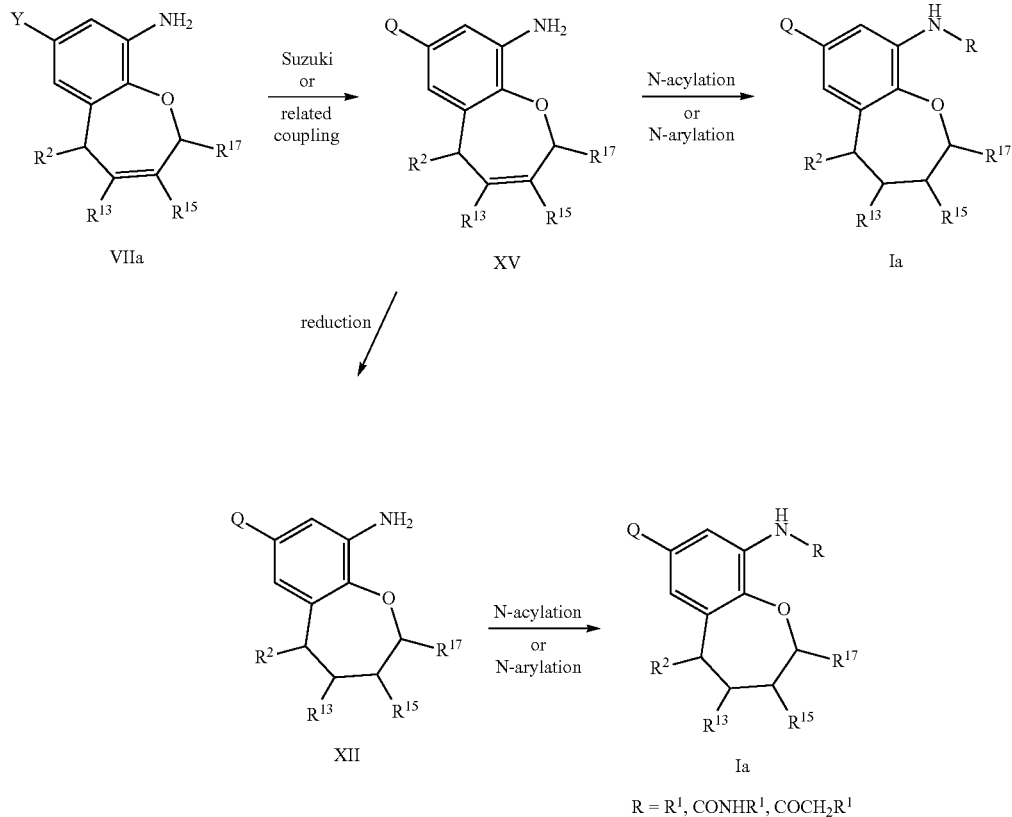

Scheme 4 provides methods for the preparation of compounds of the invention in which the core bicyclic ring system is 2,5-dihydrobenzo[b]oxepine. Bromoanilines VIIa are suitable intermediates for the preparation of intermediates XV by Suzuki or related coupling methods. Finally, compounds of the invention may be prepared from XV by the N-acylation and N-arylation reactions described above. Reduction of the olefin in XV also affords intermediates XII which may be transformed to compounds of the invention as in Scheme 2.

Intermediate VIIe or other intermediates can be functionalized by olefin oxidation (hydroboration, dihydroxylation, epoxidation, etc.) to provide hydroxylated intermediates (Scheme 5). These analogs (XIII, shown here for $R^{13}$=H, $R^{15}$=OH) can be further functionalized to provide alcohols XIV. Oxidation provides ketones XVI which can be transformed by electrophilic fluorinating agents to gem-difluorides XVII. Suzuki or related coupling reactions afford compounds of the invention (Ia). The same sequence could be performed on the regioisomeric alcohols XIII, ($R^{13}$=OH, $R^{15}$=H) to provide regioisomeric gem-difluoride compounds of the invention. Additionally, the intermediates shown as well as the regioisomeric alcohol XIII, ($R^{13}$=OH, $R^{15}$=H) and diol (XIII, $R^{13}$=OH, $R^{15}$=OH) intermediates can be transformed by methods taught above into compounds of the invention (Ia).

Scheme 5

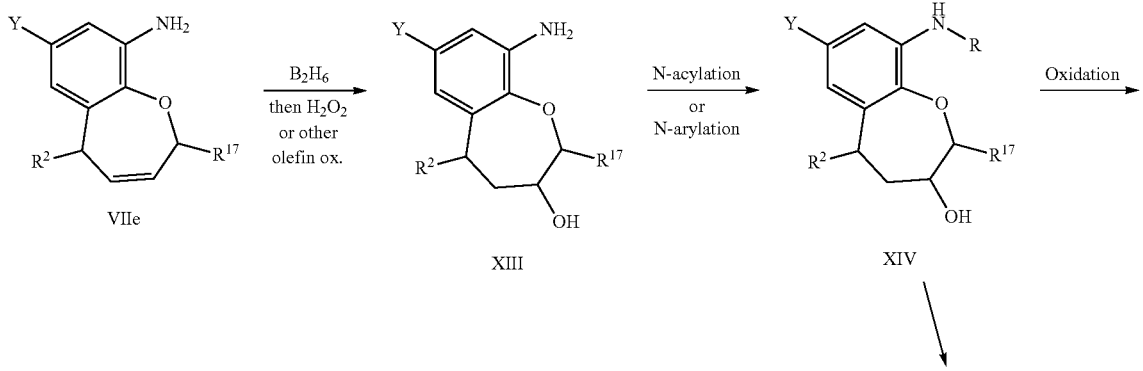

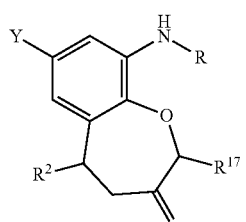 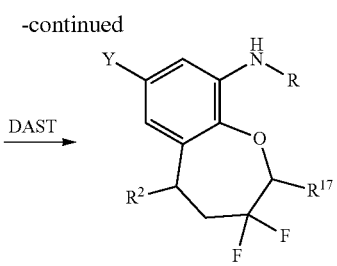

While many of the groups Q in the compounds of the invention described herein can be introduced directly, for some it is more convenient to use a protected form which is functionalized at a later stage. Additionally, certain carboxylic acid isosteres are prepared at the end of a synthetic sequence, often from a carboxylic acid or ester which may itself be a compound of the invention. Some examples of this are shown in Scheme 6, with more complete descriptions provided in the experimental section.

affords tetrazole compounds of the invention. Another carboxylic acid isostere is the 5-oxo-2,5-dihydro-1,2,4-oxatriazol group. These compounds are prepared from XVIII in the two-step sequence shown in Scheme 6.

Many compounds of the invention can be prepared in which the core ring system is a dihydrobenzofuran (Scheme 7). Allylic ethers III can undergo Claisen rearrangement to afford phenols IV. These phenols cyclize to ethers XIX at RT upon exposure to a strong acid, ideally triflic acid, in a

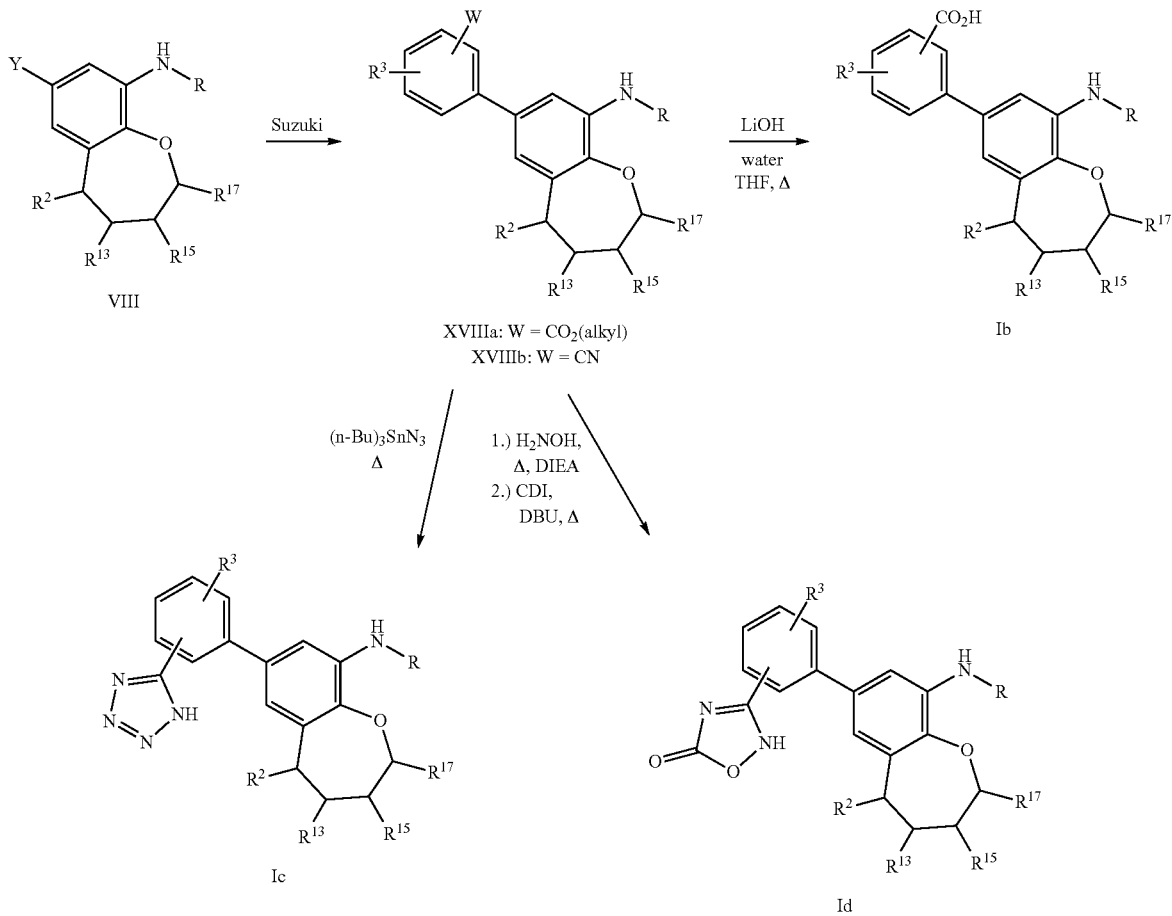

In one such embodiment, an ester XVIII can be saponified to afford carboxylic acid compounds of the invention (Ib). Where XVIII is a nitrile, heating with an azide such as tributlytin azide in a high-boiling solvent such as toluene solvent such as dichloroethane. Alternatively, the cyclization may be performed by heating to a temperature of around 100° C. with formic acid as the solvent/catalyst. These two steps can be accomplished in tandem by heating III and MgCl₂ to around 180° C. Reduction of XIX using conditions described above affords anilines XX which may be further derivatized to give ureas, amides, diarylanilines and the like. Finally, these intermediates may be transformed to compounds of the invention (Ie) by Suzuki or related couplings.

Scheme 7

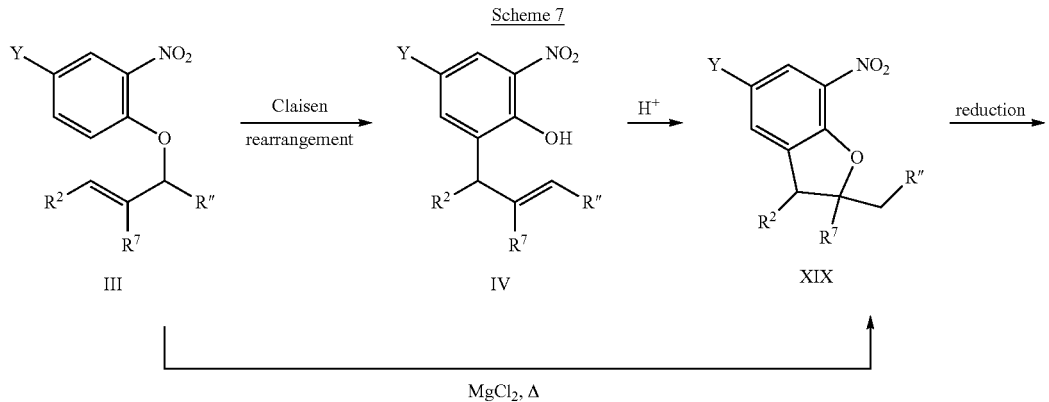

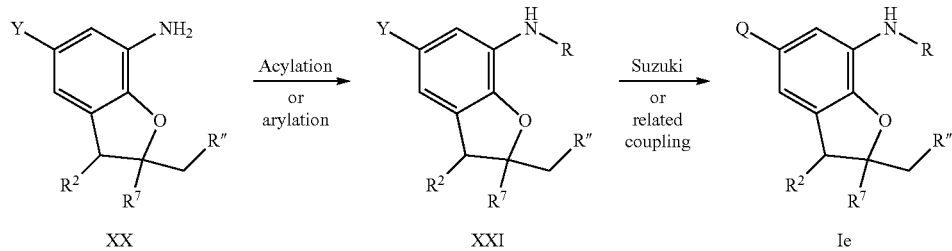

Another route to dihydrobenzofurans is shown in Scheme 8. Under Suzuki reaction conditions, N-acylated intermediates VIIb and VIIc undergo ring contraction to afford additional trans (major) and cis (minor) 2,3-disubstituted dihydrobenzofurans I. As with other intermediates and compounds of the invention, these can be further functionalized by, for instance, reduction or oxidation of the olefin group. This ring contraction reaction may also be performed on 9-nitro-2,5-dihydrobenzo[b]oxepine intermediates VI to provide intermediates XXII. Reduction of the nitro group and derivitization of the resulting aniline XXIII affords I. Performing the ring contraction with the exclusion of a boronate ester/boronic acid component affords intermediates XIX, which are shown in Scheme 7 to be useful for late introductions of the group Q.

Scheme 8

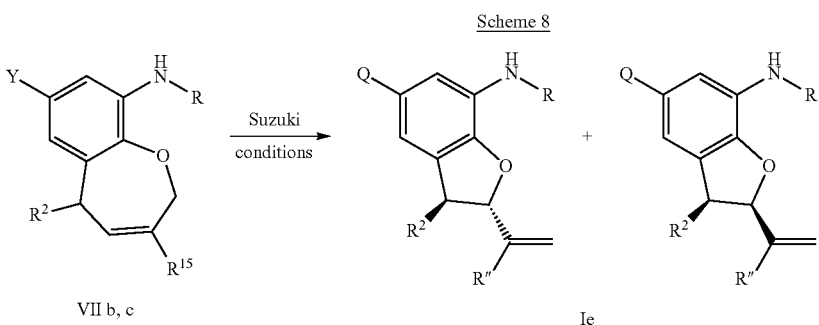

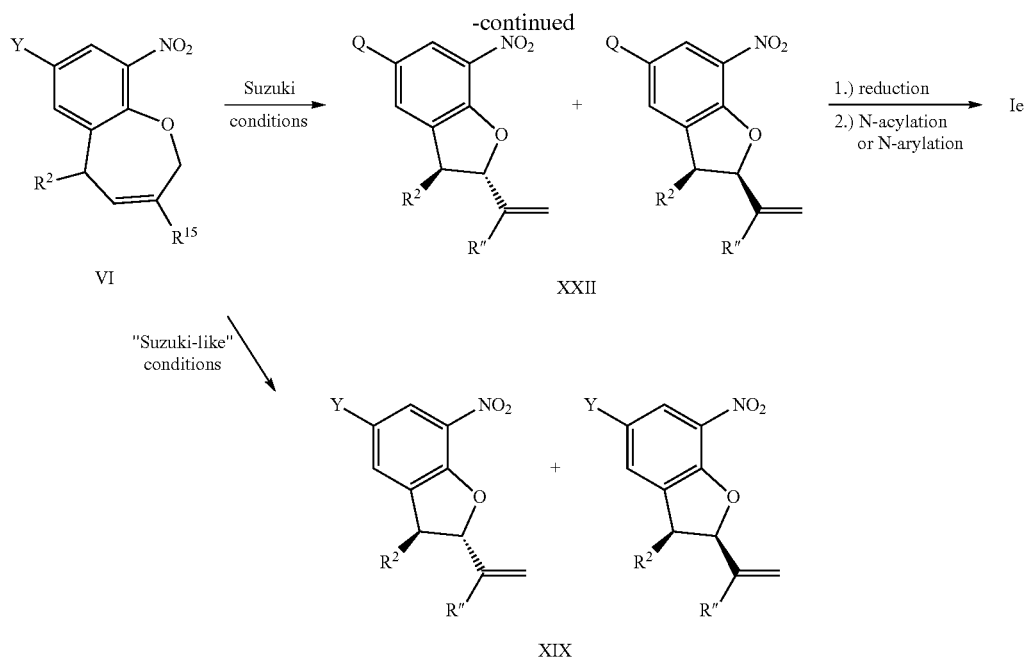

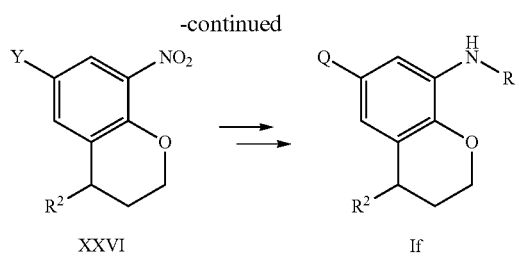

Unsaturated acids and esters XXIII (Scheme 9) are known in the literature and may be easily prepared by those of ordinary skill in the art or organic/medicinal chemistry. These olefins undergo Rhodium (II)-mediated coupling with boronate esters to provide β-substituted dihydrocinnamates XXIV. Reduction with a reagent such as DIBAL-H affords primary alcohols XXV which can undergo intramolecular Mitsunobu reactions (or other ether-forming reaction sequences) to afford substituted chroman derivatives XXVI. Conversion to compounds of the invention proceeds by similar methods to those employed for the 5- and 7-membered ethers above.

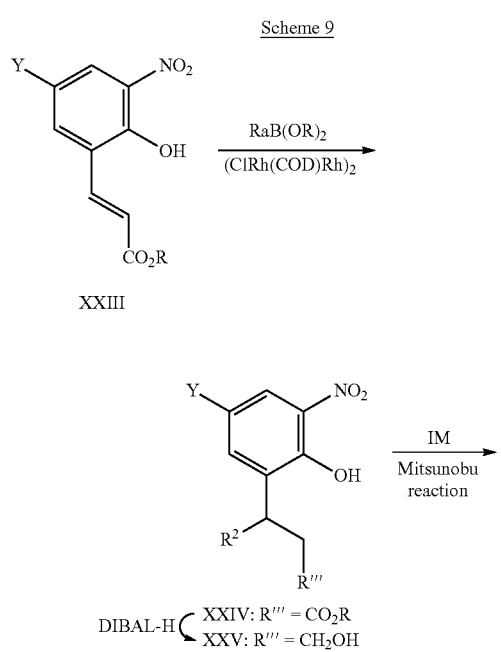

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: 1×=once; 2×=twice; 3×=thrice; rt or RT=room temperature; $T_r$=retention time; wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar;

kDa=kilodalton; i.m.=intramuscular(ly); i.p.=intraperitoneal(ly); SC or SQ=subcutaneous(ly); QD=daily; BID=twice daily; QW=weekly; QM=monthly; BW=body weight; U=unit; ns=not statistically significant; PBS=phosphate-buffered saline; IHC=immunohistochemistry; DMEM=Dulbecco's Modification of Eagle's Medium; LG=leaving group; conc.=concentrate or concentrated; aq=aqueous; sat or sat'd=saturated; MW=molecular weight; mp=melting point; MS or Mass Spec=mass spectrometry; ESI=electrospray ionization mass spectroscopy; HR=high resolution; HRMS=high resolution mass spectrometry; LCMS liquid chromatography mass spectrometry; HPLC=high performance liquid chromatography; RP HPLC=reverse phase HPLC; SFC=Supercritical Fluid Chromatography; TLC or tlc=thin layer chromatography; NMR=nuclear magnetic resonance spectroscopy; "$^1$H" for proton, "δ" for delta, "s" for singlet, "d" for doublet, "t" for triplet, "q" for quartet, "m" for multiplet, "br" for broad, "Hz" for hertz; and "a", "P", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
BOP (benzotriazol-1-yloxy)tris(dimethylamino)phosphonium hexafluorophosphate
$CDCl_3$ deutero-chloroform
$CHCl_3$ chloroform
cDNA complimentary DNA
DAST diethylaminosulfur trifluoride
DBU 2,3,4,6,7,8,9,10-octahydropyrimidol[1,2-a]azepine
DCEDCM 1,2-dichloroethane
DIAD dichloromethane
DIBAL-H dissopropyl azodicarboxylate
DIPEA diisobutyl aluminum hydride
DMF N,N-diisopropylethylamine dimethyl formamide
DMSO dimethyl sulfoxide
DIAD diisopropyl azodicarboxylate
EDTA ethylenediaminetetraacetic acid
EtOAc ethyl acetate
$Et_2O$ diethyl ether
$AlCl_3$ aluminum chloride
Boc tert-butyloxycarbonyl
$CH_2Cl_2$ dichloromethane
$CH_3CN$ or ACN acetonitrile
$Cs_2CO_3$ cesium carbonate
CDI carbonyldiimidazole
HCl hydrochloric acid
$H_2SO_4$ sulfuric acid
Hunig's base diisopropylethylamine
KF solution potassium fluoride
$K_2CO_3$ potassium carbonate
KOAc potassium acetate
mCPBA or m-CPBA meta-chloroperbenzoic acid
Pd/C palladium on carbon
PS polystyrene
$SiO_2$ silica oxide
$SnCl_2$ tin(II) chloride
TBTU 2-(1H-benzotriazole-1-yl)-1,1,3,3-tetramethylaminium tetrafluoroborate
TEA triethylamine
TFA trifluoroacetic acid
TFAA trifluoroacetic anhydride
THF tetrahydrofuran
$TMSCHN_2$ trimethylsilyldiazomethane
LHMDS lithium hexamethyldisilazide
MTBE methyl tert-butyl ether
$MgSO_4$ magnesium sulfate
NMP N-methylpyrrolidone
MsOH or MSA methylsulfonic acid
NaCl sodium chloride
NaH sodium hydride
$NaHCO_3$ sodium bicarbonate
NaOH sodium hydroxide
$Na_2SO_3$ sodium sulfite
$Na_2SO_4$ sodium sulfate
$NH_3$ ammonia
$NH_4Cl$ ammonium chloride
$NH_4OH$ ammonium hydroxide
Rochelle salt Potassium sodium tartrate tetrahydrate,
XantPhos 4,5-bis(diphenylphosphino)-9,9-dimethylxanthene
GrubbsII catalyst dichloro[1,3-bis(2,4,6-trimethylphenyl)-2-imidazolidinylidene] (2-isopropoxyphenylmethylene)ruthenium(II)
TMSOTf trimethylsilyltriflate NMR Employed in Characterization of Examples $^1$H NMR spectra (unless otherwise noted) were obtained with JEOL or Bruker FOURIER® transform spectrometers operating at 400 MHz or 500 MHz.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$). Abbreviations used in the description of NMR peaks: "a"=apparent, "br. s."=broad singlet.

HPLC/MS and Preparatory/Analytical HPLC Methods Employed in Characterization or Purification of Examples Method A: YMC S5 ODS 4.6×50 mm, 4 mL/min flow rate with gradient of 10% B-100% B over 4 minutes (A: 0.02% $H_3PO_4$ in water/MeOH (90:10), B: 0.02% $H_3PO_4$ in water/MeOH (10:90) monitoring at 220, oven temperature 40° C.

Method B: Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 1.11 ml/min; Mobile phase A: 100% Water, 0.05% TFA; Mobile phase B: 100% Acetonitrile, 0.05% TFA.

Method C: Waters Acquity using the following method: Linear Gradient of 0% to 95% solvent B over 2 min; UV visualization at 220 nm; Column: Luna C18 4.6 mm×30 mm; 3 um particle; Flow rate: 4 ml/min; Mobile phase A: 90:10 Water/MeOH with 0.05% TFA; Mobile phase B: 10:90 Water/MeOH with 0.05% TFA.

Method N: Kinetex XB-C18 (75×3) mm, 2.6 μm; Mobile Phase A: 10 mM $NH_4OAc$ in Water: Acetonitrile (98:02); Mobile Phase B: 10 mM $NH_4OAc$ in Water: Acetonitrile (02:98); Gradient: 20-100% B over 4 minutes, flow rate 1 mL/min, then a 0.6 minute hold at 100% B flow rate 1.5 mL/min; then Gradient: 100-20% B over 0.1 minutes, flow rate 1.5 mL/min.

Method O: Column: Ascentis Express C18 (50×2.1) mm, 2.7 µm; flow rate 1.1 mL/min; gradient time 3 min; Temperature: 50° C., 0% Solvent B to 100% Solvent B; monitoring at 220 nm (Solvent A: 95% Water: 5% Acetonitrile; 10 mM $NH_4OAc$; Solvent B: 5% Water: 95% Acetonitrile; 10 mM $NH_4OAc$).

Method P: Column: Ascentis Express C18 (50×4.6) mm, 2.7 µm, flow rate 4 mL/min; gradient: 0 to 100% solvent B over 4 min; Temperature: 50° C. Monitoring at 220 nm (Solvent A: 95:05 water: $CH_3CN$ with 10 mM $NH_4OAc$ and Solvent B: 05:95 water: $CH_3CN$ with 10 mM $NH_4OAc$)

Method Q: Column: Ascentis Express $C_{1-8}$ (50×4.6) mm, 2.7 µm, flow rate 4 mL/min; gradient: 0 to 100% solvent B over 4 min; Temperature: 50° C.; monitoring at 220 nm (Solvent A: 95:05 water: $CH_3CN$ with 0.1% TFA and Solvent B: 05:95 water: $CH_3CN$ with 0.1% TFA)

Method R: Column: Ascèntis Express C18 (50×2.1) mm, 2.7 µm, flow rate 1.1 mL/min; gradient: 0 to 100% solvent B over 3 min; Temperature: 50° C.; monitoring at 220 nm (Solvent A: 95:05 water: $CH_3CN$ with 0.1% TFA and Solvent B: 05:95 water: $CH_3CN$ with 0.1% TFA)

Method S: Column: Chiralpak AS-H (250×4.6) mm, 5.0 µm; Isocratic Mode, $CO_2$: Co-Solvent (85:15), Co-Solvent: 0.2% DEA in Methanol; Co-Solvent percentage: 15%, Column Temperature: 22.1° C.; Back Pressure: 100 bars; Total Flow: 3 g/min; $CO_2$ flow: 2.55 g/min; Co-Solvent flow: 0.45 g/min.

Method T: Column: Acquity BEH C18 (2.1×50 mm) 1.7 um; Mobile phase A: Buffer:ACN (95:5); Mobile phase B:Buffer:ACN (5:95), Buffer:5 mM Ammonium Acetate; Gradient: 20-90% B over 1.1 minutes, then a 0.6 minute hold at 90% B, flow rate 0.5 mL/min.

Method U: Column: Kinetex XB-C18 (75×3) mm, 2.6 µmL; Mobile Phase A: 10 mM $NH_4COOH$ in Water: Acetonitrile (98:02; Mobile Phase B: 10 mM $NH_4COOH$ in Water: Acetonitrile (02:98); Gradient: 20-100% B over 4 minutes, flow rate 1 mL/min, then a 0.6 minute hold at 100% B flow rate 1.5 mL/min; then Gradient: 100-20% B over 0.1 minutes, flow rate 1.5 mL/min.

Method V: Column: Chiralpak ASH (250×4.6) mm, 5.0 µm; Isocratic Mode, Co-Solvent: 0.2% DEA in Methanol; Co-Solvent percentage: 20%, Column Temperature: 20.2° C.; Back Pressure: 100 bars; Total Flow: 3 g/min; $CO_2$ flow: 2.4 g/min; Co-Solvent flow: 0.6 g/min.

Method W: Column: Chiralpak ASH (250×4.6) mm, 5.0 µm; Isocratic Mode, Co-Solvent: 0.2% DEA in Methanol; Co-Solvent percentage: 30%, Column Temperature: 20.2° C.; Back Pressure: 100 bars; Total Flow: 3 g/min; $CO_2$ flow: 2.1 g/min; Co-Solvent flow: 0.9 g/min.

Method X: Column: Chiralpak ASH (250×4.6) mm, 5.0 µm; Isocratic Mode, Co-Solvent: 0.2% DEA in Methanol; Co-Solvent percentage: 25%, Column Temperature: 24.3° C.; Back Pressure: 100 bars; Total Flow: 3 g/min; $CO_2$ flow: 2.5 g/min; Co-Solvent flow: 0.75 g/min.

Method Y: Column: Chiralpak ASH (250×4.6) mm, 5.0 µm; Isocratic Mode, Co-Solvent: 0.2% DEA in Methanol; Co-Solvent percentage: 25%, Column Temperature: 27.1° C.; Back Pressure: 100 bars; Total Flow: 3 g/min; $CO_2$ flow: 2.25 g/min; Co-Solvent flow: 0.75 g/min.

Method Z: Column: Chiralcel-OJH (250×4.6) mm, 5.0 µm; Isocratic Mode, Co-Solvent: 0.2% DEA in Methanol; Co-Solvent percentage: 30%, Column Temperature: 26° C.; Back Pressure: 100 bars; Total Flow: 3 g/min; $CO_2$ flow: 2.1 g/min; Co-Solvent flow: 0.9 g/min.

Method AA: Column: Acquity BEH C18 (2.1×50 mm) 1.7 urn; Mobile phase A: water; Mobile phase B: Acetonitrile; 0.05% TFA in both phases; Gradient: 2-98% B over 1 minutes, then a 0.6 minute hold at 98% B.

Method AB: Column: Lux Cellulose-4 (250×4.6) mm, 5.0 µm; Isocratic Mode, Co-Solvent: 0.2% DEA in Methanol; Co-Solvent percentage: 30%, Column Temperature: 24.2° C.; Back Pressure: 100 bars; Total Flow: 3 g/min; $CO_2$ flow: 2.1 g/min; Co-Solvent flow: 0.9 g/min.

Method AC: Column: Chiralcel-ASH (250×4.6) mm, 5.0 µm; Isocratic Mode, Co-Solvent: 0.2% DEA in Methanol; Co-Solvent percentage: 30%, Column Temperature: 26° C.; Back Pressure: 100 bars; Total Flow: 3 g/min; $CO_2$ flow: 2.1 g/min; Co-Solvent flow: 0.9 g/min Method AD: Kinetex XB-C18 (75×3) mm, 2.6 µmL; Mobile Phase A: 0.1% HCOOH in Water: Mobile Phase B: 100% Acetonitrile Gradient: 20-100% B over 4 minutes, flow rate 1 mL/min, then a 0.6 minute hold at 100% B flow rate 1.5 mL/min; flow rate 1.5 mL/min.

Method AE: Column: HP-5MS (Part Number: Agilent 19091S-433); (250×30) mm; 0.25 µm; Injection volume 3 (al, runtime 17 min (GCMS).

Method AF: Column: Chiralpak AD-H (250×4.6) mm, 5.0 (am; Isocratic Mode, Co-Solvent: 0.25% DEA in Methanol; Co-Solvent percentage: 30%, Column Temperature: 25° C.; Back Pressure: 100 bars; Total Flow: 3 g/min; $CO_2$ flow: 2.1 g/min; Co-Solvent flow: 0.9 g/min.

Method AH: Column: Chiralcel-ASH (250×4.6) mm, 5.0 µm; Isocratic Mode, Co-Solvent: 0.2% DEA in Methanol; Co-Solvent percentage: 40%, Column Temperature: 25° C.; Back Pressure: 100 bars; Total Flow: 4 g/min.

Method AK: Column: Chiralpak AD-H (250×4.6) mm, 5.0 µm; Isocratic Mode, Co-Solvent: 0.25% DEA in Methanol; Co-Solvent percentage: 40%, Column Temperature: 25° C.; BackPressure: 100 bars; Total Flow: 4 g/min; $CO_2$ flow: 2.4 g/min; Co-Solvent flow: 1.6 g/min.

Method AM: Column: Chiralpak IA (250×4.6) mm, 5.0 µm; Isocratic Mode, Co-Solvent: 0.2% DEA in Methanol; Co-Solvent percentage: 30%, Column Temperature: 21° C.; Back Pressure: 100 bars; Total Flow: 3 g/min; $CO_2$ flow: 2.1 g/min; Co-Solvent flow: 0.9 g/min.

Method AN: Column: Chiralpak IA (250×4.6) mm, 5.0 µm; Isocratic Mode, Co-Solvent: 0.2% DEA in Methanol; Co-Solvent percentage: 20%, Column Temperature: 21° C.; Back Pressure: 100 bars; Total Flow: 3 g/min; $CO_2$ flow: 2.4 g/min; Co-Solvent flow: 0.6 g/min.

Method AO: Column: Chiralpak AS-H (250×4.6) mm, 5.0 µm; Isocratic Mode, Co-Solvent: 0.2% DEA in Methanol; Co-Solvent percentage: 10%, Column Temperature: 24° C.; Back Pressure: 99 bars; Total Flow: 3 g/min; $CO_2$ flow: 2.7 g/min; Co-Solvent flow: 0.3 g/min.

Method AZ: Column: Acquity BEH C8 (2.1×50 mm) 1.7 um; Mobile phase A: Buffer-ACN (95:5); Mobile phase B: Buffer-ACN (5:95), Buffer: 5 mM Ammonium Acetate; Gradient: 5-95% B over 1.1 minutes, then a 0.6 minute hold at 95% B, flow rate 0.8 mL/min.

Method BA: Column: Luna C18 4.6×30 mm 3p, Gradient: 10 to 90% MeOH/water (0.05% TFA in both phases) from 0 to 4 min. Flowrate: 4.0 mL/min.

Unless otherwise stated, enantiomers prepared from resolved starting materials or by chiral chromatographic resolution are of unknown absolute stereochemistry.

Example 1

1-(7-(2-(1H-tetrazol-5-yl)phenyl)-5-phenyl-2,3,4,5-tetrahydrobenzo[b]oxepin-9-yl)-3-(p-tolyl)urea

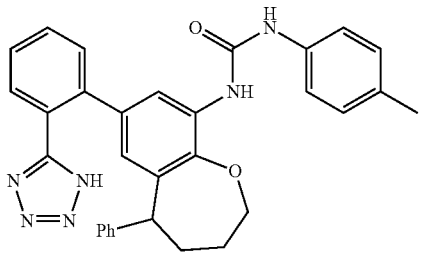 [SMILES: Cc1ccc(NC(=O)Nc2cc(-c3ccccc3-c3nnn[nH]3)cc3c2OCCCC3c2ccccc2)cc1]

1A. 4-bromo-1-(cinnamyloxy)-2-nitrobenzene

To a stirred solution of (E)-3-phenylprop-2-en-1-ol (3.69 g, 27.5 mmol), 4-bromo-2-nitrophenol (5.0 g, 22.94 mmol) and triphenylphosphine (7.22 g, 27.5 mmol) in THF (15 mL) at 0° C. was added DIAD (5.35 mL, 27.5 mmol) over 1 min. The reaction was stirred for 2 h, warmed to ambient temperature, then concentrated under reduced pressure. Purification of the residue by flash chromatography gave 1A (pale yellow solid, 4.5 g, 12.79 mmol, 56% yield). LC-MS Anal. Calc'd for $C_{15}H_{12}BrNO_3$ 333.00, found [M−H] 332.03, $T_r$=3.81 min (Method U).

1B. 4-bromo-2-nitro-6-(1-phenylallyl)phenol

A solution of 1A (5.0 g, 14.96 mmol) in diethylene glycol dimethyl ether (25 mL) was refluxed for 18 h. The reaction was cooled to RT, diluted with water, and extracted with ethyl acetate (2×100 mL). The combined organic layers was washed with brine (50 mL), dried over $Na_2SO_4$ and concentrated. Purification of the residue by flash chromatography gave 1B (yellow liquid, 3.0 g, 7.90 mmol, 53% yield). LC-MS Anal. Calc'd for $C_{15}H_{12}BrNO_3$ 333.00, found [M−H] 332.03, $T_r$=3.77 min (Method U).

1C. 2-(allyloxy)-5-bromo-1-nitro-3-(1-phenylallyl)benzene

A solution of 1B (3.0 g, 8.98 mmol) in DMF (30 mL) was treated with $K_2CO_3$ (3.72 g, 26.9 mmol) and allyl bromide (0.932 mL, 10.77 mmol), and the resulting mixture was heated at 45° C. for 1 h. The reaction mixture was poured into cold water and extracted with EtOAc (2×100 mL). The combined organic phase was washed with brine, dried over $Na_2SO_4$ and concentrated under reduced pressure. Purification of the residue by flash chromatography gave 1C (pale yellow liquid, 2.5 g, 6.58 mmol, 73% yield). LC-MS Anal. Calc'd for $C_{18}H_{16}BrNO_3$ 373.03, found [M+H] 374.0, $T_r$=4.04 min (Method U).

1D. 7-bromo-9-nitro-5-phenyl-2,5-dihydrobenzo[b]oxepine

A solution of 1C (2.5 g, 6.68 mmol) in dichloroethane (500 mL) was purged with nitrogen for 30 min. then treated with Grubbs II (0.284 g, 0.334 mmol) under nitrogen. Nitrogen gas was bubbled through this solution for 15 min, and it was then heated at 55° C. for 2 h. The reaction was concentrated under reduced pressure and purified by flash chromatography to afford 1D (Pale yellow solid, 2.0 g, 5.52 mmol, 83% yield). LC-MS Anal. Calc'd for $C_{16}H_{12}BrNO_3$ 345.00, found [M+H] 346.0, $T_r$=3.48 min (Method U).

1E. 7-bromo-5-phenyl-2,5-dihydrobenzo[b]oxepin-9-amine

To a solution of 1D (800 mg, 2.311 mmol) in ethanol (10 mL) and THF (2.0 mL) was added water (0.8 mL), followed by ammonium chloride (1854 mg, 34.7 mmol). The mixture was stirred for 5 min and then treated with zinc (2266 mg, 34.7 mmol) at 0° C. The mixture was stirred at RT for 3 h. The reaction mixture was diluted with dichloromethane (200 mL), washed with water (50 mL) then brine (50 mL), dried over $Na_2SO_4$ and concentrated under reduced pressure. The residue so obtained was purified by flash chromatography to afford 1E (off-white solid, 500 mg, 1.581 mmol, 68% yield). LC-MS Anal. Calc'd for $C_{16}H_{14}BrNO$ 315.02, found [M−H] 314.0, $T_r$=2.94 min (Method U).

1F. 1-(7-bromo-5-phenyl-2,5-dihydrobenzo[b]oxepin-9-yl)-3-(p-tolyl)urea

A solution of 1E (500 mg, 1.581 mmol) in DCM (5.0 mL) was treated with 1-isocyanato-4-methylbenzene (232 mg, 1.739 mmol), and the reaction mixture was stirred at ambient temperature for 18 h. The reaction was then concentrated under reduced pressure to afford 1F (off-white solid, 550 mg, 0.930 mmol, 59% yield). LC-MS Anal. Calc'd for $C_{24}H_{21}BrN_2O_2$ 448.07, found [M+H] 449.0, $T_r$=3.38 min (Method U).

1G. 1-(7-bromo-5-phenyl-2,3,4,5-tetrahydrobenzo[b]oxepin-9-yl)-3-(p-tolyl)urea A solution of 1F (500 mg, 1.113 mmol) in ethyl acetate (15 mL) was treated with palladium on carbon (50 mg, 0.047 mmol), and the resulting mixture was stirred at rt under an atmosphere of $H_2$ for 3 h. The reaction mixture was filtered to remove Pd/C, and the filtrate was concentrated under reduced pressure. Purification of the residue by flash chromatography afforded 1G (off-white solid, 350 mg, 0.620 mmol, 56% yield). LC-MS Anal. Calc'd for $C_{24}H_{23}BrN_2O_2$ 450.09, found [M+H] 451.0, $T_r$=4.04 min (Method U).

Example 1

To a suspension of (2-(1H-tetrazol-5-yl)phenyl)boronic acid (63.1 mg, 0.332 mmol), 1G (50 mg, 0.111 mmol) and tetrakis(triphenylphosphine)palladium (6.40 mg, 5.54 µmol) in DMF (1 mL), was added aq. $K_2CO_3$ (0.22 mL, 0.443 mmol). The mixture was placed under nitrogen and heated at 95° C. for 4 h. The reaction mixture was cooled to RT, diluted with water, and brought to pH 4 with glacial acetic acid. The reaction mixture was extracted with DCM (2×20 mL). The combined organic layer was washed with aq. 10% $NaHCO_3$ then brine, dried over $Na_2SO_4$ and concentrated under reduced pressure. The residue was purified by Prep HPLC to afford Example 1 (off white solid, 40 mg, 0.067 mmol, 60.7% yield). LC-MS Anal. Calc'd for $C_{31}H_{28}N_6O_2$ 516.22, found [M+H] 517.2, $T_r$=2.75 min (Method U). $^1$H NMR (400 MHz, DMSO-$d_6$) δ δ 9.24 (s, 1H), 8.44 (s, 1H), 8.08 (s, 1H), 7.17-7.59 (m, 9H), 7.09 (d, J=8.4 Hz, 2H), 6.99 (d, J=7.2 Hz, 2H), 5.86 (d, J=2.0 Hz, 1H), 4.14 (d, J=12 Hz, 2H), 3.87-3.92 (m, 1H), 2.24 (s, 3H), 1.90-2.07 (m, 4H).

Racemate Example 2 and Example 2 Enantiomer 1 and Example 2 Enantiomer 2

N-(7-(2-(1H-tetrazol-5-yl)phenyl)-5-phenyl-2,3,4,5-tetrahydrobenzo[b]oxepin-9-yl)-2-(p-tolyl)acetamide

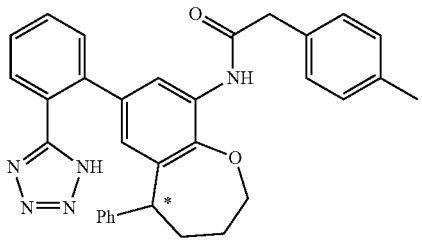 [SMILES: Cc1ccc(CC(=O)Nc2cc(-c3ccccc3-c3nnn[nH]3)cc3c2OCCCC3c2ccccc2)cc1]

2A. N-(7-bromo-5-phenyl-2,5-dihydrobenzo[b]oxepin-9-yl)-2-(p-tolyl)acetamide To a solution of 1E (400 mg, 1.265 mmol) and 2-(p-tolyl)acetic acid (380 mg, 2.53 mmol) in ethyl acetate (4.0 mL) was added DIEA (0.442 mL, 2.53 mmol), followed by T3P (1.130 mL, 1.898 mmol) at 0° C. The reaction was brought to RT and stirred for 4 h. The reaction was diluted with ethyl acetate (100 mL), washed with aq. 10% NaHCO$_3$ (30 mL) then brine (30 mL), dried over Na$_2$SO$_4$, and concentrated under reduced pressure. Purification of the residue by flash chromatography gave 2A (off white solid, 500 mg, 1.086 mmol, 86% yield). LC-MS Anal. Calc'd for C$_{25}$H$_{22}$BrNO$_2$ 447.08, found [M+H] 448.0. T$_r$=3.93 min (Method U).

Example 2

Racemate Example 2 was prepared from 2A following the procedures described for the conversion of 1F to Example 1. LC-MS Anal. Calc'd for C$_{32}$H$_{29}$N$_5$O$_2$ 515.23, found [M+H] 516.3. T$_r$=2.13 min (Method R). $^1$H NMR (400 MHz, DMSO-d$_6$) δ 9.19 (s, 1H), 7.96 (d, J=1.60 Hz, 1H), 7.54-7.59 (m, 2H), 7.45-7.49 (m, 1H), 7.37-7.39 (m, 1H), 7.25-7.27 (m, 4H), 7.14-7.19 (m, 3H), 6.96 (d, J=7.2 Hz, 2H), 6.00 (d, J=2.0 Hz, 1H), 4.13 (d, J=7.2 Hz, 1H), 4.00-4.04 (m, 1H), 3.79-3.83 (m, 1H), 3.73 (s, 2H), 3.17 (s, 1H), 2.29 (s, 3H), 2.04-2.07 (m, 1H), 1.87-1.94 (m, 3H).

Chiral separation of Racemate Example 2 gave Example 2 Enantiomer 1 and Example 2 Enantiomer 2 as single enantiomers (Method V). Enantiomer 1 T$_r$=4.25 min and Enantiomer 2 T$_r$=6.93 min (Method V).

Example 2 Enantiomer 1: LC-MS Anal. Calc'd for C$_{32}$H$_{29}$N$_5$O$_2$ 515.23, found [M+H] 516.2. T$_r$=2.55 min (Method U). $^1$H NMR (400 MHz, DMSO-d$_6$) δ 9.19 (s, 1H), 7.96 (d, J=1.60 Hz, 1H), 7.54-7.59 (m, 2H), 7.45-7.49 (m, 1H), 7.37-7.39 (m, 1H), 7.25-7.27 (m, 4H), 7.14-7.19 (m, 3H), 6.96 (d, J=7.2 Hz, 2H), 6.00 (d, J=2.0 Hz, 1H), 4.13 (d, J=7.2 Hz, 1H), 4.00-4.04 (m, 1H), 3.79-3.83 (m, 1H), 3.73 (s, 2H), 3.17 (s, 1H), 2.29 (s, 3H), 2.04-2.07 (m, 1H), 1.87-1.94 (m, 3H).

Example 2 Enantiomer 2: LC-MS Anal. Calc'd for C$_{32}$H$_{29}$N$_5$O$_2$ 515.23, found [M+H] 516.2. T$_r$=2.56 min (Method U). $^1$H NMR (400 MHz, DMSO-d$_6$) δ 9.19 (s, 1H), 7.96 (d, J=1.60 Hz, 1H), 7.54-7.59 (m, 2H), 7.45-7.49 (m, 1H), 7.37-7.39 (m, 1H), 7.25-7.27 (m, 4H), 7.14-7.19 (m, 3H), 6.96 (d, J=7.2 Hz, 2H), 6.00 (d, J=2.0 Hz, 1H), 4.13 (d, J=7.2 Hz, 1H), 4.00-4.04 (m, 1H), 3.79-3.83 (m, 1H), 3.73 (s, 2H), 3.17 (s, 1H), 2.29 (s, 3H), 2.04-2.07 (m, 1H), 1.87-1.94 (m, 3H).

Example 3 Enantiomer 1

1-(7-(2-(1H-tetrazol-5-yl)phenyl)-5-phenyl-2,3,4,5-tetrahydrobenzo[b]oxepin-9-yl)-3-(5-methylpyridin-2-yl)urea

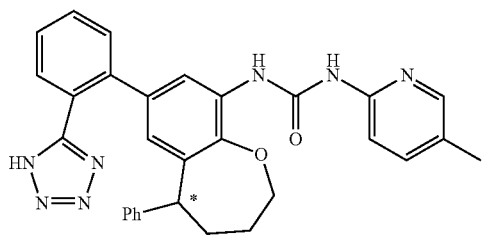 [SMILES: Cc1ccc(NC(=O)Nc2cc(-c3ccccc3-c3nnn[nH]3)cc3c2OCCCC3c2ccccc2)nc1]

Example 3 Enantiomer 1 was prepared from 23A Enantiomer 1 following the procedures for the conversion of 5A to Example 5, and utilizing 2-amino-5-methylpyridine in the final step. LC-MS Anal. Calc'd for C$_{30}$H$_{27}$N$_7$O$_2$ 517.22, found [M+H] 518.2. T$_r$=2.17 min (Method U). $^1$H NMR (400 MHz, DMSO-d$_6$) δ 9.80 (s, 1H), 8.17 (d, J=2.40 Hz, 2H), 7.45-7.63 (m, 5H), 7.17-7.30 (m, 4H), 6.98 (d, J=9.60 Hz, 2H), 5.91 (d, J=2.80 Hz, 1H), 4.16-4.23 (m, 2H), 3.90-4.00 (m, 2H), 2.24 (s, 3H), 1.92-2.12 (m, 4H), 1.14 (s, 1H).

Example 4

1-(7-(2-(1H-tetrazol-5-yl)phenyl)-5-phenyl-2,3,4,5-tetrahydrobenzo[b]oxepin-9-yl)-3-(4-cyclopropyl-3-fluorophenyl)urea

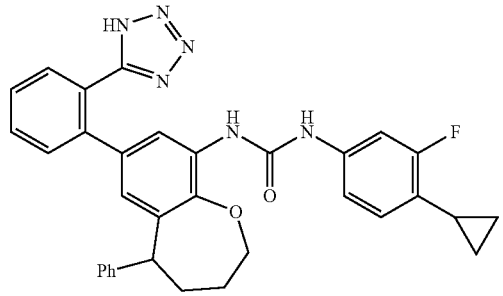 [SMILES: O=C(Nc1ccc(C2CC2)c(F)c1)Nc1cc(-c2ccccc2-c2nnn[nH]2)cc2c1OCCCC2c1ccccc1]

Example 4 was prepared from 5E and 4-cyclopropyl-3-fluoroaniline following the procedure for the conversion of 5E to Example 5. LC-MS Anal. Calc'd for C$_{33}$H$_{29}$FN$_6$O$_2$ 560.23, found [M+H] 561.2. T$_r$=2.53 min (Method U). $^1$H NMR (400 MHz, DMSO-d$_6$) δ 9.47 (s, 1H), 8.50 (s, 1H), 8.06 (s, 1H), 7.42-7.62 (m, 5H), 7.19-7.28 (m, 3H), 6.89-6.99 (m, 4H), 5.86 (s, 1H), 4.14-4.16 (m, 2H), 3.80-3.90 (m, 1H), 1.80-2.10 (m, 4H), 0.80-0.90 (m, 3H), 0.63-0.66 (m, 2H).

Example 5

1-(7-(2-(1H-tetrazol-5-yl)phenyl)-5-phenyl-2,3,4,5-tetrahydrobenzo[b]oxepin-9-yl)-3-(3-methylisoxazol-5-yl)urea

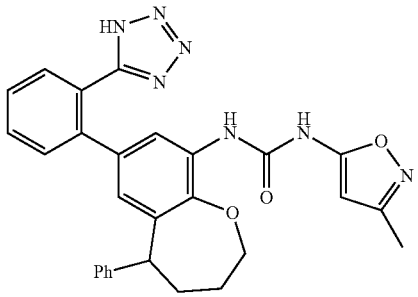 [SMILES: Cc1cc(NC(=O)Nc2cc(-c3ccccc3-c3nnn[nH]3)cc3c2OCCCC3c2ccccc2)on1]

5A. tert-butyl (7-bromo-5-phenyl-2,5-dihydrobenzo[b]oxepin-9-yl)carbamate

To a solution of 1E (2.0 g, 6.33 mmol) in acetonitrile (20 mL) was added $BOC_2O$ (0.099 mL, 0.426 mmol) at ambient temperature. The reaction mixture was stirred at 80° C. for 18 h. The solvent was removed under vacuum. The crude product was recrystallized from methanol to afford 5A (off white solid, 2.2 g, 5.23 mmol, 83% yield). LC-MS Anal. Calc'd for $C_{21}H_{22}BrNO_3$ 415.1, found [M+H] 416.1, $T_r$=4.15 min (Method U).

5B. tert-butyl (7-bromo-5-phenyl-2,3,4,5-tetrahydrobenzo[b]oxepin-9-yl)carbamate A solution of 5A (0.5 g, 1.201 mmol) in ethyl acetate (20 mL) was treated with palladium on carbon (50 mg, 0.047 mmol), and the resulting mixture was stirred at rt under an atmosphere of $H_2$ for 24 h. The reaction mixture was filtered to remove Pd/C, and the resulting solution was concentrated under reduced pressure to afford a brown residue. Purification by flash chromatography afforded 5B (off white solid, 0.4 g, 0.918 mmol, 76% yield). LC-MS Anal. Calc'd for $C_{21}H_{24}BrNO_3$ 417.1, found [M−H] 416.0, $T_r$=4.38 min (Method U).

5C. tert-butyl (5-phenyl-7-(2-(1-trityl-1H-tetrazol-5-yl)phenyl)-2,3,4,5-tetrahydrobenzo[b]oxepin-9-yl)carbamate In a 25 mL tube equipped with a screw cap, under argon were combined 5B (200 mg, 0.478 mmol), (2-(1-trityl-1H-tetrazol-5-yl)phenyl)boronic acid (413 mg, 0.956 mmol), tripotassium phosphate (304 mg, 1.434 mmol) and dioxane (4.0 mL). Then 0.2 mL of water was added to the reaction mixture. This mixture was purged with argon gas for 20 min., and $PdCl_2$(dppf)-$CH_2Cl_{1-2}$ adduct (39.0 mg, 0.048 mmol) was added. The reaction mixture was heated at 85° C. in an oil bath for 18 h. then concentrated under reduced pressure. The residue was dissolved in DCM (10 mL), filtered through celite and purified by flash chromatography to afford 5C (yellow solid, 300 mg, 0.413 mmol, 86% yield). LC-MS Anal. Calc'd for $C_{42}H_{35}N_5O$ 625.3, found [M+H] 626.2, $T_r$=1.66 min (Method T).

5D. 5-phenyl-7-(2-(1-trityl-1H-tetrazol-5-yl)phenyl)-2,3,4,5-tetrahydrobenzo[b]oxepin-9-amine To a solution of 5C (0.3 g, 0.413 mmol) in DCE (3.0 mL) was added TMS-OTf (0.224 mL, 1.240 mmol) followed by 2,6-lutidine (0.144 mL, 1.240 mmol) at 0° C. The reaction mixture was brought to RT and was stirred for 1 h. The solvent was evaporated under vacuum, and the residue was partitioned between aq. 10% $NaHCO_3$ (50 mL) and $CHCl_3$ (100 mL). The organic layer was separated, and the aqueous layer was further extracted with $CHCl_3$ (100 mL). The combined organic extract was dried ($Na_2SO_4$) and concentrated under reduced pressure. Purification of the residue by flash chromatography afforded 5D (yellow solid, 200 mg, 0.233 mmol, 56.5% yield). LC-MS Anal. Calc'd for $C_{47}H_{43}N_5O_3$ 725.3, found [M+H] 726.0, $T_r$=2.94 min (Method U).

5E. 7-(2-(1H-tetrazol-5-yl)phenyl)-5-phenyl-2,3,4,5-tetrahydrobenzo[b]oxepin-9-amine To a solution of 5D (200 mg, 0.320 mmol) in DCE (2.0 mL) was added TFA (1.231 mL, 15.98 mmol) at RT. The reaction mixture was heated at 45° C. with stirring for 18 h. The reaction mixture was cooled to RT and concentrated under reduced pressure to afford the crude product. Purification by flash chromatography afforded 5E (yellow solid, 100 mg, 0.258 mmol, 81% yield). LC-MS Anal. Calc'd for $C_{23}H_{21}N_5O$ 383.1, found [M+H] 383.9, $T_r$=1.86 min (Method U).

Example 5

To a solution of 5E (20 mg, 0.052 mmol) and 3-methylisoxazol-5-amine (6.14 mg, 0.063 mmol) in DCE (1.0 mL) was added CDI (16.91 mg, 0.104 mmol). The reaction mixture was then warmed to 45° C. and stirred for 20 h. The solvent was removed under vacuum, and the residue was purified by preparative HPLC to afford Example 5 (off white solid, 16 mg, 0.031 mmol, 59% yield). LC-MS Anal. Calc'd for $C_{28}H_{25}N_7O_3$ 507.20, found [M+H] 508.2 $T_r$=1.83 min (Method U). $^1$H NMR (400 MHz, DMSO-$d_6$) δ 10.70 (s, 1H), 8.73 (s, 1H), 8.03 (d, J=2.00 Hz, 1H), 7.42-7.63 (m, 4H), 7.18-7.29 (m, 3H), 6.98 (d, J=7.60 Hz, 2H), 5.94 (d, J=6.40 Hz, 2H), 4.16 (d, J=7.60 Hz, 2H), 3.87-3.92 (m, 1H), 2.17 (s, 3H), 1.94-2.10 (m, 4H).

Example 6

1-(7-(2-(1H-tetrazol-5-yl)phenyl)-5-phenyl-2,3,4,5-tetrahydrobenzo[b]oxepin-9-yl)-3-(4-cyclopropyl-2-fluorophenyl)urea

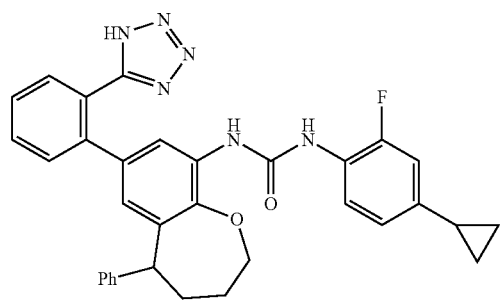 [SMILES: O=C(Nc1ccc(C2CC2)cc1F)Nc1cc(-c2ccccc2-c2nnn[nH]2)cc2c1OCCCC2c1ccccc1]

Example 6 was prepared from 5E and 4-cyclopropyl-2-fluoroaniline following the procedure for the conversion of 5E to Example 5. LC-MS Anal. Calc'd for $C_{33}H_{29}FN_6O_2$ 560.23, found [M+H] 561.2. $T_r$=2.74 min (Method U). $^1$H NMR (400 MHz, DMSO-$d_6$) δ 9.16 (s, 1H), 8.89 (s, 1H), 8.07 (s, 1H), 8.00 (t, J=8.40 Hz, 1H), 7.40-7.57 (m, 4H), 7.18-7.28 (m, 3H), 6.89-7.00 (m, 4H), 5.89 (s, 1H), 4.14 (d, J=7.60 Hz, 2H), 3.80-3.90 (m, 1H), 1.86-1.97 (m, 4H), 1.24 (s, 1H), 0.89-0.93 (m, 2H), 0.64-0.66 (m, 2H).

Example 7

2-(5-phenyl-9-(3-(p-tolyl)ureido)-2,3,4,5-tetrahydrobenzo[b]oxepin-7-yl)benzamide

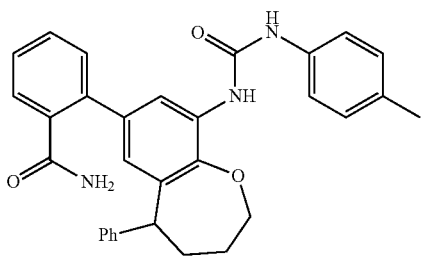 [SMILES: Cc1ccc(NC(=O)Nc2cc(-c3ccccc3C(N)=O)cc3c2OCCCC3c2ccccc2)cc1]

7A. 1-(7-(2-cyanophenyl)-5-phenyl-2,3,4,5-tetrahydrobenzo[b]oxepin-9-yl)-3-(p-tolyl)urea A suspension of 1-(7-bromo-5-phenyl-2,3,4,5-tetrahydrobenzo[b]oxepin-9-yl)-3-(p-tolyl)urea (1G) (200 mg, 0.443 mmol), (2-cyanophenyl)boronic acid (130 mg, 0.886 mmol), and tripotassium phosphate (282 mg, 1.329 mmol) in dioxane (2.0 mL) was treated with 5 drops of water. This mixture was degassed for 20 min. with argon and treated with PdCl$_2$(dppf)-CH$_2$C$_{1-2}$ Adduct (36.2 mg, 0.044 mmol). The reaction mixture was heated at 85° C. in an oil bath overnight. The reaction was concentrated under reduced pressure, suspended in DCM (100 ml) and filtered through celite. The resulting solution was concentrated, and the residue was purified by combi flash 24 g silica gel chromatography by using 0-50% EtOAc/Hexane as eluent. Concentration of the appropriate fractions afforded 1-(7-(2-cyanophenyl)-5-phenyl-2,3,4,5-tetrahydrobenzo[b]oxepin-9-yl)-3-(p-tolyl)urea (7A) (150 mg, 0.288 mmol, 64.9% yield) as an off-white solid. LC-MS Anal. Calc'd for $C_{31}H_{27}N_3O_2$ 473.2, found [M+H] 474.4, $T_r$=1.23 min (Method AZ).

Example 7

A stirred solution of 7A (200 mg, 0.422 mmol), hydroxylamine hydrochloride (58.7 mg, 0.845 mmol) and DIPEA (0.221 mL, 1.267 mmol) in ethanol (4.0 mL) was heated to 80° C. overnight. Solvent was removed under vacuum, and the crude mixture was purified by combiflash using 10% MeOH: Chloroform as solvent. Concentration afforded material which was further purified by reverse phase HPLC. The appropriate fractions were stripped, and the residue was dissolved in acetonitrile-water (1:3), frozen, and lyophilized to afford Example 7 (15 mg, 0.030 mmol) as an off white solid. LC-MS Anal. Calc'd for $C_{31}H_{29}N_3O_3$ 491.22, found [M+H] 492.2. $T_r$=2.93 min (Method U). $^1$H NMR (400 MHz, DMSO-$d_6$) δ 9.25 (s, 1H), 8.45 (s, 1H), 8.22 (d, J=2.8 Hz, 1H), 7.54 (s, 1H), 7.20-7.43 (m, 12H), 7.09 (d, J=10.8 Hz, 2H), 6.51 (d, J=2.8 Hz, 1H), 4.30 (d, J=8.4 Hz, 1H), 4.06 (s, 2H), 2.24-2.27 (m, 4H), 2.30-2.07 (m, 3H).

Racemate Example 8 and Example 8 Enantiomer 1

2-(5-phenyl-9-(3-(p-tolyl)ureido)-2,3,4,5-tetrahydrobenzo[b]oxepin-7-yl)benzoic acid

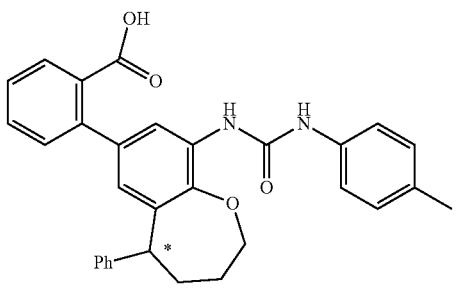 [SMILES: Cc1ccc(NC(=O)Nc2cc(-c3ccccc3C(=O)O)cc3c2OCCCC3c2ccccc2)cc1]

8A. methyl 2-(5-phenyl-9-(3-(p-tolyl)ureido)-2,3,4,5-tetrahydrobenzo[b]oxepin-7-yl)benzoate In a 25 mL tube equipped with screw cap, under argon were combined 1G (150 mg, 0.332 mmol), (2-(methoxycarbonyl)phenyl)boronic acid (120 mg, 0.665 mmol), tripotassium phosphate (212 mg, 0.997 mmol) and dioxane (3.0 mL). Then 0.2 mL of water was added to the reaction mixture. This mixture was purged with argon for 20 min., and PdCl$_2$(dppf)-CH$_2$Cl$_2$ adduct (27.1 mg, 0.033 mmol) was added. The reaction mixture was heated at 85° C. in an oil bath for 18 h. The reaction mixture was concentrated under reduced pressure, and the residue was dissolved in DCM (100 mL) and filtered through celite. The filtrate was concentrated under reduced pressure, and the residue was purified by flash chromatography to afford 8A (off white solid, 50 mg, 0.096 mmol, 29% yield). LC-MS Anal. Calc'd for $C_{32}H_{30}N_2O_4$ 506.2, found [M+H] 507.2. $T_r$=3.81 min (Method U).

Racemate Example 8

A solution of methyl 2-(5-phenyl-9-(3-(p-tolyl)ureido)-2,3,4,5-tetrahydrobenzo[b]oxepin-7-yl)benzoate (8A) (50 mg, 0.099 mmol) in THF (1.0 mL)/MeOH (0.5 mL) was treated with lithium hydroxide (11.8 mg, 0.493 mmol) in water (1.0 mL). The reaction was stirred at 70° C. for 16 h. Hydrochloric acid (3 mL, 1M aqueous solution) was then added and THF was removed in vacuo. The aqueous solution was decanted, and the residue was washed with water (10 mL). The residue was then azeotroped with methanol (10 mL) to afford the crude compound. Prep HPLC gave Example 8 (off-white solid, 2 mg, 0.004 mmol, 4% yield). LC-MS Anal. Calc'd for $C_{31}H_{28}N_2O_4$ 492.20, found [M+H] 493.3. $T_r$=2.21 min (Method R). $^1$H NMR (400 MHz, DMSO-$d_6$) δ 9.37 (s, 1H), 8.51 (s, 1H), 8.14 (s, 1H), 7.17-7.55 (m, 11H), 7.07 (d, J=8.0 Hz, 2H), 6.40 (s, 1H), 4.29 (d, J=6.8 Hz, 1H), 4.03-4.10 (m, 2H), 2.24 (s, 3H), 2.30-2.22 (m, 1H), 2.03-2.07 (m, 1H), 1.80-2.00 (m, 2H).

Example 8 Enantiomer 1 was prepared from 58A Enantiomer 1 following the procedure for the conversion of 1G to Racemate Example 8. $T_r$=4.87 min (Method W). LC-MS Anal. Calc'd for $C_{31}H_{28}N_2O_4$ 492.20, found [M+H] 493.3.

$T_r$=3.27 min (Method U). $^1$H NMR (400 MHz, DMSO-$d_6$) δ 9.37 (s, 1H), 8.51 (s, 1H), 8.14 (s, 1H), 7.17-7.55 (m, 11H), 7.07 (d, J=8.00 Hz, 2H), 6.40 (s, 1H), 4.29 (d, J=6.80 Hz, 1H), 4.03-4.10 (m, 2H), 2.24 (s, 3H), 2.30-2.22 (m, 1H), 2.03-2.07 (m, 1H), 1.80-2.00 (m, 2H).

Example 9 Enantiomer 1 and Example 9 Enantiomer 2

1-(7-(2-(1H-tetrazol-5-yl)phenyl)-3,4-dihydroxy-5-phenyl-2,3,4,5-tetrahydrobenzo[b]oxepin-9-yl)-3-(p-tolyl)urea

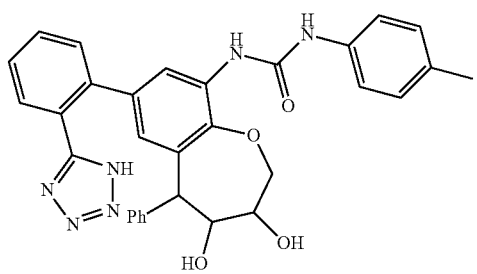 [SMILES: Cc1ccc(NC(=O)Nc2cc(-c3ccccc3-c3nnn[nH]3)cc3c2OCC(O)C(O)C3c2ccccc2)cc1]

9A. Racemic Diasteromer 1; 7-bromo-9-nitro-5-phenyl-2,3,4,5-tetrahydrobenzo[b]oxepine-3,4-diol & Racemic Diasteromer 2; 7-bromo-9-nitro-5-phenyl-2,3,4,5-tetrahydrobenzo[b]oxepine-3,4-diol To a solution of 1D (500 mg, 1.444 mmol) in acetone (3.0 mL)/water (1.0 mL) was added a solution of NMO (338 mg, 2.89 mmol) in $H_2O$ (1.5 mL, 50% wt/v), followed by a solution of osmium tetroxide (0.091 mL, 0.289 mmol) in 2-methyl-2-propanol. The mixture was stirred at RT for 16 h. Saturated $Na_2SO_3$ aqueous solution (50 mL) was added, and the mixture was stirred for an additional 15 min. Water (10 mL), followed by EtOAc (30 mL) was added, and the mixture was stirred a further 5 min. The aqueous phase was extracted with EtOAc (4×30 mL). The combined organic phase was washed with brine (20 mL) and dried over anhydrous $Na_2SO_4$. The solution was concentrated in vacuum to give the crude product. Purification by flash chromatography gave 9A Racemic Diasteromer 1 (Off white solid, 450 mg, 1.098 mmol, 76% yield) and 9A Racemic Diasteromer 2 (Off white solid, 70 mg, 0.180 mmol, 13% yield). 9A Racemic Diasteromer 1, LC-MS Anal. Calc'd for $C_{16}H_{14}BrNO_5$ 379.0, found [M+H] 380.2. $T_r$=0.92 min (Method AA). 9A Racemic Diasteromer 2, LC-MS Anal. Calc'd for $C_{16}H_{14}BrNO_5$ 379.0, found [M+H] 380.2. $T_r$=0.96 min (Method AA).

9B. Racemic Diasteromer 1. 9-amino-7-bromo-5-phenyl-2,3,4,5-tetrahydrobenzo[b]oxepine-3,4-diol To a solution of 9A Racemic Diasteromer 1 (400 mg, 1.052 mmol) in ethanol (10 mL) and THF (2.000 mL) was added water (0.800 mL) followed by ammonium chloride (844 mg, 15.78 mmol). The mixture was stirred for 5 min and was treated with zinc (1032 mg, 15.78 mmol) at 0° C. The mixture was stirred at RT for 24 h. The reaction mixture was diluted with DCM (500 mL), washed with water (50 mL), brine (50 mL), dried over $Na_2SO_4$ and concentrated under reduced pressure. Purification by flash chromatography afforded 9B Racemic Diasteromer 1 (Off white solid, 350 mg, 0.969 mmol, 92% yield). LC-MS Anal. Calc'd for $C_{16}H_{16}BrNO_3$ 349.0, found [M+H] 350.0. $T_r$=1.93 min (Method U).

9C. Racemic Diasteromer 1. 7-bromo-3,4-dihydroxy-5-phenyl-2,3,4,5-tetrahydrobenzo[b]oxepin-9-yl)-3-(p-tolyl)urea To a solution of 9B Racemic Diasteromer 1 (150 mg, 0.428 mmol) in THF (2.0 mL) was added 1-isocyanato-4-methylbenzene (62.7 mg, 0.471 mmol) at RT. The reaction mixture was stirred at 45° C. for 18 h. The reaction mixture was cooled to RT and concentrated under reduced pressure. The resultant solid was washed with hexane and air-dried to afford 9C Racemic Diasteromer 1 (Off white solid, 150 mg, 0.270 mmol, 63.0% yield). LC-MS Anal. Calc'd for $C_{24}H_{23}BrN_2O_4$ 482.1, found [M+H] 483.2. $T_r$=1.16 min (Method T).

Racemate Example 9

Racemate Example 9 was prepared from 9C Racemic Diasteromer 1 following the procedures for the conversion of 5C to 5B and 24A to Racemic Example 24. LC-MS Anal. Calc'd for $C_{31}H_{28}N_6O_4$ 548.21, found [M+H] 549.2. $T_r$=1.73 min (Method U). $^1$H NMR (400 MHz, DMSO-$d_6$) δ 9.17 (s, 1H), 8.39 (s, 1H), 7.98 (d, J=2.00 Hz, 1H), 7.56-7.58 (m, 1H), 7.49-7.51 (m, 1H), 7.32-7.37 (m, 4H), 7.24-7.32 (m, 2H), 7.15-7.19 (m, 1H), 7.09 (d, J=8.00 Hz, 4H), 6.40 (s, 1H), 4.83-4.87 (m, 2H), 4.20-4.27 (m, 2H), 3.95-3.98 (m, 1H), 3.80 (t, J=10.80 Hz, 1H), 3.63-3.66 (m, 1H), 2.25 (s, 3H).

Chiral separation of Racemate Example 9 gave Example 9 Enantiomer 1 and Example 9 Enantiomer 2 as single enantiomers (Method X). Enantiomer 1: $T_r$=2.55 min and Enantiomer 2: $T_r$=2.69 min (Method X).

Example 9 Enantiomer 1: LC-MS Anal. Calc'd for $C_{31}H_{28}N_6O_4$ 548.21, found [M+H] 549.2. $^1$H NMR (400 MHz, DMSO-$d_6$) δ 9.17 (s, 1H), 8.39 (s, 1H), 7.98 (d, J=2.0 Hz, 1H), 7.56-7.58 (m, 1H), 7.49-7.51 (m, 1H), 7.32-7.37 (m, 4H), 7.24-7.32 (m, 2H), 7.15-7.19 (m, 1H), 7.09 (d, J=8.0 Hz, 4H), 6.40 (s, 1H), 4.83-4.87 (m, 2H), 4.20-4.27 (m, 2H), 3.95-3.98 (m, 1H), 3.80 (t, J=10.8 Hz, 1H), 3.63-3.66 (m, 1H), 2.25 (s, 3H).

Example 9 Enantiomer 2: LC-MS Anal. Calc'd for $C_{31}H_{28}N_6O_4$ 548.21, found [M+H] 549.2. $^1$H NMR (400 MHz, DMSO-$d_6$) δ 9.17 (s, 1H), 8.39 (s, 1H), 7.98 (d, J=2.0 Hz, 1H), 7.56-7.58 (m, 1H), 7.49-7.51 (m, 1H), 7.32-7.37 (m, 4H), 7.24-7.32 (m, 2H), 7.15-7.19 (m, 1H), 7.09 (d, J=8.0 Hz, 4H), 6.40 (s, 1H), 4.83-4.87 (m, 2H), 4.20-4.27 (m, 2H), 3.95-3.98 (m, 1H), 3.80 (t, J=10.8 Hz, 1H), 3.63-3.66 (m, 1H), 2.25 (s, 3H).

Racemate Example 10, Example 10 Enantiomer 1, and Example 10 Enantiomer 2

1-(7-(2-(1H-tetrazol-5-yl)phenyl)-5-phenyl-2,3,4,5-tetrahydrobenzo[b]oxepin-9-yl)-3-(2-fluorophenyl)urea

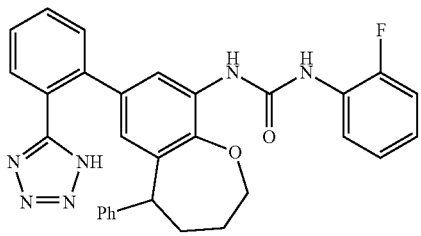 [SMILES: O=C(Nc1ccccc1F)Nc1cc(-c2ccccc2-c2nnn[nH]2)cc2c1OCCCC2c1ccccc1]

Racemate Example 10 was prepared from 5E following the procedure for the conversion of 1E to 1F utilizing 2-flurophenylisocyanate. LC-MS Anal. Calc'd for $C_{30}H_{25}FN_6O_2$ 520.20, found [M+H] 521.2. $T_r$=2.12 min (Method U). $^1$H NMR (300 MHz, DMSO-$d_6$) δ 9.28 (d, J=2.1 Hz, 1H), 8.95 (s, 1H), 8.12-8.18 (m, 1H), 8.04 (d, J=2.1 Hz, 1H), 6.98-7.60 (m, 12H), 5.95 (d, J=1.8 Hz, 1H), 4.14 (d, J=7.50 Hz, 2H), 3.85-3.95 (m, 1H), 1.80-2.20 (m, 4H).

Chiral separation of Racemate Example 10 gave Example 10 Enantiomer 1 and Example 10 Enantiomer 2 as single enantiomers (Method Y). Enantiomer 1 $T_r$=2.42 min and Enantiomer 2 $T_r$=3.80 min (Method Y).

Example 10 Enantiomer 1: LC-MS Anal. Calc'd for $C_{30}H_{25}FN_6O_2$ 520.20, found [M+H] 521.2. $T_r$=2.12 min (Method U). $^1$H NMR (300 MHz, DMSO-$d_6$) δ 9.28 (d, J=2.1 Hz, 1H), 8.95 (s, 1H), 8.12-8.18 (m, 1H), 8.04 (d, J=2.1 Hz, 1H), 6.98-7.60 (m, 12H), 5.95 (d, J=1.8 Hz, 1H), 4.14 (d, J=7.5 Hz, 2H), 3.85-3.95 (m, 1H), 1.80-2.20 (m, 4H).

Example 10 Enantiomer 2: LC-MS Anal. Calc'd for $C_{30}H_{25}FN_6O_2$ 520.20, found [M+H] 521.2. $T_r$=2.15 min (Method U). $^1$H NMR (300 MHz, DMSO-$d_6$) δ 9.28 (d, J=2.10 Hz, 1H), 8.95 (s, 1H), 8.12-8.18 (m, 1H), 8.04 (d, J=2.1 Hz, 1H), 6.98-7.60 (m, 12H), 5.95 (d, J=1.80 Hz, 1H), 4.14 (d, J=7.5 Hz, 2H), 3.85-3.95 (m, 1H), 1.80-2.20 (m, 4H).

Examples 11, 12, 15, 17 and 18 were prepared from 5E following the procedure for Example 5 using the corresponding amines.

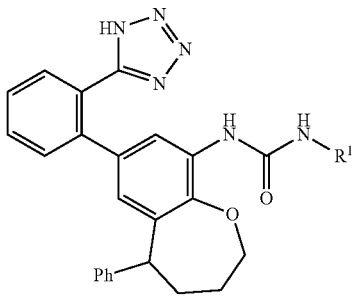

| Ex. No. | Name | R | Tr (min) Method R | [M + H]$^+$ |
|---|---|---|---|---|
| 11 | 1-(7-(2-(1H-tetrazol-5-yl)phenyl)-5-phenyl-2,3,4,5-tetrahydrobenzo[b]oxepin-9-yl)-3-(1,3,4-thiadiazol-2-yl)urea | | 1.60 | 511.3 |
| 12 | 1-(7-(2-(1H-tetrazol-5-yl)phenyl)-5-phenyl-2,3,4,5-tetrahydrobenzo[b]oxepin-9-yl)-3-(4-methylthiazol-2-yl)urea | | 1.74 | 524.3 |
| 15 | 1-(7-(2-(1H-tetrazol-5-yl)phenyl)-5-phenyl-2,3,4,5-tetrahydrobenzo[b]oxepin-9-yl)-3-(5-methylisoxazol-3-yl)urea | | 1.86 | 508.3 |
| 17 | 1-(7-(2-(1H-tetrazol-5-yl)phenyl)-5-phenyl-2,3,4,5-tetrahydrobenzo[b]oxepin-9-yl)-3-(5-methylpyridin-2-yl)urea | | 1.62 | 518.3 |

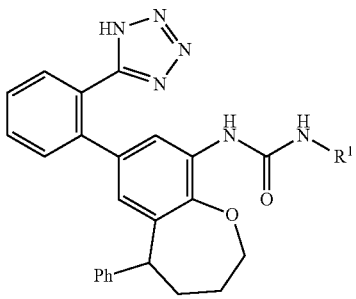

| Ex. No. | Name | R | Tr (min) Method R | [M + H]+ |
|---|---|---|---|---|
| 18 | 1-(7-(2-(1H-tetrazol-5-yl)phenyl)-5-phenyl-2,3,4,5-tetrahydrobenzo[b]oxepin-9-yl)-3-(benzo[d]thiazol-2-yl)urea | | 2.07 | 560.3 |

Example 21

1-(7-(2-(1H-tetrazol-5-yl)phenyl)-5-phenyl-2,3,4,5-tetrahydrobenzo[b]oxepin-9-yl)-3-(2,4-difluorophenyl)urea

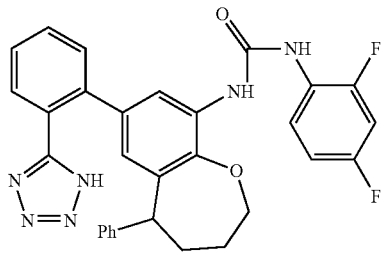 [SMILES: O=C(Nc1ccc(F)cc1F)Nc1cc(-c2ccccc2-c2nnn[nH]2)cc2c1OCCCC2c1ccccc1]

Example 21 was prepared from 5E following the procedure for the conversion of 1E to 1F utilizing 2,4-difluoro-1-isocyanatobenzene. LC-MS Anal. Calc'd for $C_{30}H_{24}F_2N_6O_2$ 538.19, found [M+H] 539.2. $T_r$=2.22 min (Method U). $^1$H NMR (300 MHz, DMSO-$d_6$) δ 9.27 (s, 1H), 8.94 (s, 1H), 8.08-8.15 (m, 2H), 7.43-7.62 (m, 4H), 7.19-7.36 (m, 4H), 6.97-7.08 (m, 3H), 5.87 (d, J=2.1 Hz, 1H), 4.15-4.17 (m, 2H), 3.80-3.95 (m, 1H), 1.94-2.08 (m, 4H).

Example 23 Enantiomer 1 and Example 23 Enantiomer 2

1-(7-(2-(1H-tetrazol-5-yl)phenyl)-5-phenyl-2,3,4,5-tetrahydrobenzo[b]oxepin-9-yl)-3-cyclopropylurea

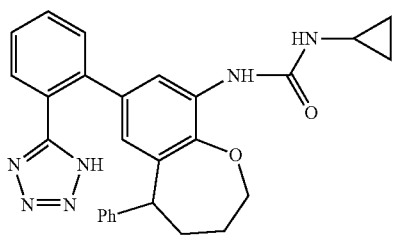 [SMILES: O=C(Nc1cc(-c2ccccc2-c2nnn[nH]2)cc2c1OCCCC2c1ccccc1)NC1CC1]

23A. Enantiomer 1 and 23A Enantiomer 2. (homochiral) tert-butyl (7-bromo-5-phenyl-2,5-dihydrobenzo[b]oxepin-9-yl)carbamate Chiral separation of 5A gave 23A Enantiomer 1 and 23A Enantiomer 2 as single enantiomers (Method Z). Enantiomer 1 $T_r$=2.39 min and Enantiomer 2 $T_r$=3.97 min.

23B. Enantiomer 1 and Enantiomer: (homochiral) 7-(2-(1H-tetrazol-5-yl)phenyl)-5-phenyl-2,3,4,5-tetrahydrobenzo[b]oxepin-9-amine 23B Enantiomer 1 was prepared from 23A Enantiomer 1 using the procedures for the conversion of 5A to 5E. LC-MS Anal. Calc'd for $C_{23}H_{21}N_5O$ 383.1, found [M+H]383.9, $T_r$=1.86 min (Method U). 23B Enantiomer 2 was prepared from 23A Enantiomer 2 using the procedures for the conversion of 5A to 5E. LC-MS Anal. Calc'd for $C_{23}H_{21}N_5O$ 383.1, found [M+H] 383.9, $T_r$=1.43 min (Method U).

Example 23 Enantiomer 1 and Enantiomer 2

Example 23 Enantiomer 1 was prepared from 23B Enantiomer 1 and isocyanatocyclopropane following the procedure for the conversion of 1E to 1F. LC-MS Anal. Calc'd for $C_{27}H_{26}N_6O_2$ 466.21, found [M+H] 467.2. $T_r$=2.02 min (Method R). $^1$H NMR (400 MHz, DMSO-$d_6$) δ 8.09 (d, J=1.6 Hz, 1H), 8.06 (s, 1H), 7.47-7.63 (m, 3H), 7.42 (d, J=7.6 Hz, 1H), 7.16-7.28 (m, 3H), 7.09 (d, J=2.0 Hz, 1H), 6.96 (d, J=7.2 Hz, 2H), 5.78 (d, J=2.0 Hz, 1H), 3.97-4.12 (m, 2H), 3.81-3.86 (m, 1H), 2.51-2.55 (m, 1H), 1.90-2.03 (m, 4H), 0.65-0.66 (m, 2H), 0.39-0.42 (m, 2H).

Example 23 Enantiomer 2 was prepared from 23B Enantiomer 2 and isocyanatocyclopropane following the procedure for the conversion of 1E to 1F. LC-MS Anal. Calc'd for $C_{27}H_{26}N_6O_2$ 466.21, found [M+H] 467.2. $T_r$=2.01 min (Method R). $^1$H NMR (400 MHz, DMSO-$d_6$) δ 8.09 (d, J=1.6 Hz, 1H), 8.06 (s, 1H), 7.47-7.63 (m, 3H), 7.42 (d, J=7.6 Hz, 1H), 7.16-7.28 (m, 3H), 7.09 (d, J=2.0 Hz, 1H), 6.96 (d, J=7.2 Hz, 2H), 5.78 (d, J=2.0 Hz, 1H), 3.97-4.12 (m, 2H), 3.81-3.86 (m, 1H), 2.51-2.55 (m, 1H), 1.90-2.03 (m, 4H), 0.65-0.66 (m, 2H), 0.39-0.42 (m, 2H).

Racemate Example 24, Example 24 Enantiomer 1, and Example 24 Enantiomer 2

1-(7-(2-(1H-tetrazol-5-yl)phenyl)-5-isopropyl-2,3,4,5-tetrahydrobenzo[b]oxepin-9-yl)-3-(p-tolyl)urea

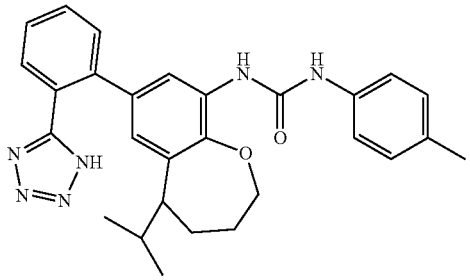 [SMILES: Cc1ccc(NC(=O)Nc2cc(-c3ccccc3-c3nnn[nH]3)cc3c2OCCCC3C(C)C)cc1]

24A. 1-(5-isopropyl-7-(2-(1-trityl-1H-tetrazol-5-yl)phenyl)-2,3,4,5-tetrahydrobenzo[b]oxepin-9-yl)-3-(p-tolyl)urea 24A was prepared starting from (E)-4-methylpent-2-en-1-ol and 4-bromo-2-nitrophenol following the procedure for the preparation of Example 1 and using (2-(1-trityl-1H-tetrazol-5-yl)phenyl)boronic acid in the final step. LC-MS Anal. Calc'd for $C_{47}H_{44}N_6O_2$ 724.4, found [M+H] 725.6, $T_r$=1.50 min (Method AZ).

Racemate Example 24

To a solution of 24A (156 mg, 0.215 mmol) in DCM (1.5 mL) was added TFA (0.829 mL, 10.76 mmol) at 0° C. The reaction mixture was brought to RT and stirred for 18 h. The reaction was concentrated under reduced pressure and the residue was then evaporated again from DCM. Purification by prep. HPLC afforded, after removal of solvent, Racemate Example 24. LC-MS Anal. Calc'd for $C_{28}H_{30}N_6O_2$ 482.2, found [M+H] 483.2. $T_r$=2.29 min (Method U). $^1$H NMR (300 MHz, DMSO-$d_6$) δ 9.22 (s, 1H), 8.34 (s, 1H), 8.07 (d, J=2.4 Hz, 1H), 7.63-7.58 (m, 2H), 7.49 (t, J=7.8 Hz, 2H), 7.32 (d, J=8.4 Hz, 2H), 7.06 (d, J=8.4 Hz, 2H), 6.19 (d, J=2.1 Hz, 1H), 4.43 (d, J=10.8 Hz, 1H), 3.47-3.39 (m, 1H), 2.27 (s, 3H), 2.24-1.96 (m, 4H), 2.09-2.01 (m, 1H), 1.97-1.72 (m, 1H), 0.9 (d, J=5.6 Hz, 3H), 0.4 (d, J=5.6 Hz, 3H).

Chiral SFC separation of Racemate Example 24 gave Example 24 Enantiomer 1 and Example 24 Enantiomer 2 as single enantiomers. Enantiomer 1 $T_r$=9.46 min and Enantiomer 2 $T_r$=13.43 min (Method S).

Example 24 Enantiomer 1: LC-MS Anal. Calc'd for $C_{28}H_{30}N_6O_2$ 482.2, found [M+H] 483.2. $T_r$=2.29 min (Method U). $^1$H NMR (300 MHz, DMSO-$d_6$) δ 9.22 (s, 1H), 8.35 (s, 1H), 8.08 (d, J=2.4 Hz, 1H), 7.64-7.57 (m, 2H), 7.49 (t, J=7.8 Hz, 2H), 7.32 (d, J=8.4 Hz, 2H), 7.07 (d, J=8.4 Hz, 2H), 6.19 (d, J=2.1 Hz, 1H), 4.43 (d, J=10.8 Hz, 1H), 3.47-3.39 (m, 1H), 2.27 (s, 3H), 2.24-1.96 (m, 4H), 2.09-2.01 (m, 1H), 1.96-1.71 (m, 1H), 0.90 (d, J=5.6 Hz, 3H), 0.40 (d, J=5.6 Hz, 3H).

Example 24 Enantiomer 2: LC-MS Anal. Calc'd for $C_{28}H_{30}N_6O_2$ 482.2, found [M+H] 483.2. $T_r$=2.29 min (Method U). $^1$H NMR (300 MHz, DMSO-$d_6$) δ 9.22 (s, 1H), 8.34 (s, 1H), 8.07 (d, J=2.4 Hz, 1H), 7.63-7.58 (m, 2H), 7.49 (t, J=7.8 Hz, 2H), 7.32 (d, J=8.4 Hz, 2H), 7.06 (d, J=8.4 Hz, 2H), 6.19 (d, J=2.1 Hz, 1H), 4.43 (d, J=10.8 Hz, 1H), 3.47-3.39 (m, 1H), 2.27 (s, 3H), 2.24-1.96 (m, 4H), 2.09-2.01 (m, 1H), 1.97-1.72 (m, 1H), 0.9 (d, J=5.6 Hz, 3H), 0.4 (d, J=5.6 Hz, 3H).

Racemate Example 25, Example 25 Enantiomer 1, and Example 25 Enantiomer 2

N-(7-(2-(1H-tetrazol-5-yl)phenyl)-5-isopropyl-2,3,4,5-tetrahydrobenzo[b]oxepin-9-yl)-2-(p-tolyl)acetamide

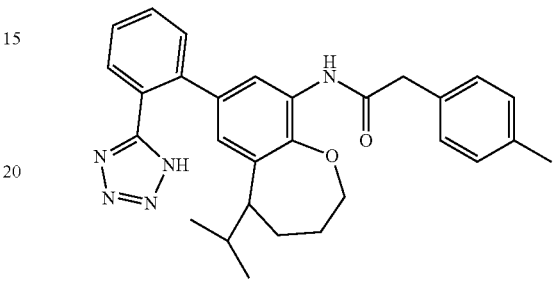

25A. 7-bromo-5-isopropyl-2,5-dihydrobenzo[b]oxepin-9-amine 25A was prepared starting from (E)-4-methylpent-2-en-1-ol and 4-bromo-2-nitrophenol following the procedures for the conversion of 4-bromo-2-nitrophenol into 1E.

25B. N-(5-isopropyl-7-(2-(1-trityl-1H-tetrazol-5-yl)phenyl)-2,3,4,5-tetrahydrobenzo[b]oxepin-9-yl)-2-(p-tolyl)acetamide 25B was prepared starting from 25A and p-tolylacetic acid following the procedure for the conversion of 1E to Example 2 and using (2-(1-trityl-1H-tetrazol-5-yl)phenyl)boronic acid in the final step. LC-MS Anal. Calc'd for $C_{47}H_{44}N_6O_2$ 723.4, found [M+H] 724.4, $T_r$=1.56 min (Method AZ).

Racemate Example 25

Racemate Example 25 was prepared from 25B by the procedure described for the conversion of 24A to Racemate Example 24. LC-MS Anal. Calc'd for $C_{29}H_{31}N_5O_2$ 481.2, found [M+H] 482.2. $T_r$=2.25 min (Method U). $^1$H NMR (300 MHz, DMSO-$d_6$) δ 9.02 (s, 1H), 7.85 (s, 1H), 7.53-7.52 (m, 1H), 7.50-7.27 (m, 3H), 7.22 (d, J=8.1 Hz, 2H), 7.13 (d, J=8.1 Hz, 2H), 6.37 (d, J=1.8 Hz, 1H), 4.24 (d, J=10.8 Hz, 1H), 3.71-3.62 (m, 2H), 2.28 (s, 3H), 2.07-1.98 (m, 3H), 1.65-1.63 (m, 1H), 1.46-1.43 (m, 1H), 0.88 (d, J=6.1 Hz, 3H), 0.44 (d, J=6.1 Hz, 3H). (Note: one singlet CH$_2$ buried under solvent peak).

Chiral SFC separation of Racemate Example 25 gave Example 25 Enantiomer 1 and Example 25 Enantiomer 2 as single enantiomers. Enantiomer 1 $T_r$=11 min and Enantiomer 2 $T_r$=16.6 min (Method AO).

Example 25 Enantiomer 1: LC-MS Anal. Calc'd for $C_{29}H_{31}N_5O_2$ 481.2, found [M+H] 482.2. $T_r$=2.39 min (Method U). $^1$H NMR (300 MHz, DMSO-$d_6$) δ 9.02 (s, 1H), 7.85 (s, 1H), 7.53-7.52 (m, 1H), 7.50-7.27 (m, 3H), 7.22 (d, J=8.1 Hz, 2H), 7.13 (d, J=8.1 Hz, 2H), 6.37 (d, J=1.8 Hz, 1H), 4.24 (d, J=10.8 Hz, 1H), 3.71-3.62 (m, 2H), 2.28 (s, 3H), 2.07-1.98 (m, 3H), 1.65-1.63 (m, 1H), 1.46-1.43 (m, 1H), 0.88 (d, J=6.1 Hz, 3H), 0.44 (d, J=6.1 Hz, 3H). (Note: one singlet CH$_2$ buried under solvent peak).

Example 25 Enantiomer 2: LC-MS Anal. Calc'd for C$_{29}$H$_{31}$N$_5$O$_2$ 481.2, found [M+H] 482.2. T$_r$=2.38 min (Method U). $^1$H NMR (300 MHz, DMSO-d$_6$) δ 9.02 (s, 1H), 7.85 (s, 1H), 7.53-7.52 (m, 1H), 7.50-7.27 (m, 3H), 7.22 (d, J=8.1 Hz, 2H), 7.13 (d, J=8.1 Hz, 2H), 6.37 (d, J=1.8 Hz, 1H), 4.24 (d, J=10.8 Hz, 1H), 3.71-3.62 (m, 2H), 2.28 (s, 3H), 2.07-1.98 (m, 3H), 1.65-1.63 (m, 1H), 1.46-1.43 (m, 1H), 0.88 (d, J=6.1 Hz, 3H), 0.44 (d, J=6.1 Hz, 3H). (Note: one singlet CH$_2$ buried under solvent peak).

Example 26 Enantiomer 1 and Example 26 Enantiomer 2

N-(7-(2-(1H-tetrazol-5-yl)phenyl)-5-phenyl-2,3,4,5-tetrahydrobenzo[b]oxepin-9-yl)-3-(p-tolyl)-1,2,4-oxadiazol-5-amine

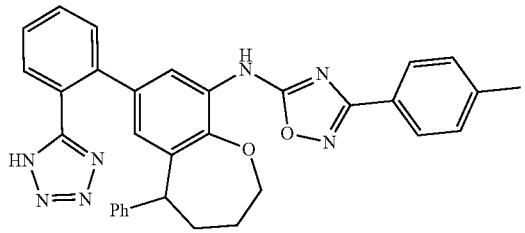 [SMILES: Cc1ccc(-c2noc(Nc3cc(-c4ccccc4-c4nnn[nH]4)cc4c3OCCCC4c3ccccc3)n2)cc1]

26A. N-(7-bromo-5-phenyl-2,3,4,5-tetrahydrobenzo[b]oxepin-9-yl)-3-(p-tolyl)-1,2,4-oxadiazol-5-amine A solution of 53A Enantiomer 1 (70 mg, 0.220 mmol) in DMF (2 mL) was treated with DIPEA (0.115 mL, 0.660 mmol) followed by 5-chloro-3-(p-tolyl)-1,2,4-oxadiazole (42.8 mg, 0.220 mmol). The reaction was heated to 100° C. and stirred for 2 h. Another 1.0 equivalent 5-chloro-3-(p-tolyl)-1,2,4-oxadiazole (42.8 mg, 0.220 mmol) was added, and the reaction mixture was stirred overnight at the same temperature. The solvent was removed under reduced pressure, and the residue was purified by flash chromatography to afford 26A (yellow solid, 35 mg, 0.073 mmol, 33% yield). LC-MS Anal. Calc'd for C$_{25}$H$_{22}$BrN$_3$O$_2$ 475.0, found [M+H] 476.1. T$_r$=1.57 min (Method T).

26B. N-(5-phenyl-7-(2-(1-trityl-1H-tetrazol-5-yl)phenyl)-2,3,4,5-tetrahydrobenzo[b]oxepin-9-yl)-3-(p-tolyl)-1,2,4-oxadiazol-5-amine Compound 26B was prepared from 26A following the procedure for the conversion of 5B to 5C. LC-MS Anal. Calc'd for C$_{51}$H$_{41}$N$_7$O$_2$ 783.3, found [M–H] 782.2. T$_r$=4.43 min (Method U).

Example 26 Enantiomer 1 and Enantiomer 2

Example 26 Enantiomer 1 was prepared following the procedure described for the conversion of 24A to Racemic Example 24. LC-MS Anal. Calc'd for C$_{32}$H$_{27}$N$_7$O$_2$ 541.2, found [M+H] 542.2. T$_r$=2.37 min (Method U). $^1$H NMR (300 MHz, DMSO-d$_6$) δ 10.4 (bs, 1H), 7.89-7.84 (m, 3H), 7.64-7.49 (m, 4H), 7.37 (d, J=7.2 Hz, 2H), 7.31-7.19 (m, 3H), 7.04 (d, J=7.2 Hz, 2H), 6.15 (d, J=0.6 Hz, 1H), 4.22-4.13 (m, 2H), 3.94-3.92 (m, 1H), 2.31 (s, 3H), 2.11-1.92 (m, 4H).

Example 26 Enantiomer 2 was prepared from 53A Enantiomer 2 following the procedures for the conversion of 53A Enantiomer 1 to Example 26 Enantiomer 1. LC-MS Anal. Calc'd for C$_{32}$H$_{27}$N$_7$O$_2$ 541.2, found [M+H] 542.2. T$_r$=2.36 min (Method U). $^1$H NMR (300 MHz, DMSO-d$_6$) δ 10.4 (bs, 1H), 7.89-7.84 (m, 3H), 7.64-7.49 (m, 4H), 7.37 (d, J=7.2 Hz, 2H), 7.31-7.19 (m, 3H), 7.04 (d, J=7.2 Hz, 2H), 6.15 (d, 0.6 Hz, 1H), 4.22-4.13 (m, 2H), 3.94-3.92 (m, 1H), 2.31 (s, 3H), 2.11-1.92 (m, 4H).

Example 27

N-(7-(2-(1H-tetrazol-5-yl)phenyl)-5-cyclopropyl-2,3,4,5-tetrahydrobenzo[b]oxepin-9-yl)-5-fluorobenzo[d]oxazol-2-amine

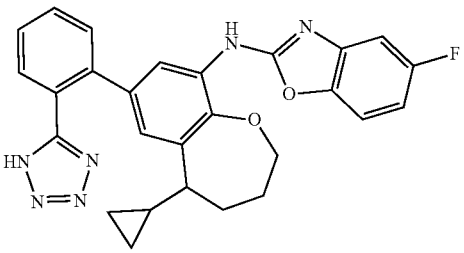 [SMILES: Fc1ccc2oc(Nc3cc(-c4ccccc4-c4nnn[nH]4)cc4c3OCCCC4C3CC3)nc2c1]

27A. tert-butyl (7-bromo-5-cyclopropyl-2,3,4,5-tetrahydrobenzo[b]oxepin-9-yl)carbamate A stirred solution of 38A (2.2 g, 5.79 mmol)) in dry ethyl acetate (30 mL) was purged with nitrogen, treated with Pd/C (0.220 g, 0.207 mmol), and placed under an atmosphere of H$_2$. The reaction mixture was stirred at RT for 12 h, filtered through celite, and the filtrate was concentrated under reduced pressure. Purification by flash chromatography gave 27A (off-white solid, 2.0 g, 5.23 mmol, 90% yield). LC-MS Analysis Calc'd for C$_{18}$H$_{24}$BrNO$_3$ 381.2 found [M+H-t-Bu] 326.2. T$_r$=1.41 min (Method AZ).

27B. 7-bromo-5-cyclopropyl-2,3,4,5-tetrahydrobenzo[b]oxepin-9-amine

A solution of 27A (300 mg, 0.785 mmol) in 1,4-DCM (5 mL) was treated with 2,6-lutidine (0.274 mL, 2.354 mmol), followed by TMSOTf (0.425 mL, 2.354 mmol) in a drop wise manner. The reaction was stirred overnight at RT then concentrated under reduced pressure. Purification of the residue by flash chromatography afforded 27B (Off white solid, 215 mg, 0.762 mmol, 97% yield). LC-MS Anal. Calc'd for C$_{13}$H$_{16}$BrNO 281.04, found [M+H] 282.2. T$_r$=4.16 min (Method U).

27C. N-(7-bromo-5-cyclopropyl-2,3,4,5-tetrahydrobenzo[b]oxepin-9-yl)-5-fluorobenzo[d]oxazol-2-amine A solution of 27B (100 mg, 0.354 mmol) in pyridine (2 mL) was added dropwise over 5 min to a solution of di(1H-imidazol-1-yl)methanethione (63.2 mg, 0.354 mmol) in pyridine (2 mL) at 0° C. The reaction was stirred at 0° C.

for 1.5 h then treated with 2-amino-4-fluorophenol (49.6 mg, 0.390 mmol) and stirred for 3 h at RT. EDC (81 mg, 0.425 mmol) was added, and the reaction was heated for two days at 55° C. The reaction was concentrated and the residue was partitioned between ethyl acetate (50 mL) and water (20 mL), washed with sat NaHCO$_3$ (20 mL) then water (20 ml) then brine (20 ml), dried over Na$_2$SO$_4$ and concentrated under reduced pressure. Purification of the residue by flash chromatography gave 27C (pink solid, 60 mg, 0.144 mmol, 41% yield). LC-MS Anal. Calc'd for C$_{20}$H$_{18}$BrFN$_2$O$_2$ 416.1, found [M+H] 417.2. T$_r$=4.11 min (Method U).

27D. N-(5-cyclopropyl-7-(2-(1-trityl-1H-tetrazol-5-yl)phenyl)-2,3,4,5-tetrahydrobenzo[b]oxepin-9-yl)-5-fluorobenzo[d]oxazol-2-amine Compound 27D was prepared from 27C by following the procedure for the preparation of 5C from 5B. LC-MS Anal. Calc'd for C$_{46}$H$_{37}$FN$_6$O$_2$ 724.3, found [M–H]723.0. T$_r$=4.55 min (Method U).

Example 27

A stirred solution of 27D (90 mg, 0.12 mmol) in dichloromethane (3 mL) was treated with TFA (1.5 mL, 19.47 mmol). The reaction was stirred for 4 h at RT then purified by prep. HPLC to afford Example 27 (17 mg, 0.035 mmol, 28% yield). LC-MS Anal. Calc'd for C$_{27}$H$_{23}$FN$_6$O$_2$ 482.2, found [M+H] 483.2. T$_r$=2.7 min (Method U). $^1$H NMR (300 MHz, DMSO-d$_6$) δ 11.9 (bs, 1H), 9.88 (s, 1H), 8.07 (s, 1H), 7.63-7.46 (m, 5H), 7.32-7.28 (m, 1H), 6.97-6.93 (m, 1H), 6.53 (s, 1H), 4.05-3.89 (m, 3H), 2.14-2.10 (m, 1H), 1.91-1.69 (m, 3H), 1.07-1.05 (m, 1H), 0.5-0.13 (m, 4H).

Example 28

N-(7-(2-(1H-tetrazol-5-yl)phenyl)-5-cyclopropyl-2,3,4,5-tetrahydrobenzo[b]oxepin-9-yl)-4-fluorobenzo[d]oxazol-2-amine

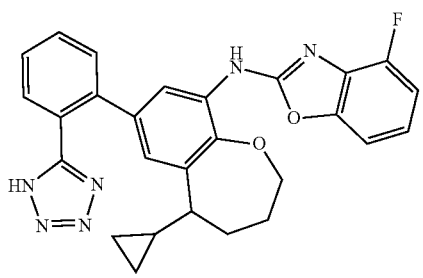 [SMILES: Fc1cccc2oc(Nc3cc(-c4ccccc4-c4nnn[nH]4)cc4c3OCCCC4C3CC3)nc12]

Example 28 was prepared from 27B and 2-amino-3-fluorophenol following the procedures for the conversion of 27B into Example 27. LC-MS Anal. Calc'd for C$_{27}$H$_{23}$FN$_6$O$_2$ 482.2, found [M+H] 483.2. T$_r$=2.13 min (Method U). $^1$H NMR (400 MHz, DMSO-d$_6$) δ 10.05 (s, 1H), 8.19 (s, 1H), 7.74-7.57 (m, 4H), 7.38 (dd, J=7.6, 1.6 Hz, 1H), 7.18-7.09 (m, 2H), 6.54 (d, J=2.0 Hz, 1H), 4.05-3.94 (m, 2H), 2.14-2.10 (m, 1H), 1.82-1.65 (m, 4H), 1.02-0.95 (m, 1H), 0.5-0.48 (m, 1H), 0.29-0.27 (m, 1H), 0.13-0.11 (m, 1H), –0.18-0.20 (m, 1H).

Example 29 Enantiomer 1 and Example 29 Diastereomer Mixture 1-(7-(2-(1H-tetrazol-5-yl)phenyl)-5-(sec-butyl)-2,3,4,5-tetrahydrobenzo[b]oxepin-9-yl)-3-(p-tolyl)urea

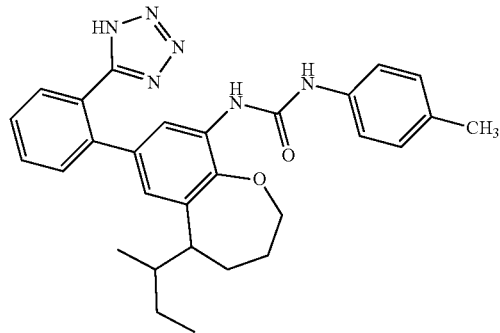 [SMILES: CCC(C)C1CCCOc2c(NC(=O)Nc3ccc(C)cc3)cc(-c3ccccc3-c3nnn[nH]3)cc21]

29A. (E)-4-bromo-1-((4-methylhex-2-en-1-yl)oxy)-2-nitrobenzene

To a stirred solution of NaH (0.702 g, 27.8 mmol) in THF (100 mL) under nitrogen atmosphere at 0° C. was added (E)-4-methylhex-2-en-1-ol (2.93 g, 25.6 mmol) in THF (10 mL) in a dropwise manner. The reaction mixture was cooled to 0° C., stirred 1 h, and treated dropwise with 4-bromo-1-fluoro-2-nitrobenzene (4.7 g, 21.36 mmol) in THF (90 mL). The reaction mixture was then warmed to RT with stirring over 2 h. The reaction mixture was poured into saturated ammonium chloride (~ 100 mL) solution and extracted with ethyl acetate (2×150 mL). The combined organic layer was washed with brine (100 mL), dried over anhydrous sodium sulphate, and concentrated under reduced pressure. The residue was purified by flash chromatography to afford 29A (pale yellow liquid, 6 g, 19.1 mmol, 89% yield). $^1$H NMR (400 MHz, CHLOROFORM-d) δ 7.90-8.00 (m, 1H), 7.52-7.66 (m, 1H), 7.18-7.32 (m, 1H), 6.98 (d, J=8.9 Hz, 1H), 5.52-5.81 (m, 1H), 4.63 (d, J=5.7 Hz, 2H), 1.95-2.17 (m, 1H), 1.33 (m, J=7.2 Hz, 2H), 0.99 (d, J=6.8 Hz, 3H), 0.85 (t, J=1A Hz, 3H).

29B. 4-bromo-2-(4-methylhex-1-en-3-yl)-6-nitrophenol

A solution of 29A (4 g, 12.73 mmol) in diglyme (20 mL) was placed under nitrogen and heated at 165° C. for 72 h. The reaction was cooled to RT and poured into water (200 mL). The resulting mixture was extracted with MTBE (2×200 mL), and the combined phase was washed with brine (100 mL), dried over anhydrous sodium sulphate, and concentrated under reduced pressure. The residue was purified by flash chromatography to afford 29B brown liquid, 1.1 g, 3.50 mmol, 27% yield). $^1$H NMR (300 MHz, DMSO-d$_6$) δ 10.63 (s, 1H), 7.99 (d, J=2.5 Hz, 1H), 7.65-7.83 (m, 1H), 5.90-6.17 (m, 1H), 4.86-5.17 (m, 2H), 3.53-3.68 (m, 1H), 1.75-1.94 (m, 1H), 1.07-1.31 (m, 2H), 0.76-0.93 (m, 6H).

29C. 2-(allyloxy)-5-bromo-1-(4-methylhex-1-en-3-yl)-3-nitrobenzene

A stirred solution of 29B (1.1 g, 3.50 mmol) in DMF (11 mL) under nitrogen atmosphere was treated with K$_2$CO$_3$ (1.452 g, 10.50 mmol) followed by 3-bromoprop-1-ene (0.364 mL, 4.20 mmol). The reaction mixture was heated at 65° C. for 2 h, cooled to RT, and then quenched with water (50 mL). The resulting mixture was extracted with ethyl acetate (2×40 mL), and the combined organic phase was washed with water (30 mL) then brine (20 mL), dried over anhydrous sodium sulphate, and concentrated under reduced pressure to afford 29C (brown liquid, 1.2 g, 3.39 mmol, 97% yield). $^1$H NMR (300 MHz, CHLOROFORM-d) δ 7.80 (d, J=2.46 Hz, 1H), 7.50-7.59 (m, 1H), 5.79-6.14 (m, 2H), 5.27-5.48 (m, 2H), 5.03-5.18 (m, 2H), 4.37-4.60 (m, 2H), 3.56 (t, J=9.02 Hz, 1H), 1.69 (s, 1H), 1.07-1.31 (m, 2H), 0.79-1.01 (m, 6H).

29D. 7-bromo-5-(sec-butyl)-9-nitro-2,5-dihydrobenzo[b]oxepine

A stirred solution of 29C (0.500 g, 1.411 mmol) in 1,2-Dichloroethane (150 mL) was purged with Argon for 20 min. and treated with Hoveyda-Grubbs catalyst $2^{nd}$ generation (0.044 g, 0.071 mmol). The reaction was stirred under argon at 55° C. for 3 h. then cooled to RT and concentrated under reduced pressure. The crude product was purified by flash chromatography to afford 29D (pale yellow liquid, 310 mg, 0.950 mmol, 67% yield). $^1$H NMR (300 MHz, CHLOROFORM-d) δ 7.78 (d, J=2.5 Hz, 1H), 7.40 (s, 1H), 5.83-6.00 (m, 1H), 5.49-5.64 (m, 1H), 4.76-4.89 (m, 1H), 4.52-4.67 (m, 1H), 2.86-3.05 (m, 1H), 2.05-2.23 (m, 1H), 1.18-1.36 (m, 1H), 0.89-1.07 (m, 4H), 0.68-0.87 (m, 3H).

29E. 7-bromo-5-(sec-butyl)-2,5-dihydrobenzo[b]oxepin-9-amine

A solution of 29D (0.310 g, 0.950 mmol) in EtOH (7 mL)-THF (0.6 mL)-water (0.2 mL) was treated with ammonium chloride (0.763 g, 14.26 mmol), and the reaction mixture was stirred at RT for 10 min. Zinc (0.932 g, 14.26 mmol) was added to the reaction mixture, and it was stirred at RT for 12 h. The reaction mixture was filtered through a pad of celite (4×15 mL ethyl acetate rinse). The combined organic phase was washed with brine (15 mL), dried over anhydrous sodium sulphate, and concentrated under reduced pressure to afford 29E (viscous liquid, 230 mg, 0.776 mmol, 82% yield). $^1$H NMR (400 MHz, DMSO-d$_6$) δ 6.64-6.74 (m, 1H), 6.30-6.40 (m, 1H), 5.77-5.91 (m, 1H), 5.39-5.56 (m, 1H), 5.07-5.25 (m, 2H), 4.49-4.63 (m, 1H), 4.00-4.16 (m, 1H), 2.64-2.81 (m, 1H), 1.93-2.09 (m, 1H), 1.12-1.30 (m, 1H), 0.82-0.97 (m, 4H), 0.58-0.79 (m, 3H).

29F. 1-(7-bromo-5-(sec-butyl)-2,5-dihydrobenzo[b]oxepin-9-yl)-3-(p-tolyl)urea A stirred solution of 29E (0.230 g, 0.776 mmol) in THF (3 mL) under nitrogen atmosphere was treated with 1-isocyanato-4-methylbenzene (0.124 g, 0.932 mmol) in THF (1 mL). The reaction mixture was refluxed for 3 h at 60° C., cooled to RT, and concentrated under reduced pressure. The residue was purified by flash chromatography to afford 29F (off white solid, 280 mg, 0.652 mmol, 84% yield). LC-MS Anal. Calc'd for $C_{22}H_{25}BrN_2O_2$ 428.11, found [M+H] 429.1. $T_r$=1.43 min. (Method T).

29G. 1-(7-bromo-5-(sec-butyl)-2,3,4,5-tetrahydrobenzo[b]oxepin-9-yl)-3-(p-tolyl)urea To a stirred solution of 29F (0.280 g, 0.652 mmol) in ethyl acetate (10 mL) was added palladium on carbon (0.035 g, 0.033 mmol). The reaction was placed under an atmosphere of hydrogen and stirred 12 h. The reaction mixture was then filtered through a pad of celite, and the celite pad was rinsed with methanol (5×30 mL). The filtrate and rinses were combined and concentrated under reduced pressure to afford 29G (off white solid, 270 mg, 0.626 mmol, 96% yield). LC-MS Anal. Calc'd for $C_{22}H_{27}BrN_2O_2$ 430.12, found [M+H] 431.1. $T_r$=1.43 min. (Method T).

29H. 1-(5-(sec-butyl)-7-(2-(1-trityl-1H-tetrazol-5-yl)phenyl)-2,3,4,5-tetrahydrobenzo[b]oxepin-9-yl)-3-(p-tolyl)urea Compound 29H was prepared from 29G following the procedure for the conversion of 5B to 5C. $^1$H NMR (300 MHz, DMSO-d$_6$) δ 9.13-9.25 (m, 1H), 8.29-8.42 (m, 1H), 7.82-7.93 (m, 1H), 7.65-7.76 (m, 1H), 7.44-7.60 (m, 2H), 7.21-7.35 (m, 15H), 7.07 (d, J=8.22 Hz, 3H), 6.78-6.95 (m, 3H), 6.38-6.55 (m, 1H), 2.73 (t, J=1.75 Hz, 1H), 2.49 (s, 3H), 2.13-2.33 (m, 6H), 1.14-1.29 (m, 2H), 0.78-0.99 (m, 6H).

Example 29

To a stirred solution of 29H (120 mg, 0.162 mmol) in dichloromethane (3 mL) under nitrogen atmosphere was added TFA (1.5 mL, 19.47 mmol). The reaction was stirred for 4 h at RT, concentrated, and purified by prep HPLC. The racemic material was further purified by chiral SFC to give Example 29 Enantiomer 1 and a Example 29 Diastereomer mixture. Enantiomer 1 $T_r$=11.55 min, (Method AM); Diastereomer mixture 1 $T_r$=5.94 min (major peak), (Method AM).

Example 29 Enantiomer 1 (off white solid, 18 mg, 0.032 mmol, 20% yield). LC-MS Anal. Calc'd for $C_{29}H_{32}N_6O_2$ 496.25, found [M+H] 497.2. $T_r$=2.43 min (Method U). $^1$H NMR (400 MHz, DMSO-d$_6$) δ 9.20 (s, 1H), 8.34 (d, J=8.5 Hz, 1H), 8.07 (dd, J=6.1, 2.2 Hz, 1H), 7.56 (d, J=7.4 Hz, 2H), 7.41-7.50 (m, 2H), 7.33 (d, J=8.47 Hz, 2H), 7.08 (d, J=8.4 Hz, 2H), 6.19 (dd, J=5.84, 2.13 Hz, 1H), 4.40 (s, 1H), 3.47 (s, 1H), 2.67 (dt, J=3.6, 1.76 Hz, 1H), 2.33 (dt, J=3.6, 1.82 Hz, 1H), 2.24 (s, 3H), 1.23 (s, 1H), 1.15 (t, J=7.3 Hz, 1H), 0.79-0.91 (m, 4H), 0.67 (t, J=7.12 Hz, 3H), 0.39 (d, J=6.7 Hz, 3H).

Example 29 Diasteromer mixture (off white solid, 17 mg, 0.025 mmol, 15% yield): LC-MS Anal. Calc'd for $C_{29}H_{32}N_6O_2$ 496.25, found [M+H] 497.2. $T_r$=2.42 min (Method U). $^1$H NMR (400 MHz, DMSO-d$_6$) δ 9.12-9.27 (m, 1H), 8.32-8.43 (m, 1H), 7.96-8.22 (m, 1H), 7.52-7.65 (m, 2H), 7.41-7.51 (m, 2H), 7.27-7.38 (m, 2H), 7.08 (d, J=8.5 Hz, 2H), 6.39 (d, J=2.0 Hz, 1H), 6.18 (d, J=2.2 Hz, 1H), 4.28-4.56 (m, 1H), 3.44-3.59 (m, 1H), 2.83-3.01 (m, 1H), 2.18 (s, 3H), 1.97-2.15 (m, 1H), 1.42-1.58 (m, 1H), 1.06-1.23 (m, 1H), 0.90-0.98 (m, 3H), 0.51-0.74 (m, 3H).

Example 30 Enantiomer 1, Example 30 Diastereomer Mixture 1 and Example 30 Diastereomer Mixture 2

N-(7-(2-(1H-tetrazol-5-yl)phenyl)-5-(sec-butyl)-2,3,4,5-tetrahydrobenzo[b]oxepin-9-yl)-2-(p-tolyl)acetamide

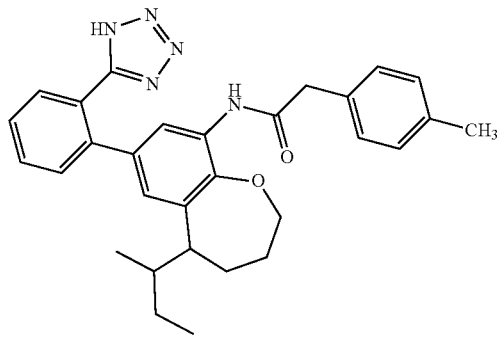 [SMILES: CCC(C)C1CCCOc2c(NC(=O)Cc3ccc(C)cc3)cc(-c3ccccc3-c3nnn[nH]3)cc21]

30A. N-(7-bromo-5-(sec-butyl)-2,5-dihydrobenzo[b]oxepin-9-yl)-2-(p-tolyl)acetamide A solution of 29E (0.380 g, 2.53 mmol) in ethyl acetate (10 mL) was placed under nitrogen, cooled to 0° C., and treated with T3P (3.22 g, 5.06 mmol). The reaction was stirred at RT for 12 h, diluted with water (30 mL) and extracted with ethyl acetate (2×20 mL). The combined organic phase was washed with brine (20 mL), dried over anhydrous sodium sulphate, and concentrated under reduced pressure. The residue was purified by flash chromatography to afford 30A (Off white solid, 700 mg, 1.634 mmol, 97% yield). LC-MS Anal. Calc'd for $C_{23}H_{26}BrNO_2$ 427.11, found [M+H] 428.1. $T_r$=1.45 min. (Method T).

30B. N-(7-bromo-5-(sec-butyl)-2,3,4,5-tetrahydrobenzo[b]oxepin-9-yl)-2-(p-tolyl)acetamide Compound 30B was prepared from 30A following the procedure for the conversion of 29F to 29G. LC-MS Anal. Calc'd for $C_{23}H_{28}BrNO_2$ 429.13, found [M+H]430.1. $T_r$=1.48 min. (Method T).

30C. N-(5-(sec-butyl)-7-(2-(1-trityl-1H-tetrazol-5-yl)phenyl)-2,3,4,5-tetrahydrobenzo[b]oxepin-9-yl)-2-(p-tolyl)acetamide Compound 30C was prepared from 30B following the procedure for the conversion of 5B to 5C. LC-MS Anal. Calc'd for $C_{49}H_{47}N_5O_2$ 737.37, found [M+H]738.4. $T_r$=1.79 min. (Method T).

Example 30

Example 30 was prepared from 30C following the procedure for the conversion of 29H to Example 29. Chiral SFC separation of Example 30 gave Example 30 Enantiomer 1, Example 30 Diastereomer mixture 1, and Example 30 Diastereomer mixture 2. Enantiomer 1 $T_r$=13.27 min (Method AN); Diastereomer mixture 1 $T_r$=3.06 min (major peak), (Method AN); Diastereomer mixture 2 $T_r$=14.85 min (55%) & 17.48 min (32%), (Method AN).

Example 30 Enantiomer 1: LC-MS Anal. Calc'd for $C_{30}H_{33}N_5O_2$ 495.26, found [M+H] 496.2. $T_r$=2.45 min (Method U). $^1$H NMR (400 MHz, DMSO-$d_6$) δ 9.13 (s, 1H), 8.00 (s, 1H), 7.39-7.70 (m, 5H), 7.09-7.27 (m, 3H), 6.28 (s, 1H), 4.29 (s, 1H), 3.63-3.78 (m, 2H), 2.36 (s, 3H), 2.09-2.18 (m, 1H), 1.88-2.06 (m, 2H), 1.83 (d, J=10.04 Hz, 1H), 1.64 (m, 1H), 1.44 (m, 1H), 1.08-1.37 (m, 3H), 0.89 (d, J=6.4 Hz, 3H), 0.61 (t, J=7.2 Hz, 3H).

Example 30 Diastereomer mixture 1: LC-MS Anal. Calc'd for $C_{30}H_{33}N_5O_2$ 495.26, found [M+H] 497.2. $T_r$=2.44 min (Method U). $^1$H NMR (400 MHz, DMSO-$d_6$) δ 9.00-9.20 (m, 1H), 7.91-8.05 (m, 1H), 7.56-7.65 (m, 2H), 7.39-7.52 (m, 2H), 7.19-7.28 (m, 2H), 7.06-7.18 (m, 2H), 6.18-6.35 (m, 1H), 4.20-4.40 (m, 1H), 3.63-3.79 (m, 2H), 2.36 (s, 3H), 1.92-2.16 (m, 2H), 1.79-1.88 (m, 2H), 1.64 (m, 1H), 1.13-1.33 (m, 1H), 0.79-0.91 (m, 3H), 0.58-0.74 (m, 3H), 0.42-0.55 (m, 3H).

Example 30 Diastereomer mixture 2: LC-MS Anal. Calc'd for $C_{30}H_{33}N_5O_2$ 495.26, found [M+H] 497.2. $T_r$=2.47 min (Method U). $^1$H NMR (400 MHz, DMSO-$d_6$) δ 9.05-9.20 (m, 1H), 7.92-8.06 (m, 1H), 7.54-7.66 (m, 2H), 7.40-7.52 (m, 2H), 7.05-7.30 (m, 4H), 6.06-6.39 (m, 1H), 4.29 (d, J=11.73 Hz, 1H), 3.62-3.79 (m, 2H), 2.60-2.74 (m, 1H), 2.36 (s, 3H), 2.07-2.16 (m, 1H), 1.37-1.56 (m, 2H), 1.23 (s, 2H), 0.92-1.15 (m, 3H), 0.80-0.87 (m, 3H), 0.65 (t, J=7.12 Hz, 3H).

Example 31

1-(7-(2-(1H-tetrazol-5-yl) phenyl)-5-methyl-2,3,4,5-tetrahydrobenzo[b]oxepin-9-yl)-3-(p-tolyl)urea

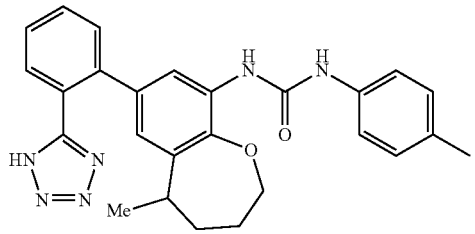 [SMILES: Cc1ccc(NC(=O)Nc2cc(-c3ccccc3-c3nnn[nH]3)cc3c2OCCCC3C)cc1]

31A. 4-bromo-1-(but-2-en-1-yloxy)-2-nitrobenzene

To a stirred solution of 4-bromo-2-nitrophenol (7.0 g, 32.1 mmol) in DMF (35 mL) was added potassium carbonate (6.66 g, 48.2 mmol) at RT. The mixture was stirred for 2-3 min, and then treated with (E)-1-bromobut-2-ene (5.20 g, 38.5 mmol). The reaction was heated to 60° C. and maintained for 30 min. The reaction mixture was cooled to RT, diluted with water, and extracted with ethyl acetate (2×50 ml). The combined organic layer was washed with brine, dried over $Na_2SO_4$, and concentrated under reduced pressure. The residue was purified by flash chromatography to afford 31A (pale yellow liquid, 8.25 g, 30.0 mmol, 93% yield). LC-MS Anal. Calc'd for $C_{10}H_{10}BrNO_3$ 272.0 found [M−H] 271.0, $T_r$=3.2 min (Method O).

31B. 4-bromo-2-(but-3-en-2-yl)-6-nitrophenol

A solution of 31A (8.3 g, 30.5 mmol) in diglyme (50 mL) was stirred overnight at 165° C. The reaction was cooled to RT, diluted with MTBE (200 mL), and washed with water (100 mL) then brine (100 mL). The organic phase was dried over sodium sulfate and concentrated under reduced pressure. The residue was purified by flash chromatography to afford 31B (Light yellow liquid, 4.5 g, 15.1 mmol, 56% yield). GC-MS Anal. Calc'd for $C_{10}H_{10}BrNO_3$ 272.1, found 273.0. $T_r$=9.1 min (Method AE).

31C. 2-(allyloxy)-5-bromo-1-(but-3-en-2-yl)-3-nitrobenzene

A stirred solution of 31B (5.0 g, 18.38 mmol) in dry DMF (50.0 mL) was treated with $K_2CO_3$ (7.62 g, 55.3 mmol) and 3-bromoprop-1-ene (1.75 mL, 20.21 mmol). The reaction mixture was heated to 65° C. and maintained for 2 h. The reaction was cooled to RT, diluted with ethyl acetate (100 mL), and washed with water (2×50 mL). The aqueous layer was back extracted with ethyl acetate (2×50 mL), and the combined organic phase was dried over sodium sulfate and concentrated under reduced pressure to afford 31C (brown liquid, 5.2 g, 16.3 mmol, 89% yield). LC-MS Analysis Calc'd for $C_{13}H_{14}BrNO_3$ 312.1, found [M+H] 313.1. $T_r$=3.82 min (Method U).

31D. 7-bromo-5-methyl-9-nitro-2,5-dihydrobenzo[b]oxepine

A solution of 31C (5.0 g, 16.02 mmol) in DCE (1000 mL) was degassed with argon for 15 min. and treated with Grubbs II (0.615 g, 0.73 mmol) catalyst. The reaction was then placed under argon and heated to 55° C. for 2 h. The reaction was concentrated under reduced pressure and purified by flash chromatography afford 31D (off-white semi solid, 4.3 g, 15 mmol, 94% yield). LC-MS Analysis Calc'd for $C_{11}H_{10}BrNO_3$ 284.1, found [M+H] 285.1. $T_r$=3.5 min (Method U).

31E. 7-bromo-5-methyl-2,5-dihydrobenzo[b]oxepin-9-amine

A solution of 31D (0.200 g, 0.704 mmol) in ethanol (4.0 mL)-THF (0.4 mL)-water (0.1 mL) was treated with ammonium chloride (0.565 g, 10.56 mmol). This mixture was stirred 15 min. then treated with zinc (0.690 g, 10.56 mmol) and stirred overnight. The reaction mixture was diluted with ethyl acetate (10 mL), washed with water (5 mL) then brine (5 mL), dried over $Na_2SO_4$, and concentrated under reduce pressure. Purification by flash chromatography afforded 31E (off-white solid, 150 mg, 0.590 mmol, 84% yield. LC-MS Analysis 1. Calc'd for $C_{11}H_{12}BrNO$ 254.1 found [M+H] 255.1. $T_r$=2.8 min (Method U).

31F. 1-(7-bromo-5-methyl-2,5-dihydrobenzo[b]oxepin-9-yl)-3-(p-tolyl)urea

A stirred solution of 1E (150 mg, 0.590 mmol), 1-isocyanato-4-methylbenzene (94 mg, 0.708 mmol) in dry THF (2.0 mL) was heated to 60° C. for 1 h. The reaction mixture was filtered through a pad of celite and (ethyl acetate rinse). The filtrate was washed with water, dried over sodium sulfate, and concentrated to afford 31F (off-white solid, 155 mg, 0.40 mmol, 68% yield). LC-MS Analysis Calc'd for $C_{19}H_{19}BrN_2O_2$ 387.2 found [M+H] 388.2. $T_r$=3.56 min (Method U).

31G. 1-(7-bromo-5-methyl-2,3,4,5-tetrahydrobenzo[b]oxepin-9-yl)-3-(p-tolyl)urea A stirred solution of 31F (0.150 g, 0.387 mmol) in dry ethyl acetate (2.0 mL) was purged with nitrogen, treated with Pd/C (0.062 g, 0.058 mmol) under $N_2$ atmosphere and then placed under an atmosphere of hydrogen. The reaction mixture was stirred at RT for 6 h, then filtered through celite to remove Pd/C, and the filtrate was concentrated under reduced pressure. Purification by flash chromatography gave 31G (off-white solid, 100 mg, 0.18 mmol, 45% yield). LC-MS Analysis 1. Calc'd for $C_{21}H_{21}BrN_2O_2$ 389.2 found [M+H] 390.2. $T_r$=3.8 min (Method U).

31H. 1-(7-(2-cyanophenyl)-5-methyl-2,3,4,5-tetrahydrobenzo[b]oxepin-9-yl)-3-(p-tolyl)urea A stirred solution of 31G (0.100 g, 0.257 mmol), 2-(5,5-dimethyl-1,3,2-dioxaborinan-2-yl) benzonitrile (0.110 g, 0.514 mmol) in DME (3.0 mL)-water (0.750 mL) was treated with $Cs_2CO_3$ (0.209 g, 0.642 mmol). The mixture was purged with argon for 5 min, and tetrakis (triphenylphosphine) palladium (O) (0.018 g, 0.015 mmol) was added. The reaction mixture was heated at 90° C. for 3 h, cooled to RT, and diluted with water. The resulting mixture was extracted with DCM (2×20 mL), and the combined organic layer was washed with brine (20 mL), dried over $Na_2SO_4$ and concentrated under reduced pressure. The residue was purified by flash chromatography to afford 31H (off-white solid, 85 mg, 0.21 mmol, 80% yield). LC-MS Anal. Calc'd for $C_{26}H_{25}N_3O_2$ 411.4 found [M+H] 412.2, $T_r$=3.5 min (Method U).

Example 31

A stirred solution of 31H (0.080 g, 0.194 mmol) in dry toluene (2.5 mL) was treated with tributyl tin azide (0.646 g, 1.944 mmol). The reaction was heated to reflux for 48 h. The reaction was then diluted with DCM and washed with saturated KF solution. The organic layer was dried over sodium sulfate, concentrated under reduced pressure, and purified by preparative HPLC to afford Example 31 (off-white solid, 25 mg, 0.053 mmol, 34% yield). LC-MS Anal. Calc'd for $C_{26}H_{26}N_6O_2$ 454.5 found [M+H]455.2. $T_r$=2.9 min (Method U). $^1$H NMR (300 MHz, DMSO-$d_6$) δ 9.21 (s, 1H), 8.34 (s, 1H), 8.04 (d, J=2.1 Hz, 1H), 7.68-7.55 (m, 2H), 7.53-7.43 (m, 2H), 7.33 (d, J=8.4 Hz, 2H), 7.08 (d, J=8.3 Hz, 2H), 6.29 (d, J=1.8 Hz, 1H), 3.97 (brs, 2H), 2.85-2.82 (m, 1H), 2.29-2.22 (m, 3H), 1.98 (m, 1H), 1.90 (m, 1H), 1.68 (m, 1H), 1.46 (m, 1H), 1.06 (d, J=7.2 Hz, 3H).

Example 32

N-(7-(2-(1H-tetrazol-5-yl) phenyl)-5-methyl-2,3,4,5-tetrahydrobenzo[b]oxepin-9-yl)-2-(p-tolyl)acetamide

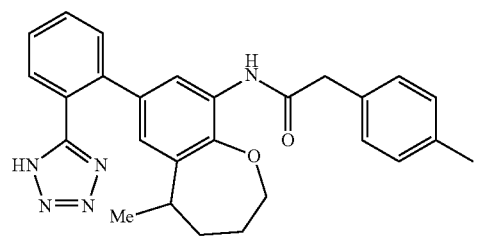 [SMILES: Cc1ccc(CC(=O)Nc2cc(-c3ccccc3-c3nnn[nH]3)cc3c2OCCCC3C)cc1]

32A. N-(7-bromo-5-methyl-2,5-dihydrobenzo[b]oxepin-9-yl)-2-(p-tolyl)acetamide A stirred, cooled (0° C.) solution of 31E (0.100 g, 0.394 mmol), 2-(p-tolyl)acetic acid (0.071 g, 0.472 mmol) in dry ethyl acetate (1.5 mL) was placed under nitrogen and treated with 2,4,6-tripropyl-1,3,5,2,4,6-trioxatriphosphorinane-2,4,6-trioxide (0.232 mL, 0.787 mmol). The reaction was then warmed to RT with stirring over 3 h. The reaction was diluted with ethyl acetate (100 mL) and washed with 10% NaHCO$_3$ solution (30 mL) then brine (30 mL). The organic phase was dried over Na$_2$SO$_4$, and concentrated under reduced pressure. Purification by flash chromatography gave 32A (off white solid, 125 mg, 0.324 mmol, 82% yield). LC-MS Anal. Calc'd for C$_{20}$H$_{20}$BrNO$_2$ 386.2, found [M+H] 387.2. T$_r$=3.82 min (Method U).

32B. N-(7-bromo-5-methyl-2,3,4,5-tetrahydrobenzo[b]oxepin-9-yl)-2-(p-tolyl)acetamide Compound 32B was prepared from 32A following the procedure described for the conversion of 31F to 31G (0.120 g, 0.311 mmol). LC-MS Anal. Calc'd for C$_{20}$H$_{22}$BrNO$_2$ 388.3, found [M+H] 389.3 T$_r$=3.9 min (Method U).

Example 32

Example 32 was prepared from 32B following the procedures described for the conversion of 31G to Example 31. LC-MS Anal. Calc'd for C$_{27}$H$_{27}$N$_5$O$_2$ 453.5, found [M+H] 454.3. T$_r$=2.0 min (Method Q). $^1$H NMR (400 MHz, DMSO-d$_6$) δ 9.11 (s, 1H), 7.89 (d, J=1.6 Hz, 1H), 7.62-7.48 (m, 2H), 7.47-7.37 (m, 2H), 7.24 (d, J=8.0 Hz, 2H), 7.15 (d, J=8.0 Hz, 2H), 6.43 (d, J=2.0 Hz, 1H), 3.85 (t, J=5.0 Hz, 2H), 3.70 (m, 2H), 2.81 (m, 1H), 2.29 (s, 3H), 2.01-1.93 (m, 1H), 1.87-1.76 (m, 1H), 1.69-1.59 (m, 1H), 1.49-1.39 (m, 1H), 1.04 (d, J=7.0 Hz, 3H).

Racemate Example 33, Example 33 Enantiomer 1, and Example 33 Enantiomer 2

1-(5-cyclopropyl-7-(2-(5-oxo-2,5-dihydro-1,2,4-oxadiazol-3-yl)phenyl)-2,3,4,5-tetrahydrobenzo[b]oxepin-9-yl)-3-(p-tolyl)urea

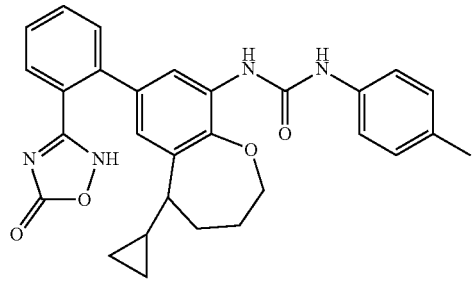 [SMILES: Cc1ccc(NC(=O)Nc2cc(-c3ccccc3-c3nc(=O)o[nH]3)cc3c2OCCCC3C2CC2)cc1]

33A. 3-cyclopropylprop-2-en-1-ol

A stirred, cooled (−78° C.) solution of methyl 3-cyclopropylacrylate (6.5 g, 51.5 mmol) in dry diethyl ether (65.0 mL) was treated with DIBAL-H (129 mL, 129 mmol) over 20 min. The reaction was stirred for 1 h then slowly warmed to RT and stirred for 1 h. The reaction was cooled to 0° C. and quenched with methanol (5 mL). Rochelle salt (20 mL) was added slowly over 5 min, and the resulting mixture was diluted with diethyl ether (25 mL). This biphasic mixture was stirred for 1 h at RT, and the layers were separated. The organic layer was dried over sodium sulfate and concentrated under reduced pressure to afford 33A (colorless liquid 4.8 g, 49 mmol, 95% yield). GC-MS Anal. Calc'd for C$_6$H$_{10}$O 98.14, found 98.0 T$_r$=5.3 min (Method AE).

33B. 4-bromo-1-((3-cyclopropylallyl)oxy)-2-nitrobenzene

A stirred suspension of NaH (3.26 g, 82 mmol) in dry THF (60 mL) at 0° C. under nitrogen atmosphere was treated with 33A (4.8 g, 48.9 mmol) in THF (15 mL). The reaction was stirred 30 min at 0° C. then treated with 4-bromo-1-fluoro-2-nitrobenzene (8.97 g, 40.8 mmol) in THF (15 mL). The reaction was stirred 2 h at RT for, cooled to 0° C. and quenched with ice water. The aqueous layer was extracted with ethyl acetate (2×75 mL), and the combined organic layer was dried over sodium sulfate and concentrated under reduced pressure. The residue was purified by flash chromatography to afford 33B (orange semi solid, 11.2 g, 38 mmol, 92% yield). LC-MS Analysis 1. Calc'd for C$_{12}$H$_{12}$BrNO$_3$ 298.1 found [M−H] 299.2 T$_r$=3.2 min (Method U).

33C. 4-bromo-2-(1-cyclopropylallyl)-6-nitrophenol

A stirred solution of 33B (8.0 g, 26.8 mmol) in diglyme (50 mL) was heated overnight at 165° C. The reaction was cooled to RT, diluted with MTBE (200 mL), and washed with water (100 mL) then brine (100 mL). The organic layer was dried with sodium sulfate and concentrated under reduced pressure. Purification by flash chromatography gave 33C (pale yellow liquid, 4.5 g, 15.09 mmol, 56% yield). LC-MS Analysis Calc'd for C$_{12}$H$_{12}$BrNO$_3$ 298.1 found [M+H] 299.1 Tr=3.5 min (Method U).

33D. 2-(allyloxy)-5-bromo-1-(1-cyclopropylallyl)-3-nitrobenzene

A stirred suspension of 33C (4.5 g, 15.09 mmol) and K$_2$CO$_3$ (6.26 g, 45.3 mmol) in dry DMF (45.0 mL) was treated with 3-bromoprop-1-ene (1.437 mL, 16.60 mmol). The reaction mixture was heated to 65° C. for 2 h, cooled to RT, and diluted with ethyl acetate (100 mL). The resulting mixture was washed with water (2×50 mL), and the combined aqueous layer was back extracted with ethyl acetate (2×50 mL). The combined organic layer was dried over sodium sulfate and concentrated under reduced pressure to afford 33D (orange liquid, 4.85 g, 14.34 mmol, 95% yield). LC-MS Analysis Calc'd for C$_{15}$H$_{16}$BrNO$_3$ 338.18, found [M+H] 339.5. T$_r$=3.82 min (Method U).

33E. 7-bromo-5-cyclopropyl-9-nitro-2,5-dihydrobenzo[b]oxepine

A stirred solution of 33D (4.9 g, 14.49 mmol) in dichloromethane (1000 mL) was purged with argon for 15 min. This solution was treated with Grubbs II (0.615 g, 0.724 mmol) catalyst and placed under argon. The reaction was heated to 55° C. for 2 h then concentrated under reduced pressure. Purification by flash chromatography gave 33E (off-white semi solid, 4.15 g, 13.4 mmol, 92% yield). LC-MS Analysis Calc'd for C$_{13}$H$_{12}$BrNO$_3$ 310.1, found [M+H] 311.0. T$_r$=3.6 min (Method U).

33F. 7-bromo-5-cyclopropyl-2,5-dihydrobenzo[b]oxepin-9-amine

A stirred solution of 33E (4.15 g, 13.38 mmol) in ethanol (40.0 mL)-THF (8.0 mL)-water (2.0 mL) was treated with ammonium chloride (10.74 g, 201 mmol). This mixture was stirred 15 min and then treated with zinc (13.12 g, 201 mmol). The reaction was stirred overnight at RT then diluted with ethyl acetate (100 mL). This mixture was washed with water (50 mL) then brine (50 mL), dried over $Na_2SO_4$, and concentrated under reduce pressure. The residue was purified by flash chromatography to afford 33F (off-white solid, 3.72 g, 13.28 mmol, 99% yield). LC-MS Analysis Calc'd for $C_{13}H_{14}BrNO$ 280.1 found [M+H] 281.0. $T_r=2.9$ min (Method U).

33G. 1-(7-bromo-5-cyclopropyl-2,5-dihydrobenzo[b]oxepin-9-yl)-3-(p-tolyl)urea A stirred solution of 33F (350 mg, 1.249 mmol) in THF (4 mL) was treated with 1-isocyanato-4-methylbenzene (200 mg, 1.499 mmol) and heated to 60° C. for 1 h. The reaction was filtered through a pad of celite (ethyl acetate rinse). The combined organic layer was washed with water, dried over sodium sulfate, and concentrated to afford 33G (off-white solid, 410 mg, 0.99 mmol, 79% yield). LC-MS Analysis Calc'd for $C_{21}H_{21}BrN_2O_2$ 413.3 found [M+H] 414.3. $T_r=1.8$ min (Method T).

33H. 1-(7-bromo-5-cyclopropyl-2,3,4,5-tetrahydrobenzo[b]oxepin-9-yl)-3-(p-tolyl)urea A stirred solution of 33G (0.900 g, 2.178 mmol) in dry ethyl acetate (10.0 mL) was purged with nitrogen, treated with Pd/C (0.090 g, 0.085 mmol) under $N_2$, and placed under an atmosphere of $H_2$. The reaction was stirred at RT for 6 h then filtered through celite, and the filtrate was concentrated under reduced pressure. The residue was purified by flash chromatography to afford 33H (off-white solid, 850 mg, 2.1 mmol, 94% yield). LC-MS Analysis Calc'd for $C_{21}H_{23}BrN_2O_2$ 415.3, found [M+H] 416.2. $T_r=3.8$ min (Method U).

33I. 1-(7-(2-cyanophenyl)-5-cyclopropyl-2,3,4,5-tetrahydrobenzo[b]oxepin-9-yl)-3-(p-tolyl)urea A stirred mixture of 33H (400 mg, 0.963 mmol), 2-(4,4,5,5-tetramethyl-1,3,2-dioxaborolan-2-yl)benzonitrile (441 mg, 1.926 mmol), and $K_2CO_3$ (784 mg, 2.408 mmol) in DMF (8.0 mL) was purged with argon for 5 min. Tetrakis(triphenylphosphine) palladium (O) (66.8 mg, 0.058 mmol) was added, and the reaction was purged with argon for 5 min. The reaction mixture was heated at 90° C. for 4 h, cooled to RT, and filtered through celite (ethyl acetate rinse). The organic layer was washed with water then brine, dried over sodium sulfate, and concentrated under reduced pressure. Purification by flash chromatography gave 33I (off-white solid, 450 mg, 1.028 mmol, 86% yield). LC-MS Analysis 1. Calc'd for $C_{28}H_{27}N_3O_2$ 437.5 found [M+H] 438.0. $T_r=4.1$ min (Method U).

33J. (Z)-2-(5-cyclopropyl-9-(3-(p-tolyl) ureido)-2,3,4,5-tetrahydrobenzo[b]oxepin-7-yl)-N'-hydroxybenzimidamide To a stirred mixture of 33I (0.450 g, 1.028 mmol) and hydroxylamine hydrochloride (0.143 g, 2.057 mmol) in ethanol (10.0 mL), was added DIPEA (0.539 mL, 3.09 mmol). The reaction mixture was heated overnight at 80° C., cooled to RT, and diluted with ethyl acetate (20 mL). This mixture was washed with water (5 mL) then brine (5 mL), dried over sodium sulfate, and concentrated under reduced pressure. The residue was purified by flash chromatography to afford 33 J (Off-white solid, 150 mg, 0.319 mmol, 31% yield). LC-MS Analysis Calc'd for $C_{28}H_{30}N_4O_3$ 470.5 found [M+H]471.2. $T_r=2.8$ min (Method U).

Racemate Example 33

A stirred solution of 33J (145 mg, 0.308 mmol) and CDI (74.9 mg, 0.462 mmol) in dry dioxane (3.0 mL) was treated with DBU (0.056 mL, 0.370 mmol). The reaction mixture was placed under nitrogen and heated to 110° C. for 1 h. The reaction was diluted with ethyl acetate (30 mL) then washed with water (10 mL) and brine (10 mL). The organic layer was dried over sodium sulfate, concentrated under reduced pressure, and purified by flash chromatography to afford Racemate Example 33 (off-white solid, 85 mg 53% yield). LC-MS Anal. Calc'd for $C_{29}H_{28}N_4O_4$ 496.5, found [M+H] 497.2. $T_r=1.07$ min (Method T).

Chiral separation of Racemate Example 33 gave Example 33 Enantiomer 1 and Example 33 Enantiomer 2 (Method AB). Enantiomer 1 $T_r=10.43$ min, Enantiomer 2 $T_r=13.21$ min (Method AB).

Example 33 Enantiomer 1: (Off-white solid, 11.0 mg, 0.022 mmol, 7% yield). LC-MS Anal. Calc'd for $C_{29}H_{28}N_4O_4$ 496.5, found [M+H] 497.2. $T_r=3.08$ min (Method N). $^1$H NMR (400 MHz, DMSO-$d_6$) δ 9.23 (s, 1H), 8.36 (s, 1H), 8.14 (d, J=2.4 Hz, 1H), 7.55-7.48 (m, 2H), 7.44-7.31 (m, 4H), 7.09 (d, J=8.4 Hz, 2H), 6.83 (d, J=2.0 Hz, 1H), 4.04 (m, 1H), 3.97 (m, 1H), 2.25 (s, 3H), 2.13 (m, 1H), 1.93-1.78 (m, 3H), 1.71 (m., 1H), 1.18-1.08 (m, 1H), 0.53 (m, 1H), 0.45 (m, 1H), 0.15 (m, 1H), 0.09-0.02 (m, 1H).

Example 33 Enantiomer 2: (Off-white solid, 11.5 mg, 0.023 mmol, 7% yield). LC-MS Anal. Calc'd for $C_{29}H_{28}N_4O_4$ 496.5, found [M+H] 497.2. $T_r=3.08$ min (Method N). $^1$H NMR (400 MHz, DMSO-$d_6$) δ 9.23 (s, 1H), 8.37 (s, 1H), 8.14 (d, J=2.4 Hz, 1H), 7.54-7.52 (m, 2H), 7.43-7.19 (m, 2H), 7.40-7.34 (m, 2H), 7.09 (d, J=8.0 Hz, 2H), 6.83 (d, J=2.0 Hz, 1H), 4.08-3.90 (m, 2H), 2.25 (s, 3H), 2.13 (m, 1H), 1.94-1.75 (m, 4H), 1.17-1.06 (m, 1H), 0.58-0.41 (m, 2H), 0.23-0.12 (m, 1H), 0.09-0.02 (m, 1H).

Racemate Example 34, Example 34 Enantiomer 1, and Example 34 Enantiomer 2

1-(7-(2-(1H-tetrazol-5-yl) phenyl)-5-cyclopropyl-2,3,4,5-tetrahydrobenzo[b]oxepin-9-yl)-3-(2-fluorophenyl)urea

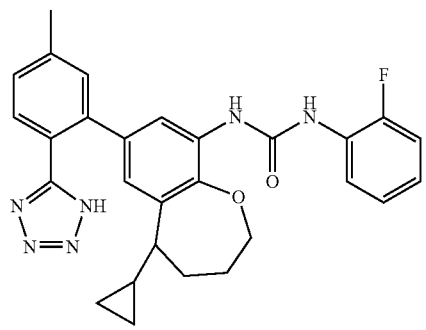 [SMILES: Cc1ccc(-c2nnn[nH]2)c(-c2cc(NC(=O)Nc3ccccc3F)c3c(c2)C(C2CC2)CCCO3)c1]

34A. 1-(7-bromo-5-cyclopropyl-2,5-dihydrobenzo[b]oxepin-9-yl)-3-(2-fluorophenyl)urea Compound 34A was prepared from 33F and 1-fluoro-2-isocyanatobenzene following the procedure for the conversion of 33F to 33G. LC-MS Anal. Calc'd for $C_{20}H_{18}BrFN_2O_2$ 417.2, found [M+H] 418.2. $T_r$=1.11 min (Method R).

34B. 1-(7-bromo-5-cyclopropyl-2,3,4,5-tetrahydrobenzo[b]oxepin-9-yl)-3-(2-fluorophenyl)urea Compound 34B was prepared from 34A following the procedure for the conversion of 33G to 33H. LC-MS Anal. Calc'd for $C_{20}H_{20}BrFN_2O_2$ 419.2, found [M+H] 420.0. $T_r$=3.7 min (Method U).

Racemate Example 34

Racemate Example 34 was prepared in DMF from 34B and 5-(4-methyl-2-(4,4,5,5-tetramethyl-1,3,2-dioxaborolan-2-yl)phenyl)-1H-tetrazole following the procedure described for the conversion of 31G to 31H. LC-MS Anal. Calc'd for $C_{28}H_{27}FN_6O_2$ 498.2, found [M+H] 499.2. $T_r$=2.3 min (Method U).

Chiral separation of Racemate Example 34 gave Example 34 Enantiomer 1 and Example 34 Enantiomer 2 (Method W). Enantiomer 1 $T_r$=3.61 min, Enantiomer 2 $T_r$=6.33 min (Method W).

Example 34 Enantiomer 1: LC-MS Anal. Calc'd for $C_{28}H_{27}FN_6O_2$ 498.2, found [M+H] 499.2. $T_r$=2.11 min (Method U). $^1$H NMR (400 MHz, DMSO-$d_6$) δ 9.28 (s, 1H), 8.93 (s, 1H), 8.19-8.11 (m, 2H), 7.50 (d, J=8.0 Hz, 1H), 7.49-7.32 (m, 2H), 7.23 (dd, J=9.54, 11.54 Hz, 1H), 7.13 (t, J=7.40 Hz, 1H), 7.00 (m, 1H), 6.38 (s, 1H), 3.99-3.92 (m, 2H)), 2.19-2.06 (m, 3H), 2.19-2.06 (m, 1H), 1.87-1.78 (m, 3H), 1.67 (m, 1H), 0.97 (m, 1H), 0.47 (m, 1H), 0.26 (m, 1H), 0.09 (m, 1H), −0.24 (m, 1H).

Example 34 Enantiomer 2: LC-MS Anal. Calc'd for $C_{28}H_{27}FN_6O_2$ 498.2, found [M+H] 499.2. $T_r$=2.13 min (Method U). $^1$H NMR (400 MHz, DMSO-$d_6$) δ 9.28 (s, 1H), 8.93 (s, 1H), 8.19-8.11 (m, 2H), 7.50 (d, J=8.0 Hz, 1H), 7.49-7.32 (m, 2H), 7.23 (dd, J=9.54, 11.54 Hz, 1H), 7.13 (t, J=7.40 Hz, 1H), 7.00 (m, 1H), 6.38 (s, 1H), 3.99-3.92 (m, 2H)), 2.19-2.06 (m, 3H), 2.19-2.06 (m, 1H), 1.87-1.78 (m, 3H), 1.67 (m, 1H), 0.97 (m, 1H), 0.47 (m, 1H), 0.26 (m, 1H), 0.09 (m, 1H), −0.24 (m, 1H).

Example 35

1-(5-cyclopropyl-7-(2-(5-oxo-4,5-dihydro-1,2,4-oxadiazol-3-yl)phenyl)-2,3,4,5-tetrahydrobenzo[b]oxepin-9-yl)-3-(2-fluorophenyl)urea

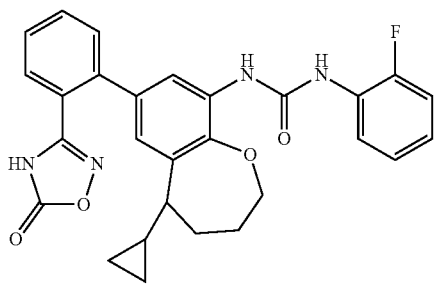 [SMILES: O=C(Nc1ccccc1F)Nc1cc(-c2ccccc2-c2noc(=O)[nH]2)cc2c1OCCCC2C1CC1]

Example 35 was prepared from 34B following the procedure for the conversion of 33H to Example 33. LC-MS Anal. Calc'd for $C_{28}H_{25}FN_4O_4$, 500.521, found [M+H] 501.2. $T_r$=3.34 min (Method U). $^1$H NMR (300 MHz, DMSO-$d_6$) δ 12.32 (s, 1H), 9.32 (s, 1H), 9.00 (s, 1H), 8.31-8.14 (m, 2H), 7.76-7.61 (m, 2H), 7.55 (m, 2H), 7.30-7.19 (m, 1H), 7.13-7.07 (m, 1H), 7.04-6.95 (m, 1H), 6.82 (d, J=2.1 Hz, 1H), 4.14-3.90 (m, 2H), 2.22-2.07 (m, 1H), 1.95-1.86 (m, 4H), 1.16-1.02 (m, 1H), 0.55-0.53 (m, 1H), 0.45-0.44 (m, 1H), 0.19-0.18 (m, 1H), 0.01-0.00 (m, 1H).

Racemate Example 36, Example 36 Enantiomer 1, and Example 36 Enantiomer 2

1-(7-(2-(1H-tetrazol-5-yl)phenyl)-5-cyclopropyl-2,3,4,5-tetrahydrobenzo[b]oxepin-9-yl)-3-(p-tolyl)urea

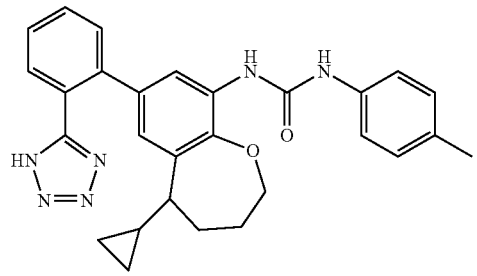 [SMILES: Cc1ccc(NC(=O)Nc2cc(-c3ccccc3-c3nnn[nH]3)cc3c2OCCCC3C2CC2)cc1]

36A. 1-(5-cyclopropyl-7-(2-(1-trityl-1H-tetrazol-5-yl)phenyl)-2,3,4,5-tetrahydrobenzo[b]oxepin-9-yl)-3-(p-tolyl)urea A solution of 33H (0.300 g, 0.722 mmol) and (2-(1-trityl-1H-tetrazol-5-yl) phenyl) boronic acid (0.468 g, 1.083 mmol) in dioxane (15.0 mL) was treated with potassium phosphate tribasic (0.460 g, 2.167 mmol). Water, 0.5 mL, was added, and the resulting mixture was purged with argon for 10 min. $PdCl_2$ (dppf)-$CH_2Cl_{1-2}$ Adduct (0.059 g, 0.072 mmol) was added, and the reaction was heated overnight at 85° C. The reaction was cooled to RT, diluted with ethyl acetate (50 mL), and washed with water then brine. The organic layer was dried over sodium sulfate and concentrated under reduced pressure. Purification of the residue by flash chromatography gave 36A (off-white solid, 410 mg, 0.57 mmol, 79% yield). LC-MS Analysis Calc'd for $C_{47}H_{42}N_6O_2$ 722.8 found [M+H] 724.0. $T_r$=4.1 min (Method U).

Racemate Example 36

To a stirred solution of 36A (0.120 g, 0.166 mmol) in DCM (2.0 mL) was added TFA (0.500 mL, 6.49 mmol). The reaction was stirred overnight then concentrated and purified by preparative HPLC to afford Racemate Example 36 (off-white solid 45.0 mg, 0.092 mmol, 56% yield). LC-MS Anal. Calc'd for $C_{28}H_{28}N_6O_2$ 480.5, found [M+H]481.2. $T_r$=2.7 min (Method U). $^1$H NMR (400 MHz, DMSO-$d_6$) δ 9.24 (s, 1H), 8.39 (s, 1H), 8.15-8.13 (d, J=2.4 Hz, 1H), 7.67-7.50 (m, 2H), 7.57-7.50 (m, 2H), 7.47-7.31 (m, 2H), 7.10-7.08 (d, J=8.4 Hz, 2H), 6.37 (s, 1H), 4.40-3.88 (m, 2H), 2.24 (s, 3H), 2.17-2.06 (m, 1H), 1.92-1.73 (m, 3H), 1.66-1.56 (m, 1H), 0.98-0.095 (m, 1H) 0.48-0.47 (m, 1H), 0.27-0.26 (m, 1H), 0.12-0.11 (m, 1H), −0.20-0.23 (m, 1H).

Chiral separation of Racemate Example 36 gave Example 36 Enantiomer 1 and Example 36 Enantiomer 2 as single enantiomers (Method S). Enantiomer 1 $T_r$=3.9 min, Enantiomer 2 $T_r$=6.6 min (Method S).

Example 36 Enantiomer 1: LC-MS Anal. Calc'd for $C_{28}H_{28}N_6O_2$ 480.5, found [M+H] 481.2. $T_r$=2.7 min (Method U). $^1$H NMR (400 MHz, DMSO-$d_6$) δ 9.24 (s, 1H), 8.39 (s, 1H), 8.15-8.13 (d, J=2.4 Hz, 1H), 7.67-7.50 (m, 2H), 7.57-7.50 (m, 2H), 7.47-7.31 (m, 2H), 7.10-7.08 (d, J=8.4 Hz, 2H), 6.37 (s, 1H), 4.40-3.88 (m, 2H), 2.24 (s, 3H), 2.17-2.06 (m, 1H), 1.92-1.73 (m, 3H), 1.66-1.56 (m, 1H), 0.98-0.095 (m, 1H) 0.48-0.47 (m, 1H), 0.27-0.26 (m, 1H), 0.12-0.11 (m, 1H), −0.20-0.23 (m, 1H).

Example 36 Enantiomer 2: LC-MS Anal. Calc'd for $C_{28}H_{28}N_6O_2$ 480.5, found [M+H] 481.2. $T_r$=2.8 min (Method U). $^1$H NMR (400 MHz, DMSO-$d_6$) δ 9.24 (s, 1H), 8.39 (s, 1H), 8.15-8.13 (d, J=2.4 Hz, 1H), 7.67-7.50 (m, 2H), 7.57-7.50 (m, 2H), 7.47-7.31 (m, 2H), 7.10-7.08 (d, J=8.4 Hz, 2H), 6.37 (s, 1H), 4.40-3.88 (m, 2H), 2.24 (s, 3H), 2.17-2.06 (m, 1H), 1.92-1.73 (m, 3H), 1.66-1.56 (m, 1H), 0.98-0.095 (m, 1H) 0.48-0.47 (m, 1H), 0.27-0.26 (m, 1H), 0.12-0.11 (m, 1H), −0.20-0.23 (m, 1H).

Example-37 Enantiomer 1 & Enantiomer 2

N-(7-(2-(1H-tetrazol-5-yl)phenyl)-5-cyclopropyl-2,3,4,5-tetrahydrobenzo[b]oxepin-9-yl)-2-(p-tolyl)acetamide

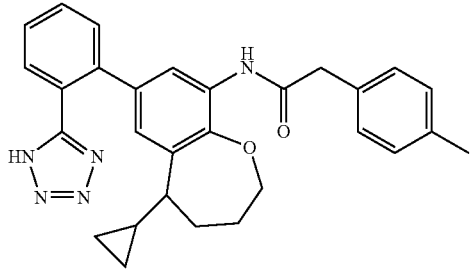 [SMILES: Cc1ccc(CC(=O)Nc2cc(-c3ccccc3-c3nnn[nH]3)cc3c2OCCCC3C2CC2)cc1]

37A. N-(7-bromo-5-cyclopropyl-2,5-dihydrobenzo[b]oxepin-9-yl)-2-(p-tolyl)acetamide 37A was prepared from 33F and 2-(p-tolyl) acetic acid following the procedure for the conversion of 32A to 32B. LC-MS Anal. Calc'd for $C_{22}H_{22}BrNO_2$ 412.3, found [M+H] 413.0. $T_r$=1.0 min (Method R).

37B. N-(7-bromo-5-cyclopropyl-2,3,4,5-tetrahydrobenzo[b]oxepin-9-yl)-2-(p-tolyl) acetamide 37B was prepared from 37A following the procedure for the conversion of 33G to 33H. LC-MS Anal. Calc'd for $C_{22}H_{24}BrNO_2$ 414.3 found [M+H] 415.2. $T_r$=3.9 min (Method U).

37C. N-(5-cyclopropyl-7-(2-(1-trityl-1H-tetrazol-5-yl) phenyl)-2,3,4,5-tetrahydrobenzo[b]oxepin-9-yl)-2-(p-tolyl)acetamide 37C was prepared from 37B following the procedure for the conversion of 33H to 36A. LC-MS Analysis Calc'd for $C_{48}H_{43}N_5O_2$ 721.8 found [M+H] 723.1. $T_r$=2.8 min (Method T).

Racemate Example 37

Racemate Example 37 was prepared from 37C following the procedure for the conversion of 36A to Racemate Example 36. LC-MS Anal. Calc'd for $C_{29}H_{29}N_5O_2$ 479.6, found [M+H] 480.2. $T_r$=2.1 min (Method U). $^1$H NMR (400 MHz, DMSO-$d_6$) δ 9.14 (s, 1H), 7.99 (d, J=1.5 Hz, 1H), 7.63-7.58 (m, 2H), 7.52-7.45 (m, 2H), 7.27-7.20 (d, J=7.6 Hz, 2H), 7.15-7.14 (J=7.6 Hz, 2H), 6.50 (d, J=2.0 Hz, 1H), 3.99-3.88 (m, 2H), 3.85-3.76 (m, 2H), 2.28 (s, 3H), 2.14-2.01 (m, 1H), 1.86-1.55 (m, 4H), 0.90-0.85 (m, 1H), 0.45-0.38 (m, 1H), 0.25-0.22 (m, 1H), 0.15-0.12 (m, 1H), −0.23--0.28 (m, 1H).

Chiral separation of Racemate Example 37 gave Example 37 Enantiomer 1 and Example 37 Enantiomer 2 as single enantiomers (Method AC). Enantiomer 1 $T_r$=2.41 min (Method AC); Enantiomer 2 $T_r$=5.16 min (Method AC).

Example 37 Enantiomer 1: LC-MS Anal. Calc'd for $C_{29}H_{29}N_5O_2$ 479.5, found [M+H] 480.2. $T_r$=2.4 min (Method U). $^1$H NMR (400 MHz, DMSO-$d_6$) δ 9.15 (s, 1H), 7.99 (d, J=1.5 Hz, 1H), 7.63-7.58 (m, 2H), 7.52-7.45 (m, 2H), 7.27-7.20 (d, J=7.6 Hz, 2H), 7.15-7.14 (J=7.6 Hz, 2H), 6.50-6.48 (d, J=2.0 Hz, 1H), 3.99-3.88 (m, 2H), 3.85-3.76 (m, 2H), 2.28 (s, 3H), 2.14-2.01 (m, 1H), 1.86-1.55 (m, 4H), 0.97-0.95 (m, 1H), 0.45-0.44 (m, 1H), 0.25-0.23 (m, 1H), 0.09-0.07 (m, 1H), −0.23--0.27 (m, 1H).

Example 37 Enantiomer 2: LC-MS Anal. Calc'd for $C_{29}H_{29}N_5O_2$ 479.5 found [M+H] 480.2. $T_r$=2.1 min (Method U $^1$H NMR (400 MHz, DMSO-$d_6$) δ 9.15 (s, 1H), 7.99 (d, J=1.5 Hz, 1H), 7.63-7.58 (m, 2H), 7.52-7.45 (m, 2H), 7.27-7.20 (d, J=7.6 Hz, 2H), 7.15-7.14 (J=7.6 Hz, 2H), 6.50-6.48 (d, J=2.0 Hz, 1H), 3.99-3.88 (m, 2H), 3.85-3.76 (m, 2H), 2.28 (s, 3H), 2.14-2.01 (m, 1H), 1.86-1.55 (m, 4H), 0.97-0.95 (m, 1H), 0.45-0.44 (m, 1H), 0.25-0.23 (m, 1H), 0.09-0.07 (m, 1H), −0.23--0.27 (m, 1H).

Example 38 Enantiomer 1 and Example 38 Enantiomer 2

1-(7-(2-(1H-tetrazol-5-yl) phenyl)-5-cyclopropyl-2,3,4,5-tetrahydrobenzo[b]oxepin-9-yl)-3-(2-fluorophenyl)urea

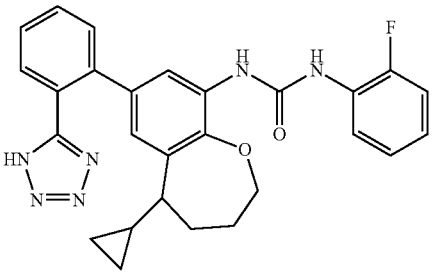

38A. tert-butyl (7-bromo-5-cyclopropyl-2,5-dihydrobenzo[b]oxepin-9-yl)carbamate A stirred solution of 33F (1.80 g, 6.42 mmol) and $BOC_2O$ (4.48 mL, 19.27 mmol) in dry acetonitrile (40.0 mL) was heated overnight at 80° C. The reaction was concentrated under reduced pressure and purified by flash chromatography to afford 38A (Off white semi solid, 2.05 g, 5.39 mmol, 84% yield). LC-MS Anal. Calc'd for $C_{18}H_{22}BrNO_3$ 380.2, found [M−H] 379.0, $T_r$=4.0 min (Method U).

38B. tert-butyl (7-bromo-5-cyclopropyl-2,3,4,5-tetrahydrobenzo[b]oxepin-9-yl)carbamate 38B was prepared from 38A following the procedure for the conversion of 33G to 33H. LC-MS Anal. Calc'd for $C_{18}H_{24}BrNO_3$ 382.2, found [M+H] 383.3, $T_r$=4.2 min (Method U).

38C. tert-butyl (5-cyclopropyl-7-(2-(1-trityl-1H-tetrazol-5-yl) phenyl)-2,3,4,5-tetrahydrobenzo[b]oxepin-9-yl)carbamate 38C was prepared from 38B following the procedure for the conversion of 33H to 36A. LC-MS Anal. Calc'd for $C_{44}H_{43}N_5O_3$ 689.8; found [M−H] 688.4. $T_r$=3.2 min (Method U).

38D. 5-cyclopropyl-7-(2-(1-trityl-1H-tetrazol-5-yl) phenyl)-2,3,4,5-tetrahydrobenzo[b]oxepin-9-amine A stirred solution of 38C (2.3 g, 3.33 mmol) in dry DCM (25 mL) was cooled to 0° C. and treated with 2,6-lutidine (1.165 mL, 10.00 mmol) followed by trimethylsilyl trifluoromethanesulfonate (1.810 mL, 10.00 mmol). The reaction was stirred for 1 h then slowly brought to RT. The reaction was diluted with DCM (50 mL), washed with 10% aq. sodium bicarbonate, and dried over sodium sulfate. Concentration and purification of the residue by flash chromatography gave 38D (Off-white solid, 1.30 g, 2.204 mmol, 66% yield). LC-MS Anal. Calc'd for $C_{39}H_{35}N_5O$ 589.7 found [M+H] 591.2, $T_r$=3.0 min (Method U).

38E. 7-(2-(1H-tetrazol-5-yl) phenyl)-5-cyclopropyl-2,3,4,5-tetrahydrobenzo[b]oxepin-9-amine 38E was prepared from 38D following the procedure following the procedure for the conversion of 36A to Racemate Example 36. LC-MS Anal. Calc'd for $C_{20}H_{21}N_5O$ 347.4, found [M+H] 348.4, $T_r$=1.2 min (Method U). Chiral separation of Racemate 38E gave 38E Enantiomer 1 and 38E Enantiomer 2 as single enantiomers (Method AC). Enantiomer 1 $T_r$=3.5 min (Method AC) and Enantiomer 2 $T_r$=4.9 min. (Method AC).

Example 38 Enantiomer 1

Example 38 Enantiomer 1 was prepared from 38E Enantiomer 1 and 1-fluoro-2-isocyanatobenzene following the procedure as for the conversion of 33F to 33G. (Method AC). Enantiomer 1 $T_r$=4.7 min (Method AC). LC-MS Anal. Calc'd for $C_{27}H_{25}FN_6O_2$ 484.5, found [M+H] 485.2. $T_r$=2.1 min (Method U). $^1$H NMR (400 MHz, DMSO-d$_6$) δ 9.26 (s, 1H), 8.89 (s, 1H), 8.18-8.14 (t, J=7.2 Hz, 1H), 8.08 (s, 1H), 7.61-7.39 (m, 4H), 7.28-7.18 (m, 1H), 7.16-7.08 (m, 1H), 6.98-6.96 (m, 1H), 6.44 (s, 1H), 4.08-3.84 (m, 2H), 2.10-2.05 (m, 1H), 192-1.56 (m, 4H), 0.99-0.88 (m, 1H), 0.46 (m, 1H) 0.26-0.22 (m, 1H) 0.10-0.08 (m, 1H) −0.18-0.22 (m, 1H).

Example 38 Enantiomer 2

Example 38 Enantiomer 2 was prepared from 38E Enantiomer 2 and 1-fluoro-2-isocyanatobenzene following the procedure as for the conversion of 33F to 33G. (Method AC). Enantiomer 2 $T_r$=8.4 min (Method AC). LC-MS Anal. Calc'd for $C_{27}H_{25}FN_6O_2$ 484.5, found [M+H] 485.2. $T_r$=2.12 min (Method U). 9.26 (s, 1H), 8.89 (s, 1H), 8.18-8.14 (t, J=7.2 Hz, 1H), 8.08 (s, 1H), 7.61-7.39 (m, 4H), 7.28-7.18 (m, 1H), 7.16-7.08 (m, 1H), 6.98-6.96 (m, 1H), 6.44 (s, 1H), 4.08-3.84 (m, 2H), 2.10-2.05 (m, 1H), 192-1.56 (m, 4H), 0.99-0.88 (m, 1H), 0.46 (m, 1H) 0.26-0.22 (m, 1H) 0.10-0.08 (m, 1H) −0.18-0.22 (m, 1H).

Example 39 Enantiomer 1 and Example 39 Enantiomer 2

1-(7-(2-(1H-tetrazol-5-yl) phenyl)-5-cyclopropyl-2,3,4,5-tetrahydrobenzo[b]oxepin-9-yl)-3-(2-fluoro-4-methylphenyl)urea

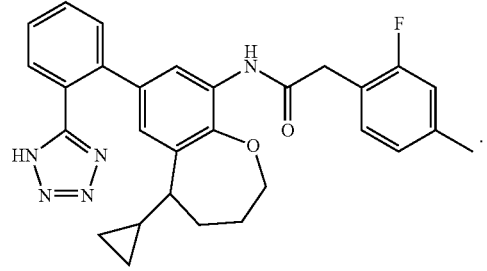 [SMILES: Cc1ccc(CC(=O)Nc2cc(-c3ccccc3-c3nnn[nH]3)cc3c2OCCCC3C2CC2)c(F)c1]

Example 39 Enantiomer 1 was prepared from 38E Enantiomer 1 and 2-(2-fluoro-4-methylphenyl) acetic acid following the procedure for the conversion of 32A to 32B. Enantiomer 1 $T_r$=3.2 min (Method AC). LC-MS Anal. Calc'd for $C_{29}H_{28}FN_5O_2$ 497.5 found [M+H] 498.2. $T_r$=3.2 min (Method U). $^1$H NMR (400 MHz, DMSO-d$_6$) δ 9.21 (s, 1H), 7.97 (s, 1H), 7.57-7.44 (m, 4H), 7.28-7.24 (t, J=8.0 Hz 1H), 7.06-6.96 (m, 2H), 6.55-6.48 (m, 1H), 3.96 (m, 1H), 3.80-3.74 (m, 3H), 2.30 (s, 3H), 2.13-2.03 (m, 1H), 1.88-1.78 (m, 1H), 1.77-1.67 (m, 2H), 1.65-153 (m, 1H), 0.97-0.85 (m, 1H), 0.46-0.44 (m, 1H) 0.26-0.24 (m, 1H) 0.10-0.08 (m, 1H) −0.23-−0.28 (m, 1H).

Example 39 Enantiomer 2 was prepared from 38E Enantiomer 2 and 2-(2-fluoro-4-methylphenyl) acetic acid following the procedure for the conversion of 32A to 32B. Enantiomer 2 $T_r$=6.1 min (Method AC). LC-MS Anal. Calc'd for $C_{29}H_{28}FN_5O_2$ 497.5, found [M+H] 498.2. $T_r$=2.23 min (Method U). $^1$H NMR (400 MHz, DMSO-d$_6$) δ 9.21 (s, 1H), 7.97 (s, 1H), 7.57-7.44 (m, 4H), 7.28-7.24 (t, J=8.0 Hz 1H), 7.06-6.96 (m, 2H), 6.55-6.48 (m, 1H), 3.96 (m, 1H), 3.80-3.74 (m, 3H), 2.30 (s, 3H), 2.13-2.03 (m, 1H), 1.88-1.78 (m, 1H), 1.77-1.67 (m, 2H), 1.65-153 (m, 1H), 0.97-0.85 (m, 1H), 0.46-0.44 (m, 1H) 0.26-0.24 (m, 1H) 0.10-0.08 (m, 1H) −0.23-−0.28 (m, 1H).

Example 40 Enantiomer 1 and Example 40 Enantiomer 2

N-(7-(2-(1H-tetrazol-5-yl) phenyl)-5-cyclopropyl-2,3,4,5-tetrahydrobenzo[b]oxepin-9-yl)-2-(2-fluorophenyl)acetamide

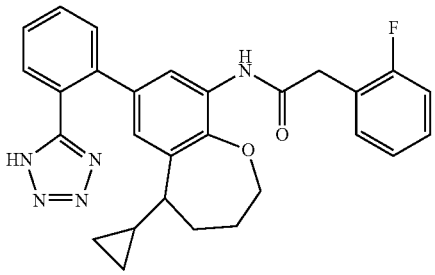 [SMILES: O=C(Cc1ccccc1F)Nc1cc(-c2ccccc2-c2nnn[nH]2)cc2c1OCCCC2C1CC1]

Example 40 Enantiomer 1 was prepared from 38E Enantiomer 1 and 2-(2-fluorophenyl) acetic acid following the procedure for the conversion of 32A to 32B. $T_r$=3.4 min (Method AC). LC-MS Anal. Calc'd for $C_{28}H_{26}FN_5O_2$, 483.5, found [M+H] 484.2. $T_r$=2.0 min (Method U). $^1$H NMR (400 MHz, DMSO-$d_6$) δ 9.28 (s, 1H), 7.99 (s, 1H), 7.67-7.44 (m, 4H), 7.40 (t, J=7.78 Hz, 1H), 7.35-7.29 (m, 1H), 7.23-7.14 (m, 2H), 6.51 (s, 1H), 3.97-3.92 (m, 1H), 3.85 (m, 3H), 2.13-2.03 (m, 1H), 1.88-1.78 (m, 1H), 1.77-1.67 (m, 2H), 1.65-1.53 (m, 1H), 0.99-0.93 (m, 1H), 0.46-0.44 (m, 1H) 0.26-0.24 (m, 1H) 0.10-0.08 (m, 1H) −0.23-−0.28 (m, 1H).

Example 40 Enantiomer 2 was prepared from 38E Enantiomer 2 and 2-(2-fluorophenyl) acetic acid following the procedure for the conversion of 32A to 32B. $T_r$=7.3 min (Method AC). LC-MS Anal. Calc'd for $C_{28}H_{26}FN_5O_2$, 483.5, found [M+H]484.2. $T_r$=2.0 min (Method U). $^1$H NMR (400 MHz, DMSO-$d_6$) δ 9.28 (s, 1H), 7.99 (s, 1H), 7.67-7.44 (m, 4H), 7.40 (t, J=7.78 Hz, 1H), 7.35-7.29 (m, 1H), 7.23-7.14 (m, 2H), 6.51 (s, 1H), 3.97-3.92 (m, 1H), 3.85 (m, 3H), 2.13-2.03 (m, 1H), 1.88-1.78 (m, 1H), 1.77-1.67 (m, 2H), 1.65-1.53 (m, 1H), 0.99-0.93 (m, 1H), 0.46-0.44 (m, 1H) 0.26-0.24 (m, 1H) 0.10-0.08 (m, 1H) −0.23-−0.28 (m, 1H).

Example 41 Enantiomer 1 and Example 41 Enantiomer 2

1-(7-(2-(1H-tetrazol-5-yl) phenyl)-5-cyclopropyl-2,3,4,5-tetrahydrobenzo[b]oxepin-9-yl)-3-(4-chloro-2-fluorophenyl)urea

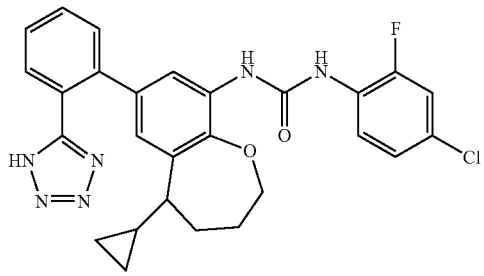 [SMILES: O=C(Nc1ccc(Cl)cc1F)Nc1cc(-c2ccccc2-c2nnn[nH]2)cc2c1OCCCC2C1CC1]

Example 41 Enantiomer 1 was prepared from 38E Enantiomer 1 and 4-chloro-2-fluoro-1-isocyanato benzene following the procedure for the conversion of 32A to 32B. $T_r$=3.6 min (Method AC). LC-MS Anal. Calc'd for $C_{27}H_{24}ClFN_6O_2$, 518.9, found [M+H] 520.2. $T_r$=2.3 min (Method U). $^1$H NMR (400 MHz, DMSO-$d_6$) δ 9.35 (s, 1H), 8.92 (s, 1H), 8.22 (t, J=9.04 Hz, 1H), 8.09-7.99 (m, 1H), 7.46 (m, 5H), 7.23 (d, J=8.4 Hz, 1H), 6.46 (d, J=2.0 Hz, 1H), 3.97-3.85 (m, 2H), 2.13-2.03 (m, 1H), 1.88-1.78 (m, 1H), 1.77-1.67 (m, 2H), 1.65-1.53 (m, 1H), 0.99-0.95 (m, 1H), 0.46-0.44 (m, 1H) 0.26-0.24 (m, 1H) 0.10-0.08 (m, 1H) −0.23-−0.28 (m, 1H).

Example 41 Enantiomer 2 was prepared from 38E Enantiomer 2 and 4-chloro-2-fluoro-1-isocyanato benzene following the procedure for the conversion of 32A to 32B. $T_r$=1.8 min (Method AC). LC-MS Anal. Calc'd for $C_{27}H_{24}ClFN_6O_2$, 518.9, found [M+H]520.2. $T_r$=2.3 min (Method U). $^1$H NMR (400 MHz, DMSO-$d_6$) δ 9.35 (s, 1H), 8.92 (s, 1H), 8.22 (t, J=9.0 Hz, 1H), 8.09-7.99 (m, 1H), 7.46 (m, 5H), 7.23 (d, J=8.4 Hz, 1H), 6.46 (d, J=2.0 Hz, 1H), 3.97-3.85 (m, 2H), 2.13-2.03 (m, 1H), 1.88-1.78 (m, 1H), 1.77-1.67 (m, 2H), 1.65-1.53 (m, 1H), 0.99-0.95 (m, 1H), 0.46-0.44 (m, 1H) 0.26-0.24 (m, 1H) 0.10-0.08 (m, 1H) −0.23-−0.28 (m, 1H).

Example 42

1-(7-(2-(1H-tetrazol-5-yl) phenyl)-5-methyl-2,3,4,5-tetrahydrobenzo[b]oxepin-9-yl)-3-(pyrimidin-2-yl)urea

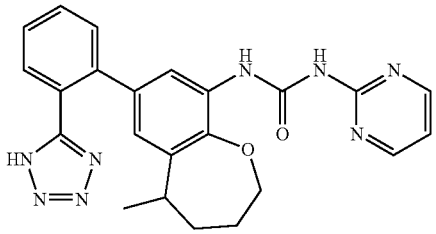 [SMILES: CC1CCCOc2c(NC(=O)Nc3ncccn3)cc(-c3ccccc3-c3nnn[nH]3)cc21]

42A. 1-(7-bromo-5-methyl-2,5-dihydrobenzo[b]oxepin-9-yl)-3-(pyrimidin-5-yl)urea

A stirred solution of 7-bromo-5-methyl-2,5-dihydrobenzo[b]oxepin-9-amine (31E) (0.450 g, 1.771 mmol) and pyrimidin-5-amine (0.202 g, 2.125 mmol) in DCE (10.0 mL) was treated with CDI (0.861 g, 5.31 mmol), and the resulting solution was stirred overnight. The reaction was concentrated under reduced pressure, and the residue was partitioned between water (10 ml) and EtOAc (30 ml). The organic layer was separated, dried over $Na_2SO_4$ and concentrated under reduced pressure to afford the crude product. Purification by flash chromatography gave 42A. LC-MS Anal. Calc'd for $C_{16}H_{15}BrN_4O_2$ 375.2, found [M+H] 376.5. $T_r$=2.9 min (Method U).

42B. 1-(1-(7-bromo-5-methyl-2,3,4,5-tetrahydrobenzo[b]oxepin-9-yl)-3-(pyrimidin-5-yl)urea 42B was prepared from 42A following the procedure for the conversion of 31G to 31H. LC-MS Anal. Calc'd for $C_{16}H_{17}BrN_4O_2$ 377.2, found [M+H] 378.5. $T_r$=2.6 min (Method U).

42C. 1-(5-methyl-7-(2-(1-trityl-1H-tetrazol-5-yl) phenyl)-2,3,4,5-tetrahydrobenzo[b]oxepin-9-yl)-3-(pyrimidin-5-yl)urea 42C was prepared from 42B and (2-(1-trityl-1H-tetrazol-5-yl) phenyl) boronic acid following the procedure for the conversion of 33H to 36A. LC-MS Anal. Calc'd for $C_{42}H_{36}N_8O_2$ 684.8, found [M+H] 685.5. $T_r$=4.0 min (Method U).

Example 42

Example 42 was prepared from 42C following the procedure for the conversion of 36A to Racemate Example 36. LC-MS Anal. Calc'd for $C_{23}H_{22}N_8O_2$ 442.47, found [M+H] 443.3. $T_r$=1.44 min (Method R). $^1$H NMR (400 MHz, DMSO-$d_6$) δ 9.67 (s, 1H), 8.55 (s, 1H), 7.95 (s, 1H), 7.55 (d, J=1.5 Hz, 2H), 7.39 (m, 4H), 6.42 (d, J=2.0 Hz, 1H), 3.86-4.09 (m, 2H), 2.76-2.90 (m, 1H), 1.95-1.85 (m, 1H), 1.68 (m, 1H), 1.41-1.52 (m, 1H), 1.14-1.20 (m, 1H), 1.06 (s, 3H).

Example 43

(homochiral) 1-(7-(2-(1H-tetrazol-5-yl)phenyl)-4-methyl-5-phenyl-2,3,4,5-tetrahydrobenzo[b]oxepin-9-yl)-3-(p-tolyl)urea (Homochiral, Relative and Absolute Stereochemistry Unknown)

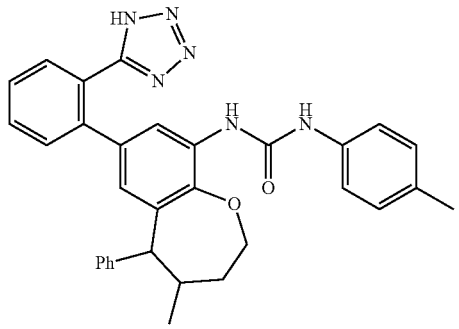 [SMILES: Cc1ccc(NC(=O)Nc2cc(-c3ccccc3-c3nnn[nH]3)cc3c2OCCC(C)C3c2ccccc2)cc1]

43A. (E)-2-methyl-3-phenylprop-2-en-1-ol

A stirred suspension of copper(I) iodide (7.21 g, 37.8 mmol) in THF (dry) (35 mL) was placed under nitrogen, cooled to −35° C., and treated with methylmagnesium bromide (3M in diethylether) (25.2 mL, 76 mmol) dropwise over 30 min. The reaction was warmed to 10° C. with stirring over 1 h, re-cooled to 5° C., and treated with 3-phenylprop-2-yn-1-ol (1 g, 7.57 mmol) drop wise over 5 min. The reaction mixture was then slowly warmed to 20° C. and stirred 4 h. The reaction was quenched with saturated aq. NH$_4$Cl solution (25 mL) drop wise over 30 min., and the resulting mixture was extracted with ethyl acetate (2×100 mL). The combined organic layer was dried over sodium sulphate and concentrated under reduced pressure. Purification of the residue by flash chromatography gave 43A (yellow liquid, 0.81 g, 5.47 mmol, 72% yield). $^1$H NMR (400 MHz, CHLOROFORM-d) δ 7.33-7.39 (m, 2H), 7.28-7.31 (m, 2H) 7.22-7.26 (m, 1H), 6.54 (s, 1H), 4.21 (s, 2H), 1.92 (d, J=1.5 Hz, 3H).

43B. (E)-4-bromo-1-((2-methyl-3-phenylallyl)oxy)-2-nitrobenzene

A suspension of NaH (3.55 g, 89 mmol) in THF (100 mL) at 0° C. was treated by dropwise addition with 43A (11.12 g, 75 mmol) in THF (25 mL), and the resulting mixture was stirred at 0° C. for 1 h. Then 4-bromo-1-fluoro-2-nitrobenzene (15 g, 68.2 mmol) in THF (25 mL) was added dropwise, and the reaction was slowly warmed to RT and stirred overnight. The reaction mixture was quenched with brine (50 mL) and extracted with ethyl acetate (2×50 mL). The combined organic layer was dried over sodium sulphate and concentrated under reduced pressure. Purification by flash chromatography gave 43B (yellow solid, 19 g, 52.9 mmol, 78% yield). $^1$H NMR (400 MHz, DMSO-$d_6$) δ 8.14 (d, J=3.6 Hz, 1H), 7.85 (m, 1H), 7.26-7.44 (m, 6H), 6.67 (s, 1H), 4.82 (s, 2H), 1.89 (d, J=1.6 Hz, 3H).

43C. 4-bromo-2-(2-methyl-1-phenylallyl)-6-nitrophenol

A solution of 43B (9.5 g, 27.3 mmol) in diglyme (100 ml, 704 mmol) was heated to 165° C. for 36 h. The reaction was concentrated under reduced pressure, and the residue was purified by flash chromatography to afford 43C (yellow gum, 4.5 g, 12.41 mmol, 46% yield). LC-MS Anal. Calc'd for $C_{16}H_{14}BrNO_3$ 347.06, found [M+H] 348.2. $T_r$=1.3 min (Method T).

43D. 2-(allyloxy)-5-bromo-1-(2-methyl-1-phenylallyl)-3-nitrobenzene

A solution of 43C (5.25 g, 15.08 mmol) in DMF (70 mL) was treated with K$_2$CO$_3$ (6.25 g, 45.2 mmol) followed by allyl bromide (1.435 mL, 16.59 mmol). The reaction was heated to 50° C. for 3 h then cooled to RT and poured into ice water (50 mL). The resulting mixture was extracted with ethyl acetate (2×50 mL), and the combined organic layer was dried over sodium sulphate and concentrated under reduced pressure to afford 43D (brown gum, 5.25 g, 13.52 mmol, 90% yield). LC-MS Anal. Calc'd for $C_{19}H_{18}BrNO_3$ 387.07, found [M+H] 405.2 (ammonia adduct). $T_r$=4.17 min (Method U).

43E. 7-bromo-4-methyl-9-nitro-5-phenyl-2,5-dihydrobenzo[b]oxepine

A solution of 43D (6 g, 15.45 mmol) in DCE (1500 mL) was purged with nitrogen for 15 min and treated with GrubbsII (0.656 g, 0.773 mmol). The reaction was heated to 60° C. overnight then concentrated under reduced pressure. The residue was purified by flash chromatography to afford 43E (pale yellow solid, 4.75 g, 12.53 mmol, 81% yield). LC-MS Anal. Calc'd for $C_{17}H_{14}BrNO_3$ 359.06, found [M−H] 358.2. $T_r$=1.27 min (Method T).

43F. 7-bromo-4-methyl-5-phenyl-2,5-dihydrobenzo[b]oxepin-9-amine

To a solution of 43E (4.75 g, 13.19 mmol) in ethanol (100 mL)-THF (20 mL)-water (10 mL) was added ammonium chloride (10.58 g, 198 mmol). This mixture was stirred at RT for 5 min then treated with zinc (12.93 g, 198 mmol). The reaction was stirred overnight at RT, filtered through celite and concentrated under reduced pressure. The residue was diluted with water (100 mL) and extracted with ethyl acetate (2×100 mL). The combined organic layer was dried over sodium sulphate and concentrated under reduced pressure to afford 43F (brown gum, 4 g, 11.75 mmol, 89% yield). LC-MS Anal. Calc'd for $C_{17}H_{16}BrNO$ 329.04, found [M+H] 330.2. $T_r$=3.22 min (Method U).

43G. 7-bromo-4-methyl-5-phenyl-2,3,4,5-tetrahydrobenzo[b]oxepin-9-amine (Diastereomer Mixture)

A solution of 43F (4 g, 12.11 mmol) in ethyl acetate (400 mL) was treated with platinum(IV) oxide (1 g, 4.40 mmol) and stirred overnight under an atmosphere of hydrogen. The reaction mixture was filtered through celite and concentrated under reduced pressure to afford the crude product. Purification by flash chromatography gave 43G (brown gum, 1.5 g, 4.47 mmol, 36.9% yield). LC-MS Anal. Calc'd for $C_{17}H_{18}BrNO$ 331.23, found [M+H] 332.2. $T_r$=3.585 min (Method U).

Chiral separation of diastereomer mixture 43 G (Method AF) gave diastereomer 1 $T_r$=5.83 min (Method AF), diastereomer 2 $T_r$=7.16 min (Method AF), diastereomer 3 $T_r$=9.3 min (Method AF), and diastereomer 4 $T_r$=11.84 min (Method AF).

Compound 43G isomer 1: LC-MS Anal. Calc'd for $C_{17}H_{18}BrNO$ 331.05, found [M+H] 332.2, $T_r$=3.36 min (Method U). $^1$H NMR (300 MHz, DMSO-d6) δ 7.15-7.31 (m, 5H), 6.72 (d, J=2.40 Hz, 1H), 6.32 (d, J=2.40 Hz, 1H), 5.18 (s, 2H), 4.01-4.06 (m, 1H), 3.85 (d, J=7.20 Hz, 1H), 3.78-3.81 (m, 1H), 2.41-2.43 (m, 1H), 1.82-1.86 (m, 1H), 1.45-1.51 (m, 1H), 0.95 (d, J=6.90 Hz, 3H).

Compound 43G isomer 2: LC-MS Anal. Calc'd for $C_{17}H_{18}BrNO$ 331.05, found [M+H] 332.2, $T_r$=3.4 min (Method U). $^1$H NMR (300 MHz, DMSO-d6) δ 7.42 (d, J=120 Hz, 2H), 7.16-7.29 (m, 3H), 6.67 (d, J=2.70 Hz, 1H), 6.40 (d, J=2.40 Hz, 1H), 5.21 (s, 2H), 4.35 (m, 1H), 3.96 (d, J=3.00 Hz, 1H), 3.63 (t, J=21.60 Hz, 1H), 2.14-2.20 (m, 1H), 1.77-1.83 (m, 1H), 1.57 (d, J=13.80 Hz, 1H), 0.88 (d, J=6.90 Hz, 3H).

Compound 43G isomer 3: LC-MS Anal. Calc'd for $C_{17}H_{18}BrNO$ 331.05, found [M+H] 332.2, $T_r$=3.36 min (Method U). $^1$H NMR (300 MHz, DMSO-d6) δ 7.15-7.31 (m, 5H), 6.72 (d, J=2.40 Hz, 1H), 6.32 (d, J=2.40 Hz, 1H), 5.18 (s, 2H), 4.01-4.06 (m, 1H), 3.85 (d, J=120 Hz, 1H), 3.78-3.81 (m, 1H), 2.41-2.43 (m, 1H), 1.82-1.86 (m, 1H), 1.45-1.51 (m, 1H), 0.95 (d, J=6.90 Hz, 3H).

Compound 43G isomer 4: LC-MS Anal. Calc'd for $C_{17}H_{18}BrNO$ 331.05, found [M+H] 332.2, $T_r$=3.4 min (Method U). $^1$H NMR (300 MHz, DMSO-d6) 7.42 (d, J=7.20 Hz, 2H), 7.16-7.29 (m, 3H), 6.67 (d, J=2.70 Hz, 1H), 6.40 (d, J=2.40 Hz, 1H), 5.21 (s, 2H), 4.35 (m, 1H), 3.96 (d, J=3.00 Hz, 1H), 3.63 (t, J=21.60 Hz, 1H), 2.14-2.20 (m, 1H), 1.77-1.83 (m, 1H), 1.57 (d, J=13.80 Hz, 1H), 0.88 (d, J=6.90 Hz, 3H).

43H. 1-(7-bromo-4-methyl-5-phenyl-2,3,4,5-tetrahydrobenzo[b]oxepin-9-yl)-3-(p-tolyl)urea A solution of 43G isomer 2 (0.05 g, 0.150 mmol) in DCM (2 mL) was treated with 1-isocyanato-4-methylbenzene (0.024 g, 0.181 mmol) and the resulting solution was stirred overnight at RT. The reaction was concentrated under reduced pressure and purified by flash chromatography to afford 43H (off white solid, 0.07 g, 0.147 mmol, 98% yield). LC-MS Anal. Calc'd for $C_{25}H_{25}BrN_2O_2$ 464.1, found [M+H] 465.2, $T_r$=3.972 min (Method U).

Example 43 (Homochiral, Relative and Absolute Stereochemistry Unknown)

A suspension of 43H (0.07 g, 0.150 mmol), 5-(2-(4,4,5,5-tetramethyl-1,3,2-dioxaborolan-2-yl)phenyl)-1H-tetrazole (0.123 g, 0.451 mmol) and $K_2CO_3$ (0.083 g, 0.602 mmol) in DMF (4 mL)-water (1 mL) was purged with nitrogen for 15 min then treated with tetrakis(triphenylphosphine)palladium (0) (8.69 mg, 7.52 μmol). The reaction was heated overnight at 90° C. then concentrated under reduced pressure. The residue was treated with water (10 mL), and this mixture was extracted with ethylacetate (2×15 mL). The combined organic layer was dried over sodium sulphate, concentrated under reduced pressure, and purified by prep HPLC to afford Example 43 (white solid, 27 mg, 0.050 mmol, 33% yield). LC-MS Anal. Calc'd for $C_{32}H_{30}N_6O_2$ 530.24, found [M+H] 531.2. $T_r$=2.35 min (Method U). $^1$H NMR (400 MHz, DMSO-d6) δ 9.33 (s, 1H) 7.90 (d, J=2.0 Hz, 1H), 7.85 (s, 1H), 7.36 (d, J=8.0 Hz, 2H), 7.08 (d, J=8.0 Hz, 2H), 6.77 (m, 1H), 5.50 (s, 2H), 3.11 (d, J=4.8 Hz, 2H), 2.60-2.67 (m, 6H), 2.42 (s, 4H), 2.24 (s, 6H), 2.11-2.15 (m, 1H), 2.10 (s, 3H), 1.61-1.64 (m, 2H), 1.48-1.50 (m, 1H), 1.38-1.41 (m, 1H), 0.84 (d, J=4.0 Hz, 6H), 0.82 (d, J=3.6 Hz, 6H).

Example 44

1-(7-(2-(1H-tetrazol-5-yl)phenyl)-4-methyl-5-phenyl-2,3,4,5-tetrahydrobenzo[b]oxepin-9-yl)-3-(p-tolyl)urea (Homochiral, Relative and Absolute Stereochemistry Unknown)

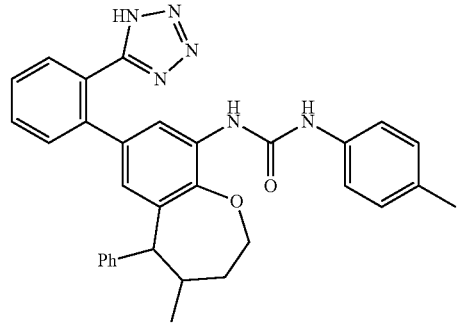 [SMILES: Cc1ccc(NC(=O)Nc2cc(-c3ccccc3-c3nnn[nH]3)cc3c2OCCC(C)C3c2ccccc2)cc1]

Example 44 was prepared from 43 G isomer 4 following the procedures for the conversion of 43G isomer 2 to Example 43. LC-MS Anal. Calc'd for $C_{32}H_{30}N_6O_2$ 530.24, found [M+H] 531.2. $T_r$=2.35 min (Method U). $^1$H NMR (400 MHz, DMSO-d6) δ 9.33 (s, 1H) 7.90 (d, J=2.0 Hz, 1H), 7.85 (s, 1H), 7.36 (d, J=8.0 Hz, 2H), 7.08 (d, J=8.0 Hz, 2H), 6.77 (d, J=10.4, Hz, 1H), 5.50 (s, 2H), 3.11 (d, J=4.8 Hz, 2H), 2.60-2.67 (m, 6H), 2.42 (s, 4H), 2.24 (s, 6H), 2.11-2.15 (m, 1H), 2.10 (s, 3H), 1.61-1.64 (m, 2H), 1.48-1.50 (m, 1H), 1.38-1.41 (m, 1H), 0.84 (d, J=4.0 Hz, 6H), 0.82 (d, J=3.6 Hz, 6H).

Example 45

1-(7-(2-(1H-tetrazol-5-yl)phenyl)-4-methyl-5-phenyl-2,3,4,5-tetrahydrobenzo[b]oxepin-9-yl)-3-(p-tolyl)urea (Homochiral, Relative and Absolute Stereochemistry Unknown)

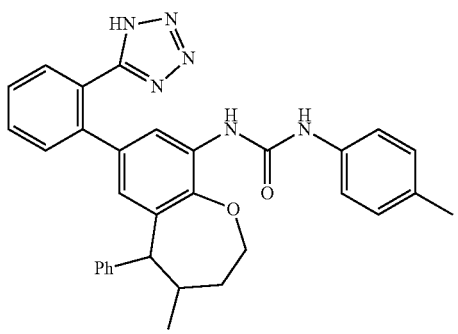 [SMILES: Cc1ccc(NC(=O)Nc2cc(-c3ccccc3-c3nnn[nH]3)cc3c2OCCC(C)C3c2ccccc2)cc1]

Example 45 was prepared from 43 G isomer 1 following the procedures for the conversion of 43G isomer 2 to Example 43. LC-MS Anal. Calc'd for $C_{32}H_{30}N_6O_2$ 530.24, found [M+H] 531.2. $T_r$=2.40 min (Method U). $^1$H NMR (400 MHz, DMSO-$d_6$) δ 9.25 (s, 1H), 8.46 (s, 1H), 8.18 (d, J=2.00 Hz, 1H), 7.58-7.65 (m, 2H), 7.48-7.53 (m, 2H), 7.34 (d, J=8.40 Hz, 2H), 7.25 (t, J=14.80 Hz, 2H), 7.14-7.17 (m, 1H), 7.04-7.08 (m, 4H), 6.10 (d, J=2.40 Hz, 1H), 4.16 (d, J=12.00, Hz, 1H), 3.96 (t, J=21.20 Hz, 1H), 3.77 (d, J=6.00 Hz, 1H), 2.39-2.42 (m, 1H), 2.25 (s, 3H), 1.90-1.93 (m, 1H), 1.51 (d, J=13.20 Hz, 1H), 0.86 (d, J=7.20 Hz, 3H).

Example 46

1-(7-(2-(1H-tetrazol-5-yl)phenyl)-4-methyl-5-phenyl-2,3,4,5-tetrahydrobenzo[b]oxepin-9-yl)-3-(p-tolyl)urea (Homochiral, Relative and Absolute Stereochemistry Unknown)

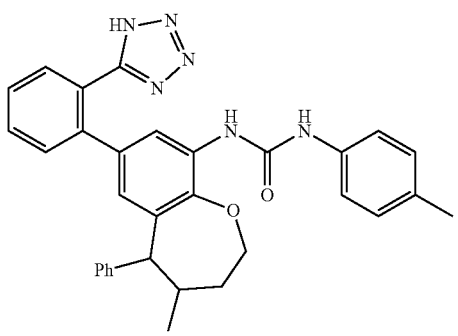 [SMILES: Cc1ccc(NC(=O)Nc2cc(-c3ccccc3-c3nnn[nH]3)cc3c2OCCC(C)C3c2ccccc2)cc1]

Example 46 was prepared from 43 G isomer 3 following the procedures for the conversion of 43G isomer 2 to Example 43. LC-MS Anal. Calc'd for $C_{32}H_{30}N_6O_2$ 530.24, found [M+H] 531.2. $T_r$=2.40 min (Method U). $^1$H NMR (400 MHz, DMSO-d6) δ 9.25 (s, 1H), 8.46 (s, 1H), 8.18 (d, J=2.00 Hz, 1H), 7.58-7.65 (m, 2H), 7.48-7.53 (m, 2H), 7.34 (d, J=8.40 Hz, 2H), 7.25 (t, J=14.80 Hz, 2H), 7.14-7.17 (m, 1H), 7.04-7.08 (m, 4H), 6.10 (d, J=2.40 Hz, 1H), 4.16 (d, J=12.00, Hz, 1H), 3.96 (t, J=21.20 Hz, 1H), 3.77 (d, J=6.00 Hz, 1H), 2.39-2.42 (m, 1H), 2.25 (s, 3H), 1.90-1.93 (m, 1H), 1.51 (d, J=13.20 Hz, 1H), 0.86 (d, J=7.20 Hz, 3H).

Example 47

N-(7-(2-(1H-tetrazol-5-yl)phenyl)-4-methyl-5-phenyl-2,3,4,5-tetrahydrobenzo[b]oxepin-9-yl)-2-(p-tolyl)acetamide (Homochiral, Relative and Absolute Stereochemistry Unknown)

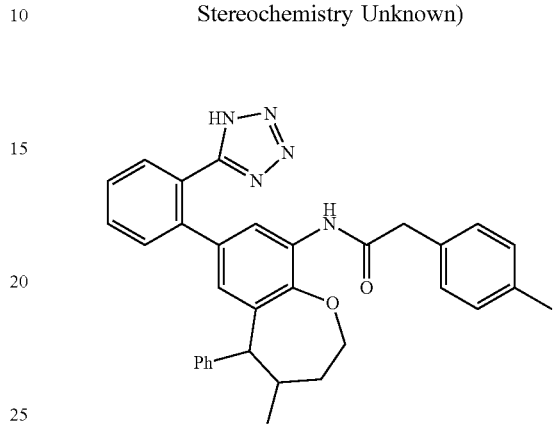

47A. N-(7-bromo-4-methyl-5-phenyl-2,3,4,5-tetrahydrobenzo[b]oxepin-9-yl)-2-(p-tolyl) acetamide A stirred solution of 43G isomer 2 (0.060 g, 0.181 mmol) and 2-(p-tolyl)acetic acid (0.035 g, 0.235 mmol) in dry DMF (1.5 mL) was treated with DIPEA (0.095 mL, 0.542 mmol) followed by 2,4,6-tripropyl-1,3,5,2,4,6-trioxatriphosphorinane-2,4,6-trioxide (0.172 g, 0.271 mmol). The reaction was stirred for 30 min., diluted with ethyl acetate (10 mL), and washed with water (5 mL). The organic layer was dried over sodium sulfate and concentrated under reduced pressure to afford 47A (off-white solid, 75 mg, 0.162 mmol, 89% yield). LC-MS Anal. Calc'd for $C_{33}H_{31}N_5O_2$ 529.24, found [M+H] 530.2. $T_r$ 10=1.44 min (Method T).

Example 47 (Homochiral, Relative and Absolute Stereochemistry Unknown)

A solution of 47A (0.06 g, 0.129 mmol) in DMF (3 mL) was treated with 5-(2-(4,4,5,5-tetramethyl-1,3,2-dioxaborolan-2-yl)phenyl)-1H-tetrazole (0.105 g, 0.388 mmol) followed by $K_2CO_3$ (0.071 g, 0.517 mmol) in water (1 mL). This mixture was purged with nitrogen for 15 min, treated with tetrakis(triphenylphosphine)palladium(0) (7.46 mg, 6.46 μmol) and heated overnight at 90° C. The reaction was concentrated under reduced pressure, and the residue was partitioned between water (10 mL) and ethyl acetate. The organic layer was dried over sodium sulphate and concentrated under reduced pressure to afford the crude product. Purification by prep. HPLC afforded Example 47 (white solid, 18 mg, 0.034 mmol, 26% yield). LC-MS Anal. Calc'd for $C_{33}H_{31}N_5O_2$ 529.24, found [M+H] 530.2. $T_r$=3.35 min (Method U). $^1$H NMR (400 MHz, DMSO-d6) δ 9.23 (s, 1H), 7.85 (s, 1H), 7.55-7.59 (m, 2H), 7.45-7.49 (m, 1H), 7.39 (d, J=7.6 Hz, 1H), 7.23-7.29 (m, 6H), 7.15-7.19 (m, 3H), 4.27 (d, J=12.4 Hz, 1H), 4.01 (d, J 25=2.4 Hz, 1H), 3.71-3.80 (m, 3H), 2.29 (s, 3H), 2.16-2.19 (m, 1H), 1.81-1.91 (m, 1H), 1.71-1.79 (m, 1H), 0.85 (d, J=7.2 Hz, 3H).

Example 48

N-(7-(2-(1H-tetrazol-5-yl)phenyl)-4-methyl-5-phenyl-2,3,4,5-tetrahydrobenzo[b]oxepin-9-yl)-2-(p-tolyl)acetamide (Homochiral, Relative and Absolute Stereochemistry Unknown)

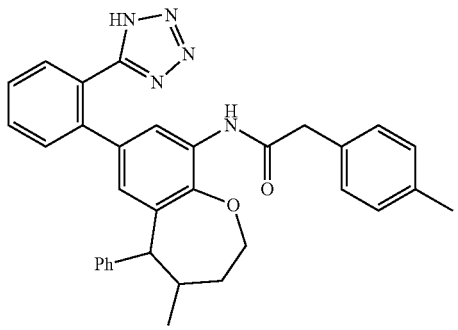 [SMILES: Cc1ccc(CC(=O)Nc2cc(-c3ccccc3-c3nnn[nH]3)cc3c2OCCC(C)C3c2ccccc2)cc1]

Example 48 was prepared from 43G isomer 4 following the procedure for the conversion of 43G isomer 2 into Example 47. LC-MS Anal. Calc'd for $C_{33}H_{31}N_5O_2$ 529.24, found [M+H] 530.2. $T_r$=3.35 min (Method U). $^1$H NMR (400 MHz, DMSO-d6) δ 9.23 (s, 1H), 7.85 (s, 1H), 7.55-7.59 (m, 2H), 7.45-7.49 (m, 1H), 7.39 (d, 7.6 Hz, 1H), 7.23-7.29 (m, 6H), 7.15-7.19 (m, 3H), 4.27 (d, J=12.4 Hz, 1H), 4.01 (d, J=2.4 Hz, 1H), 3.71-3.80 (m, 3H), 2.29 (s, 3H), 2.16-2.19 (m, 1H), 1.81-1.91 (m, 1H), 1.71-1.79 (m, 1H), 0.85 (d, J=7.2 Hz, 3H).

Example 49

N-(7-(2-(1H-tetrazol-5-yl)phenyl)-4-methyl-5-phenyl-2,3,4,5-tetrahydrobenzo[b]oxepin-9-yl)-2-(p-tolyl)acetamide (Homochiral, Relative and Absolute Stereochemistry Unknown)

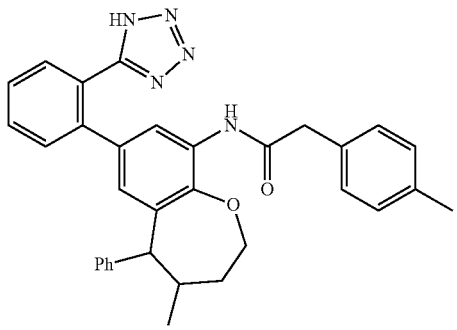 [SMILES: Cc1ccc(CC(=O)Nc2cc(-c3ccccc3-c3nnn[nH]3)cc3c2OCCC(C)C3c2ccccc2)cc1]

Example 49 was prepared from 43G isomer 1 following the procedure for the conversion of 43G isomer 2 into Example 47. LC-MS Anal. Calc'd for $C_{33}H_{31}N_5O_2$ 529.24, found [M+H] 530.2. $T_r$=3.305 min (Method U). $^1$H NMR (400 MHz, DMSO-d6) δ 9.23 (s, 1H), 8.06 (s, 1H), 7.57-7.61 (m, 2H), 7.47-7.51 (m, 1H), 7.44 (d, J=8.0 Hz, 1H), 7.22-7.26 (m, 4H), 7.13-7.16 (m, 3H), 7.04 (d, J=7.6 Hz, 2H), 4.04-4.07 (m, 1H), 3.71-3.87 (m, 4H), 2.40-2.43 (m, 1H), 2.28 (s, 3H), 1.87-1.93 (m, 1H), 1.47 (d, J=12.8 Hz, 1H), 0.83 (d, J=6.8 Hz, 3H).

Example 50

N-(7-(2-(1H-tetrazol-5-yl)phenyl)-4-methyl-5-phenyl-2,3,4,5-tetrahydrobenzo[b]oxepin-9-yl)-2-(p-tolyl)acetamide (Homochiral, Relative and Absolute Stereochemistry Unknown)

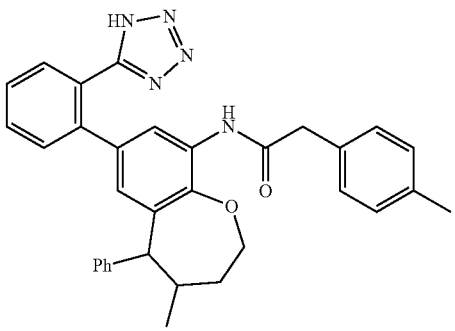 [SMILES: Cc1ccc(CC(=O)Nc2cc(-c3ccccc3-c3nnn[nH]3)cc3c2OCCC(C)C3c2ccccc2)cc1]

Example 50 was prepared from 43 G isomer 3 following the procedure for the conversion of 43G isomer 2 into Example 47. LC-MS Anal. Calc'd for $C_{33}H_{31}N_5O_2$ 529.24, found [M+H] 530.2. $T_r$=3.305 min (Method U). $^1$H NMR (400 MHz, DMSO-d6) δ 9.23 (s, 1H), 8.06 (s, 1H), 7.57-7.61 (m, 2H), 7.47-7.51 (m, 1H), 7.44 (d, J=8.0 Hz, 1H), 7.22-7.26 (m, 4H), 7.13-7.16 (m, 3H), 7.04 (d, J=7.6 Hz, 2H), 4.04-4.07 (m, 1H), 3.71-3.87 (m, 4H), 2.40-2.43 (m, 1H), 2.28 (s, 3H), 1.87-1.93 (m, 1H), 1.47 (d, J=12.8 Hz, 1H), 0.83 (d, J=6.8 Hz, 3H).

Example 51

N-(7-(2-(1H-tetrazol-5-yl)phenyl)-4-methyl-5-phenyl-2,3,4,5-tetrahydrobenzo[b]oxepin-9-yl)benzo[d]oxazol-2-amine (Homochiral, Relative and Absolute Stereochemistry Unknown)

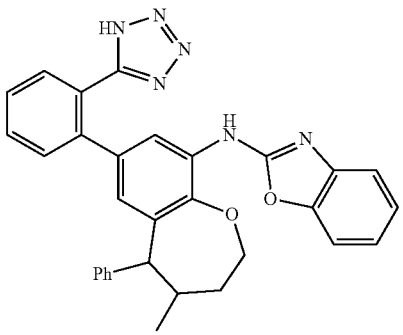 [SMILES: CC1CCOc2c(Nc3nc4ccccc4o3)cc(-c3ccccc3-c3nnn[nH]3)cc2C1c1ccccc1]

51A. N-(7-bromo-4-methyl-5-phenyl-2,3,4,5-tetrahydrobenzo[b]oxepin-9-yl)benzo[d]oxazol-2-amine A solution of 43G isomer 4 (100 mg, 0.301 mmol) in xylene (10 mL) was treated with 2-chlorobenzo[d]oxazole (50.8 mg, 0.331 mmol) and heated overnight at 150° C. The reaction was concentrated under reduced pressure and purified by flash chromatography to afford 51A (brown solid, 0.1 g, 0.191 mmol, 64% yield). LC-MS Anal. Calc'd for $C_{24}H_{21}BrN_2O_2$ 448.07, found [M+H] 449.2. $T_r$=4.2 min (Method U).

Example 51 (Homochiral, Relative and Absolute Stereochemistry Unknown)

A solution of 51A (25 mg, 0.056 mmol) in 1,4-dioxane (2 mL) was treated with 5-(2-(4,4,5,5-tetramethyl-1,3,2-dioxaborolan-2-yl)phenyl)-1H-tetrazole (45.4 mg, 0.167 mmol) and $K_2CO_3$ (23.07 mg, 0.167 mmol) in water (0.5 mL). This mixture was purged with nitrogen for 15 min, treated with tetrakis(triphenylphosphine)palladium(0) (6.43 mg, 5.56 µmol), and was heated overnight at 110° C. The reaction was concentrated under reduced pressure, and the residue was partitioned between water (10 mL) and ethyl acetate. The organic layer was dried over sodium sulphate and concentrated under reduced pressure to afford the crude product. Purification by prep. HPLC afforded Example 51 (white solid, 6 mg, 9.35 µmol, 17% yield). LC-MS Anal. Calc'd for $C_{31}H_{26}N_6O_2$ 514.21, found [M+H] 515.2. $T_r$=1.544 min (Method U). $^1$H NMR (400 MHz, DMSO-d6) δ 400 MHz, DMSO-d6: δ 9.86 (s, 1H), 8.08 (s, 1H), 7.46-7.66 (m, 6H), 7.34-7.36 (m, 2H), 7.12-7.28 (m, 5H), 6.53 (s, 1H), 4.40-4.41 (m, 1H), 4.11 (d, J=2.4 Hz, 1H), 3.86 (t, J=21.2 Hz, 1H), 2.23-2.24 (m, 1H), 1.82-1.84 (m, 1H), 1.71-1.73 (m, 1H), 0.89 (d, J=7.2 Hz, 3H).

Example 52

N-(7-(2-(1H-tetrazol-5-yl)phenyl)-4-methyl-5-phenyl-2,3,4,5-tetrahydrobenzo[b]oxepin-9-yl)-1H-benzo[d]imidazol-2-amine (Homochiral, Relative and Absolute Stereochemistry Unknown)

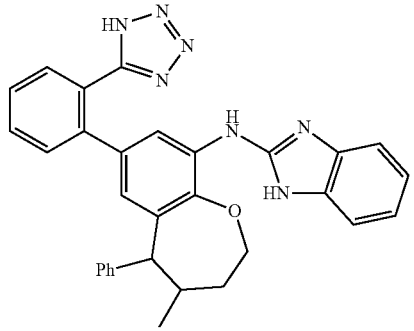 [SMILES: CC1CCOc2c(Nc3nc4ccccc4[nH]3)cc(-c3ccccc3-c3nnn[nH]3)cc2C1c1ccccc1]

52A. N-(7-bromo-4-methyl-5-phenyl-2,3,4,5-tetrahydrobenzo[b]oxepin-9-yl)-1H-benzo[d] imidazol-2-amine To a solution of 43G isomer 4 (50 mg, 0.150 mmol) in 1,4-dioxane (2 mL) was added 2-chloro-1H-benzo[d]imidazole (27.6 mg, 0.181 mmol) followed by 4M HCl in dioxane (0.038 mL, 0.150 mmol). The reaction was heated overnight at 95° C., cooled to RT and quenched with sodium bicarbonate (10%) solution (10 mL). The resulting mixture was extracted with ethyl acetate (2×10 mL), and the combined organic layer was dried over sodium sulphate and concentrated under reduced pressure. The residue was purified by flash chromatography to afford 52A (brown solid, 60 mg, 0.106 mmol, 70.2% yield). LC-MS Anal. Calc'd for $C_{24}H_{22}BrN_3O$ 447.09, found [M+H] 448.2. $T_r$=3.815 min (Method U).

Example 52 (Homochiral, Relative and Absolute Stereochemistry Unknown)

A solution of 52A (30 mg, 0.067 mmol) in 1,4-dioxane (2 mL) was treated with 5-(2-(4,4,5,5-tetramethyl-1,3,2-dioxaborolan-2-yl)phenyl)-1H-tetrazole (54.6 mg, 0.201 mmol) and $K_2CO_3$ (27.7 mg, 0.201 mmol) in water (0.5 mL). This mixture was purged with nitrogen for 15 min, treated with tetrakis(triphenylphosphine)palladium(0) (7.73 mg, 6.69 µmol), and heated overnight at 110° C. The reaction was concentrated under reduced pressure, and the residue was partitioned between water (10 mL) and ethyl acetate. The organic layer was dried over sodium sulphate and concentrated under reduced pressure to afford the crude product. Purification by prep. HPLC afforded Example 52 (white solid, 5 mg, 7.6 µmol, 11% yield). LC-MS Anal. Calc'd for $C_{31}H_{27}N_7O$ 513.22, found [M+H] 514.2. $T_r$=2.334 min (Method U). $^1$H NMR (400 MHz, DMSO-d6) δ 10.50 (s, 1H), 7.63-7.68 (m, 2H), 7.53-7.59 (m, 2H), 7.40-7.43 (m, 2H), 7.19-7.23 (m, 7H), 6.98 (s, 1H), 6.67 (s, 1H), 4.29 (d, J=12.8 Hz, 1H), 4.15 (d, J=2.0 Hz, 1H), 3.93 (t, J=9.8 Hz, 1H), 2.23-2.27 (m, 1H), 1.70-1.84 (m, 2H), 0.88 (d, J=6.8 Hz, 3H).

Racemate Example 53, Example 53 Enantiomer 1 and Example 53 Enantiomer 2

N-(7-(2-(1H-tetrazol-5-yl)phenyl)-5-phenyl-2,3,4,5-tetrahydrobenzo[b]oxepin-9-yl) benzo[d] oxazol-2-amine

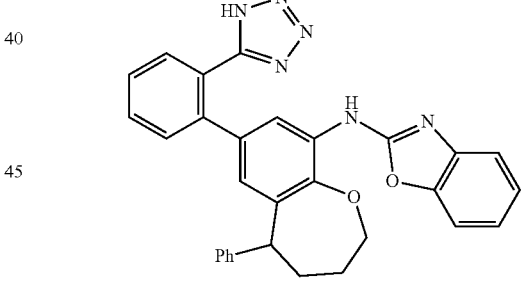

53A. 7-bromo-5-phenyl-2,3,4,5-tetrahydrobenzo[b] oxepin-9-amine

A solution of 5B (0.7 g, 1.673 mmol) in 1,4-dioxane (5 mL) was treated with 4M HCl in dioxane (5 ml, 20.00 mmol) and stirred overnight at RT. The reaction was concentrated under reduced pressure, treated with 100 mL of 10% aq. sodium bicarbonate, and extracted twice with ethyl acetate. The combined organic layer was dried over sodium sulfate and concentrated under reduced pressure to afford 53A (brown solid, 0.45 g, 1.358 mmol, 81% yield). LC-MS Anal. Calc'd for $C_{16}H_{16}BrNO$ 317.04, found [M+H] 318.2. $T_r$=3.17 min (Method U). Chiral separation of racemic 53A (Method AK) gave 53A Enantiomer 1 $T_r$=2.66 min (Method AK) and 53A Enantiomer 2 $T_r$=3.43 min (Method AK). Enantiomer 1: LC-MS Anal. Calc'd for $C_{16}H_{16}BrNO$

53B. N-(7-bromo-5-phenyl-2,3,4,5-tetrahydrobenzo[b]oxepin-9-yl)benzo[d]oxazol-2-amine 53B was prepared from 53A following the procedure for the conversion of 43G isomer 4 to 51A. LC-MS Anal. Calc'd for $C_{23}H_{19}BrN_2O_2$ 434.06, found [M+H] 435.2. $T_r$=4.26 min (Method U).

Example 53

Racemate Example 53 was prepared from 53B following the procedure for the conversion of 51A to Example 51. LC-MS Anal. Calc'd for $C_{31}H_{27}N_7O$ 500.19, found [M+H] 501.2. $T_r$=2.056 min (Method U). $^1$H NMR (400 MHz, DMSO-d6) δ 400 MHz, DMSO-d6: δ 9.83 (s, 1H), 8.17 (d, J=2.00 Hz, 1H), 7.61 (d, J=8.00 Hz, 2H), 7.46-7.54 (m, 4H), 7.12-7.31 (m, 5H), 7.05 (d, J=7.20 Hz, 2H), 6.12 (s, 1H), 4.22 (d, J=7.20 Hz, 1H), 4.12-4.15 (m, 1H), 3.93-3.96 (m, 1H), 2.33-2.35 (m, 1H), 1.92-1.97 (m, 3H).

Chiral separation of Racemate Example 53 (Method AH) gave enantiomer 1 $T_r$=2.00 min (Method AH) and enantiomer 2 $T_r$=4.06 min (Method AH).

Example 53 Enantiomer 1: LC-MS Anal. Calc'd for $C_{31}H_{27}N_7O$ 500.19, found [M+H] 501.2. $T_r$=2.264 min (Method U). $^1$H NMR (400 MHz, DMSO-d6) δ 400 MHz, DMSO-d6: δ 9.83 (s, 1H), 8.17 (d, 2.0 Hz, 1H), 7.61 (d, J=8.0 Hz, 2H), 7.46-7.54 (m, 4H), 7.12-7.31 (m, 5H), 7.05 (d, J=7.2 Hz, 2H), 6.12 (s, 1H), 4.22 (d, J=7.2 Hz, 1H), 4.12-4.15 (m, 1H), 3.93-3.96 (m, 1H), 2.33-2.35 (m, 1H), 1.92-1.97 (m, 3H).

Example 53 Enantiomer 2: LC-MS Anal. Calc'd for $C_{31}H_{27}N_7O$ 500.19, found [M+H] 501.2. $T_r$=2.24 min (Method U). $^1$H NMR (400 MHz, DMSO-d6) δ 400 MHz, DMSO-d6: δ 9.83 (s, 1H), 8.17 (d, J=2.0 Hz, 1H), 7.61 (d, J=8.0 Hz, 2H), 7.46-7.54 (m, 4H), 7.12-7.31 (m, 5H), 7.05 (d, J=7.2 Hz, 2H), 6.12 (s, 1H), 4.22 (d, J=7.2 Hz, 1H), 4.12-4.15 (m, 1H), 3.93-3.96 (m, 1H), 2.33-2.35 (m, 1H), 1.92-1.97 (m, 3H).

Example 54

N-(7-(2-(1H-tetrazol-5-yl)phenyl)-5-phenyl-2,3,4,5-tetrahydrobenzo[b]oxepin-9-yl)-5-(trifluoromethyl)pyrimidin-2-amine

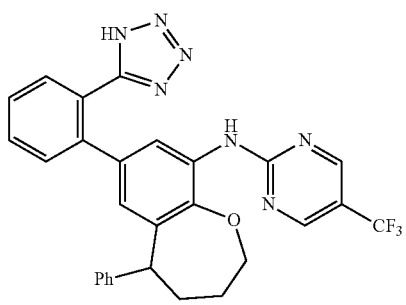 [SMILES: FC(F)(F)c1cnc(Nc2cc(-c3ccccc3-c3nnn[nH]3)cc3c2OCCCC3c2ccccc2)nc1]

54A. N-(7-bromo-5-phenyl-2,3,4,5-tetrahydrobenzo[b]oxepin-9-yl)-5-(trifluoromethyl)pyrimidin-2-amine Compound 54A was prepared from 53A and 2-chloro-5-trifluoromethylpyridine following the procedure for the conversion of 43G isomer 4 to 52A. LC-MS Anal. Calc'd for $C_{21}H_{17}BrF_3N_3O$ 463.05 found [M+H] 464.2, $T_r$=4.345 min (Method U).

Example 54

Example 54 was prepared from 54A following the procedure for the conversion of 51A to Example 51. LC-MS Anal. Calc'd for $C_{28}H_{22}F_3N_7O$ 529.18 found [M+H] 530.2. $T_r$=2.282 min (Method U). $^1$H NMR (400 MHz, DMSO-d6) δ 9.17 (s, 1H), 8.78 (s, 2H), 7.68 (d, J=2.0 Hz, 1H), 7.54-7.57 (m, 2H), 7.45-7.48 (m, 1H), 7.39-7.44 (m, 1H), 7.29 (t, J=7.6 Hz, 2H), 7.20 (t, J=7.2 Hz, 1H), 7.08 (d, J=7.2 Hz, 2H), 6.28 (d, J=2.0 Hz, 1H), 4.23 (d, J=6.8 Hz, 1H), 4.08-4.10 (m, 1H), 3.91-3.95 (m, 1H), 2.12-2.15 (m, 1H), 1.98-2.01 (m, 1H), 1.86-1.95 (m, 2H).

Racemate Example 55, Example 55 Enantiomer 1 and Example 55 Enantiomer 2

N-(7-(2-(1H-tetrazol-5-yl)phenyl)-5-phenyl-2,3,4,5-tetrahydrobenzo[b]oxepin-9-yl)-5-methylpyrimidin-2-amine

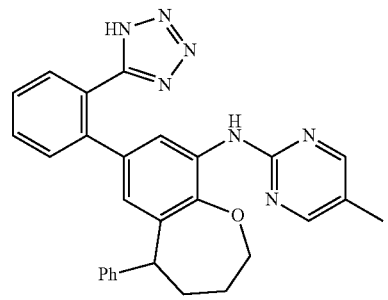 [SMILES: Cc1cnc(Nc2cc(-c3ccccc3-c3nnn[nH]3)cc3c2OCCCC3c2ccccc2)nc1]

Racemate Example 55 was prepared from 53A and 2-chloro-5-methylpyrimidine following the procedures for the conversion of 53A to Example 54. LC-MS Anal. Calc'd for $C_{28}H_{25}N_7O$ 475.21 found [M+H] 476.2. $T_r$=3.07 min (Method AD), hi NMR (400 MHz, DMSO-d6) δ 8.33 (s, 2H), 8.12 (d, J=2.0 Hz, 1H), 8.08 (s, 1H), 7.56-7.62 (m, 2H), 7.43-7.50 (m, 2H), 7.28 (t, J=7.4 Hz, 2H), 7.20 (t, J=7.4 Hz, 1H), 7.06 (d, J=7.6 Hz, 1H), 6.08 (d, J=2.0 Hz, 1H), 4.21 (d, J=7.2 Hz, 1H), 4.11-4.15 (m, 1H), 3.96-3.98 (m, 1H), 2.16 (s, 3H), 2.12-2.16 (m, 1H), 1.91-2.00 (m, 3H).

Example 55 Enantiomer 1 was prepared from 53A Enantiomer 1 following the procedure for the conversion of 53A to Example 55. LC-MS Anal. Calc'd for $C_{28}H_{25}N_7O$ 475.21 found [M+H] 476.2. $T_r$=1.95 min (Method U). $^1$H NMR (400 MHz, DMSO-d6) δ 8.33 (s, 2H), 8.12 (d, J=2.00 Hz, 1H), 8.08 (s, 1H), 7.56-7.62 (m, 2H 7.43-7.50 (m, 2H), 7.28 (t, J=7.4 Hz, 2H), 7.20 (t, J=7.4 Hz, 1H), 7.06 (d, J=7.6 Hz, 1H), 6.08 (d, J=2.0 Hz, 1H), 4.21 (d, J=7.2 Hz, 1H), 4.11-4.15 (m, 1H), 3.96-3.98 (m, 1H), 2.16 (s, 3H), 2.12-2.16 (m, 1H), 1.91-2.00 (m, 3H).

Example 55 Enantiomer 2 was prepared from 53A Enantiomer 2 following the procedure for the conversion of 53A to Example 55. LC-MS Anal. Calc'd for $C_{28}H_{25}N_7O$ 475.21 found [M+H] 476.2. $T_r$=2.837 min (Method U). $^1$H NMR (400 MHz, DMSO-d6) δ 8.33 (s, 2H), 8.12 (d, J=2.0 Hz, 1H), 8.08 (s, 1H), 7.56-7.62 (m, 2H), 7.43-7.50 (m, 2H), 7.28 (t, J=7.4 Hz, 2H), 7.20 (t, J=7.4 Hz, 1H), 7.06 (d, J=7.6 Hz, 1H), 6.08 (d, J=2.0 Hz, 1H), 4.21 (d, J=7.2 Hz, 1H), 4.11-4.15 (m, 1H), 3.96-3.98 (m, 1H), 2.16 (s, 3H), 2.12-2.16 (m, 1H), 1.91-2.00 (m, 3H).

Example 56

N-(7-(2-(1H-tetrazol-5-yl)phenyl)-5-phenyl-2,3,4,5-tetrahydrobenzo[b]oxepin-9-yl)-4-phenylthiazol-2-amine (Homochiral, Absolute Stereochemistry Unknown)

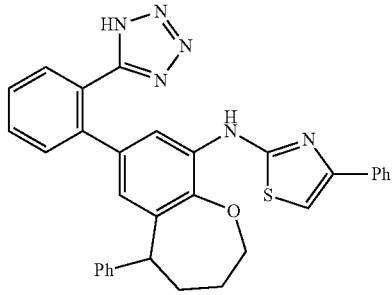 [SMILES: c1ccc(-c2csc(Nc3cc(-c4ccccc4-c4nnn[nH]4)cc4c3OCCCC4c3ccccc3)n2)cc1]

Example 56 was prepared from 53A Enantiomer 2 and 2-bromo-4-phenylthiazole at 120° C., otherwise following the procedures for the conversion of 43 G isomer 4 to Example 52. LC-MS Anal. Calc'd for $C_{32}H_{26}N_6OS$ 542.19 found [M+H] 543.2. $T_r$=2.954 min (Method U). $^1$H NMR (400 MHz, DMSO-d6) δ 8.41 (s, 1H), 7.85 (d, J=8.4 Hz, 2H), 7.58-7.63 (m, 3H), 7.47 (m, 1H), 7.36 (t, J=7.6 Hz, 2H), 7.27 (t, J=8.2 Hz, 3H), 7.18 (t, J=7.4 Hz, 1H), 7.10 (s, 1H), 6.99 (d, J=7.2 Hz, 2H), 5.85 (d, J=2.0 Hz, 1H), 4.30-4.33 (m, 1H), 4.17-4.18 (m, 1H), 3.91-3.93 (m, 1H), 1.99-2.10 (m, 4H).

Example 57 Enantiomer 1 and Example 57 Enantiomer 2

N-(7-(2-(1H-tetrazol-5-yl)phenyl)-5-phenyl-2,3,4,5-tetrahydrobenzo[b]oxepin-9-yl)-6-fluorobenzo[d]thiazol-2-amine

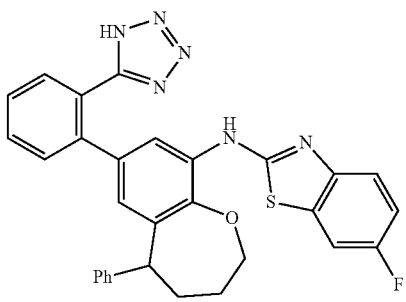 [SMILES: Fc1ccc2nc(Nc3cc(-c4ccccc4-c4nnn[nH]4)cc4c3OCCCC4c3ccccc3)sc2c1]

Example 57 Enantiomer 1 was prepared from 53A enantiomer 1 and 2-chloro-6-fluorobenzo[d]thiazole at 140° C., otherwise following the procedures for the conversion of 43G isomer 4 to Example 52. LC-MS Anal. Calc'd for $C_{30}H_{23}FN_6OS$ 534.16 found [M+H] 535.0. $T_r$=2.866 min (Method U). $^1$H NMR (400 MHz, DMSO-d6) δ 9.96 (s, 1H), 8.36 (d, J=2.0 Hz, 1H), 7.72 (d, J=11.2, Hz, 1H), 7.59-7.63 (m, 3H), 7.45-7.53 (m, 2H), 7.29 (t, J=7.6 Hz, 2H), 7.21 (d, J=7.2 Hz, 1H), 7.15 (m, 1H), 7.08 (d, J=7.2 Hz, 2H), 6.17 (d, J=2.0 Hz, 1H), 4.25 (d, J=6.8 Hz, 1H), 4.11-4.14 (m, 1H), 3.93-3.97 (m, 1H), 2.12-2.16 (m, 1H), 1.91-2.02 (m, 3H).

Example 57 Enantiomer 2 was prepared from 53A enantiomer 2 and 2-chloro-6-fluorobenzo[d]thiazole at 140° C., otherwise following the procedures for the conversion of 43G isomer 4 to Example 52. LC-MS Anal. Calc'd for $C_{30}H_{23}FN_6OS$ 534.16 found [M+H] 535.0. $T_r$=2.857 min (Method U). $^1$H NMR (400 MHz, DMSO-d6) δ 9.96 (s, 1H), 8.36 (d, J=2.0 Hz, 1H), 7.72 (d, J=11.2, Hz, 1H), 7.59-7.63 (m, 3H), 7.45-7.53 (m, 2H), 7.29 (t, J=7.6 Hz, 2H), 7.21 (d, J=7.2 Hz, 1H), 7.15 (m, 1H), 7.08 (d, J=12 Hz, 2H), 6.17 (d, J=2.0 Hz, 1H), 4.25 (d, J=6.80 Hz, 1H), 4.11-4.14 (m, 1H), 3.93-3.97 (m, 1H), 2.12-2.16 (m, 1H), 1.91-2.02 (m, 3H).

Example 58

N-((2-(5-phenyl-9-(3'-(p-tolyl)ureido)-2,3,4,5-tetrahydrobenzo[b]oxepin-7-yl) phenyl)sulfonyl)acetamide (Homochiral, Stereochemistry Unknown)

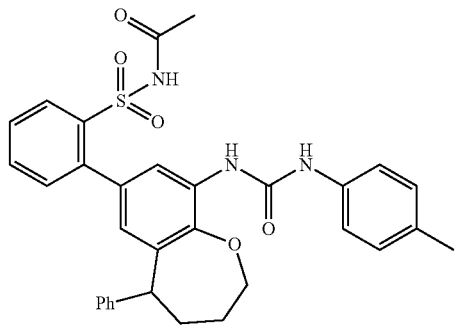 [SMILES: CC(=O)NS(=O)(=O)c1ccccc1-c1cc(NC(=O)Nc2ccc(C)cc2)c2c(c1)C(c1ccccc1)CCCO2]

58A Enantiomer 1. 1-(7-bromo-5-phenyl-2,3,4,5-tetrahydrobenzo[b]oxepin-9-yl)-3-(p-tolyl)urea A solution of 53A Enantiomer 1 (50 mg, 0.157 mmol) in DCM (2 mL) was treated with 1-isocyanato-4-methylbenzene (41.8 mg, 0.314 mmol), and the reaction was stirred overnight at RT. The reaction was quenched with water (10 mL) and extracted with DCM (2×15 mL). The combined organic layer was dried over sodium sulphate and concentrated under reduced pressure to afford 58A Enantiomer 1 (yellow solid, 70 mg, 0.144 mmol, 92% yield). LC-MS Anal. Calc'd for $C_{24}H_{23}BrN_2O_2$ 450.09, found [M+H] 451.2. $T_r$=4.07 min (Method U).

58B. N-(tert-butyl)-2-(5-phenyl-9-(3-(p-tolyl)ureido)-2,3,4,5-tetrahydro benzo[b]oxepin-7-yl)benzenesulfonamide A solution of 58A Enantiomer 1 (100 mg, 0.222 mmol) in DMF (2 mL) was treated with 2-(tert-butyl amino)sulfonylphenylboronic acid (171 mg, 0.665 mmol) and $K_2CO_3$ (122 mg, 0.886 mmol) in water (0.5 mL). This mixture was purged with nitrogen for 15 min, treated with tetrakis (triphenylphosphine)palladium(0) (25.6 mg, 0.022 mmol), and heated overnight at 90° C. The reaction was concentrated under reduced pressure, suspended in water (10 mL), and extracted with ethyl acetate (2×15 mL). The combined organic layer was dried over sodium sulphate, concentrated under reduced pressure, and purified by flash chromatography to afford 58B (brown solid, 55 mg, 0.086 mmol, 38.7% yield). LC-MS Anal. Calc'd for $C_{34}H_{37}N_3O_4S$ 583.25, found [M+H] 584.2. $T_r$=1.11 min (Method AA).

58C. 2-(5-phenyl-9-(3-(p-tolyl)ureido)-2,3,4,5-tetrahydrobenzo[b]oxepin-7-yl) benzene sulfonamide A solution of 58B (50 mg, 0.086 mmol) in DCM (2 mL) was treated with TFA (2 mL, 26.0 mmol), and the reaction was stirred overnight at RT. The reaction was concentrated under reduced pressure and evaporated from DCM to afford 58C (brown solid, 45 mg, 0.081 mmol, 95% yield). LC-MS Anal. Calc'd for $C_{30}H_{29}N_3O_4S$ 527.18, found [M+H] 528.2. $T_r$=3.66 min (Method U).

Example 58 (Homochiral, Stereochemistry Unknown)

A solution of 58C (20 mg, 0.038 mmol) in DCM (2 mL) was treated with TEA (0.037 mL, 0.265 mmol) followed by acetyl chloride (0.013 mL, 0.190 mmol). The reaction was stirred overnight at 50° C. The reaction was diluted with DCM (10 mL) and washed with 10% aq. sodium bicarbonate solution (10 mL). The organic layer was dried over sodium sulphate, concentrated under reduced pressure, and purified by prep HPLC afford Example 58 (white solid, 7 mg, 10.14 µmol, 27% yield). LC-MS Anal. Calc'd for $C_{32}H_{31}N_3O_5S$ 569.19, found [M+H] 570.2. $T_r$=3.728 min (Method U). $^1$H NMR (400 MHz, DMSO-d6) δ 11.34 (s, 1H), 9.26 (s, 1H), 8.50 (s, 1H), 8.11 (d, J=2.0 Hz, 1H), 8.02 (dd, J=8.0 Hz, 1H), 7.63 (td, J=7.6, 1.5 Hz, 1H), 7.56 (td, J=7.6, 1.3 Hz, 1H), 7.27-7.33 (m, 4H), 7.16-7.24 (m, 4H), 7.07 (d, J=8.0 Hz, 2H), 6.30 (d, J=1.6 Hz, 1H), 4.33 (d, J=5.6 Hz, 1H), 4.09-4.10 (m, 2H), 2.21-2.25 (m, 4H), 2.04-2.08 (m, 1H), 1.93-1.95 (m, 2H), 1.69 (s, 3H).

Example 59

N-((2-(5-phenyl-9-(3-(p-tolyl)ureido)-2,3,4,5-tetrahydrobenzo[b]oxepin-7-yl) phenyl)sulfonyl)acetamide (Homochiral, Stereochemistry Unknown)

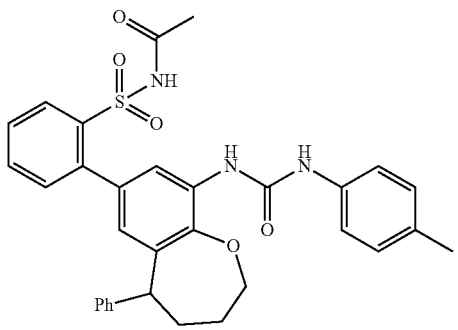 [SMILES: CC(=O)NS(=O)(=O)c1ccccc1-c1cc(NC(=O)Nc2ccc(C)cc2)c2c(c1)C(c1ccccc1)CCCO2]

Example 59 was prepared from 53A Enantiomer 2 following the procedures for the conversion of 53A Enantiomer 1 to Example 58. LC-MS Anal. Calc'd for $C_{32}H_{31}N_3O_5S$ 569.19, found [M+H] 570.2. $T_r$=3.653 min (Method U). $^1$H NMR (400 MHz, DMSO-d6) δ 11.34 (s, 1H), 9.26 (s, 1H), 8.50 (s, 1H), 8.11 (d, J=2.0 Hz, 1H), 8.02 (dd, J=8.00, Hz, 1H), 7.63 (dt, J=7.4, 1.3 Hz, 1H), 7.4 (dt, J=7.4, 1.5 Hz, 1H), 7.27-7.33 (m, 4H), 7.16-7.24 (m, 4H), 7.07 (d, J=8.0 Hz, 2H), 6.30 (d, J=1.60 Hz, 1H), 4.33 (d, J=5.6 Hz, 1H), 4.09-4.10 (m, 2H), 2.21-2.25 (m, 4H), 2.04-2.08 (m, 1H), 1.93-1.95 (m, 2H), 1.69 (s, 3H).

Example 60

N-((2-(5-phenyl-9-(3-(p-tolyl)ureido)-2,3,4,5-tetrahydrobenzo[b]oxepin-7-yl) phenyl)sulfonyl)benzamide (Homochiral, Stereochemistry Unknown)

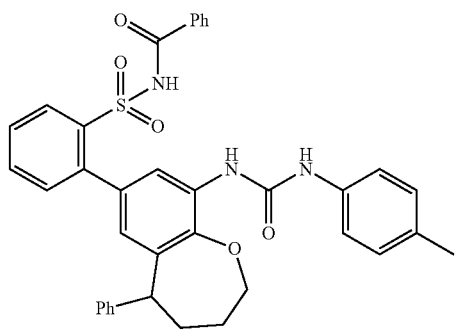 [SMILES: Cc1ccc(NC(=O)Nc2cc(-c3ccccc3S(=O)(=O)NC(=O)c3ccccc3)cc3c2OCCCC3c2ccccc2)cc1]

A solution of 58C (25 mg, 0.047 mmol) in DCM (1 mL) was treated with TEA (0.033 mL, 0.237 mmol) followed by benzoyl chloride (0.016 mL, 0.142 mmol), and the reaction was stirred overnight at RT. The reaction was diluted with DCM (10 mL) and washed with 10% aq. sodium hydroxide solution (2×10 mL). The organic layer was dried over sodium sulphate, concentrated under reduced pressure, and purified by prep HPLC to afford Example 60 (white solid, 6 mg, 9.12 µmol, 19% yield). LC-MS Anal. Calc'd for $C_{37}H_{33}N_3O_5S$ 631.21, found [M+H] 632.2. $T_r$=3.297 min (Method U). $^1$H NMR (400 MHz, DMSO-d6) δ 11.82 (s, 1H), 9.18 (s, 1H), 8.38 (s, 1H), 8.12 (dd, J=7.8, 1.4 Hz, 1H), 8.08 (d, J=2.0 Hz, 1H), 7.70 (d, J=9.6 Hz, 2H), 7.52-7.64 (m, 2H), 7.37 (t, J=7.6 Hz, 2H), 7.27 (d, J=8.4 Hz, 2H), 7.12-7.22 (m, 4H), 7.07 (d, J=8.4 Hz, 2H), 7.00 (d, J=7.2 Hz, 2H), 6.18 (s, 1H), 3.98-4.07 (m, 3H), 2.24 (s, 3H), 1.99-2.01 (m, 1H), 1.82-1.86 (m, 3H).

Example 61

N-((2-(5-phenyl-9-(3-(p-tolyl)ureido)-2,3,4,5-tetrahydrobenzo[b]oxepin-7-yl) phenyl)sulfonyl)benzamide (Homochiral, Stereochemistry Unknown)

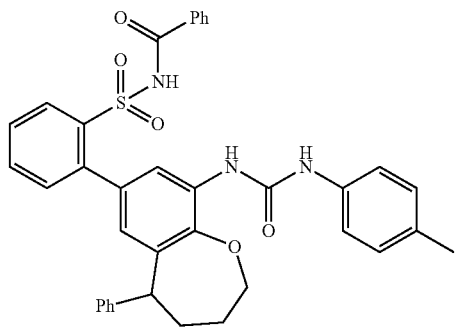 [SMILES: Cc1ccc(NC(=O)Nc2cc(-c3ccccc3S(=O)(=O)NC(=O)c3ccccc3)cc3c2OCCCC3c2ccccc2)cc1]

Example 61 Enantiomer 2 was prepared from 53A enantiomer 2 by following the procedures for the conversion of 53A enantiomer 1 to Example 60. LC-MS Anal. Calc'd for $C_{37}H_{33}N_3O_5S$ 631.21, found [M+H] 632.2. $T_r$=3.297 min (Method U). $^1$H NMR (400 MHz, DMSO-d6) δ 11.82 (s, 1H), 9.18 (s, 1H), 8.38 (s, 1H), 8.12 (dd, J=7.6, 1.2 Hz, 1H), 8.08 (d, J=2.0 Hz, 1H), 7.70 (d, J=9.6 Hz, 2H), 7.52-7.64 (m, 2H), 7.37 (t, J=7.0 Hz, 2H), 7.27 (d, J=8.4 Hz, 2H), 7.12-7.22 (m, 4H), 7.07 (d, J=8.4 Hz, 2H), 7.00 (d, J=7.2 Hz, 2H), 6.18 (s, 1H), 3.98-4.07 (m, 3H), 2.24 (s, 3H), 1.99-2.01 (m, 1H), 1.82-1.86 (m, 3H).

Example 62 Enantiomer 1 and Example 62 Enantiomer 2

N-(7-(2-(1H-tetrazol-5-yl)phenyl)-5-phenyl-2,3,4,5-tetrahydrobenzo[b]oxepin-9-yl)-5-methylpyridin-2-amine

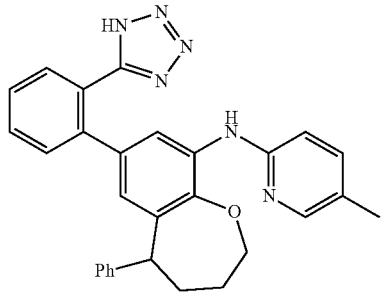 [SMILES: Cc1ccc(Nc2cc(-c3ccccc3-c3nnn[nH]3)cc3c2OCCCC3c2ccccc2)nc1]

62A. N-(7-bromo-5-phenyl-2,3,4,5-tetrahydrobenzo[b]oxepin-9-yl)-5-methylpyridin-2-amine (Homochiral, Stereochemistry Unknown)

A solution of 53A enantiomer 1 (50 mg, 0.157 mmol) in 1,4-dioxane (1 mL) was treated with 2-bromo-5-methylpyridine (32.4 mg, 0.189 mmol) followed by sodium tert-butoxide (45.3 mg, 0.471 mmol). The reaction mixture was purged with nitrogen for 10 min, treated with xantphos (18.18 mg, 0.031 mmol) and bis(dibenzylideneacetone)palladium (9.04 mg, 0.016 mmol) and heated overnight at 110° C. The reaction was concentrated under reduced pressure and purified by flash chromatography to give 62A (yellow gum, 40 mg, 0.087 mmol, 39.6% yield). LC-MS Anal. Calc'd for $C_{22}H_{21}BrN_2O$ 408.08 found [M+H] 409.2. $T_r$=3.25 min (Method U).

Example 62

Example 62 Enantiomer 1 was prepared from 62A following the procedure for the conversion of 51A to Example 51. LC-MS Anal. Calc'd for $C_{29}H_{26}N_6O$ 474.21 found [M+H] 475.2. $T_r$=2.078 min (Method U). $^1$H NMR (400 MHz, DMSO-d6) δ 7.92 (s, 1H), 7.58-7.66 (m, 4H), 7.46-7.53 (m, 2H), 7.29 (t, J=7.4 Hz, 2H), 7.21 (t, J=7.4 Hz, 1H), 7.05 (d, J=8.0 Hz, 3H), 6.12 (s, 1H), 4.23 (d, J=6.8 Hz, 1H), 4.08-4.11 (m, 1H), 3.88 (t, J=8.2 Hz, 1H), 2.22 (s, 3H), 2.09-2.13 (m, 1H), 1.98-2.02 (m, 1H), 1.89-1.92 (m, 2H).

Example 62 Enantiomer 2 was prepared from 53A Enantiomer 2 following the procedures for the conversion of 53A enantiomer 1 to Example 62 enantiomer 1. LC-MS Anal. Calc'd for $C_{29}H_{26}N_6O$ 474.21 found [M+H] 475.2. $T_r$=2.072 min (Method U). $^1$H NMR (400 MHz, DMSO-d6) δ 7.92 (s, 1H), 7.58-7.66 (m, 4H), 7.46-7.53 (m, 2H), 7.29 (t, J=7.4 Hz, 2H), 7.21 (t, J=7.4 Hz, 1H), 7.05 (d, J=8.0 Hz, 3H), 6.12 (s, 1H), 4.23 (d, J=6.8 Hz, 1H), 4.08-4.11 (m, 1H), 3.88 (t, J=8.2 Hz, 1H), 2.22 (s, 3H), 2.09-2.13 (m, 1H), 1.98-2.02 (m, 1H), 1.89-1.92 (m, 2H).

Example 63 Enantiomer 1 and Example 63 Enantiomer 2

N-(7-(2-(1H-tetrazol-5-yl)phenyl)-5-phenyl-2,3,4,5-tetrahydrobenzo[b]oxepin-9-yl)-5-fluoropyrimidin-2-amine

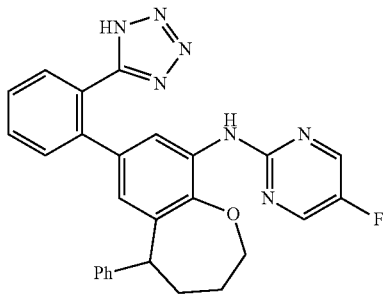 [SMILES: Fc1cnc(Nc2cc(-c3ccccc3-c3nnn[nH]3)cc3c2OCCCC3c2ccccc2)nc1]

63A. N-(7-bromo-5-phenyl-2,3,4,5-tetrahydrobenzo[b]oxepin-9-yl)-5-fluoro pyrimidine-amine (Homochiral, Stereochemistry Unknown)

A solution of 53A Enantiomer 1 (50 mg, 0.157 mmol) in 1,4-dioxane (1 mL) was added 2-chloro-5-fluoropyrimidine (24.99 mg, 0.189 mmol) followed by $Cs_2CO_3$ (154 mg, 0.471 mmol). This mixture was purged with nitrogen for 10 min, treated with xantphos (18.18 mg, 0.031 mmol) followed by $PdOAc_2$ (10.58 mg, 0.016 mmol), and heated overnight at 110° C. The reaction was concentrated under reduced pressure and purified by flash chromatography to afford 63A (brown solid, 22 mg, 0.038 mmol, 24.33% yield). LC-MS Anal. Calc'd for $C_{20}H_{17}BrFN_3O$ 413.05 found [M+H] 414.2. $T_r$=4.195 min (Method U).

Example 63

Example 63 Enantiomer 1 was prepared from 63A following the procedure for the conversion of 51A to Example 51. LC-MS Anal. Calc'd for $C_{27}H_{22}FN_7O$ 479.18 found [M+H] 480.2. $T_r$=1.82 min (Method U). $^1$H NMR (400 MHz, DMSO-d6) δ 8.55 (s, 2H), 8.40 (s, 1H), 7.98 (d, J=2.0 Hz, 1H), 7.45-7.64 (m, 4H), 7.27-7.31 (m, 2H), 7.21-7.22 (m, 1H), 7.06 (d, J=8.0 Hz, 2H), 6.12 (s, 1H), 4.22 (d, J=7.2 Hz, 1H), 4.12-4.15 (m, 1H), 3.94-3.97 (m, 1H), 2.09-2.13 (m, 1H), 1.91-2.01 (m, 3H).

Example 63 Enantiomer 2 was prepared from 53A enantiomer 2 following the procedure for the conversion of 53A Enantiomer 1 to Example 63 Enantiomer 1. LC-MS Anal. Calc'd for $C_{27}H_{22}FN_7O$ 479.18 found [M+H] 480.2. $T_r$=1.848 min (Method U). $^1$H NMR (400 MHz, DMSO-d6) 8.55 (s, 2H), 8.40 (s, 1H), 7.98 (d, J=2.0 Hz, 1H), 7.45-7.64 (m, 4H), 7.27-7.31 (m, 2H), 7.21-7.22 (m, 1H), 7.06 (d, J=8.0 Hz, 2H), 6.12 (s, 1H), 4.22 (d, J=7.2 Hz, 1H), 4.12-4.15 (m, 1H), 3.94-3.97 (m, 1H), 2.09-2.13 (m, 1H), 1.91-2.01 (m, 3H).

Example 64 Enantiomer 1 and Example 64 Enantiomer 2

N-(7-(2-(1H-tetrazol-5-yl)phenyl)-5-phenyl-2,3,4,5-tetrahydrobenzo[b]oxepin-9-yl) benzo[d]thiazol-2-amine

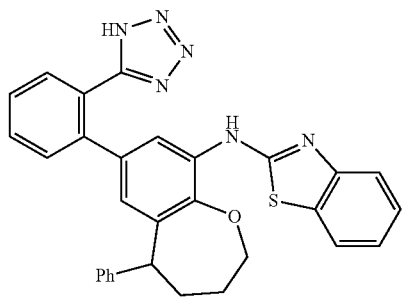 [SMILES: c1ccc(C2CCCOc3c(Nc4nc5ccccc5s4)cc(-c4ccccc4-c4nnn[nH]4)cc32)cc1]

Example 64 Enantiomer 1 was prepared from 53A Enantiomer 1 and 2-chloro-benzo[d]thiazole at 140° C., otherwise following the procedures for the conversion of 43 G isomer 4 to Example 52. LC-MS Anal. Calc'd for $C_{30}H_{24}N_6OS$ 516.17 found [M+H]517.2. $T_r$=2.21 min (Method U). $^1$H NMR (400 MHz, DMSO-d6) δ 9.97 (s, 1H), 8.44 (s, 1H), 7.80 (d, J=8.8 Hz, 1H), 7.61-7.63 (m, 3H), 7.49-7.55 (m, 2H), 7.28-7.33 (m, 3H), 7.13-7.23 (m, 3H), 7.07-7.09 (m, 2H), 6.14 (s, 1H), 4.25 (d, J=6.8 Hz, 1H), 4.12-4.16 (m, 1H), 3.94-3.97 (m, 1H), 2.12-2.15 (m, 1H), 1.91-2.08 (m, 3H).

Example 64 enantiomer 2 was prepared from 53A Enantiomer 2 and 2-chloro-benzo[d]thiazole at 140° C., otherwise following the procedures for the conversion of 43 G isomer 4 to Example 52. LC-MS Anal. Calc'd for $C_{30}H_{24}N_6OS$ 516.17 found [M+H]517.2. $T_r$=2.21 min (Method U). $^1$H NMR (400 MHz, DMSO-d6) δ 9.97 (s, 1H), 8.44 (s, 1H), 7.80 (d, J=8.8 Hz, 1H), 7.61-7.63 (m, 3H), 7.49-7.55 (m, 2H), 7.28-7.33 (m, 3H), 7.13-7.23 (m, 3H), 7.07-7.09 (m, 2H), 6.14 (s, 1H), 4.25 (d, J=6.8 Hz, 1H), 4.12-4.16 (m, 1H), 3.94-3.97 (m, 1H), 2.12-2.15 (m, 1H), 1.91-2.08 (m, 3H).

Example 65 methyl 2-methoxy-6-(5-phenyl-9-(3-(p-tolyl)ureido)-2,3,4,5-tetrahydrobenzo[b]oxepin-7-yl)benzoate

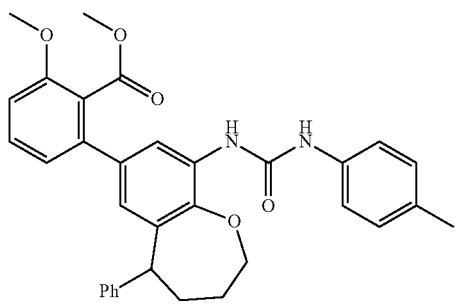

65A. tert-butyl (7-(5,5-dimethyl-1,3,2-dioxaborinan-2-yl)-5-phenyl-2,3,4,5-tetrahydrobenzo[b]oxepin-9-yl)carbamate A solution of 5B (0.5 g, 1.108 mmol) in DMSO (10 mL) was treated with 5,5,5',5'-tetramethyl-2,2'-bi(1,3,2-dioxaborinane) (0.500 g, 2.216 mmol) followed by potassium acetate (0.489 g, 4.98 mmol). This mixture was purged with nitrogen for 10 min then treated with $PdCl_2(dppf)-CH_2Cl$ Adduct (0.045 g, 0.055 mmol) and heated for 5 h at 80° C. The reaction was concentrated under reduced pressure, diluted with ethyl acetate (25 mL) and washed with brine (5×20 mL). The organic layer was dried over sodium sulphate and concentrated under reduced pressure to afford 65A (brown solid, 0.6 g, 0.892 mmol, 81% yield). LC-MS Anal. Calc'd for $C_{29}H_{33}BN_2O_4$ 484.25 found [M+H]417.2 (boronic acid fragment), $T_r$=2.82 min (Method U).

65B. methyl 2-(9-((tert-butoxycarbonyl)amino)-5-phenyl-2,3,4,5-tetrahydro benzo[b]oxepin-7-yl)-6-methoxybenzoate A solution of 65A (150 mg, 0.332 mmol) in DMF (4 mL) was treated with methyl 2-bromo-6-methoxybenzoate (81 mg, 0.332 mmol) and $K_2CO_3$ (184 mg, 1.329 mmol) in water (1 mL). This mixture was purged with nitrogen for 15 min, treated with tetrakis(triphenylphosphine)palladium(0) (19.20 mg, 0.017 mmol), and heated overnight at 90° C. The reaction was concentrated under reduced pressure, suspended in water (10 mL), and extracted with ethyl acetate (2×15 mL). The combined organic layer was dried over sodium sulphate, concentrated under reduced pressure, and purified by flash chromatography to afford 65B (white solid, 110 mg, 0.168 mmol, 50.6% yield. LC-MS Anal. Calc'd for $C_{30}H_{33}NO_6$ 503.23 found [M+NH$_4$] 521.2. $T_r$=3.99 min (Method U).

65C. methyl 2-(9-amino-5-phenyl-2,3,4,5-tetrahydrobenzo[b]oxepin-7-yl)-6-methoxy benzoate A solution of 65B (110 mg, 0.218 mmol) in 1,4-dioxane (2 mL) was treated with 4M HCl in dioxane (2 mL, 8.00 mmol) and stirred overnight at RT. The reaction was concentrated under reduced pressure, suspended in 10% aq. sodium bicarbonate (20 mL), and extracted with ethyl acetate (2×20 mL). The combined organic layer was dried over sodium sulfate and concentrated under reduced pressure to afford 65C (70 mg, 0.168 mmol, 77% yield) as brown gum. LC-MS Anal. Calc'd for $C_{25}H_{25}NO_4$ 403.17 found [M+H] 404.2, $T_r$=3.08 min (Method U).

Example 65

A solution of 65C (30 mg, 0.074 mmol) in DCM (2 mL) was treated with 1-isocyanato-4-methylbenzene (19.80 mg, 0.149 mmol) and stirred overnight at RT. The reaction was diluted with DCM (10 mL), washed with water (2×25 mL), and dried over sodium sulphate. Concentration under reduced pressure followed by purification by prep HPLC afforded Example 65 (white solid, 14 mg, 0.026 mmol, 34.7% yield). LC-MS Anal. Calc'd for $C_{33}H_{32}N_2O_5$ 536.23 found [M+H] 537.2. $T_r$=3.633 min (Method U). $^1$H NMR (400 MHz, DMSO-d6) δ 9.27 (s, 1H), 8.49 (s, 1H), 8.19 (d, J=2.40 Hz, 1H), 7.43 (t, J=8.0 Hz, 1H), 7.32-7.37 (m, 4H), 7.21-7.24 (m, 3H), 7.06-7.11 (m, 3H), 6.88 (d, J=7.6 Hz, 1H), 6.35 (d, J=2.0 Hz, 1H), 4.32 (d, J=6.0 Hz, 1H), 4.11-4.12 (m, 1H), 4.01-4.04 (m, 1H), 3.46 (s, 3H), 3.78 (s, 3H), 2.25 (s, 3H), 2.19-2.23 (m, 1H), 2.03-2.08 (m, 1H), 1.93-1.96 (m, 2H).

Example 66 methyl 2-methyl-6-(5-phenyl-9-(3-(p-tolyl)ureido)-2,3,4,5-tetrahydrobenzo[b]oxepin-7-yl)benzoate

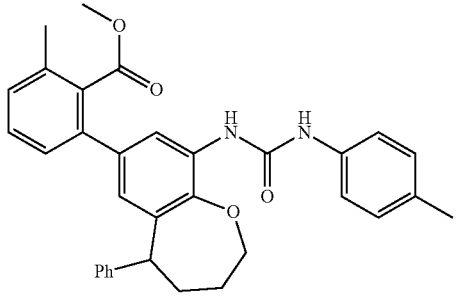 [SMILES: COC(=O)c1c(C)cccc1-c1cc(NC(=O)Nc2ccc(C)cc2)c2c(c1)C(c1ccccc1)CCCO2]

Example 66 was prepared from 65A and methyl 2-bromo-6-methylbenzoate following the procedure for the conversion of 65A to Example 65. LC-MS Anal. Calc'd for $C_{33}H_{32}N_2O_4$ 520.23 found [M+H] 521.2. $T_r$=3.8 min (Method U). $^1$H NMR (400 MHz, DMSO-d6) δ 9.27 (s, 1H), 8.49 (s, 1H), 8.19 (d, J=2.4 Hz, 1H), 7.43 (t, J=8.0 Hz, 1H), 7.32-7.37 (m, 4H), 7.21-7.24 (m, 3H), 7.06-7.11 (m, 3H), 6.88 (d, J=7.6 Hz, 1H), 6.35 (d, J=2.0 Hz, 1H), 4.32 (d, J=6.0 Hz, 1H), 4.11-4.12 (m, 1H), 4.01-4.04 (m, 1H), 3.46 (s, 3H), 3.78 (s, 3H), 2.25 (s, 3H), 2.19-2.23 (m, 1H), 2.03-2.08 (m, 1H), 1.93-1.96 (m, 2H).

Example 67

1-(7-(2-(5-oxo-4,5-dihydro-1,2,4-oxadiazol-3-yl)phenyl)-5-phenyl-2,3,4,5-tetrahydrobenzo[b]oxepin-9-yl)-3-(p-tolyl)urea (Homochiral, Stereochemistry Unknown)

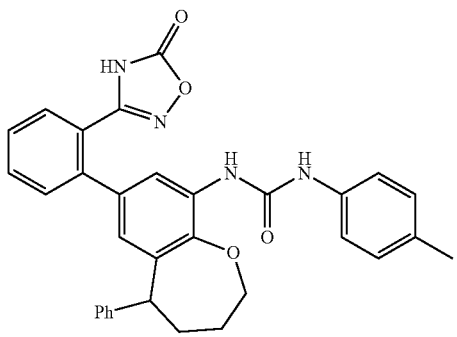 [SMILES: Cc1ccc(NC(=O)Nc2cc(-c3ccccc3-c3noc(=O)[nH]3)cc3c2OCCCC3c2ccccc2)cc1]

67A. 1-(7-bromo-5-phenyl-2,3,4,5-tetrahydrobenzo[b]oxepin-9-yl)-3-(p-tolyl)urea Compound 67A was prepared from 53A Enantiomer 2 by the procedure used for the preparation of 58A Enantiomer 1 from 53A Enantiomer 1. (brown solid, 650 mg, 1.09 mmol, 76% yield). LC-MS Anal. Calc'd for $C_{24}H_{23}BrN_2O_2$ 452.1, found [M+H]453.0. $T_r$=4.06 min (Method U).

67B. 1-(7-(5,5-dimethyl-1,3,2-dioxaborinan-2-yl)-5-phenyl-2,3,4,5-tetrahydrobenzo[b]oxepin-9-yl)-3-(p-tolyl)urea Compound 67B was prepared from 67A by the procedure used for the preparation of 65A from 5B. (brown solid, 0.6 g, 0.892 mmol, 81% yield). LC-MS Anal. Calc'd for $C_{29}H_{33}BN_2O_4$ 484.25 found [M+H] 417.2 (boronic acid fragment), $T_r$=2.83 min (Method U).

Example 67 (Homochiral, Stereochemistry Unknown)

Example 67 was prepared from 67B and 3-(2-bromophenyl)-1,2,4-oxadiazol-5(4H)-one by the procedure used for the preparation of 65B from 65A. LC-MS Anal. Calc'd for $C_{32}H_{28}N_4O_4$ 532.21 found [M+H] 533.2. $T_r$=3.11 min (Method U). $^1$H NMR (400 MHz, DMSO-d6) δ 12.20 (s, 1H), 9.28 (s, 1H), 8.50 (s, 1H), 8.22 (d, J=2.4 Hz, 1H), 7.62 (t, J=7.4 Hz, 1H), 7.55 (d, J=7.6 Hz, 1H), 7.47 (t, J=7.6 Hz, 1H), 7.42 (d, J=8.0 Hz, 1H), 7.34-7.37 (m, 2H), 7.31 (d, J=8.0 Hz, 2H), 7.22 (t, J=7.2 Hz, 1H), 7.15 (d, J=7.2 Hz, 2H), 7.10 (d, J=8.0 Hz, 2H), 6.19 (d, J=1.6 Hz, 1H), 4.28 (d, J=7.6 Hz, 1H), 4.21-4.25 (m, 1H), 3.92 (t, J=8.6 Hz, 1H), 2.25 (s, 3H), 1.92-2.07 (m, 4H).

Example 68

4-methyl-2-(5-phenyl-9-(3-(p-tolyl)ureido)-2,3,4,5-tetrahydrobenzo[b]oxepin-7-yl)benzoic acid (Homochiral, Stereochemistry Unknown)

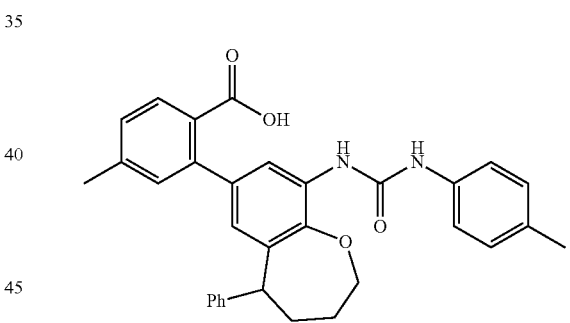

68A. methyl 4-methyl-2-(5-phenyl-9-(3-(p-tolyl)ureido)-2,3,4,5-tetrahydro benzo[b]oxepin-7-yl)benzoate A solution of 67A (50 mg, 0.103 mmol) in DMF (2 mL) was treated with methyl 2-bromo-4-methylbenzoate (35.5 mg, 0.155 mmol) and $K_2CO_3$ (57.1 mg, 0.413 mmol) in water (0.5 mL). This mixture was purged with nitrogen for 15 min and treated with tetrakis(triphenylphosphine)palladium(0) (5.96 mg, 5.16 μmol). The reaction was then heated overnight at 90° C. and concentrated under reduced pressure. The residue was suspended in water (10 mL) and extracted with ethyl acetate (2×15 mL). The combined organic layer was dried over sodium sulphate, concentrated under reduced pressure, and purified by flash chromatography to afford 68A (white solid, 35 mg, 0.067 mmol, 64.5% yield). LC-MS Anal. Calc'd for $C_{33}H_{32}N_2O_4$ 520.23 found [M−H] 521.2. $T_r$=3.99 min (Method U).

Example 68 (Homochiral, Stereochemistry Unknown)

A solution of methyl 68A (35 mg, 0.067 mmol) in THF (1 mL)-MeOH (1 mL) was treated with LiOH·H$_2$O (14.12 mg, 0.336 mmol) in water (0.5 mL), and the reaction was heated overnight at 75° C. The reaction was concentrated under reduced pressure, suspended in water (10 mL), and acidified with solid citric acid. The resulting mixture was extracted with ethyl acetate (2×25 mL), and the combined organic layer was dried over sodium sulphate and concentrated under reduced pressure. The residue was purified by prep HPLC to afford Example 68 (white solid, 11 mg, 0.021 mmol, 32.0% yield). LC-MS Anal. Calc'd for C$_{32}$H$_{30}$N$_2$O$_4$ 506.22 found [M−H] 505.2. T$_r$=3.11 min (Method AD). $^1$H NMR (400 MHz, DMSO-d6) δ 12.51 (s, 1H), 9.26 (s, 1H), 8.46 (s, 1H), 8.14 (d, J=2.4 Hz, 1H), 7.56 (d, J=8.0 Hz, 1H), 7.30-7.36 (m, 4H), 7.19-7.23 (m, 4H), 7.07-7.10 (m, 3H), 6.36 (d, J=2.4 Hz, 1H), 4.33 (d, J=6.0 Hz, 1H), 4.06 (t, J=4.8 Hz, 2H), 2.34 (s, 3H), 2.22-2.26 (m, 4H), 2.03-2.07 (m, 1H), 1.92-1.93 (m, 2H).

Example 69

1-(7-(2-(1H-tetrazol-5-yl)phenyl)-4,5-dimethyl-2,3,4,5-tetrahydrobenzo[b]oxepin-9-yl)-3-(p-tolyl)urea (Mixture of Stereoisomers)

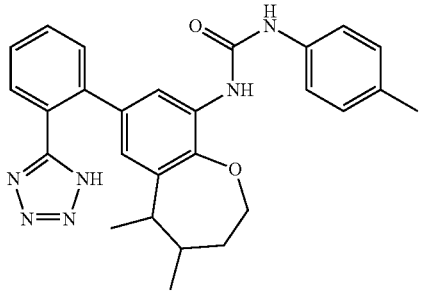 [SMILES: Cc1ccc(NC(=O)Nc2cc(-c3ccccc3-c3nnn[nH]3)cc3c2OCCC(C)C3C)cc1]

69A. 1-(7-bromo-4,5-dimethyl-2,3,4,5-tetrahydrobenzo[b]oxepin-9-yl)-3-(p-tolyl)urea (Mixture of Stereoisomers)

Diastereomeric 69A was prepared from (E)-2-methylbut-2-en-1-ol and 4-bromo-1-fluoro-2-nitrobenzene following the procedures for the conversion of (E)-2-methyl-3-phenylprop-2-en-1-ol and 4-bromo-1-fluoro-2-nitrobenzene to 43H. LC-MS Anal. Calc'd for C$_{32}$H$_{28}$N$_4$O$_4$ 402.1 found [M+H] 403.1. T$_r$=1.30 min (Method T).

Example 69

A mixture of 69A (100 mg, 0.248 mmol), (2-(1-trityl-1H-tetrazol-5-yl)phenyl)boronic acid (236 mg, 0.545 mmol) and K$_2$CO$_3$ (188 mg, 1.364 mmol) in in DMF (1 mL)-water (0.25 mL). was degassed by purging with N$_2$ for 10 min. This mixture was treated with tetrakis(triphenylphosphine)palladium(0) (17.19 mg, 0.015 mmol) and heated for 16 h at 90° C. The reaction was quenched with water and extracted with ethyl acetate (2×25 mL). The combined organic layer was dried over sodium sulphate and concentrated under reduced pressure. The residue was purified by prep HPLC to afford Example 69 (16 mg, 0.034 mmol, 14% yield) as an off-white solid. LC-MS Anal. Calc'd for C$_{27}$H$_{28}$N$_6$O$_2$ 468.5, found [M+H] 469.5. T$_r$=1.56 min (Method O). $^1$H NMR (400 MHz, DMSO-d$_6$) δ 8.35 (s, 1H), 8.08 (d, J=2.0 Hz, 1H), 7.67 (t, J=8.0 Hz, 1H), 7.65 (d, J=1.2 Hz, 1H), 7.51-7.55 (m, 2H), 7.34 (d, J=2.0 Hz, 1H), 7.31 (d, J=2.0 Hz, 1H), 7.09 (s, 1H), 7.01 (s, 1H), 6.21 (d, J=2.0 Hz, 1H), 4.09-4.12 (m, 1H), 3.81-3.84 (m, 1H), 3.17 (s, 1H), 2.66-2.67 (m, 1H), 2.23 (s, 3H), 1.83 (s, 3H), 1.01 (d, J=6.40 Hz, 1H), 0.76 (d, J=6.80 Hz, 1H).

Example 70

1-(7-(2-(1H-tetrazol-5-yl)phenyl)-5-(4-fluorophenyl)-2,3,4,5-tetrahydrobenzo[b]oxepin-9-yl)-3-(2-fluorophenyl)urea

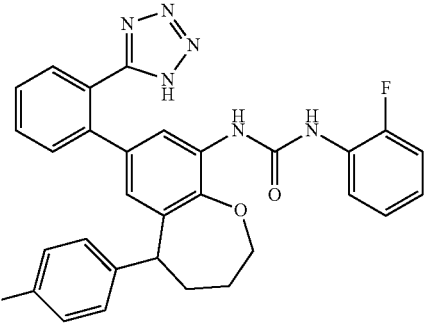

70A. 7-bromo-5-(4-fluorophenyl)-2,5-dihydrobenzo[b]oxepin-9-amine

Compound 70A was prepared from (E)-3-(4-fluorophenyl)prop-2-en-1-ol and 4-bromo-2-nitrophenol following the procedures for the conversion of (E)-3-phenylprop-2-en-1-ol to 1E. (brown solid). LC-MS Anal. Calc'd for C$_{16}$H$_{13}$BrFNO 335.0, found [M+H]336.0. T$_r$=3.15 min (Method U).

70B. 1-(7-bromo-5-(4-fluorophenyl)-2,5-dihydrobenzo[b]oxepin-9-yl)-3-(2-fluorophenyl)urea Compound 70B was prepared from 70A and 2-fluorophenylisocyanate by the procedure used for the conversion of 1E to 1F. (white solid, 0.27 g, 0.573 mmol, 96% yield). LC-MS Anal. Calc'd for C$_{23}$H$_{17}$BrF$_2$N$_2$O$_2$ 472.0 found [M+H] 473.0, T$_r$=3.73 min (Method U).

Example 70

Example 70 was prepared from 70B following the procedures for the conversion of 1F to Example 1. LC-MS Anal. Calc'd for C$_{30}$H$_{24}$F$_2$N$_6$O$_2$ 538.2, found [M+H] 539. T$_r$=2.55 min (Method U). $^1$H NMR (400 MHz, DMSO-d$_6$) δ 9.30 (s, 1H), 8.98 (s, 1H), 8.21-8.08 (m, 2H), 7.75-7.65 (m, 1H), 7.62-7.54 (m, 2H), 7.51-7.40 (m, 2H), 7.24 (ddd, J=11.7, 8.2, 1.3 Hz, 1H), 7.16-6.96 (m, 5H), 5.86 (s, 1H), 4.20-4.11 (m, 2H), 3.95-3.83 (m, 1H), 2.11-1.85 (m, 4H), 1.39-1.22 (m, 2H).

Example 71

N-(7-(2-(1H-tetrazol-5-yl)phenyl)-5-phenyl-2,3,4,5-tetrahydrobenzo[b]oxepin-9-yl)-2-methylbenzo[d]thiazol-6-amine (Homochiral, Stereochemistry Unknown)

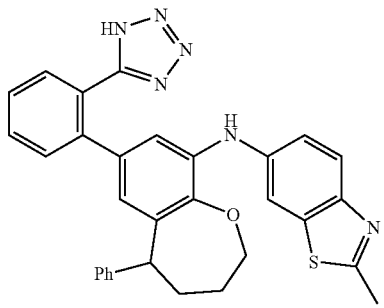 [SMILES: Cc1nc2ccc(Nc3cc(-c4ccccc4-c4nnn[nH]4)cc4c3OCCCC4c3ccccc3)cc2s1]

71A. 7-(2-(1H-tetrazol-5-yl)phenyl)-5-phenyl-2,3,4,5-tetrahydrobenzo[b]oxepin-9-amine To a solution of 53A Enantiomer 2 in DMF (5 mL) were added 5-(2-(4,4,5,5-tetramethyl-1,3,2-dioxaborolan-2-yl)phenyl)-1H-tetrazole (534 mg, 1.964 mmol) and $K_2CO_3$ (326 mg, 2.357 mmol) in water (1 mL). The reaction mixture was purged with nitrogen for 15 min, treated with tetrakis(triphenylphosphine)palladium(0) (91 mg, 0.079 mmol), and heated overnight at 110° C. The reaction was concentrated under reduced pressure and purified by flash chromatography to afford 71A (brown gum, 220 mg, 0.413 mmol, 52.6% yield). LC-MS Anal. Calc'd for $C_{23}H_{21}N_5O$ 383.17, found [M+H] 384.2. $T_r$=2.07 min (Method U).

Example 71 (Homochiral, Absolute Stereochemistry Unknown)

A solution of 71A (50 mg, 0.130 mmol) and 6-bromo-2-methylbenzo[d]thiazole (35.7 mg, 0.156 mmol) in 1,4-dioxane (2 mL) was treated with sodium tert-butoxide (37.6 mg, 0.391 mmol), and the resulting mixture was purged with nitrogen for 15 min. Xantphos (37.7 mg, 0.065 mmol) and bis(dibenzylideneacetone)palladium (7.50 mg, 0.013 mmol) were added, and the reaction was heated overnight at 110° C. The reaction was filtered and concentrated under reduced pressure, and the residue was purified by prep HPLC to give Example 71 (pale yellow solid, 6.1 mg, 0.011 mmol, 8.64% yield). LC-MS Anal. Calc'd for $C_{31}H_{26}N_6OS$ 530.97, found [M+H] 531.2. $T_r$=1.849 min (Method P). $^1$H NMR (400 MHz, DMSO-d6) δ 7.68 (d, J=8.8 Hz, 1H), 7.62 (s, 1H), 7.51 (d, J=8.4 Hz, 1H), 7.37-7.39 (m, 2H), 7.26-7.33 (m, 3H), 7.16-7.22 (m, 3H), 7.03 (d, J=8.4 Hz, 1H), 6.83 (d, J=2.0 Hz, 1H), 6.51 (s, 1H), 6.09 (s, 1H), 4.25 (d, J=6.8 Hz, 1H), 4.05-4.09 (m, 1H), 3.91-3.93 (m, 1H), 2.73 (s, 3H), 2.14-2.18 (m, 1H), 2.02-2.06 (m, 1H), 1.90-1.92 (m, 2H).

Examples 72 and 73 (homochiral, absolute stereochemistry unknown) were prepared from 71A and the appropriate bromobenzene ($R^1$-Br) following the procedure for the conversion of 71A to Example 71.

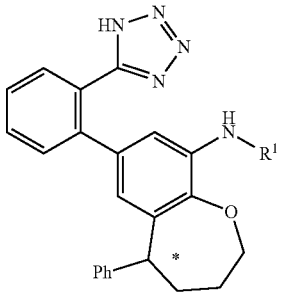

| Ex. No. | Name | $R^1$ | $T_r$ (min) Method P | [M + H]$^+$ |
|---|---|---|---|---|
| 72 | 7-(2-(1H-tetrazol-5-yl)phenyl)-N-(4-chloro-3-fluorophenyl)-5-phenyl-2,3,4,5-tetrahydrobenzo[b]oxepin-9-amine | 4-Cl-3-F-phenyl | 2.15 | 512.2 |
| 73 | 7-(2-(1H-tetrazol-5-yl)phenyl)-N-(4-chloro-2-fluorophenyl)-5-phenyl-2,3,4,5-tetrahydrobenzo[b]oxepin-9-amine | 4-Cl-2-F-phenyl | 2.1 | 512.2 |

Example 74

2-methyl-N-(7-(5-methyl-2-(1H-tetrazol-5-yl)phenyl)-5-phenyl-2,3,4,5-tetrahydrobenzo[b]oxepin-9-yl)benzo[d]thiazol-6-amine (Homochiral, Absolute Stereochemistry Unknown)

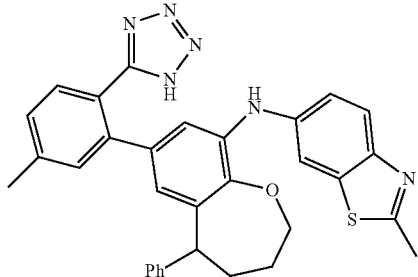

74A. 7-(5-methyl-2-(1H-tetrazol-5-yl)phenyl)-5-phenyl-2,3,4,5-tetrahydrobenzo[b]oxepin-9-amine To a solution of 53A Enantiomer 2 in DMF (8 mL) were added 5-(4-methyl-2-(4,4,5,5-tetramethyl-1,3,2-dioxaborolan-2-yl)phenyl)-1H-tetrazole (1124 mg, 3.93 mmol) and $K_2CO_3$ (651 mg, 4.71 mmol) in water (2 mL). The reaction mixture was purged with nitrogen for 15 min, treated with tetrakis(triphenylphosphine) palladium(0) (182 mg, 0.157 mmol) and heated overnight at 110° C. The reaction was concentrated under reduced pressure and purified by flash chromatography to afford 74A (brown gum, 600 mg, 1.042 mmol, 66.3% yield). LC-MS Anal. Calc'd for $C_{24}H_{23}N_5O$ 397.2, found [M+H]398.2. $T_r$=2.33 min (Method U).

Example 74 (Homochiral, Absolute Stereochemistry Unknown)

A solution of 74A (50 mg, 0.126 mmol) and 6-bromo-2-methylbenzo[d]thiazole (34.4 mg, 0.151 mmol) in 1,4-dioxane (2 mL) was treated with sodium tert-butoxide (36.3 mg, 0.377 mmol), and the resulting mixture was purged with nitrogen for 15 min. Xantphos (36.4 mg, 0.063 mmol) and bis(dibenzylideneacetone)palladium (7.23 mg, 0.013 mmol) were added, and the reaction was heated overnight at 110° C. The reaction was filtered, concentrated under reduced pressure, and purified by prep HPLC to afford Example 74 (pale yellow solid, 4 mg, 7.12 μmol, 5.7% yield). LC-MS Anal. Calc'd for $C_{32}H_{28}N_6OS$ 544.2, found [M+H] 545.2. $T_r$=2.02 min (Method P). $^1$H NMR (400 MHz, DMSO-d6) δ 7.72 (s, 1H), 7.69 (s, 1H), 7.43-7.45 (m, 2H), 7.19-7.32 (m, 5H), 7.07-7.13 (m, 3H), 6.84 (d, J=2.0 Hz, 1H), 6.05 (s, 1H), 4.24 (d, J=6.0 Hz, 1H), 4.01-4.03 (m, 1H), 3.95-3.97 (m, 1H), 2.74 (s, 3H), 2.33 (s, 3H), 2.15-2.16 (m, 1H), 1.99-2.04 (m, 1H), 1.89-1.92 (m, 2H).

Examples 75 to 79 (homochiral, absolute stereochemistry unknown) were prepared from 74A and the appropriate bromobenzene ($R^1$-Br) following the procedure for the conversion of 74A to Example 74.

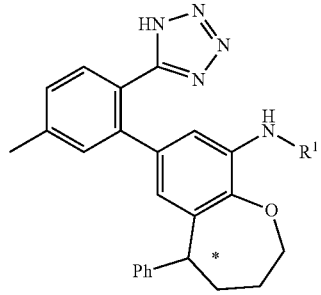

| Ex. No. | Name | $R^1$ | $T_r$ (min) Method P | [M + H]⁺ |
|---|---|---|---|---|
| 75 | N-(4-chloro-2-fluorophenyl)-7-(5-methyl-2-(1H-tetrazol-5-yl)phenyl)-5-phenyl-2,3,4,5-tetrahydrobenzo[b]oxepin-9-amine | | 2.31 | 526.2 |
| 76 | N-(4-chloro-3-fluorophenyl)-7-(5-methyl-2-(1H-tetrazol-5-yl)phenyl)-5-phenyl-2,3,4,5-tetrahydrobenzo[b]oxepin-9-amine | | 2.25 | 526.2 |
| 77 | N-(3,4-difluorophenyl)-7-(5-methyl-2-(1H-tetrazol-5-yl)phenyl)-5-phenyl-2,3,4,5-tetrahydrobenzo[b]oxepin-9-amine | | 2.15 | 510.2 |

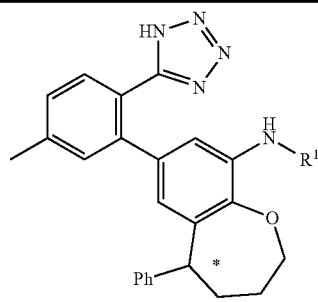

| Ex. No. | Name | R¹ | T_r (min) Method P | [M + H]⁺ |
|---|---|---|---|---|
| 78 | N-(4-chlorophenyl)-7-(5-methyl-2-(1H-tetrazol-5-yl)phenyl)-5-phenyl-2,3,4,5-tetrahydrobenzo[b]oxepin-9-amine | 4-chlorophenyl | 2.19 | 508.2 |
| 79 | N-(4-(difluoromethoxy)phenyl)-7-(5-methyl-2-(1H-tetrazol-5-yl)phenyl)-5-phenyl-2,3,4,5-tetrahydrobenzo[b]oxepin-9-amine | 4-(OCHF₂)phenyl | 2.17 | 540.2 |

Examples 80 to 82 (homochiral, absolute stereochemistry unknown) were prepared from 53A Enantiomer 1 and the appropriate chlorides (R¹-Cl) following the procedure for the conversion of 53A to Example 54.

Examples 83 & 84 (homochiral, absolute stereochemistry unknown) were prepared from 53A Enantiomer 2 and the appropriate chlorides (R¹-Cl) following the procedure for the conversion of 53A to Example 54.

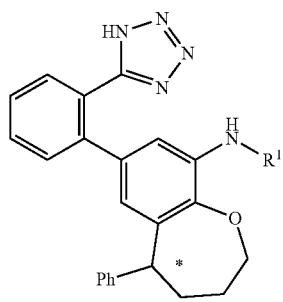

| Ex. No. | Name | R¹ | T_r (min) Method O | [M + H]⁺ |
|---|---|---|---|---|
| 81 | N-(7-(2-(1H-tetrazol-5-yl)phenyl)-5-phenyl-2,3,4,5-tetrahydrobenzo[b]oxepin-9-yl)pyrazolo[1,5-a]pyrimidin-7-amine | pyrazolo[1,5-a]pyrimidin-7-yl | 1.48 | 501.3 |
| 83 | N-(7-(2-(1H-tetrazol-5-yl)phenyl)-5-phenyl-2,3,4,5-tetrahydrobenzo[b]oxepin-9-yl)quinolin-2-amine | quinolin-2-yl | 1.99 | 511.2 |

-continued

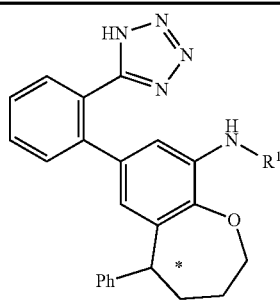

| Ex. No. | Name | R[1] | T$_r$ (min) Method O | [M + H]$^+$ |
|---|---|---|---|---|
| 84 | N-(7-(2-(1H-tetrazol-5-yl)phenyl)-5-phenyl-2,3,4,5-tetrahydrobenzo[b]oxepin-9-yl) pyrazolo[1,5-a]pyrimidin-5-amine | | 1.63 | 501.2 |

Example 85

(+/−)-1-((trans)-5-(2-(1H-tetrazol-5-yl)phenyl)-3-phenyl-2-vinyl-2,3-dihydrobenzofuran-7-yl)-3-(p-tolyl)urea

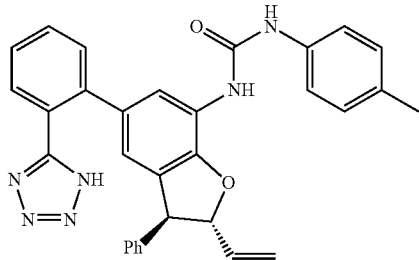 [SMILES: C=C[C@H]1Oc2c(NC(=O)Nc3ccc(C)cc3)cc(-c3ccccc3-c3nnn[nH]3)cc2[C@@H]1c1ccccc1]

To a suspension of (2-(1H-tetrazol-5-yl)phenyl)boronic acid (0.482 g, 2.54 mmol), 1F (0.38 g, 0.846 mmol), and tetrakis(triphenylphosphine)palladium(0) (0.049 g, 0.042 mmol) in degassed DMF (6 mL) was added aq. potassium carbonate (2.255 mL, 3.38 mmol). The mixture was placed under nitrogen and heated at 95° C. for 2 h. The reaction was cooled, brought to pH4 with glacial HOAc, filtered, and purified by prep. HPLC. Concentration of the appropriate fraction afforded (+/−)-1-((trans)-5-(2-(1H-tetrazol-5-yl) phenyl)-3-phenyl-2-vinyl-2,3-dihydrobenzofuran-7-yl)-3-(p-tolyl)urea (Example 85) (0.195 g, 44% yield) as an off-white powder. MS (ESI): m/z=515 [M+H]$^+$. T$_r$=4.63 (Method BA). $^1$H NMR (400 MHz, DMSO-d$_6$) δ 9.05 (s, 1H), 8.27 (s, 1H), 7.90 (s, 1H), 7.63 (t, 1H, J=7.8 Hz), 7.57 (d, 1H, J=7.3 Hz), 7.49 (t, 2H, J=7.7 Hz), 7.25-7.36 (m, 5H), 7.02-7.11 (m, 4H), 6.20 (ddd, 1H, J=17.4, 10.3, 7.4 Hz), 6.09 (s, 1H), 5.34 (d, 1H, J=17.2 Hz), 5.32 (d, 1H, J=10.1 Hz), 5.00 (dd, 1H, J=8.4, 7.7 Hz), 4.47 (d, 1H, J=8.6 Hz), 2.24 (s, 3H).

Example 86

(+/−)-1-((cis)-5-(2-(1H-tetrazol-5-yl)phenyl)-3-phenyl-2-vinyl-2,3-dihydrobenzofuran-7-yl)-3-(p-tolyl)urea

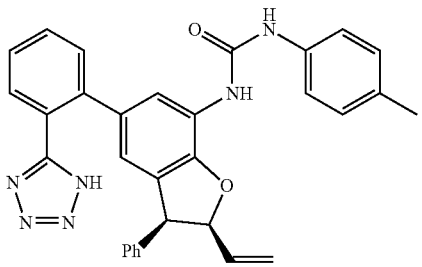 [SMILES: C=C[C@@H]1Oc2c(NC(=O)Nc3ccc(C)cc3)cc(-c3ccccc3-c3nnn[nH]3)cc2[C@@H]1c1ccccc1]

Example 87

(+/−)-1-(7-(2-(1H-tetrazol-5-yl)phenyl)-5-phenyl-2,5-dihydrobenzo[b]oxepin-9-yl)-3-(p-tolyl)urea

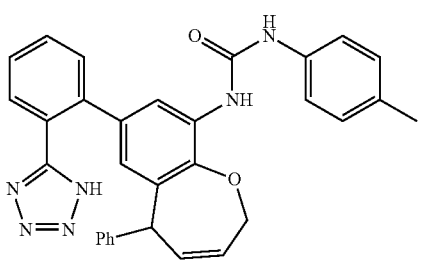 [SMILES: Cc1ccc(NC(=O)Nc2cc(-c3ccccc3-c3nnn[nH]3)cc3c2OCC=CC3c2ccccc2)cc1]

The chromatographic separation described in Example 85 provided a fraction which contained both (+/−)-1-((cis)-5-(2-(1H-tetrazol-5-yl)phenyl)-3-phenyl-2-vinyl-2,3-dihydrobenzofuran-7-yl)-3-(p-tolyl)urea and (+/−)-1-(7-(2-(1H-tetrazol-5-yl)phenyl)-5-phenyl-2,5-dihydrobenzo[b]oxepin- 9-yl)-3-(p-tolyl)urea. This fraction was concentrated under reduced pressure and chromatographed on silica gel (gradient elution with ether-hexanes+1% glacial acetic acid). Concentration of the appropriate (earlier eluting) fractions afforded Example 86 (0.013 g, 3% yield) as a white powder. MS (ESI): m/z=515 [M+H]$^+$. T$_r$=4.55 (Method BA). $^1$H NMR (400 MHz, DMSO-d$_6$) δ 9.05 (s, 1H), 8.27 (s, 1H), 7.99 (s, 1H), 7.61 (t, 1H, J=7.6 Hz), 7.57 (d, 1H, J=6.6 Hz), 7.48 (t, 2H, J=7.0 Hz), 7.20-7.33 (m, 5H), 7.08 (d, 2H, J=8.4 Hz), 6.85 (d, 2H, J=6.8 Hz), 6.20 (s, 1H), 5.50-5.57 (m, 1H), 5.28-5.39 (m, 2H), 5.04-09 (m, 1H), 4.80 (d, 1H, J=9.0 Hz), 2.24 (s, 3H). Concentration of the later-eluting fractions afforded Example 87 as a white powder. MS (ESI): m/z=515 [M+H]$^+$. T$_r$=4.51 (Method BA). $^1$H NMR (400 MHz, DMSO-d$_6$) δ 9.14 (s, 1H), 8.39 (s, 1H), 8.06 (d, 1H, J=2.0 Hz), 7.47-7.63 (m, 4H), 7.23-7.33 (m, 4H), 7.14-7.20 (m, 3H), 7.07 (d, 2H, J=8.4 Hz), 6.36 (d, 1H, J=2.0 Hz), 5.95 (dd, 1H, J=11.9, 6.4 Hz), 5.78 (br. d, 1H, J=11.4 Hz), 4.75 (br. d, 1H, J=17.0 Hz), 4.59 (d, 1H, J=6.2 Hz), 4.46 (br. d, 1H, J=17.6 Hz), 2.23 (s, 3H).

Example 88

1-((trans)-5-(2-(1H-tetrazol-5-yl)phenyl)-3-phenyl-2-vinyl-2,3-dihydrobenzofuran-7-yl)-3-(p-tolyl)urea (Enantiomer 1, Absolute Stereochemistry Unknown)

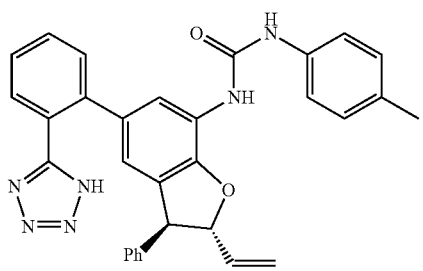

Example 89

1-((trans)-5-(2-(1H-tetrazol-5-yl)phenyl)-3-phenyl-2-vinyl-2,3-dihydrobenzofuran-7-yl)-3-(p-tolyl)urea (Enantiomer 2, Absolute Stereochemistry Unknown)

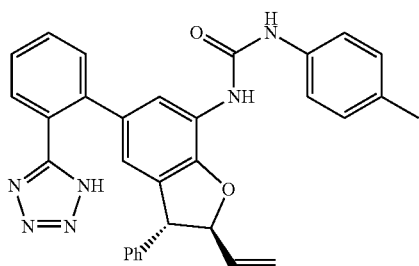 [SMILES: C=C[C@@H]1Oc2c(NC(=O)Nc3ccc(C)cc3)cc(-c3ccccc3-c3nnn[nH]3)cc2[C@H]1c1ccccc1]

Racemic Example 85 material (0.19 g) was purified by chiral SFC (20% MeOH in CO$_2$, Chiralpak AS-H column, 3 ml/min, 40° C., 140 bars) Concentration of the appropriate (earlier eluting) fraction followed by re-purification by reverse-phase HPLC afforded Example 88 (0.053 g) as a colorless solid. MS (ESI): m/z=515 [M+H]$^+$. $^1$H NMR (400 MHz, DMSO-d$_6$): superimposable upon racemate NMR. Concentration of the later-eluting fractions afforded Example 89 (0.073 g) as a white powder. MS (ESI): m/z=515 [M+H]$^+$. $^1$H NMR (400 MHz, DMSO-d$_6$): superimposable upon racemate NMR.

Example 90

(+/−)-1-((trans)-5-(2-(1H-tetrazol-5-yl)phenyl)-3-phenyl-2-ethyl-2,3-dihydrobenzofuran-7-yl)-3-(p-tolyl)urea

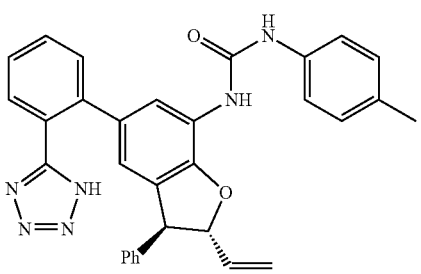 [SMILES: C=C[C@H]1Oc2c(NC(=O)Nc3ccc(C)cc3)cc(-c3ccccc3-c3nnn[nH]3)cc2[C@@H]1c1ccccc1]

To a solution of (+/−)-1-((trans)-5-(2-(1H-tetrazol-5-yl)phenyl)-3-phenyl-2-vinyl-2,3-dihydrobenzofuran-7-yl)-3-(p-tolyl)urea (Example 85) (4.00 mg, 7.77 μmol) in Ethanol (1.5 mL) under nitrogen was added palladium on carbon (4.14 mg, 3.89 μmol). The reaction was placed under 1 atm. of H$_2$ and stirred for 2 h. The reaction was diluted with dichloromethane, treated with a bit of MgSO$_4$, and filtered. The filtrate was stripped, and the residue was dissolved in benzene (1 mL). This solution was frozen and lyophilized to afford Example 90 (0.004 g, 100% yield) as a white powder. MS (ESI): m/z=517 [M+H]$^+$. T$_r$=4.67 (Method BA). $^1$H NMR (400 MHz, DMSO-d$_6$) δ 9.08 (s, 1H), 8.14 (s, 1H), 7.94 (d, 1H, J=1.3 Hz), 7.61 (td, 1H, J=7.5, 1.3 Hz), 7.56 (br. d, 1H, J=6.8 Hz), 7.44-7.51 (m, 2H), 7.23-7.36 (m, 5H), 7.04-7.11 (m, 4H), 6.07 (s, 1H), 4.55 (dt, 1H, J=7.9, 5.9 Hz), 4.33 (d, 1H, J=7.9 Hz), 2.24 (s, 3H), 1.88-1.90 (m, 2H), 1.03 (t, 3H, J=7.3 Hz).

Example 91

(+/−)-N-((trans)-5-(2-(1H-tetrazol-5-yl)phenyl)-3-phenyl-2-vinyl-2,3-dihydrobenzofuran-7-yl)-2-(p-tolyl)acetamide

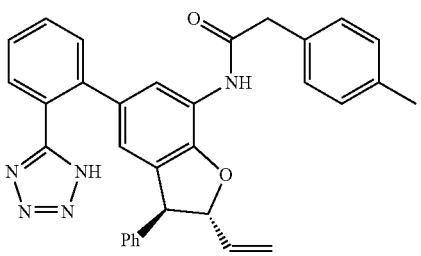 [SMILES: C=C[C@H]1Oc2c(NC(=O)Cc3ccc(C)cc3)cc(-c3ccccc3-c3nnn[nH]3)cc2[C@@H]1c1ccccc1]

91A. (+/−)-N-(7-bromo-5-phenyl-2,5-dihydrobenzo[b]oxepin-9-yl)-2-(p-tolyl)acetamide To a solution of 1E (0.06 g, 0.190 mmol) in DMF (1 mL) was added 4-methylphenylacetic acid (0.031 g, 0.21 mmol) and triethylamine (0.053 mL, 0.380 mmol) followed by BOP (0.101 g, 0.228 mmol). The solution was stirred overnight at 40° C. then diluted with ether and washed with aq. HCl then aq. sodium bicarbonate then water. The organic phase was dried and stripped to afford 91A (0.085 g, 95% yield) as a sticky tan foam. MS (ESI): m/z=450 [M+H]$^+$. T$_r$=4.97 (Method BA).

Example 91

Tandem Suzuki coupling/ring contraction of 91A under the conditions used for the conversion of 1F to Example 85 afforded Example 91 in 47% yield as a white powder. MS (ESI): m/z=514 [M+H]$^+$. T$_r$=4.52 (Method BA). $^1$H NMR (400 MHz, DMSO-d$_6$) δ 9.71 (s, 1H), 7.78 (s, 1H), 7.53-7.63 (m, 2H), 7.41-7.51 (m, 2H), 7.25-7.35 (m, 3H), 7.20 (d, 2H, J=7.9 Hz), 7.11 (d, 2H, J=7.9 Hz), 7.04 (d, 2H, J=8.1 Hz), 6.12-6.22 (m, 2H), 5.27-5.36 (m, 2H), 4.96 (br. t, 1H, J=7.9 Hz), 4.45 (d, 1H, J=8.6 Hz), 3.67 (s, 2H), 2.27 (s, 3H).

Example 92

(+/−)-1-(7-(2-(1H-tetrazol-5-yl)phenyl)-3-methyl-5-phenyl-2,5-dihydrobenzo[b]oxepin-9-yl)-3-(p-tolyl)urea

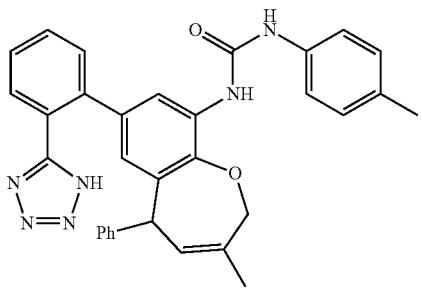 [SMILES: CC1=CC(c2ccccc2)c2cc(-c3ccccc3-c3nnn[nH]3)cc(NC(=O)Nc3ccc(C)cc3)c2OC1]

92A. (+/−)-5-bromo-2-((2-methylallyl)oxy)-1-nitro-3-(1-phenylallyl)benzene

To a stirred, cooled (0° C.) solution of 2-methylprop-2-en-1-ol (0.087 g, 1.206 mmol) and (+/−)-4-bromo-2-nitro-6-(1-phenylallyl)phenol (1B) (0.31 g, 0.928 mmol) and triphenylphosphine (0.316 g, 1.206 mmol) in THF (3 mL) was added DIAD (0.234 mL, 1.206 mmol) over 1 min. The reaction was stirred 2 h, warming to RT. The reaction was partially concentrated and purified by flash chromatography (gradient elution with ether-heptane). Concentration of the appropriate fractions afforded 92A (0.37 g, 98% yield) as an amber oil. $^1$H NMR (400 MHz, DMSO-d$_6$) δ 8.09 (d, 1H, J=2.6 Hz), 7.69 (d, 1H, J=2.4 Hz), 7.34 (t, 2H, J=7.4 Hz), 7.24 (t, 1H, J=7.4 Hz), 7.18 (d, 2H, J=7.0 Hz), 6.40 (ddd, 1H, J=17.0, 10.1, 7.5 Hz), 5.27 (d, 1H, J=10.1 Hz), 5.11 (d, 1H, J=7.3 Hz), 4.95-5.04 (m, 3H), 4.21 (ABq, 2H, J$_{AB}$=11.4 Hz, Δν=45.8 Hz), 1.72 (s, 3H).

92B. (+/−)-7-bromo-3-methyl-5-phenyl-2,5-dihydrobenzo[b]oxepin-9-amine

Compound 92B was prepared from 92A using the methods for the conversion of 1C to 1E MS (ESI): m/z=330 [M+H]$^+$. T$_r$=4.17 (Method BA).

92C. (+/−)-1-(7-bromo-3-methyl-5-phenyl-2,5-dihydrobenzo[b]oxepin-9-yl)-3-(p-tolyl)urea Compound 92C was prepared from 92B using the method for the conversion of 1E to 1F MS (ESI): m/z=465 [M+H]$^+$. T$_r$=5.14 (Method BA).

Example 92

Example 92 was prepared as a white powder in 14% yield from 92C using the methods for the conversion of 1F to Example 87. MS (ESI): m/z=529 [M+H]$^+$. T$_r$=4.67 (Method BA). $^1$H NMR (400 MHz, DMSO-d$_6$) δ 9.13 (s, 1H), 8.39 (s, 1H), 8.05 (d, 1H, J=2.0 Hz), 7.65 (t, 1H, J=8.0 Hz), 7.60 (d, 1H, J=6.8 Hz), 7.54 (d, 1H, J=8.4 Hz), 7.50 (t, 1H, J=7.2 Hz), 7.30 (d, 2H, J=8.4 Hz), 7.25 (t, 2H, J=7.4 Hz), 7.18 (t, 1H, J=6.5 Hz), 7.13 (d, 2H, J=7.3 Hz), 7.07 (d, 2H, 8.4 Hz), 6.30 (d, 1H, 2.0 Hz), 5.73 (br. d, 1H, J=~6.6 Hz), 4.55 (br d, 1H, J=~5.5 Hz), 4.46 (ABq, 2H, J$_{AB}$=16.1 Hz, Δν=83.4 Hz), 2.23 (s, 3H), 1.66 (s, 3H).

Example 93

(+/−)-1-((trans)-5-(2-(1H-tetrazol-5-yl)phenyl)-3-phenyl-2-(prop-1-en-2-yl)-2,3-dihydrobenzofuran-7-yl)-3-(p-tolyl)urea

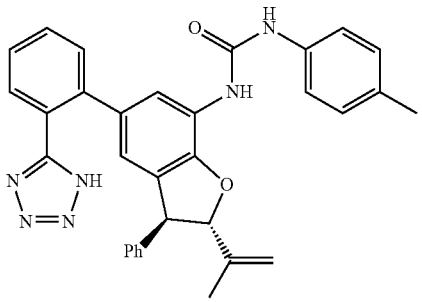 [SMILES: C=C(C)[C@H]1Oc2c(NC(=O)Nc3ccc(C)cc3)cc(-c3ccccc3-c3nnn[nH]3)cc2[C@@H]1c1ccccc1]

Concentration of the later-eluting fraction from the prep. HPLC purification of Example 92 afforded 23% of Example 93 as a white powder. MS (ESI): m/z=529 [M+H]$^+$. T$_r$=4.75 (Method BA). $^1$H NMR (400 MHz, DMSO-d$_6$) δ 9.06 (s, 1H), 8.28 (s, 1H), 7.98 (s, 1H), 7.63 (t, 1H, J=7.8 Hz), 7.57 (d, 1H, J=7.3 Hz), 7.49 (t, 2H, J=7.5 Hz), 7.25-7.36 (m, 5H), 7.08 (d, 2H, J=8.4 Hz), 7.04 (d, 2H, J=7.0 Hz), 6.08 (s, 1H), 4.97-5.02 (m, 3H), 4.51 (d, 1H, J=8.4 Hz), 2.24 (s, 3H), 1.83 (s, 3H).

Example 94

(+/−)-1-((trans)-5-(2-(1H-tetrazol-5-yl)phenyl)-3-(3,3,3-trifluoropropyl)-2-vinyl-2,3-dihydrobenzofuran-7-yl)-3-(p-tolyl)urea

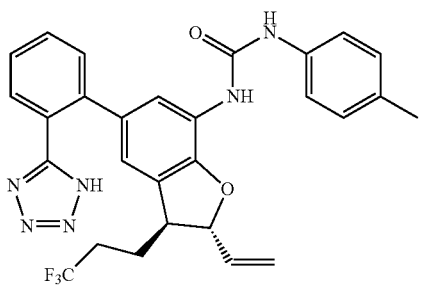 [SMILES: C=C[C@H]1Oc2c(NC(=O)Nc3ccc(C)cc3)cc(-c3ccccc3-c3nnn[nH]3)cc2[C@@H]1CCC(F)(F)F]

94A. (E)-4-bromo-2-nitro-1-((6,6,6-trifluorohex-2-en-1-yl)oxy)benzene

To a stirred, cooled (−78° C.) solution of (E)-6,6,6-trifluorohex-2-en-1-ol (Ciba-Geigy Corporation Patent: U.S. Pat. No. 4,785,004 A1, 1988) (4.29 g, 19.50 mmol) in THF (15 mL) was added BuLi (7.50 mL, 18.75 mmol), dropwise over 1-2 min. The solution was stirred 2-3 min. then treated with 4-bromo-1-fluoro-2-nitrobenzene (3.30 g, 15 mmol) as-a single portion. The dry ice bath was removed, and the solution was stirred 1 h (During this time the reaction warmed to a temperature slightly above ambient, indicating that care should be taken to avoid exotherm if this reaction is run on significantly larger scale) then quenched with aq. HOAc. The resulting mixture was extracted with ether, and the organic extract was dried, stripped, and chromatographed on silica gel (gradient elution with ether-hexanes). Concentration of the appropriate fractions afforded 94A (3.9 g, 70% yield) as a pale orange oil. $^1$H NMR (400 MHz, chloroform-d) δ 7.99 (d, J=2.4 Hz, 1H), 7.63 (dd, J=8.9, 2.4 Hz, 1H), 6.98 (d, J=8.9 Hz, 1H), 6.01-5.85 (m, 1H), 5.83-5.71 (m, 1H), 4.65 (dd, J=5.3, 1.2 Hz, 2H), 2.48-2.34 (m, 2H), 2.31-2.13 (m, 2H).

94B. (+/−)-4-bromo-2-nitro-6-(6,6,6-trifluorohex-1-en-3-yl)phenol

Compound 94A (0.2 g, 0.565 mmol) was dissolved in diglyme (1 mL) and degassed. This solution was placed under nitrogen and heated at 160° C. for 90 h. TLC and LCMS suggest that reaction has proceeded to about 50% conversion. The reaction was chromatographed on silica gel (gradient elution with ether-hexanes). Concentration of the appropriate fraction afforded 94B (0.075 g, 36% yield) as a pale yellow oil. $^1$H NMR (400 MHz, DMSO-d$_6$) δ 10.70 (br. s, 1H), 8.02 (d, J=2.4 Hz, 1H), 7.74 (d, 2.4 Hz, 1H), 5.97-6.07 (m, 1H), 5.13 (d, J=15.9 Hz, 1H), 5.12 (d, J=12.1 Hz, 1H), 3.78-3.86 (m, 1H), 2.09-2.27 (m, 2H), 1.84-1.98 (m, 2H).

94C. (+/−)-2-(allyloxy)-5-bromo-1-nitro-3-(6,6,6-trifluorohex-1-en-3-yl)benzene To a stirred, cooled (0° C.) solution of prop-2-en-1-ol (0.069 g, 1.186 mmol), 94B (0.35 g, 0.988 mmol) and triphenylphosphine (0.311 g, 1.186 mmol) in THF (1 mL) was added DIAD (0.231 mL, 1.186 mmol) over 1 min. The reaction was stirred 2 h, warming to RT. The reaction was partially concentrated and purified by flash chromatography (gradient elution with ether-heptane). Concentration of the appropriate fractions afforded 94C (0.37 g, 90% yield) as an amber oil. $^1$H NMR (400 MHz, DMSO-d$_6$) δ 8.06 (d, J=2.4 Hz, 1H), 7.91 (d, 2.4 Hz, 1H), 5.95-6.07 (m, 2H), 5.34-5.40 (m, 1H), 5.26-5.29 (m, 1H), 5.15 (d, 1H, J=9.0 Hz), 5.12 (d, J=17 Hz, 1H), 4.40-4.48 (m, 2H), 3.71-3.78 (m, 1H), 1.79-2.29 (m, 4H).

94D. (+/−)-7-bromo-9-nitro-5-(3,3,3-trifluoropropyl)-2,5-dihydrobenzo[b]oxepine A solution of 94C (0.36 g, 0.913 mmol) in ClCH$_2$CH$_2$Cl (12 ml) was degassed by bubbling nitrogen through it for 15 min. The solution was treated with the second-generation Grubbs catalyst (0.039 g, 0.046 mmol), placed under nitrogen, and heated to 55° C. for 1.h. TLC shows spot-to spot (Rf ~0.6 to Rf ~0.5 in 10% ether-hexanes) conversion. The reaction was concentrated and chromatographed on silica gel (hexanes to 30% ether-hexanes gradient). Concentration of the appropriate fractions afforded 94D (0.32 g, 91% yield) as an amber oil. $^1$H NMR (400 MHz, DMSO-d$_6$) δ 8.06 (d, J=2.4 Hz, 1H), 7.78 (d, 2.4 Hz, 1H), 5.86-5.94 (m, 1H), 5.58-5.65 (m, 1H), 4.77-4.84 (m, 1H), 4.51-4.57 (m, 1H), 3.50-3.57 (m, 1H), 1.95-2.36 (m, 4H).

94E. (+/−)-7-bromo-5-(3,3,3-trifluoropropyl)-2,5-dihydrobenzo[b]oxepin-9-amine To a solution of 94D (0.31 g, 0.847 mmol) in ethanol (5 mL) was added 0.4 mL of water followed by ammonium chloride (0.679 g, 12.70 mmol). This mixture was stirred 5 min, then treated with zinc (0.830 g, 12.70 mmol). The reaction was stirred 15 min., diluted with dichloromethane and filtered. The filtrate was washed with water, dried, and stripped to afford 94E (0.29 g, 97% yield) as an amber oil. MS (ESI): m/z=336 [M+H]$^+$. T$_r$=3.92 (Method BA).

94F. (+/−)-1-(7-bromo-5-(3,3,3-trifluoropropyl)-2,5-dihydrobenzo[b]oxepin-9-yl)-3-(p-tolyl)urea To a solution of 94E (0.24 g, 0.714 mmol) in THF (1 mL) was added 1-isocyanato-4-methylbenzene (0.133 g, 1.000 mmol). This solution was stirred at 55° C. for 1.5 h then cooled and stirred overnite at RT. The reaction was purified by flash chromatography (gradient elution with ether-hexanes). Concentration of the appropriate fractions afforded 94F (0.32 g, 91% yield) as an off-white powder. MS (ESI): m/z=469 [M+H]$^+$. T$_r$=4.98 (Method BA).

Example 94

Example 94 was prepared as a in 46% yield from 94F using the methods for the conversion of 1F to Example 85. MS (ESI): m/z=535 [M+H]$^+$. T$_r$=4.47 (Method BA). $^1$H NMR (400 MHz, DMSO-d$_6$) δ 9.01 (s, 1H), 8.19 (s, 1H), 7.88 (s, 1H), 7.59-7.64 (m, 2H), 7.49-7.53 (m, 2H), 7.30 (d, 2H, J=8.4 Hz), 7.07 (d, 2H, 8.4 Hz), 6.46 (d, 1H, 1.0 Hz), 6.00-6.08 (m, 1H), 5.47 (d, 1H, J=16.8 Hz), 5.27 (d, 1H, J=10.4 Hz), 5.06 (t, 1H, J=6.7 Hz), 3.22-3.28 (m, 1H), 2.17-2.31 (m, 5H), 1.74-1.80 (m, 2H).

Examples 95 to 99: Suzuki coupling as shown in the scheme below of bromide 92C with the appropriate aryboronic acids QB(OH)$_2$ under the conditions described for the conversion of 1F to Example 85 afforded Example 96 and Example 97 (Table 30 below). Similarly, 1F affords Example 98. Example 95 was prepared from 1E and 2-fluorophenylisocyanate using the procedures for the conversion of 1E to Example 85, and Example 99 was prepared from 94E and 4-ethylphenylisocyanate using the same protocol. (All entries are racemic).

| Ex. | Q | R² | R' | R¹ | T$_r$ (min) | (M + H)⁺ |
|---|---|---|---|---|---|---|
| 95 | 2-(1H-tetrazol-5-yl)phenyl | Ph | H | 2-fluorophenyl | 1.01$^{acgt}$ | 519 |
| 96 | 2-carboxyphenyl | Ph | Me | 4-methylphenyl | 4.87 METHOD BA | 505 |
| 97 | 3-carboxy-4-methoxyphenyl | Ph | Me | 4-methylphenyl | 4.86 METHOD BA | 535 |
| 98 | 2-carboxy-4-fluorophenyl | Ph | H | 4-methylphenyl | 4.85 METHOD BA | 509 |
| 99 | 2-(1H-tetrazol-5-yl)phenyl | CH₂CH₂CF₃ | H | 4-ethylphenyl | 4.71 METHOD BA | 549 |

Example 100

1-((trans)-5-(2-(1H-tetrazol-5-yl)phenyl)-3-(3,3,3-trifluoropropyl)-2-vinyl-2,3-dihydrobenzofuran-7-yl)-3-(p-tolyl)urea (Enantiomer 1, Absolute Stereochemistry Unknown)

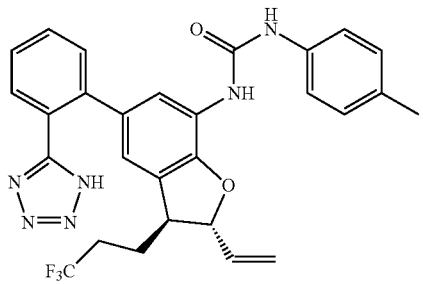 [SMILES: C=C[C@H]1Oc2c(NC(=O)Nc3ccc(C)cc3)cc(-c3ccccc3-c3nnn[nH]3)cc2[C@@H]1CCC(F)(F)F]

And

Example 101

1-((trans)-5-(2-(1H-tetrazol-5-yl)phenyl)-3-(3,3,3-trifluoropropyl)-2-vinyl-2,3-dihydrobenzofuran-7-yl)-3-(p-tolyl)urea (Enantiomer 2, Absolute Stereochemistry Unknown)

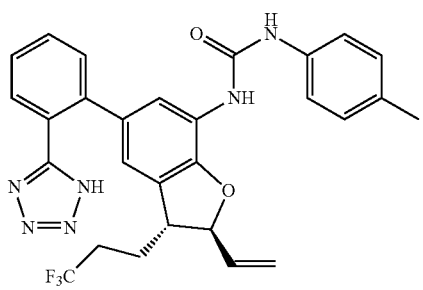 [SMILES: C=C[C@@H]1Oc2c(NC(=O)Nc3ccc(C)cc3)cc(-c3ccccc3-c3nnn[nH]3)cc2[C@H]1CCC(F)(F)F]

Racemic Example 94 material (0.144 g) was purified by chiral SFC (20% MeOH in $CO_2$, Chiralpak AS-H column, 3 ml/min, 40° C., 100 bars) Concentration of the appropriate (earlier eluting) fraction followed by re-purification by reverse-phase HPLC afforded 1-((trans)-5-(2-(1H-tetrazol-5-yl)phenyl)-3-(3,3,3-trifluoropropyl)-2-vinyl-2,3-dihydrobenzofuran-7-yl)-3-(p-tolyl)urea (Example 100) (0.053 g) as a colorless solid. MS (ESI): m/z=535 [M+H]$^+$. $t_R$=4.56$^{METHOD\ BA}$ $^1$H NMR (400 MHz, DMSO-$d_6$): superimposable upon racemate NMR. Concentration of the later-eluting fractions afforded 1-((trans)-5-(2-(1H-tetrazol-5-yl)phenyl)-3-(3,3,3-trifluoropropyl)-2-vinyl-2,3-dihydrobenzofuran-7-yl)-3-(p-tolyl)urea (Example 101) (0.073 g) as a white powder. MS (ESI): m/z=535 [M+H]$^+$. $T_r$=4.55 (Method BA). $^1$H NMR (400 MHz, DMSO-$d_6$): superimposable upon racemate NMR.

Examples 102 to 104: Hydrogenation as shown in the scheme below of the appropriate olefinic compounds prepared in the preceeding Examples and represented as XL under the conditions described for the conversion of Example 85 to Example 90 affords Examples 102 to 104 shown in the table below. (All entries are racemic).

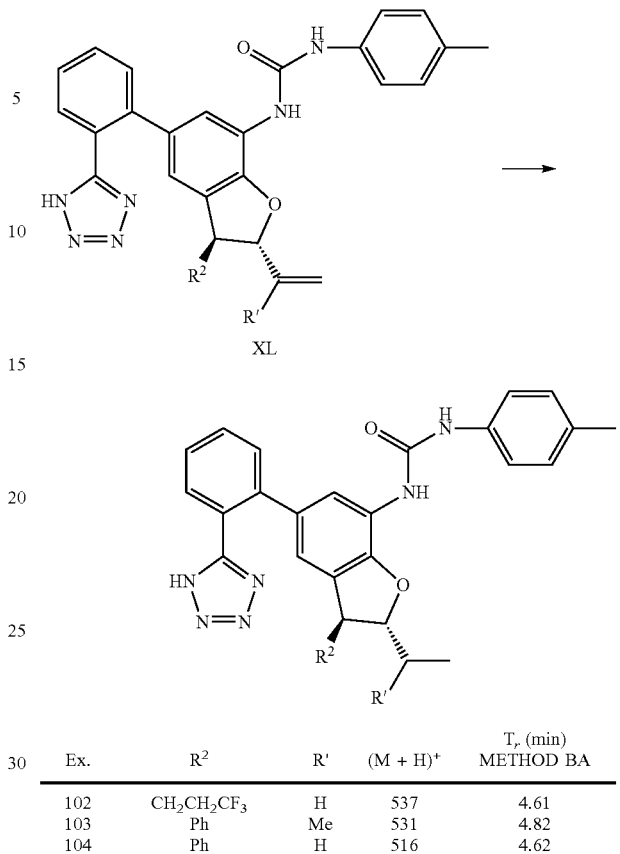

| Ex. | $R^2$ | R' | (M + H)$^+$ | $T_r$ (min) METHOD BA |
|---|---|---|---|---|
| 102 | $CH_2CH_2CF_3$ | H | 537 | 4.61 |
| 103 | Ph | Me | 531 | 4.82 |
| 104 | Ph | H | 516 | 4.62 |

Example 105

(+/−)-1-(7-(2-(1H-tetrazol-5-yl)phenyl)-5-phenyl-2,5-dihydrobenzo[b]oxepin-9-yl)-3-(4-chloro-2-fluorophenyl)urea

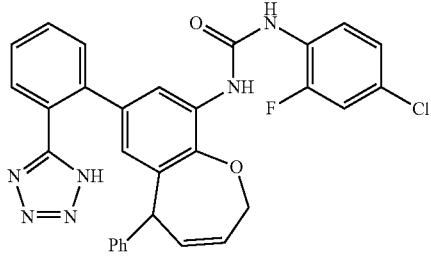 [SMILES: O=C(Nc1ccc(Cl)cc1F)Nc1cc(-c2ccccc2-c2nnn[nH]2)cc2c1OCC=CC2c1ccccc1]

105A. (+/−)-7-(2-(1H-tetrazol-5-yl)phenyl)-5-phenyl-2,5-dihydrobenzo[b]oxepin-9-amine Compound 105A was prepared as a colorless glass in 22% yield from (+/−)-7-bromo-5-phenyl-2,5-dihydrobenzo[b]oxepin-9-amine (1E) using the conditions described for the conversion of 1F to Example 85. MS (ESI): m/z=382 [M+H]$^+$. $T_r$=3.29 (Method BA).

Example 105

Example 105 was prepared from 105A and 4-chloro-2-fluoro-1-isocyanatobenzene using the procedure for the conversion of 94E to 94F. MS (ESI): m/z=553 [M+H]⁺. $T_r$=4.72 (Method BA). ¹H NMR (400 MHz, DMSO-d₆) δ 9.31 (s, 1H), 8.95 (s, 1H), 8.18 (t, 1H, J=8.9 Hz), 8.03 (s, 1H), 7.56-7.62 (m, 2H), 7.43-7.52 (m, 3H), 7.16-7.28 (m, 6H), 6.45 (d, 1H, J=2.0 Hz), 5.94-6.00 (m, 1H), 5.80 (br. d, 1H, J=11.9 Hz), 4.63 (ABq, 2H, $J_{AB}$=17.3 Hz, Δv=155 Hz), 4.58 (d, 1H, J=6.4 Hz).

Example 106

(+/−)-1-(7-(2-(1H-tetrazol-5-yl)phenyl)-5-phenyl-2,5-dihydrobenzo[b]oxepin-9-yl)-3-(4-bromophenyl)urea

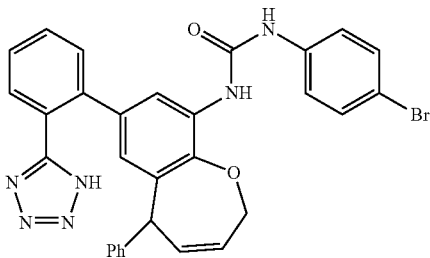 [SMILES: O=C(Nc1ccc(Br)cc1)Nc1cc(-c2ccccc2-c2nnn[nH]2)cc2c1OCC=CC2c1ccccc1]

Example 106 was prepared as a white powder in 57% yield from 105A and 4-bromo-1-isocyanatobenzene using the procedure for the conversion of 94E to 94F. MS (ESI): m/z=579 [M+H]⁺. $T_r$=4.67 (Method BA). ¹H NMR (400 MHz, DMSO-d₆) δ 9.38 (s, 1H), 8.46 (s, 1H), 8.03 (s, 1H), 7.66 (t, 1H, J=7.7 Hz), 7.61 (d, 1H, J=7.0 Hz), 7.55 (d, 1H, J=7.5 Hz), 7.51 (t, 1H, J=6.2 Hz), 7.36-7.45 (m, 4H), 7.23-7.28 (m, 2H), 7.14-7.20 (m, 3H), 6.38 (d, 1H, J=2.0 Hz), 5.92-5.99 (m, 1H), 5.79 (br. d, 1H, J=13.4 Hz), 4.62 (ABq, 2H, $J_{AB}$=15.9 Hz, Δv=118 Hz), 4.61 (br. d, 1H, J=6.6 Hz).

Example 107

(+/−)-1-(7-(2-(1H-tetrazol-5-yl)phenyl)-5-(3,3,3-trifluoropropyl)-2,5-dihydrobenzo[b]oxepin-9-yl)-3-(4-ethylphenyl)urea

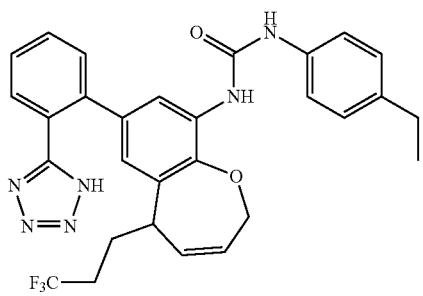 [SMILES: CCc1ccc(NC(=O)Nc2cc(-c3ccccc3-c3nnn[nH]3)cc3c2OCC=CC3CCC(F)(F)F)cc1]

107A. (+/−)-7-(2-(1H-tetrazol-5-yl)phenyl)-5-(3,3,3-trifluoropropyl)-2,5-dihydrobenzo[b]oxepin-9-amine 107A was prepared as a colorless glass in 27% yield from 94E using the conditions described for the conversion of 1F to Example 85. This aniline was taken to the next step without characterization.

Example 107

Example 107 was prepared as a white powder in 55% yield from 107A and 4-ethyl-1-isocyanatobenzene using the procedure for the conversion of 94E to 94F. MS (ESI): m/z=549 [M+H]⁺ $T_r$=4.68 (Method BA). ¹H NMR (400 MHz, DMSO-d₆) δ 9.20 (s, 1H), 8.43 (s, 1H), 8.09 (d, 1H, J=2.0 Hz), 7.61-7.68 (m, 2H), 7.51-7.57 (m, 2H), 7.33 (d, 2H, J=8.4 Hz), 7.11 (d, 2H, J=8.6 Hz), 6.29 (d, 1H, J=2.2 Hz), 5.81-5.83 (m, 1H), 5.57 (br. d, 1H, J=11.4 Hz), 4.52 (ABq, 2H, $J_{AB}$=17.2 Hz, Δv=158 Hz), 3.10-3.16 (m, 1H), −2.53 (m, integration, exact chemical shift range obscured by solvent), 1.83-2.12 (m, 4H), 1.15 (5, 3H, J=7.6 Hz).

Example 108

(+/−)-4-fluoro-2-(5-phenyl-9-(3-(p-tolyl)ureido)-2,3,4,5-tetrahydrobenzo[b]oxepin-7-yl)benzoic acid

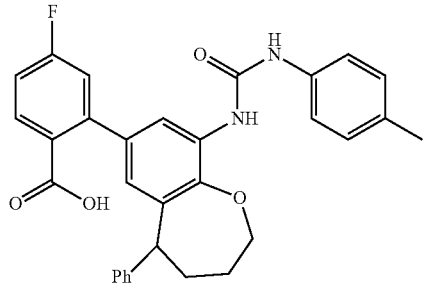 [SMILES: Cc1ccc(NC(=O)Nc2cc(-c3cc(F)ccc3C(=O)O)cc3c2OCCCC3c2ccccc2)cc1]

108A. (+/−)-1-(7-bromo-5-phenyl-2,3,4,5-tetrahydrobenzo[b]oxepin-9-yl)-3-(p-tolyl)urea A solution of 1-(7-bromo-5-phenyl-2,5-dihydrobenzo[b]oxepin-9-yl)-3-(p-tolyl)urea (0.05 g, 0.111 mmol) (1F) in ethyl acetate (2 mL) was treated with 10 wt. % palladium on carbon (24 mg) and stirred under 1 atm. of H₂ for 2 h. The reaction was then treated with an additional 9 mg of catalyst and stirred for 3 h longer. LCMS indicates almost no starting material remains, so the reaction was diluted with dichloromethane, treated with a little MgSO₄, filtered, and stripped to afford (+/−)-1-(7-bromo-5-phenyl-2,3,4,5-tetrahydrobenzo[b]oxepin-9-yl)-3-(p-tolyl)urea (108A) (0.05 g, 95% yield) as an off-white solid. MS (ESI): m/z=453 [M+H]⁺ $t_R$=5.05$^{METHOD\ BA}$.

Example 108

Example 108 was prepared in 53% yield as an off-white powder from 108A and 2-borono-4-fluorobenzoic acid using the conditions described for the conversion of 1F to Example 85. MS (ESI): m/z=511 [M+H]⁺. $T_r$=4.87 (Method BA). ¹H NMR (400 MHz, DMSO-d₆) δ 12.70 (br. s, 1H), 9.25 (s, 1H), 8.48 (s, 1H), 8.16 (d, 1H, J=2.2 Hz), 7.71 (dd, 1H, J=8.6, 5.9 Hz), 7.34 (d, 2H, J=8.4 Hz), 7.30 (d, 2H, J=7.3 Hz), 7.18-7.24 (m, 4H), 7.03-7.11 (m, 3H), 6.39 (d, 1H, J=2.0 Hz), 4.33 (br. d, 1H, J=9.0 Hz), 3.99-4.11 (m, 2H), 1.85-2.26 (m, 7H).

Example 109

(+/−)-1-((cis)-7-(2-(1H-tetrazol-5-yl)phenyl)-3-methyl-5-phenyl-2,3,4,5-tetrahydrobenzo[b]oxepin-9-yl)-3-(p-tolyl)urea

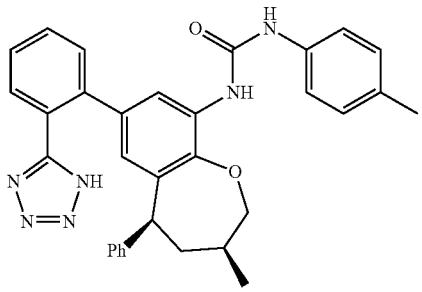 [SMILES: Cc1ccc(NC(=O)Nc2cc(-c3ccccc3-c3nnn[nH]3)cc3c2OC[C@@H](C)C[C@H]3c2ccccc2)cc1]

Example 109 was prepared as a white powder in quantitative yield as from Example 92 using the conditions described for the conversion of Example 85 to Example 90. MS (ESI): m/z=531 [M+H]+. T$_r$=4.75 (Method BA). $^1$H NMR (400 MHz, DMSO-d$_6$) δ 9.22 (s, 1H), 8.38 (s, 1H), 7.95 (s, 1H), 7.71 (dd, 1H, J=7.3, 1.5 Hz), 7.16-7.45 (m, ~6H), 7.05-7.10 (m, 4H), 6.97 (d, 2H, J=7.0 Hz), 6.62 (d, 1H, J=2.0 Hz), 4.38-4.45 (m, 2H), 4.15 (br. d, 1H, J=11.2 Hz), 2.23 (s, 3H), 1.01-1.64 (m, integration uncertain due to resonances from aliphatic impurity), 0.87 (d, 3H, J=6.6 Hz).

Example 110

(+/−) 1-(7-(2-(1H-tetrazol-5-yl)phenyl)-3,3-difluoro-5-phenyl-2,3,4,5-tetrahydrobenzo[b]oxepin-9-yl)-3-(p-tolyl)urea

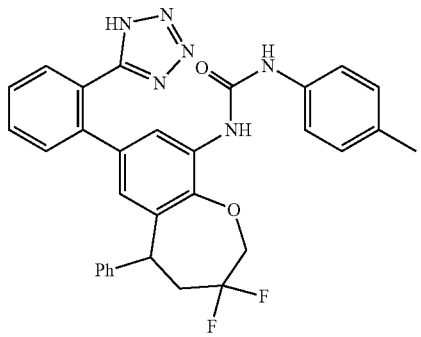 [SMILES: Cc1ccc(NC(=O)Nc2cc(-c3ccccc3-c3nnn[nH]3)cc3c2OCC(F)(F)CC3c2ccccc2)cc1]

110A: (+/−)9-amino-7-bromo-5-phenyl-2,3,4,5-tetrahydrobenzo[b]oxepin-4-ol and 110B: 9-amino-7-bromo-5-phenyl-2.3A5-tetrahydrobenzo[b]oxepin-3-ol

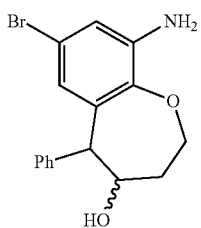 + 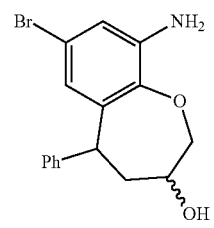

To a solution of 7-bromo-5-phenyl-2,5-dihydrobenzo[b]oxepin-9-amine (1E) (320 mg, 1.012 mmol) in THF (20 mL) at 0° C. was added 1 M BH$_3$ in THF (2.024 mL, 2.024 mmol) slowly. The mixture was stirred at 0° C. for 4 h. HPLC showed still starting material left. BH$_3$ in THF (2 mL) was added and the mixture was stirred at 0° C. for 30 min. Then 3N NaOH (3.37 mL, 10.12 mmol) was added followed by 50% H$_2$O$_2$ in water (1.376 mL, 20.24 mmol). The mixture was stirred at RT 30 min. Diluted with saturated NH$_4$Cl and EtOAc. The organic phase was separated and washed with brine, dried over MgSO$_4$, filtered and concentrated. The residue was purified with ISCO 80 g column, 65 mL/min. 0-100% EtOAC/CH$_2$Cl$_2$ in 25 min. Isomer 1 was eluted with 20% EtOAc/CH$_2$Cl$_2$ to give 110A (87 mg, 0.260 mmol, 25.7% yield) MS: Anal. Calc'd for C$_{16}$H$_{16}$BrNO$_2$ 333.036, found [M+H] 334.0, 336.0 LC: T$_r$=2.427 min (Method A) Isomer 2 was eluted with 60% EtOAc/CH$_2$C$_{1-2}$ to give 110B (76 mg, 0.227 mmol, 22.47% yield) MS: Anal. Calc'd for C$_{1-6}$H$_{16}$BrNO$_2$ 333.036, found [M+H] 334.0, 336.0 LC: T$_r$=2.733 min (Method A).

110C: 1-(7-bromo-3-hydroxy-5-phenyl-2,3,4,5-tetrahydrobenzo[b]oxepin-9-yl)-3-(p-tolyl)urea (Mixture of Diastereomers)

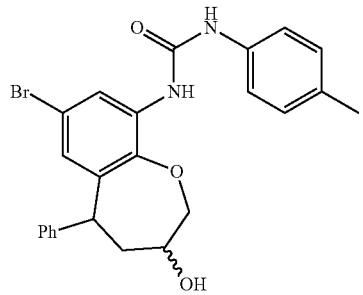 [SMILES: Cc1ccc(NC(=O)Nc2cc(Br)cc3c2OCC(O)CC3c2ccccc2)cc1]

To a solution of 110B (71 mg, 0.212 mmol) in THF (2 mL) at RT was added 1-isocyanato-4-methylbenzene (56.6 mg, 0.425 mmol), followed by triethylamine (0.089 mL, 0.637 mmol). The mixture was stirred at 50° C. for 2 h, then cooled to RT and diluted with EtOAc and water. The organic phase was separated and washed with brine, dried over MgSO$_4$, filtered and concentrated. The residue was purified by ISCO 24 g, 35 mL/min. 0-100% EtOAc/Hexane in 25 min. The desired product was eluted with 85% EtOAc/Hexane. Concentration of the appropriate fractions afforded 110C (32 mg, 0.068 mmol, 31.9% yield) as an off white solid. MS: Anal. Calc'd for C$_{24}$H$_{23}$BrN$_2$O$_3$ 466.1, found [M+H] 467.2. LC: T$_r$=1.08 min (Method AA).

110D: (+/−)1-(7-bromo-3-oxo-5-phenyl-2,3,4,5-tetrahydrobenzo[b]oxepin-9-yl)-3-(p-tolyl)urea

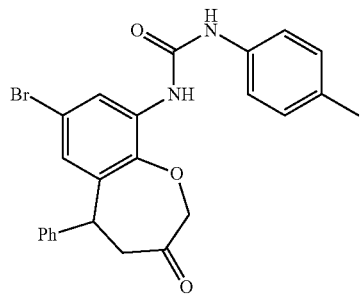 [SMILES: Cc1ccc(NC(=O)Nc2cc(Br)cc3c2OCC(=O)CC3c2ccccc2)cc1]

To a suspension of 110C (34 mg, 0.073 mmol) in CH$_2$Cl$_2$ (6 mL) at RT was added Dess-Martin periodinane (93 mg, 0.218 mmol). The mixture was stirred at RT for 4 days, treated with saturated NaHCO$_3$ and extracted with CH$_2$Cl$_2$. The organic phase was washed with brine and filtered. The filtrate was dried over MgSO$_4$, filtered, and concentrated. The residue was purified with ISCO 24 g column, 35 mL/min. 0-50% EtOAc/Hexane in 20 min. The desired product was eluted with 35% EtOAc/Hexane. to give HOD (23 mg, 0.044 mmol, 61.1% yield) as light brown solid. $^1$H NMR (400 MHz, CHLOROFORM-d) δ 8.42 (d, J=2.2 Hz, 1H), 7.58 (s, 1H), 7.40-7.16 (m, 7H), 7.09 (d, J=7.3 Hz, 2H), 6.90 (br. s., 1H), 6.71 (d, J=2.0 Hz, 1H), 4.45-4.30 (m, 2H), 4.30-4.22 (m, 1H), 3.44 (dd, J=13.2, 9.7 Hz, 1H), 3.14 (dd, J=13.2, 4.4 Hz, 1H), 2.36 (s, 3H) MS: Anal. Calc'd for C$_{24}$H$_{21}$BrN$_2$O$_3$ 464.074, found [M+H] 465.0, 467.0 LC: T$_r$=3.766 min (Method A).

110E: (+/−)1-(7-bromo-3,3-difluoro-5-phenyl-2,3,4,5-tetrahydrobenzo[b]oxepin-9-yl)-3-(p-tolyl)urea

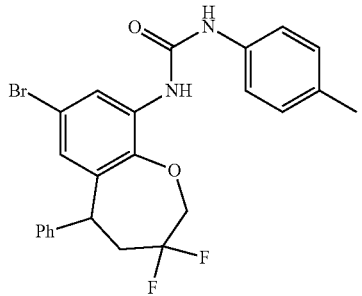 [SMILES: Cc1ccc(NC(=O)Nc2cc(Br)cc3c2OCC(F)(F)CC3c2ccccc2)cc1]

To a solution of 110D (20 mg, 0.043 mmol) in CH$_2$Cl$_2$ (1 mL) at −15° C. was added Diethylaminosulfur trifluoride (0.028 mL, 0.215 mmol). The mixture was stirred at −15° C. and slowly warmed to 0° C. for 1 h, diluted with CH$_2$Cl$_2$ and saturated NaHCO$_3$. Organic was separated and washed with brine, dried over MgSO$_4$, filtered and concentrated to give a crude mixture. The crude mixture was purified with ISCO 12 g column, 0-15% EtOAc/Hexane in 20 min. The desired product was concentrated to give 110E (9 mg, 0.018 mmol, 42.5% yield) as slight yellow solid. MS: Anal. Calc'd for C$_{24}$H$_{21}$BrF$_2$N$_2$O$_2$ 486.075, found [M+H] 487.0, 489.0 LC: T$_r$=4.00 min (Method A).

110F: (+/−) 1-(7-(2-cyanophenyl)-3,3-difluoro-5-phenyl-2,3,4,5-tetrahydrobenzo[b]oxepin-9-yl)-3-(p-tolyl)urea

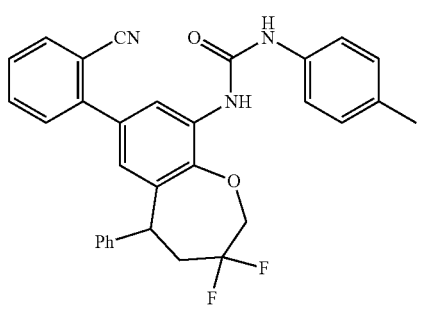 [SMILES: Cc1ccc(NC(=O)Nc2cc(-c3ccccc3C#N)cc3c2OCC(F)(F)CC3c2ccccc2)cc1]

To a solution of 110D (6 mg, 0.012 mmol) in dioxane (0.2 mL) at RT was added 2-(5,5-dimethyl-1,3,2-dioxaborinan-2-yl)benzonitrile (5.30 mg, 0.025 mmol). The mixture was purged with N$_2$ for 5 min. Then potassium phosphate, dibasic (6.43 mg, 0.037 mmol) and PdCl$_2$(dppf)-CH2Cl2 Adduct (1.005 mg, 1.231 µmol) were added. The mixture was sealed and heated at 95° C. for 17 h. The reaction was cooled to RT, diluted with MeOH, and filtered to remove insoluble material. The filtrate was purified with prep HPLC (3 injections) (Waters Xbridge C18 19×100 mm), 20 mL/min flow rate with gradient of 20% B-100% B over 10 min Hold at 100% B for 6 min. (A: 0.1% TFA in water/MeOH (90:10), B: 0.1% TFA in water/MeOH (10:90) monitoring at 220. After concentration of desired fraction, 110F (4 mg, 7.69 µmol, 62.5% yield) was obtained as off white solid. MS: Anal. Calc'd for C$_{31}$H$_{25}$F$_2$N$_3$O$_2$ 509.191, found [M+H] 510.2 LC: T$_r$=3.89 min (Method A).

110G: (+/−) 7-(2-(1H-tetrazol-5-yl)phenyl)-3,3-difluoro-5-phenyl-2,3,4,5-tetrahydrobenzo[b]oxepin-9-amine

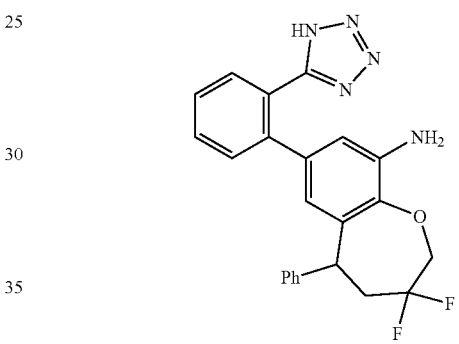

To a solution of 110F (4 mg, 7.85 µmol) in PhCH$_3$ (0.2 mL) at RT was added azidotributyltin (7.31 µl, 0.027 mmol). The mixture was stirred overnight at 105° C. then cooled to RT. The reaction was diluted with MeOH and purified by prep HPLC (2 injections) (Waters Xbridge C18 19×100 mm), 20 mL/min flow rate with gradient of 20% B-100% B over 10 min Hold at 100% B for 5 min. (A: 0.1% TFA in water/MeOH (90:10), B: 0.1% TFA in water/MeOH (10:90) monitoring at 220. After concentration, 110G (2.8 mg, 5.34 µmol, 68.0% yield) was obtained. MS: Anal. Calc'd for C$_{23}$H$_{19}$F$_2$N$_5$O 419.156, found [M+H] 420.2 LC: T$_r$=2.831 min (Method A).

Example 110

To a solution of 110G (2.8 mg, 5.39 µmol) in THF (0.1 mL) at RT was added 1-isocyanato-4-methylbenzene (1.437 mg, 10.79 µmol), followed by triethylamine (2.256 µl, 0.016 mmol). The reaction was stirred at 50° C. for 30 min., becoming a white suspension. The reaction was diluted with DMF and purified by prep HPLC (Waters Xbridge C18 19×100 mm), 20 mL/min flow rate with gradient of 20% B-100% B over 10 min Hold at 100% B for 5 min. (A: 0.1% TFA in water/MeOH (90:10), B: 0.1% TFA in water/MeOH (10:90) monitoring at 220. The desired product was eluted at 10.979 min. After concentration, Example 110 (0.38 mg, 0.688 µmol, 12.75% yield) was obtained as white solid, $^1$H NMR (500 MHz, CHLOROFORM-d) § 8.04 (d, J=2.2 Hz, 1H), 7.99-7.92 (m, 1H), 7.53-7.44 (m, 2H), 7.35 (d, J=6.9

Hz, 2H), 7.32-7.19 (m, 7H), 7.00 (d, J=7.2 Hz, 2H), 6.68 (s, 1H), 5.94 (d, J=1.7 Hz, 1H), 4.39-4.27 (m, 2H), 3.84-3.72 (m, 1H), 2.69-2.56 (m, 1H), 2.56-2.44 (m, 1H), 2.42 (s, 3H) MS: Anal. Calc'd for $C_{31}H_{26}F_2N_6O_2$ 552.209, found [M+H] 553.2 LC: $T_r$=3.675 min (Method A)

Example 111 rac-3-((2R,3S)-2-cyclopropyl-3-phenyl-7-(3-(p-tolyl)ureido)-2,3-dihydrobenzofuran-5-yl)butanoic acid

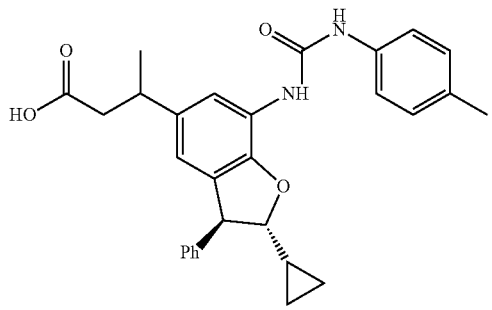 [SMILES: Cc1ccc(NC(=O)Nc2cc(C(C)CC(=O)O)cc3c2O[C@H](C2CC2)[C@H]3c2ccccc2)cc1]

111A: rac-(2R,3S)-5-bromo-7-nitro-3-phenyl-2-vinyl-2,3-dihydrobenzofuran

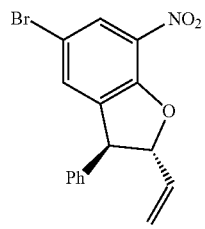 [SMILES: C=C[C@H]1Oc2c(cc(Br)cc2[N+](=O)[O-])[C@@H]1c1ccccc1]

A solution of 1D (400 mg, 1.155 mmol) in dioxane (5 mL) was purged with $N_2$ for 15 min then treated with tetrakis(triphenylphosphine)palladium(0) (66.8 mg, 0.058 mmol). This mixture was purged with $N_2$ for a further 5 min. then stirred under $N_2$ for over 2 days. The dark brown solution was concentrated, and the residue was purified by ISCO 80 g column, 60 mL/min. 0-15% EtOAc/Hexane in 30 min. Concentration of the appropriate fractions afforded 111A (140 mg, 0.400 mmol, 34.7% yield) as light yellow solid. $^1$H NMR (400 MHZ, CHLOROFORM-d) δ 8.14 (dd, J=2.0, 0.9 Hz, 1H), 7.47-7.26 (m, 4H), 7.25-7.11 (m, 2H), 6.11 (ddd, J=17.1, 10.5, 6.8 Hz, 1H), 5.45-5.34 (m, 2H), 5.34-5.24 (m, 1H), 4.43 (d, J=8.4 Hz, 1H) MS: Anal. Calc'd for $C_{16}H_{12}BrNO_3$ 345.00, found [M−H] 344.1 LC: $T_r$=3.723 min (Method A).

111B: rac-(2R,3S)-5-bromo-2-cyclopropyl-7-nitro-3-phenyl-2,3-dihydrobenzofuran

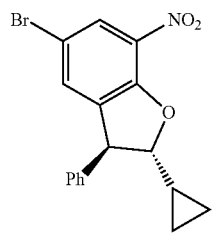 [SMILES: O=[N+]([O-])c1cc(Br)cc2c1O[C@H](C1CC1)[C@H]2c1ccccc1]

A solution of diazomethane in ether was generated by treatment of N-Methyl-N'-nitro-N-nitrosoguanidine (2378 mg, 8.09 mmol) in 10 mL of ether with 40% aqueous KOH (3 mL). The diazomethane solution was added slowly at 0° C. to a stirred solution of rac-(2R,3S)-5-bromo-7-nitro-3-phenyl-2-vinyl-2,3-dihydrobenzofuran (140 mg, 0.404 mmol) (111A) in diethyl ether (5 mL). The clear solution became blackish and bubbles evolved. After addition, the mixture was stirred at 0° C. for 30 min. then filtered through celite. The filtrate was concentrated, and the residue was purified with ISCO 24 g column, 35 mL/min. 0-10% EtOAc/Hexane in 10 min. The desired product was eluted with 5% EtOAc/Hexane. Combined tube 22-25. After concentration, 111B (125 mg, 0.330 mmol, 82% yield) was obtained as light yellow solid. $^1$H NMR (500 MHz, CHLOROFORM-d) δ 8.15 (dd, J=1.9, 0.8 Hz, 1H), 7.44-7.34 (m, 3H), 7.32-7.24 (m, 1H), 7.23-7.11 (m, 2H), 4.55 (d, J=7.8 Hz, 1H), 4.34 (t, J=8.0 Hz, 1H), 1.40-1.29 (m, 1H), 0.80-0.73 (m, 1H), 0.70-0.63 (m, 1H), 0.61-0.51 (m, 1H), 0.34-0.23 (m, 1H) MS: Anal. Calc'd for $C_{17}H_{14}BrNO_3$ 359.016, found [M+H] 360.2 LC: $T_r$=3.833 min (Method A).

111C: rac-ethyl 3-((2R,3S)-2-cyclopropyl-7-nitro-3-phenyl-2,3-dihydrobenzofuran-5-yl)but-2-enoate

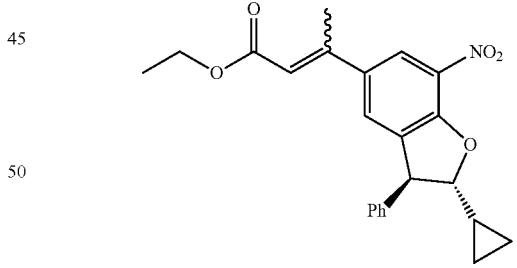

A solution of 111B (125 mg, 0.347 mmol) and (E)-ethyl but-2-enoate (0.129 mL, 1.041 mmol) in DMF (1 mL) was treated with tetrabutylammonium bromide (22.37 mg, 0.069 mmol), triethylamine (0.097 mL, 0.694 mmol), and dichlorobis(tri-o-tolylphosphine)-palladium(II) (13.64 mg, 0.017 mmol). The resulting mixture was purged with $N_2$ for 5 min. then sealed and heated for 16 h at 110° C. The reaction was cooled to RT, diluted with EtOAc, and washed with water. The organic phase was washed with water (2×) then brine, dried over $MgSO_4$, filtered, and concentrated. The residue was purified with ISCO 24 g column, 35 mL/min. 0-20% EtOAc/Hexane in 15 min, to give 111C (94 mg, 0.239 mmol, 68.8% yield) was obtained as light yellow liquid. MS: Anal. Calc'd for $C_{23}H_{23}NO_5$ 393.158, found [M+H] 394.0 LC: $T_r$=3.948 min (Method A).

111D: rac-ethyl 3-((2R,3S)-7-amino-2-cyclopropyl-3-phenyl-2,3-dihydrobenzofuran-5-yl)butanoate

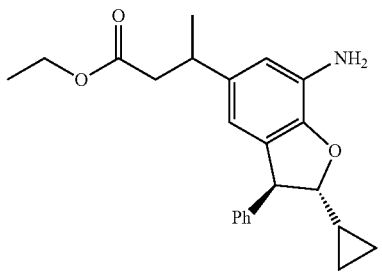 [SMILES: CCOC(=O)CC(C)c1cc(N)c2c(c1)[C@H](c1ccccc1)[C@@H](C1CC1)O2]

To a solution of 111C (14 mg, 0.036 mmol) in MeOH (5 mL) at RT was added 10% Pd/C (7.54 mg, 7.12 μmol). The mixture was evacuated with vacuum and filled with $H_2$ (Repeated 3×). Then it was stirred under $H_2$ for 2 h. The mixture was evacuated with vacuum and filled with $N_2$. It was then filtered through celite, and the filtrate was concentrated to give 111D (7 mg, 0.019 mmol, 53.8% yield). $^1$H NMR (400 MHz, CHLOROFORM-d) δ 7.38-7.15 (m, 5H), 6.50-6.41 (m, 1H), 6.26 (d, J=3.7 Hz, 1H), 4.48 (d, J=8.4 Hz, 1H), 4.11-4.00 (m, 2H), 3.98-3.81 (m, 1H), 3.60 (br. s., 2H), 3.17-2.94 (m, 1H), 2.59-2.30 (m, 2H), 1.35-1.24 (m, 2H), 1.24-1.05 (m, 6H), 0.69-0.50 (m, 2H), 0.44 (dq, J=9.6, 4.9 Hz, 1H), 0.17 (dq, J=9.7, 4.8 Hz, 1H) MS: Anal. Calc'd for $C_{23}H_{27}NO_3$ 365.199, found [M+H] 366.0 LC: $T_r$=3.128 min (Method A).

111E: rac-ethyl 3-((2R,3S)-2-cyclopropyl-3-phenyl-7-(3-(p-tolyl)ureido)-2,3-dihydrobenzofuran-5-yl)butanoate

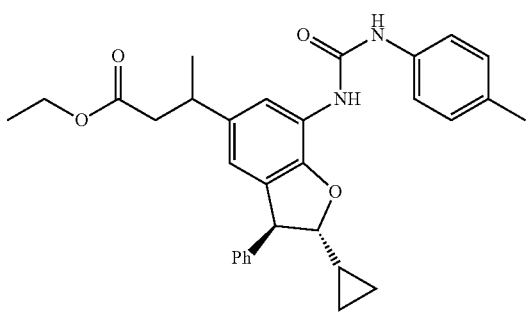 [SMILES: CCOC(=O)CC(C)c1cc(NC(=O)Nc2ccc(C)cc2)c2c(c1)[C@H](c1ccccc1)[C@@H](C1CC1)O2]

To a solution of 111D (9 mg, 0.025 mmol) in THF (1 mL) was added 1-isocyanato-4-methylbenzene (4.92 mg, 0.037 mmol), followed by triethylamine (6.86 μl, 0.049 mmol). The reaction was stirred at 50° C. for 30 min., diluted with water, and extracted with EtOAc. The organic phase was separated and washed with brine, dried over $MgSO_4$, filtered and concentrated to give crude material. This crude material was dissolved in $CH_2Cl_2$/MeOH, loaded onto a solid cartridge, and dried under vacuum for 30 min. Then it was purified with ISCO, 24 g column, 35 mL/min. 0-30% EtOAc/Hexane in 16 min. The desired product was eluted with 25% EtOAc/Hexane to give 111E (7.7 mg, 0.015 mmol, 62.1%) as a colorless liquid. $^1$H NMR (400 MHz, CHLOROFORM-d) δ 7.68 (d, J=4.4 Hz, 1H), 7.39-7.23 (m, 3H), 7.23-7.06 (m, 2H), 6.97 (d, J=7.9 Hz, 1H), 6.86 (d, J=9.0 Hz, 1H), 6.69 (d, J=7.5 Hz, 1H), 6.66-6.59 (m, 1H), 6.55 (s, 1H), 4.51 (d, J=8.1 Hz, 1H), 4.13-4.00 (m, 2H), 3.96 (td, J=8.3, 4.4 Hz, 1H), 3.25-3.09 (m, 1H), 2.64-2.40 (m, 2H), 2.33 (s, 3H), 2.25 (s, 1H), 1.37-1.21 (m, 5H), 1.17 (q, J=7.1 Hz, 3H), 0.69-0.52 (m, 2H), 0.41 (dt, J=9.5, 4.6 Hz, 1H), 0.24-0.10 (m, 1H) MS: Anal. Calc'd for $C_{31}H_{34}N_2O_4$ 498.252, found [M+H] 499.2 LC: $T_r$=4.015 min (Method A)

Example 111

To a solution of 111E (7.7 mg, 0.015 mmol) in THF (0.3 mL) was added 1N NaOH (0.154 mL, 0.154 mmol) and MeOH (0.1 mL). The mixture was stirred at RT for 16 h. The crude mixture was neutralized with 1N HCl to pH 5. Then it was diluted with DMF and purified by preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 15 min, then a 5-minute hold at 100% B; Flow: 20 mL/min. Fractions containing the desired product were combined and dried by centrifugal evaporation to give Example 111 (1.2 mg, 2.52 umol, 16%) $^1$H NMR (500 MHz, METHANOL-$d_4$) δ 7.75 (br. s., 1H), 7.59 (s, 1H), 7.35-7.29 (m, 3H), 7.27-7.17 (m, 3H), 7.10 (d, J=8.4 Hz, 2H), 6.53 (s, 1H), 4.53 (d, J=7.9 Hz, 1H), 3.96 (t, J=8.2 Hz, 1H), 2.30 (s, 3H), 0.67-0.52 (m, 2H), 0.42 (m, 1H), 0.19 (s, 1H) MS: Anal. Calc'd for $C_{29}H_{30}N_2O_4$ 470.221, found [M+H] 471.2 LC: $T_r$=3.746 min (Method A).

Example 112

(+/−)1-(5-(1-(1H-tetrazol-5-yl)cyclopropyl)-3-phenyl-2-vinyl-2,3-dihydrobenzofuran-7-yl)-3-(p-tolyl)urea

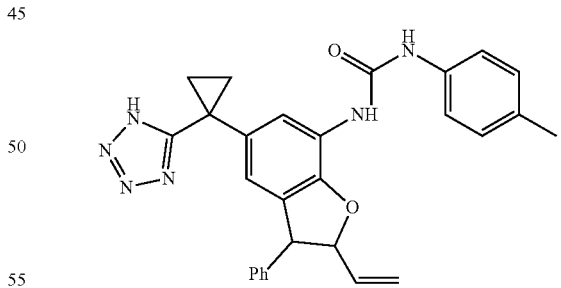

112A: 4-(bromomethyl)-1-methoxy-2-nitrobenzene

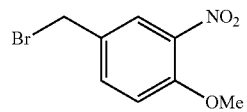 [SMILES: COc1ccc(CBr)cc1[N+](=O)[O-]]

To a solution of 1-methoxy-4-methyl-2-nitrobenzene (5 mL, 36.0 mmol) in CCl₄ (70 mL) was added N-Bromosuccinimide (6.42 g, 36.0 mmol), followed by benzoyl peroxide (0.44 g, 1.8 mmol). The reaction was sealed and heated at 70° C. for 16 h. It was then cooled to RT, poured into water, and extracted with CH₂Cl₂. The organic phase was separated and washed with brine, dried over MgSO₄, filtered and concentrated to give crude material. This crude material was triturated with hexane. The resulting solid was collected and dried under vacuum for 16 h to give 112A (7.0 g, 22.76 mmol, 63.1% yield) as a yellow solid. ¹H NMR (400 MHz, CHLOROFORM-d) δ 7.90 (d, J=2.4 Hz, 1H), 7.58 (dd, J=8.7, 2.3 Hz, 1H), 7.08 (d, J=8.8 Hz, 1H), 4.48 (s, 2H), 4.02 (s, 3H) LC: T$_r$=2.448 min (Method A).

112B: 2-(4-methoxy-3-nitrophenyl)acetonitrile

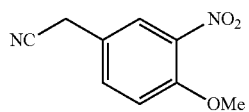

Compound 112A (7 g, 28.4 mmol) was dissolved in acetonitrile (100 ml) at 0° C., treated with tetraethylammonium cyanide (5.33 g, 34.1 mmol), and stirred for 30 min. The mixture was concentrated, diluted with water, and extracted with EtOAc. The organic phase was separated and washed 3× with brine and then dried over anhydrous MgSO₄. Filtration and concentration afforded a dark brown oil. The crude product was dissolved in a small amount of DCM and purified by flash chromatography (SiO₂, 0% EtOAc/hexanes to 50% EtOAc/hexanes, 220 g column, 100 mL/min, 30 min gradient, monitoring at 254 nm). The appropriate fractions were pooled and concentrated under reduced pressure to afford 112B (3.4 g, 17.34 mmol, 60.9% yield) as a light yellow solid. ¹H NMR (400 MHz, CHLOROFORM-d) δ 7.82 (d, J=2.4 Hz, 1H), 7.55 (dd, J=8.6, 2.4 Hz, 1H), 7.13 (d, J=8.6 Hz, 1H), 3.99 (s, 3H), 3.77 (s, 2H) LC: T$_r$=1.585 min (Method A).

112C: 1-(4-methoxy-3-nitrophenyl)cyclopropanecarbonitrile

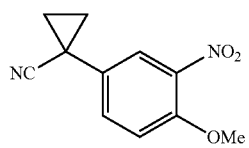 [SMILES: COc1ccc(C2(C#N)CC2)cc1[N+](=O)[O-]]

To a solution of 112B (2.1 g, 10.93 mmol) and 1-bromo-2-chloroethane (1.359 mL, 16.39 mmol) in DMF (100 mL) at 0° C. was added Sodium hydride (1.311 g, 32.8 mmol). It became dark color. The mixture was stirred at 0° C. for 10 min. and then it was stirred at RT for 16 h. The reaction was diluted with ether and washed with saturated aq. NH₄Cl. The organic phase was separated and washed with water (3×) then brine, dried over MgSO₄, filtered and concentrated. The residue was purified with ISCO 220 g column, 30 mL/min. 0-50% EtOAc/Hexane in 20 min. The desired product was eluted with 40% EtOAc/Hexane. The appropriate fractions were combined and concentrated to give 112C (1.2 g, 5.44 mmol, 49.8% yield) as light yellow solid. ¹H NMR (400 MHz, CHLOROFORM-d) δ 7.70 (d, J=2.6 Hz, 1H), 7.60 (dd, J=8.7, 2.5 Hz, 1H), 7.10 (d, J=8.8 Hz, 1H), 3.98 (s, 3H), 1.81-1.72 (m, 2H), 1.45-1.29 (m, 2H) LC: T$_r$=2.088 min (Method A).

112D: 1-(4-hydroxy-3-nitrophenyl)cyclopropanecarbonitrile

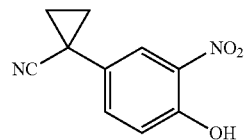 [SMILES: N#CC1(c2ccc(O)c([N+](=O)[O-])c2)CC1]

A solution of 112C (1.2 g, 5.50 mmol) in CH₂Cl₂ (50 mL) at 0° C. was treated with aluminum chloride (2.93 g, 22.00 mmol). The mixture was stirred at 0° C. and then warmed to RT and stirred at RT for 16 h. The reaction was diluted with water and extracted with EtOAc. The organic phase was separated and washed with brine, dried over MgSO₄, filtered and concentrated to give the crude product. This crude material was purified with ISCO 120 g column, 85 mL/min. 0-30% EtOAc/Hexane. The desired product was eluted with 20% EtOAc/Hexane to give 112D (760 mg, 3.68 mmol, 67.0% yield) as yellow solid. ¹H NMR (400 MHz, DMSO-d₆) δ 11.13 (s, 1H), 7.80 (d, J=2.6 Hz, 1H), 7.51 (dd, J=8.7, 2.5 Hz, 1H), 7.14 (d, J=8.8 Hz, 1H), 1.78-1.64 (m, 2H), 1.58-1.42 (m, 2H) LC: T$_r$=2.010 min (Method A).

112E: (E)-1-(4-(cinnamyloxy)-3-nitrophenyl)cyclopropanecarbonitrile

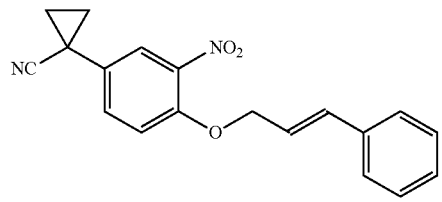 [SMILES: N#CC1(c2ccc(OC/C=C/c3ccccc3)c([N+](=O)[O-])c2)CC1]

To a solution of Ph₃P (424 mg, 1.616 mmol) in THF (2.5 mL) was added diisopropyl azodicarboxylate (0.314 mL, 1.616 mmol). The reaction was stirred at RT for 10 min. and treated with 112D (330 mg, 1.616 mmol). The reaction was stirred for another 5 min. then treated with (E)-3-phenyl-prop-2-en-1-ol (282 mg, 2.101 mmol). The resulting light brown mixture was stirred at RT for 16 h with precipitation of a light yellow solid. The reaction was concentrated and the residue was purified with ISCO 120 g, 85 mL/min, 0-40% EtOAc/Hexane in 40 min. The desired product was eluted with 25% EtOAc/Hexane to give 112E (530 mg, 1.654 mmol, 102% yield) as light yellow solid. ¹H NMR (400 MHz, CHLOROFORM-d) δ 7.71 (d, J=2.4 Hz, 1H), 7.58 (dd, J=8.7, 2.5 Hz, 1H), 7.42 (dd, J=7.1, 1.5 Hz, 2H), 7.35 (t, J=7.3 Hz, 2H), 7.32-7.24 (m, 1H), 7.15 (d, J=8.8 Hz, 1H), 6.79 (d, J=16.1 Hz, 1H), 6.37 (dt, J=16.1, 5.6 Hz, 2H), 4.88 (dd, J=5.5, 1.5 Hz, 2H), 1.81-1.71 (m, 2H), 1.48-1.38 (m, 2H) LC: tr=3.308 min (Method A).

112F: 1-(4-hydroxy-3-nitro-5-(1-phenylallyl)phenyl)cyclopropanecarbonitrile

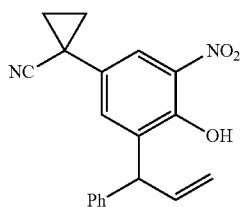 [SMILES: C=CC(c1ccccc1)c1cc(C2(C#N)CC2)cc([N+](=O)[O-])c1O]

A solution of 112E (300 mg, 0.936 mmol) in diglyme (1 mL) was heated at 150° C. for 36 h then concentrated under reduced pressure. The residue was purified with ISCO 40 g column, 40 mL/min. 0-20% EtOAc/Hexane in 20 min. The desired product was eluted with 10% EtOAc/Hexane to give 112F (80 mg, 0.247 mmol, 26.4% yield) as yellow liquid. $^1$H NMR (400 MHz, CHLOROFORM-d) δ 10.97 (s, 1H), 7.93 (d, J=2.4 Hz, 1H), 7.51 (d, J=2.4 Hz, 1H), 7.39-7.31 (m, 2H), 7.31-7.22 (m, 1H), 7.22-7.04 (m, 2H), 6.29 (ddd, J=17.0, 10.3, 6.6 Hz, 1H), 5.41-5.28 (m, 1H), 5.24 (d, J=6.6 Hz, 1H), 5.00 (dt, J=17.1, 1.3 Hz, 1H), 1.83-1.67 (m, 2H), 1.44-1.23 (m, 2H) MS: Anal. Calc'd for $C_{19}H_{16}N_2O_3$ 320.116, found [M-H] 319 LC: $T_r$=3.486 min (Method A).

112G: 1-(4-(allyloxy)-3-nitro-5-(1-phenylallyl)phenyl)cyclopropanecarbonitrile

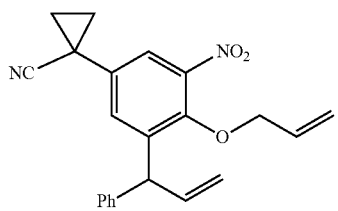 [SMILES: C=CCOc1c(C(C=C)c2ccccc2)cc(C2(C#N)CC2)cc1[N+](=O)[O-]]

To a solution of 112F (80 mg, 0.250 mmol) in DMF (3 mL) at RT was added potassium carbonate (104 mg, 0.749 mmol), followed by 3-Bromopropene (0.087 mL, 0.999 mmol). The mixture was stirred at 60° C. for 2.5 h, cooled to RT, and filtered to remove solids. The filtrate was diluted with water and extracted with EtOAc. The organic phase was washed with brine, dried over MgSO$_4$, filtered and concentrated to afford 112G (90 mg, 0.250 mmol, 100% yield) as colorless liquid, $^1$H NMR (400 MHz, CHLOROFORM-d) δ 7.60 (d, J=2.6 Hz, 1H), 7.46 (d, J=2.6 Hz, 1H), 7.39-7.31 (m, 2H), 7.30-7.23 (m, 1H), 7.21-7.12 (m, 2H), 6.28 (ddd, J=17.1, 10.3, 6.5 Hz, 1H), 6.01-5.78 (m, 1H), 5.43-5.22 (m, 4H), 4.97 (dt, J=17.1, 1.3 Hz, 1H), 4.37 (ddt, J=11.7, 5.9, 1.2 Hz, 1H), 4.25 (ddt, J=11.6, 5.9, 1.3 Hz, 1H), 1.86-1.74 (m, 2H), 1.44-1.36 (m, 2H) MS: Anal. Calc'd for $C_{22}H_{20}N_2O_3$ 360.147, found [M+NH4] 378.2 LC: $T_r$=3.638 min (Method A).

112H: 1-(9-nitro-5-phenyl-2,5-dihydrobenzo[b]oxepin-7-yl)cyclopropanecarbonitrile

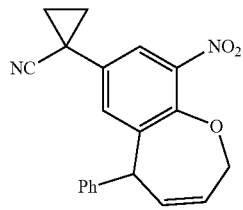 [SMILES: N#CC1(c2cc3c(c([N+](=O)[O-])c2)OCC=CC3c2ccccc2)CC1]

A solution of 112G (90 mg, 0.250 mmol) in ClCH$_2$CH$_2$Cl (20 mL) at RT was purged with N$_2$ for 10 min. Then GrubbsII (10.60 mg, 0.012 mmol) was added and the mixture was stirred at 55° C. for 30 min. The reaction was cooled to RT and the solvent was removed under reduced pressure. The residue was dissolved in minimal amount of CH$_2$Cl$_2$ and purified with ISCO 12 g column, 0-20% EtOAc/Hexane in 18 min. The desired product was eluted with 10% EtOAc/Hexane to give 112H (70 mg, 0.209 mmol, 83% yield) as white solid. $^1$H NMR (400 MHz, CHLOROFORM-d) δ 7.46 (d, J=2.4 Hz, 1H), 7.42-7.33 (m, 4H), 7.32-7.10 (m, 2H), 6.07 (ddt, J=11.7, 6.3, 2.2 Hz, 1H), 5.83-5.69 (m, 1H), 4.91 (d, J=6.6 Hz, 1H), 4.87-4.74 (m, 2H), 1.81-1.71 (m, 2H), 1.39-1.19 (m, 2H) MS: Anal. Calc'd for $C_{20}H_{16}N_2O_3$ 332.116, found [M-H] 331.4.2 LC: $T_r$=3.283 min (Method A).

112I: 5-(1-(9-nitro-5-phenyl-2,5-dihydrobenzo[b]oxepin-7-yl)cyclopropyl)-1H-tetrazole

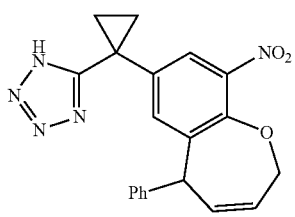 [SMILES: O=[N+]([O-])c1cc(C2(c3nnn[nH]3)CC2)cc2c1OCC=CC2c1ccccc1]

To a solution of 112H in THF (0.5 mL) at RT was added dibutyloxostannane (26.2 mg, 0.105 mmol) followed by azidotrimethylsilane (0.111 mL, 0.842 mmol). The vessel was sealed and heated to 140° C. in the microwave for 60 min (the temperature reached 100° C.). The mixture was diluted with water and EtOAc. The layers were separated and the aqueous phase extracted twice with 10 mL EtOAc. The organics were combined, washed with water and brine, then dried over anhydrous sodium sulfate. Filtration and concentration afforded 5112I (79 mg, 0.210 mmol, 100% yield) as a light brown liquid. MS: Anal. Calc'd for $C_{20}H_{17}N_5O_3$ 375.133, found [M-H] 374.4 LC: $T_r$=3.085 min (Method A).

112J: 7-(1-(1H-tetrazol-5-yl)cyclopropyl)-5-phenyl-2,5-dihydrobenzo[b]oxepin-9-amine

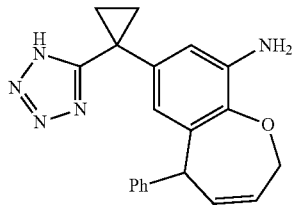 [SMILES: Nc1cc(C2(c3nnn[nH]3)CC2)cc2c1OCC=CC2c1ccccc1]

To a solution of 112I (75 mg, 0.200 mmol) in ethanol (1 mL)-water (0.1 mL) was added ammonium chloride (107 mg, 1.998 mmol), followed by zinc (131 mg, 1.998 mmol). The mixture was stirred at 55° C. for 5.5 h and left at RT for 16 h. The reaction was then diluted with EtOAc and water and filtered through a 0.45 µM membrane with celite. The filtrate was transferred to a separatory funnel, and the organic phase was separated and washed with brine, dried over MgSO$_4$, filtered and concentrated to give 112J (45 mg, 0.130 mmol, 65% yield) as an off white solid. MS: Anal. Calc'd for $C_{20}H_{19}N_5O$ 345.159, found [M+H] 346.2 LC: T$_r$=2.473 min (Method A).

112K: 1-(7-(1-(1H-tetrazol-5-yl)cyclopropyl)-5-phenyl-2,5-dihydrobenzo[b]oxepin-9-yl)-3-(p-tolyl)urea

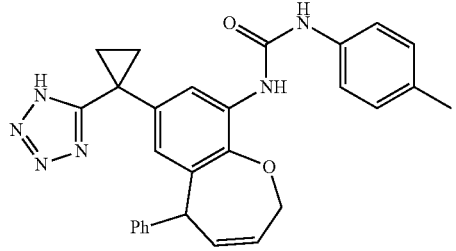 [SMILES: Cc1ccc(NC(=O)Nc2cc(C3(c4nnn[nH]4)CC3)cc3c2OCC=CC3c2ccccc2)cc1]

To 112J (45 mg, 0.130 mmol) in THF (2 mL) at RT was added 4-nitrophenyl carbonochloridate (26.3 mg, 0.130 mmol). The mixture was stirred at RT for 30 min. then treated with para-toluidine (20.94 mg, 0.195 mmol) followed by triethylamine (0.036 mL, 0.261 mmol). The mixture was warmed to 50° C. and stirred for 40 min. The reaction was then diluted with MeOH and purified with prep HPLC (5 injections) (Waters Xbridge C18 19×100 mm), 20 mL/min flow rate with gradient of 20% B-100% B over 10 min Hold at 100% B for 5 min. (A: 0.1% TFA in water/MeOH (90:10), B: 0.1% TFA in water/MeOH (10:90) monitoring at 220 nM to give 112K (35 mg, 0.072 mmol, 55% yield) $^1$H NMR (400 MHz, DMSO-d$_6$) δ 9.14 (s, 1H), 8.40 (s, 1H), 8.10 (d, J=2.2 Hz, 1H), 7.40 (d, J=7.3 Hz, 2H), 7.35-7.20 (m, 5H), 7.20-7.11 (m, 1H), 7.06 (d, J=8.1 Hz, 2H), 6.82 (d, J=2.0 Hz, 1H), 6.11-5.96 (m, 1H), 5.82-5.73 (m, 1H), 4.78 (d, J=13.9 Hz, 1H), 4.71 (d, J=7.0 Hz, 1H), 4.41 (d, J=17.4 Hz, 1H), 2.22 (s, 3H), 1.61-1.39 (m, 2H), 1.44-1.15 (m, 2H) MS: Anal. Calc'd for $C_{28}H_{26}N_6O_2$ 478.212, found [M+H] 479.3 LC: T$_r$=3.468 min (Method A).

Example 112

To a solution of 112K (12 mg, 0.025 mmol) in DMF (0.5 mL) was added (2-(1H-tetrazol-5-yl)phenyl)boronic acid (9.53 mg, 0.050 mmol), followed by tetrakis(triphenylphosphine)palladium(0) (2.90 mg, 2.508 µmol). The mixture was evacuated placed under N$_2$ and treated with potassium carbonate (17.33 mg, 0.125 mmol) in 0.125 mL of water. The mixture was placed under vacuum, filled with N$_2$, and stirred at 95° C. for 3 h. The mixture was diluted with MeOH and purified with prep HPLC (Waters Xbridge C18 19×100 mm), 20 mL/min flow rate with gradient of 30% B-100% B over 10 min Hold at 100% B for 5 min. (A: 0.1% TFA in water/MeOH (90:10), B: 0.1% TFA in water/MeOH (10:90) monitoring at 254 nm to give Example 112 (1.6 mg, 3.31 umol, 13%) $^1$H NMR (500 MHz, METHANOL-d$_4$) δ 7.83 (s, 1H), 7.35-7.29 (m, 4H), 7.26 (d, J=7.4 Hz, 1H), 7.22-7.17 (m, 2H), 7.09 (d, J=8.4 Hz, 2H), 6.71 (s, 1H), 6.11 (s, 1H), 5.34-5.16 (m, 2H), 5.00 (t, J=7.7 Hz, 1H), 4.40 (d, J=8.4 Hz, 1H), 2.29 (s, 3H), 1.50 (d, J=2.5 Hz, 2H), 1.40 (d, J=2.5 Hz, 1H), 1.32 (d, J=2.5 Hz, 1H) MS: Anal. Calc'd for $C_{28}H_{26}N_6O_2$ 478.212, found [M+H] 479.4 LC: T$_r$=3.58 min (Method A).

Example 113 rel-1-((2R,3R)-5-(2-(2H-tetrazol-5-yl)phenyl)-2-methyl-3-phenyl-2,3-dihydrobenzofuran-7-yl)-3-(p-tolyl)urea

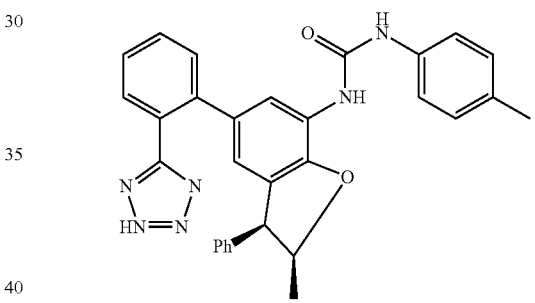

113A. rel-(2R,3S)-5-bromo-2-methyl-7-nitro-3-phenyl-2,3-dihydrobenzofuran and 113B. rel-(2R,3R)-5-bromo-2-methyl-7-nitro-3-phenyl-2,3-dihydrobenzofuran 4-Bromo-2-nitro-6-(1-phenylallyl)phenol (274 mg, 0.820 mmol) (1B) was dissolved in methylene chloride (5.0 mL) under nitrogen. Triflic acid (10 uL, 0.113 mmol) was then added. After ca. 2 h, another aliquot of triflic acid (10 uL, 0.113 mmol) was added. The reaction was then stirred overnight. TLC analysis showed the formation of two products. The reaction was then diluted with ether and washed twice with 1 N sodium hydroxide. The organic layer was then washed with water and brine. Drying with magnesium sulfate, filtration and evaporation provided the crude products. This material was applied to a 24 g Isco silica gel column and eluted with 0-25% ethyl acetate in hexanes. Evaporation of the appropriate fractions provided two products 113A (79 mg, 0.236 mmol, 28.8% yield) and 113B (80 mg, 0.239 mmol, 29.2% yield). 113A: $^1$H NMR (400 MHz, DMSO-d$_6$) δ 8.10 (dd, J=2.1, 0.8 Hz, 1H), 7.49-7.26 (m, 7H), 5.13-5.03 (m, 1H), 4.51 (d, J=7.7 Hz, 1H), 1.56 (d, J=6.4 Hz, 3H). 113B: $^1$H NMR (400 MHz, DMSO-d$_6$) δ 8.15-8.10 (m, 1H), 7.67 (dd, J=2.0, 1.1 Hz, 1H), 7.40-7.28

(m, 4H), 7.07-6.99 (m, 2H), 5.41 (dq, J=8.6, 6.6 Hz, 1H), 4.87 (d, J=8.6 Hz, 1H), 1.05 (d, J=6.6 Hz, 5H).

113C: rel-1-((2R,3R)-5-bromo-2-methyl-3-phenyl-2,3-dihydrobenzofuran-7-yl)-3-(p-tolyl)urea Compound 113B (80 mg, 0.239 mmol) was dissolved in 9:1 ethanol-water (10 mL) under nitrogen. Ammonium chloride (128 mg, 2.394 mmol) was added and stirring continued for a few min. Zinc (157 mg, 2.394 mmol) was introduced and the reaction was stirred for an hour. The reaction was then filtered and transferred to a separatory funnel. The reaction was partitioned between methylene chloride and water. The organic layer was washed with brine, dried over magnesium sulfate and filtered. Evaporation provided ca. 80 mg of the intermediate aniline as a viscous oil. This material was dissolved in THF (2 mL) and treated with p-tolyl isocyanate (36.2 µl, 0.287 mmol). The reaction was warmed to 50° C. and stirred overnight. The cooled reaction was applied to a 24 g Isco silica gel column and eluted with 0-25% ethyl acetate in hexanes. The material was further purified by flash silica gel chromatography using 3:1 hexanes-ethyl acetate. Evaporation provided 113C (71 mg, 0.157 mmol, 65%) as a colorless solid. $^1$H NMR (400 MHz, DMSO-d$_6$) δ 9.11 (s, 1H), 8.38 (s, 1H), 8.21 (d, J=2.0 Hz, 1H), 7.36-7.36 (m, 1H), 7.43-7.31 (m, 4H), 7.31-7.22 (m, 1H), 7.12 (d, J=8.4 Hz, 2H), 7.04-6.95 (m, 2H), 6.89-6.81 (m, 1H), 5.31-5.17 (m, 1H), 4.70 (d, J=8.4 Hz, 1H), 2.27 (s, 3H), 1.03 (d, J=6.6 Hz, 3H).

Example 113

A reaction vial was charged with degassed DMF (1.5 mL), 113C (30 mg, 0.069 mmol) and (2-(2H-tetrazol-5-yl)phenyl) boronic acid (39.1 mg, 0.206 mmol). Nitrogen was bubbled through the reaction for 15 min. Potassium carbonate (137 µl, 0.206 mmol) (1.5 M solution) was added and the nitrogen bubbling continued for a few more minutes. Tetrakis(triphenylphosphine)palladium(0) (7.93 mg, 6.86 µmol) was added and the vial sealed. The reaction was then heated to 95° C. After a few hours, another portion of (2-(2H-tetrazol-5-yl)phenyl)boronic acid (39.1 mg, 0.206 mmol), potassium carbonate (137 µl, 0.206 mmol), and tetrakis(triphenylphosphine)palladium(0) (7.93 mg, 6.86 µmol) were added. After heating for a few more hours, LCMS analysis did not suggest any further progress of the reaction. The cooled reaction was then partially purified by RP-HPLC (methanol-water gradient +0.1% TFA). The impure product containing fractions were concentrated on the rotary evaporator. When a precipitate formed, the material was transferred to a separatory funnel and extracted with ethyl acetate. The organic layer was washed with brine and dried over magnesium sulfate. Filtration and evaporation gave the partially purified product. This material was applied to a 0.5 mm preparative silica gel plate and eluted with 1:1 ethyl acetate-hexanes containing 1% acetic acid. The product containing band was extracted with ethyl acetate to give Example 113 (11 mg, 0.022 mmol, 31.9% yield) as a colorless solid. $^1$H NMR (400 MHz, DMSO-d$_6$) δ 11.95 (br. s., 1H), 9.05 (s, 1H), 8.22 (s, 1H), 7.97 (s, 1H), 7.58 (d, J=7.0 Hz, 2H), 7.51-7.41 (m, 2H), 7.39-7.22 (m, 5H), 7.10 (d, J=8.4 Hz, 2H), 6.91 (d, J=7.0 Hz, 2H), 6.24 (d, J=1.1 Hz, 1H), 5.30-5.15 (m, 1H), 4.66 (d, J=8.6 Hz, 1H), 2.26 (s, 3H), 0.96 (d, J=6.6 Hz, 3H). LC-MS Calculated for C$_{30}$H$_{26}$N$_6$O$_2$ 502.2, found [M+H] 503.4, T$_r$=1.07 min (Method AA).

Example 114 rel-4-fluoro-2-((2R,3R)-2-methyl-3-phenyl-7-(3-(p-tolyl)ureido)-2,3-dihydrobenzofuran-5-yl)benzoic acid

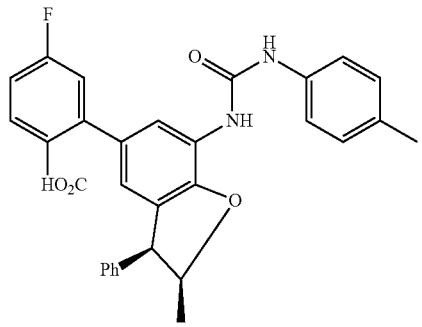 [SMILES: Cc1ccc(NC(=O)Nc2cc(-c3cc(F)ccc3C(=O)O)cc3c2O[C@@H](C)[C@H]3c2ccccc2)cc1]

A reaction vial was charged with degassed DMF (1.0 mL), 113C (20 mg, 0.046 mmol) and 2-borono-4-fluorobenzoic acid (25.2 mg, 0.137 mmol). Nitrogen was bubbled through the reaction for 15 min. Potassium carbonate (91 µl, 0.137 mmol) (1.5 M solution) was added and the nitrogen bubbling continued for a few more minutes. Tetrakis(triphenylphosphine)palladium(0) (5.28 mg, 4.57 µmol) was added and the vial sealed. The vial was then heated to 95° C. for an hour. Another portion of 2-borono-4-fluorobenzoic acid (25.2 mg, 0.137 mmol), potassium carbonate (91 µl, 0.137 mmol), and tetrakis(triphenylphosphine)palladium(0) (5.28 mg, 4.57 µmol) were added and heat continued for another hour. The cooled reaction was acidified with glacial acetic acid. Purification was accomplished by RP-HPLC (methanol-water gradient +0.1% TFA). The product containing fractions were concentrated on the rotary evaporator. The precipitate that formed was filtered, rinsed with water and hexanes. Air drying gave Example 114 (10.2 42.9% yield) as a cream colored solid. $^1$H NMR (400 MHz, DMSO-d$_6$) δ 12.73 (br mg, 0.020 mmol, s, 1H), 9.08 (s, 1H), 8.29 (s, 1H), 8.06 (d, J=1.5 Hz, 1H), 7.75 (dd, J=8.6, 6.2 Hz, 1H), 7.39-7.31, 7.31-7.19, 7.16-7.02 (integration of the ill resolved aromatic resonances is high suggesting the presence of an aromatic impurity), 6.67 (s, 1H), 5.34-5.21 (m, 1H), 4.76 (d, J=8.4 Hz, 1H), 2.26 (s, 3H), 1.03 (d, J=6.6 Hz, 4H). LC-MS Calculated for C$_{30}$H$_{25}$FN$_2$O$_4$ 496.2, found [M+H] 497.3, T$_r$=1.11 min (Method AA).

Example 115 rel-1-((2R,3S)-5-(2-(1H-tetrazol-5-yl)phenyl)-2-methyl-3-phenyl-2,3-dihydrobenzofuran-7-yl)-3-(p-tolyl)urea

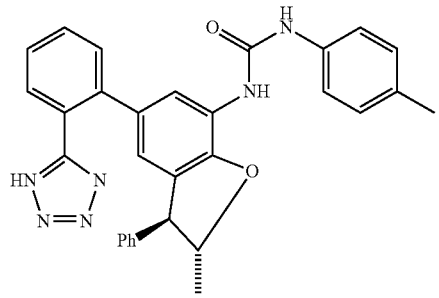 [SMILES: Cc1ccc(NC(=O)Nc2cc(-c3ccccc3-c3nnn[nH]3)cc3c2O[C@H](C)[C@H]3c2ccccc2)cc1]

Compound 113A (75 mg, 0.224 mmol) was dissolved in 9:1 ethanol-water (10 mL) under nitrogen. Ammonium chloride (120 mg, 2.244 mmol) was added and stirring continued for a few minutes. Zinc (147 mg, 2.244 mmol) was added, and the reaction was permitted to stir overnight. The completed reaction was filtered, diluted with methylene chloride and transferred to a separatory funnel. This solution was washed with water then brine. Drying over magnesium sulfate, filtration and evaporation provided the crude product. This material was dissolved in THF (2 mL) and treated with p-tolyl isocyanate (34.0 µl, 0.269 mmol). As the reaction appeared to be slow at RT, it was warmed to 50° C. and stirred overnight. The cooled reaction was applied to a 24 g Isco silica gel column and eluted with 0-25% ethyl acetate in hexanes. This material was further purified by flash silica gel chromatography using 3:1 hexanes-ethyl acetate. This provided rel-1-((2R,3S)-5-bromo-2-methyl-3-phenyl-2,3-dihydrobenzofuran-7-yl)-3-(p-tolyl)urea of sufficient purity for the next reaction. LC-MS Calculated for $C_{23}H_{21}BrN_2O_2$ 436.1, found [M+H] 437.2, $T_r$=1.21 min (Method AA). A reaction vial was charged with degassed DMF (1.0 mL), rep 1-((2R,3S)-5-bromo-2-methyl-3-phenyl-2,3-dihydrobenzofuran-7-yl)-3-(p-tolyl)urea (22.2 mg, 0.051 mmol) and (2-(1H-tetrazol-5-yl)phenyl)boronic acid (28.9 mg, 0.152 mmol). Nitrogen was bubbled through the solution for 60 minutes. Potassium carbonate (102 µl, 0.152 mmol) (1.5 M solution) was added and nitrogen bubbling continued for a few more minutes. Tetrakis(triphenylphosphine)palladium(0) (14 mg, 0.012 mmol) was added and the vial sealed. The reaction was then heated to 95° C. for ca. 2 h. The cooled reaction was acidified with glacial acetic acid and purified by RP-HPLC (methanol-water gradient +0.1% TFA). Evaporation of the appropriate fractions provided rel-1-((2R,3S)-5-(2-(1H-tetrazol-5-yl)phenyl)-2-methyl-3-phenyl-2,3-dihydrobenzofuran-7-yl)-3-(p-tolyl)urea (Example 115) (5.4 mg, 9.99 µmol, 19.69% yield) as a pale yellow solid. $^1$H NMR (400 MHz, DMSO-$d_6$) δ 9.07 (s, 1H), 8.25 (s, 1H), 7.98 (s, 1H), 7.72-7.56 (m, 2H), 7.55-7.45 (m, 2H), 7.41-7.25 (m, 5H), 7.18-7.02 (m, 4H), 6.09 (s, 1H), 4.75-4.60 (m, 1H), 4.30 (d, J=8.8 Hz, 1H), 2.26 (s, 3H), 1.55 (d, J=6.2 Hz, 3H). LC-MS Calculated for $C_{30}H_{26}N_6O_2$ 502.2, found [M+H] 503.4, $T_r$=1.05 min (Method AA).

Example 116 rel-4-fluoro-2-((2R,3S)-2-methyl-3-phenyl-7-(3-(p-tolyl)ureido)-2,3-dihydrobenzofuran-5-yl)benzoic acid

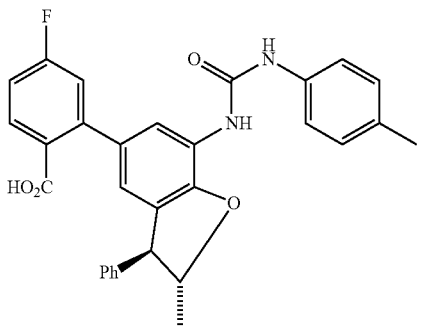 [SMILES: Cc1ccc(NC(=O)Nc2cc(-c3cc(F)ccc3C(=O)O)cc3c2O[C@H](C)[C@H]3c2ccccc2)cc1]

A reaction vial was charged with DMF (1.0 mL), rel-1-((2R,3S)-5-bromo-2-methyl-3-phenyl-2,3-dihydrobenzofuran-7-yl)-3-(p-tolyl)urea (22 mg, 0.050 mmol) and 2-borono-4-fluorobenzoic acid (27.8 mg, 0.151 mmol). Nitrogen was bubbled through the solution for 35 minutes. Potassium carbonate (101 µl, 0.151 mmol) (1.5 M solution) was added and nitrogen bubbling continued for a few more minutes. Tetrakis(triphenylphosphine)palladium(0) (5.81 mg, 5.03 µmol) was added and the vial sealed. The reaction was then heated to 95° C. for ca. 3 h. The cooled reaction was acidified with glacial acetic acid and purified by RP-HPLC (methanol-water gradient +0.1% TFA). The product containing fractions were concentrated on the rotary evaporator. The precipitate that formed was filtered, rinsed with water and hexanes. Air drying gave Example 116 (5.8 mg, 0.012 mmol, 23.22% yield) as a colorless solid. $^1$H NMR (400 MHz, DMSO-$d_6$) δ 12.75 (br. s., 1H), 9.09 (s, 1H), 8.28 (s, 1H), 8.04 (d, J=1.5 Hz, 1H), 7.74 (dd, J=8.6, 6.2 Hz, 1H), 7.47-7.19 (m, 8H), 7.15-7.01 (m, 3H), 6.52 (s, 1H), 4.88-4.72 (m, 1H), 4.41 (d, J=8.8 Hz, 1H), 2.26 (s, 3H), 1.59 (d, J=6.2 Hz, 3H). LC-MS Calculated for $C_{30}H_{25}FN_2O_4$ 496.2, found [M+H] 497.3, $T_r$=1.09 min (Method AA).

Example 117 rel-4-fluoro-2-((2R,3R)-2-methyl-7-(3-(p-tolyl)ureido)-3-(3,3,3-trifluoropropyl)-2,3-dihydrobenzofuran-5-yl)benzoic acid

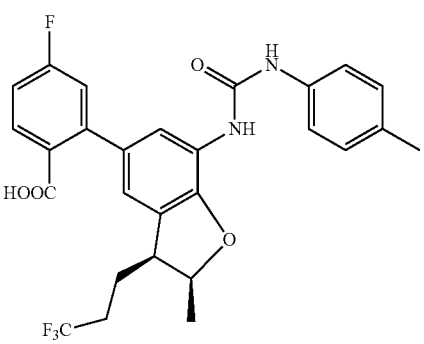 [SMILES: Cc1ccc(NC(=O)Nc2cc(-c3cc(F)ccc3C(=O)O)cc3c2O[C@@H](C)[C@H]3CCC(F)(F)F)cc1]

117A. rel-(2R,3S)-5-bromo-2-methyl-7-nitro-3-(3,3,3-trifluoropropyl)-2,3-dihydrobenzofuran and 117B. rel-(2R,3R)-5-bromo-2-methyl-7-nitro-3-(3,3,3-trifluoropropyl)-2,3-dihydrobenzofuran (+/−)-4-bromo-2-nitro-6-(6,6,6-trifluorohex-1-en-3-yl)phenol (320 mg, 0.90 mmol) (94B) was dissolved in methylene chloride (5 mL) under nitrogen. Triflic acid (20 uL, 0.226 mmol) was added and the reaction stirred for 3 h. The reaction was diluted with ether and transferred to a separatory funnel. The ether solution was washed twice with 1 N NaOH solution, once with water, and once with brine. Drying over magnesium sulfate, filtration and evaporation provided the crude products. The crude product was applied to a 24 g Isco silica gel column and eluted with 0-25% ethyl acetate in hexanes. The mixed fractions were combined and further purified on a 0.5 mm preparative silica gel plate, eluting with 3:1 hexanes-ethyl acetate. Combination of the purified isomers gave 117A (53 mg, 0.148 mmol, 16.4%) and 117B (60 mg, 0.169 mmol, 18.8%). 117A: $^1$H NMR (400 MHz, DMSO-$d_6$) δ 8.05 (dd, J=2.0, 0.7 Hz, 1H), 7.95 (dd, J=2.0, 1.1 Hz, 1H), 5.01 (quin, J=6.2 Hz, 1H), 3.31-3.24 (m, 1H), 2.49-2.26 (m, 2H), 2.11-1.94 (m, 1H), 1.92-1.75 (m, 1H), 1.45 (d, J=6.4 Hz, 3H). $^{19}$F NMR (376 MHz, DMSO-$d_6$) 5-64.70. 117B: $^1$H NMR (400 MHz, DMSO-$d_6$) δ 8.05 (d, J=1.5 Hz, 1H), 7.94 (dd, J=2.1, 1.2 Hz, 1H), 5.29-5.19 (m, 1H), 3.56 (q, J=7.3 Hz, 1H), 2.44-2.30 (m, 2H), 1.90-1.81 (m, 2H), 1.43 (d, J=6.6 Hz, 3H). $^{19}$F NMR (376 MHz, DMSO-$d_6$) 5-64.96.

117C. rel-1-((2R,3R)-5-bromo-2-methyl-3-(3,3,3-trifluoropropyl)-2,3-dihydrobenzofuran-7-yl)-3-(p-tolyl)urea rel-(2R,3R)-5-bromo-2-methyl-7-nitro-3-(3,3,3-trifluoropropyl)-2,3-dihydrobenzofuran (56 mg, 0.158 mmol) (117B) was dissolved in ethanol (5.0 mL). Water (0.5 mL) was added. Ammonium chloride (85 mg, 1.581 mmol) was added and the reaction stirred for a few minutes. Zinc (103 mg, 1.581 mmol) was added and stirring continued overnight. The reaction was then filtered and transferred to a separatory funnel. The reaction was partitioned between methylene chloride and water. The organic layer was washed with brine, dried over magnesium sulfate, filtered and evaporated. The crude aniline was dissolved in THF (1 mL) and treated with p-tolyl isocyanate (29.9 mL, 0.237 mmol). The reaction was warmed to 50° C. and stirred overnight. The cooled reaction was applied to a 24 g Isco silica gel column and eluted with 0-25% ethyl acetate in hexanes. This purification process was repeated until material of adequate purity was obtained. Compound 117C (62 mg, 0.136 mmol, 86% yield) was isolated as a colorless solid. $^1$H NMR (400 MHz, DMSO-$d_6$) δ 9.07 (s, 1H), 8.27 (s, 1H), 8.15 (d, J=2.0 Hz, 1H), 7.33 (br d, J=8.4 Hz, 2H), 7.12 (d, J=1.5 Hz, 1H), 7.10-7.07 (m, 2H), 5.09-4.96 (m, 1H), 3.41 (q, J=7.3 Hz, 1H), 2.45-2.30 (m, 2H), 2.26 (s, 3H), 1.90-1.78 (m, 1H), 1.77-1.63 (m, 1H), 1.43 (d, J=6.6 Hz, 3H).

Example 117

A reaction vial was charged with degassed DMF (1.0 mL), 117C (18 mg, 0.039 mmol) and 2-borono-4-fluorobenzoic acid (21.72 mg, 0.118 mmol). Nitrogen was bubbled through the solution for 30 minutes. Potassium carbonate (79 μl, 0.118 mmol) (1.5 M solution) and tetrakis(triphenylphosphine)palladium(0) (4.55 mg, 3.94 μmol) were added and the nitrogen bubbling continued for 5 minutes. The vial was sealed and warmed to 95° C. The reaction was stirred overnight. The cooled reaction was quenched with acetic acid and purified by RP-HPLC (methanol-water gradient +0.1% TFA). Isolate 4.5 mg of a yellow solid. The purification was repeated to give rel-4-fluoro-2-((2R,3R)-2-methyl-7-(3-(p-tolyl)ureido)-3-(3,3,3-trifluoropropyl)-2,3-dihydrobenzofuran-5-yl)benzoic acid (Example 117) (2 mg, 0.0035 mmol, 8.9%) as a colorless solid. $^1$H NMR (400 MHz, Methanol-$d_4$) δ 7.96-7.84 (m, 2H), 7.31 (d, J=7.9 Hz, 2H), 7.22-7.06 (m, 4H), 6.89 (s, 1H), 5.09-4.97 (m, 1H), 3.39 (br. s., 1H), 2.43-2.17 (m, 5H), 2.03-1.90 (m, 1H), 1.87-1.70 (m, 1H), 1.54 (d, J=6.4 Hz, 3H). LC-MS Calculated for $C_{27}H_{24}F_4N_2O_4$ 516.2, found [M+H] 517.3, $T_r$=1.05 min (Method AA).

Example 118 rel-1-((2R,3S)-5-(2-(2H-tetrazol-5-yl)phenyl)-2-methyl-3-(3,3,3-trifluoropropyl)-2,3-dihydrobenzofuran-7-yl)-3-(p-tolyl)urea

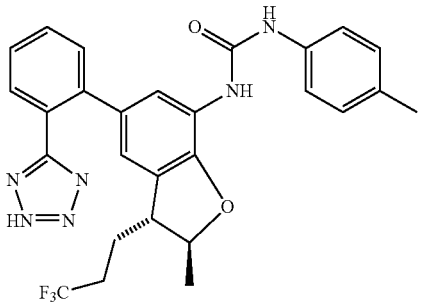 [SMILES: Cc1ccc(NC(=O)Nc2cc(-c3ccccc3-c3nnn[nH]3)cc3c2O[C@@H](C)[C@@H]3CCC(F)(F)F)cc1]

118A. rel-1-((2R,3S)-5-bromo-2-methyl-3-(3,3,3-trifluoropropyl)-2,3-dihydrobenzofuran-7-yl)-3-(p-tolyl)urea Compound 117A (52 mg, 0.147 mmol) was dissolved in ethanol (5.0 mL). Water (0.5 mL) and ammonium chloride (79 mg, 1.468 mmol) were added and the reaction stirred for a few minutes. The reaction was initiated with the addition of zinc (96 mg, 1.468 mmol). Five days later, the reaction was filtered and transferred to a separatory funnel. The reaction was partitioned between methylene chloride and water. The organic layer was washed with brine, dried over magnesium sulfate, filtered and evaporated. The crude aniline was dissolved in THF (2 mL) and treated with p-tolyl isocyanate (27.8 μl, 0.220 mmol). After two days, the reaction was applied to a 24 g Isco silica gel column and eluted with 0-5% methanol in methylene chloride. Evaporation of the product containing fractions gave 118A (59 mg, 0.129 mmol, 88% yield) as a yellow film.

Example 118

A reaction vial was charged with degassed DMF (1.0 mL), 118A (30 mg, 0.066 mmol) and (2-(2H-tetrazol-5-yl)phenyl) boronic acid (37.4 mg, 0.197 mmol). Nitrogen was bubbled through the solution for 75 min. Potassium carbonate (131 μl, 0.197 mmol) (1.5 M solution) was added and the nitrogen purge continued for 5 min. Tetrakis(triphenylphosphine) palladium(0) (14 mg, 0.012 mmol) was added, the vial given a final flush with nitrogen and sealed. The reaction was heated to 95° C. After 3 h, the cooled reaction was acidified with glacial acetic acid, diluted with methanol and filtered. This material was then purified by RP-HPLC (methanol-water gradient +0.1% TFA). Evaporation of the product containing fraction under a stream of nitrogen overnight gave Example 118 (5.7 mg, 10.69 μmol, 16.30% yield) as a pale yellow solid. $^1$H NMR (400 MHz, DMSO-d$_6$) δ 9.02 (s, 1H), 8.14 (s, 1H), 7.88 (s, 1H), 7.75-7.60 (m, 2H), 7.55 (d, J=7.0 Hz, 2H), 7.31 (d, J=8.4 Hz, 2H), 7.09 (d, J=8.4 Hz, 2H), 6.47 (s, 1H), 4.74 (t, J=6.2 Hz, 1H), 3.13-3.05 (m, 1H), 2.25 (s, 3H), 1.73 (d, J=6.2 Hz, 2H), 1.42 (d, J=6.4 Hz, 3H). $^{19}$F NMR (376 MHZ, DMSO-d$_6$) δ -64.76 (s, 3F). LC-MS Calculated for $C_{27}H_{25}F_3N_6O_2$ 522.2, found [M+H] 523.3, T$_r$=1.01 min (Method AA).

Example 119 rel-4-fluoro-2-((2R,3S)-2-methyl-7-(3-(p-tolyl) ureido)-3-(3,3,3-trifluoropropyl)-2,3-dihydrobenzofuran-5-yl)benzoic acid

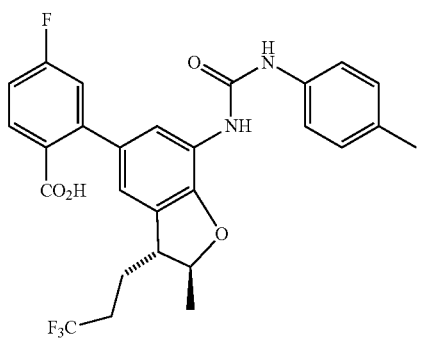 [SMILES: Cc1ccc(NC(=O)Nc2cc(-c3cc(F)ccc3C(=O)O)cc3c2O[C@@H](C)[C@@H]3CCC(F)(F)F)cc1]

A reaction vial was charged with degassed DMF (1.0 mL), 118A and 2-borono-4-fluorobenzoic acid (36.2 mg, 0.197 mmol). Nitrogen was bubbled through the solution for 75 min. Potassium carbonate (131 μl, 0.197 mmol) (1.5 M solution) was added and nitrogen purging continued for 5 min. Tetrakis(triphenylphosphine)palladium(0) (14 mg, 0.012 mmol) was added, the vial given a final flush with nitrogen and sealed. The reaction was then heated to 95° C. for 3 h. The cooled reaction was acidified with glacial acetic acid, diluted with methanol and filtered. The clarified solution was purified by RP-HPLC (methanol-water gradient +0.1% TFA). Evaporation of the product containing fraction gave rel-4-fluoro-2-((2R,3S)-2-methyl-7-(3-(p-tolyl) ureido)-3-(3,3,3-trifluoropropyl)-2,3-dihydrobenzofuran-5-yl)benzoic acid (Example 119) (6.3 mg, 10.37 μmol, 15.80% yield) as a pale yellow solid. $^1$H NMR (400 MHz, DMSO-d$_6$) δ 12.75 (s, 1H), 9.04 (s, 1H), 8.18 (s, 1H), 7.98 (d, J=1.8 Hz, 1H), 7.78 (dd, J=8.6, 5.9 Hz, 1H), 7.32 (d, J=8.4 Hz, 2H), 7.29-7.15 (m, 2H), 7.09 (d, J=8.4 Hz, 2H), 6.90 (s, 1H), 4.80 (dt, J=11.9, 6.2 Hz, 1H), 3.26-3.14 (m, 2H), 2.46-2.37 (m, 2H), 2.25 (s, 3H), 2.05-1.76 (m, 2H), 1.47 (d, J=6.4 Hz, 3H). $^{19}$F NMR (376 MHz, DMSO-d$_6$) δ -64.65 (s, 3F), -109.81 (s, 1F). LC-MS Calculated for $C_{27}H_{24}F_4N_2O_4$ 516.2, found [M+H] 517.3, T$_r$=1.06 min (Method AA).

Example 120

1-(5-(2-(1H-Tetrazol-5-yl)phenyl)-2,2-dimethyl-2,3-dihydrobenzofuran-7-yl)-3-(p-tolyl)urea

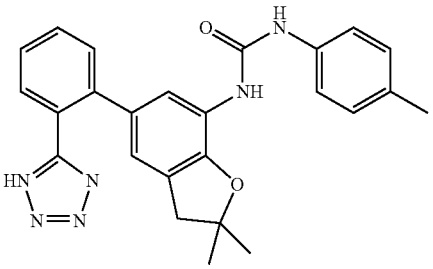 [SMILES: Cc1ccc(NC(=O)Nc2cc(-c3ccccc3-c3nnn[nH]3)cc3c2OC(C)(C)C3)cc1]

120A.
4-Bromo-1-((2-methylallyl)oxy)-2-nitrobenzene

To a mixture of 4-bromo-2-nitrophenol (3.3 g, 15.0 mmol) in anhydrous DMF (15 mL), at 60° C. under nitrogen atmosphere, was added potassium carbonate (4.2 g, 30.0 mmol). The resulting mixture was stirred for 3 min before isobutenyl chloride (2.2 mL, 22.3 mmol) was added via syringe. The resulting mixture was stirred at 60° C. for one hour before the temperature was increased to 70° C. After 16 h the reaction was allowed to cool to RT before being poured into water. The mixture was stirred for 10 min before the resultant precipitate was isolated by vacuum filtration and air dried to afford 120A as a pale yellow solid (4.0 g; 98% yield) $^1$H NMR (400 MHz, DMSO-d$_6$) δ 8.12 (d, J=2.6 Hz, 1H), 7.82 (dd, J=9.0, 2.4 Hz, 1H), 7.33 (d, J=9.0 Hz, 1H), 5.07 (d, J=0.9 Hz, 1H), 4.99 (s, 1H), 4.67 (s, 2H), 1.75 (s, 3H). T$_r$=2.08 min (Method C).

120B.
5-Bromo-2,2-dimethyl-7-nitro-2,3-dihydrobenzofuran

To a flask charged with 120A (500.0 mg, 1.8 mmol), under nitrogen atmosphere, was added anhydrous magnesium chloride (2.3 μL, 0.06 mmol). The mixture was heated at 160° C. for 30 min, then at 170° C. for 20 min, before heating at 180° C. for 14 h. The reaction mixture was cooled to RT before being passed through a RediSep RF Flash Column (SiO$_2$, 12 g), using CHCl$_3$ to elute. Fractions consistent with the presence of expected product, by HPLC/MS, were combined and concentrated in vacuo to afford 120B as an amber oil (50.6 mg; 10% yield). $^1$H NMR (400 MHz, DMSO-d$_6$) δ 7.98 (s, 1H), 7.79 (s, 1H), 3.15 (s, 2H), 1.50 (s, 6H). MS (ES): m/z=272/274 [M+H]$^+$. T$_r$=2.30 min (Method C).

120C.
5-Bromo-2,2-dimethyl-2,3-dihydrobenzofuran-7-amine

To a homogeneous mixture of 120B (50.6 mg, 0.19 mmol) in EtOH (3 mL) and water (0.5 mL), at RT under nitrogen atmosphere, was added ammonium chloride (199.0 mg, 3.7 mmol). The mixture was stirred for 5 min before zinc (243.0 mg, 3.7 mmol) was added in one portion. The mixture was stirred at ambient temperature for 30 min before being diluted with dichloromethane and filtered through a pad of Celite. The pad was thoroughly rinsed with dichloromethane before the combined filtrate was washed with water, dried (anhydrous MgSO$_4$), filtered and concentrated in vacuo to afford 120C as a crude residue which was used without further purification. MS (ES): m/z=242/244 [M+H]$^+$. T$_r$=1.48 min (Method C).

120D. 1-(5-Bromo-2,2-dimethyl-2,3-dihydrobenzofuran-7-yl)-3-(p-tolyl)urea

To a homogeneous mixture of 120C (45.0 mg, 0.19 mmol) in anhydrous THF (1 mL), at RT under nitrogen atmosphere, was added p-tolyl isocyanate (0.04 mL, 0.32 mmol). The resulting mixture was heated at 55° C. for 6 h before being allowed to slowly cool to RT. The reaction mixture was purified by Isco chromatography, using a RediSep normal phase silica flash column (12 g) and eluting from 0-50% EtOAc in hexane, to afford 120D as a solid (29.7 mg; 43% yield). $^1$H NMR (400 MHz, DMSO-d$_6$) δ 9.08 (s, 1H), 8.14 (s, 1H), 8.09 (d, J=2.0 Hz, 1H), 7.31 (d, J=8.3 Hz, 2H), 7.08 (d, J=8.2 Hz, 2H), 7.01-6.95 (m, 1H), 3.06 (s, 2H), 2.24 (s, 3H), 1.47 (s, 6H). MS (ES): m/z=375/377 [M+H]$^+$. T$_r$=2.19 min (Method C).

Example 120

To a homogeneous mixture of 120D (40.3 mg, 0.11 mmol) in anhydrous, nitrogen-purged DMF (1 mL), at RT under nitrogen atmosphere, was added (2-(1H-tetrazol-5-yl)phenyl)boronic acid (28.5 mg, 0.15 mmol), potassium carbonate (74.1 mg, 0.54 mmol) and water (0.4 mL). The heterogeneous mixture was purged with nitrogen for 15 min before tetrakis(triphenylphosphine)palladium (0) (6.2 mg; 5.4 µmol) was added, followed by 5 min of purging with nitrogen. The reaction vial was sealed and the mixture was heated at 100° C. for 2.5 h before being allowed to slowly cool to RT. The reaction mixture was treated with glacial acetic acid until pH 4, diluted with DMF, then purified by preparative HPLC. The crude material was purified via preparative HPLC/MS to afford Example 120 (8.1 mg; 17% yield). $^1$H NMR (500 MHz, 1:1 CD$_3$OD/CDCl$_3$) δ 7.98 (s, 1H), 7.72-7.68 (m, 2H), 7.62-7.57 (m, 2H), 7.53-7.46 (m, 2H), 7.31 (d, J=8.4 Hz, 2H), 7.10 (d, J=8.4 Hz, 2H), 6.34 (s, 1H), 2.92 (s, 2H), 2.30 (s, 3H), 1.48 (s, 6H). MS (ES): m/z=441 [M+H]$^+$. T$_r$=1.85 min (Method B).

Example 121

2-(2,2-Dimethyl-7-(3-(p-tolyl)ureido)-2,3-dihydrobenzofuran-5-yl)benzoic acid

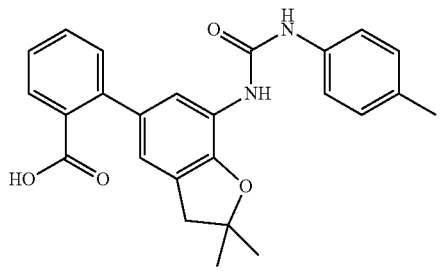 [SMILES: Cc1ccc(NC(=O)Nc2cc(-c3ccccc3C(=O)O)cc3c2OC(C)(C)C3)cc1]

Example 121 (3.8 mg; 8% yield) was prepared following a procedure analogous to that for the synthesis of Example 120, except that 2-carboxybenzeneboronic acid (24.9 mg, 0.15 mmol) was used instead of (2-(1H-tetrazol-5-yl)phenyl)boronic acid, $^1$H NMR (500 MHz, 1:1 CD$_3$OD/CDCl$_3$) δ 7.98 (s, 1H), 7.84 (d, J=1.5 Hz, 1H), 7.74-7.68 (m, 1H), 7.62 (s, 1H), 7.49-7.38 (m, 2H), 7.36-7.31 (m, 1H), 7.29 (d, J=8.4 Hz, 2H), 7.08 (d, J=8.4 Hz, 2H), 6.89 (s, 1H), 3.10 (s, 2H), 2.29 (s, 3H), 1.53 (s, 6H). MS (ES): m/z=417 [M+H]$^+$. T$_r$=1.88 min (Method B).

Example 122

3-(2,2-Dimethyl-7-(3-(p-tolyl)ureido)-2,3-dihydrobenzofuran-5-yl)benzoic acid

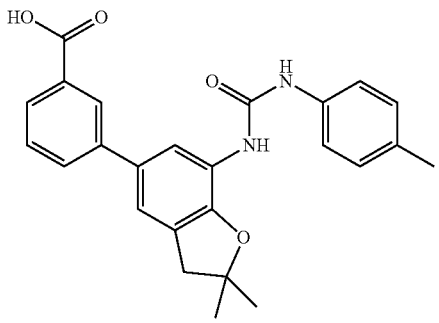 [SMILES: Cc1ccc(NC(=O)Nc2cc(-c3cccc(C(=O)O)c3)cc3c2OC(C)(C)C3)cc1]

Example 122 (5.5 mg; 12% yield) was prepared following a procedure analogous to that for the synthesis of Example 120, except that 3-boronobenzoic acid (24.9 mg, 0.15 mmol) was used instead of (2-(1H-tetrazol-5-yl)phenyl)boronic acid. $^1$H NMR (500 MHz, 1:1 CD$_3$OD/CDCl$_3$) δ 8.27-8.21 (m, 1H), 8.16 (d, J=1.5 Hz, 1H), 7.95-7.91 (m, 1H), 7.80-7.75 (m, 1H), 7.60-7.59 (m, 2H), 7.45 (t, J=7.7 Hz, 1H), 7.32 (d, J=8.4 Hz, 2H), 7.16-7.13 (m, 1H), 7.10 (d, J=8.4 Hz, 2H), 3.14 (s, 2H), 2.30 (s, 3H), 1.55 (s, 6H). MS (ES): m/z=417 [M+H]$^+$. T$_r$=1.92 min (Method B).

Example 123

(±)-1-(5-(2-(1H-Tetrazol-5-yl)phenyl)-2,2-dimethyl-3-phenyl-2,3-dihydrobenzofuran-7-yl)-3-(p-tolyl)urea

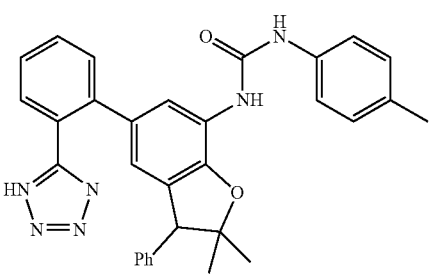 [SMILES: Cc1ccc(NC(=O)Nc2cc(-c3ccccc3-c3nnn[nH]3)cc3c2OC(C)(C)C3c2ccccc2)cc1]

123A. (E)-4-Bromo-1-((2-methyl-3-phenylallyl)oxy)-2-nitrobenzene

To a homogeneous mixture of trans-2-methyl-3-phenyl-2-propen-1-ol (5.7 mL, 37.5 mmol) and anhydrous THF (10 mL), at −78° C. under nitrogen atmosphere, was added BuLi (2.5M in hexane) (12.0 mL, 30.0 mmol) dropwise over 5 min. The resulting solution was stirred at −78° C. for one hour before 4-bromo-1-fluoro-2-nitrobenzene (5.5 g, 25.0 mmol) was added. The reaction was stirred and allowed to slowly warm to RT over one hour. The mixture was carefully poured into 1N HCl (aq) then thoroughly extracted with EtOAc. The organic extracts were combined and concentrated in vacuo to remove volatiles, before being triturated and sonicated in the presence of hexanes. The resulting precipitate was filtered through a sintered glass Buchner funnel to afford a solid which was triturated and sonicated a second time in the presence of hexane plus a small amount of methanol. Isolation by vacuum filtration afforded 123A as a bright orange solid (3.8 g; 44% yield) which was used in the next step without further purification. $^1$H NMR (400 MHz, CHLOROFORM-d) δ 8.00 (d, J=2.4 Hz, 1H), 7.63 (dd, J=9.0, 2.4 Hz, 1H), 7.39-7.34 (m, 2H), 7.32-7.23 (m, 3H), 7.05 (d, J=9.0 Hz, 1H), 6.67 (s, 1H), 4.71 (s, 2H), 1.99 (d, J=1.3 Hz, 3H). $T_r$=2.25 min (Method C).

123B. (±)-4-Bromo-2-(2-methyl-1-phenylallyl)-6-nitrophenol

A homogeneous mixture of 123A (2.0 g, 5.7 mmol) in diglyme (12 mL), under nitrogen atmosphere, was heated at 150° C. for five days before being allowed to cool to RT. The reaction mixture was purified by Isco chromatography, using a RediSep normal phase silica flash column (80 g) and eluting from 0-15% EtOAc in hexane, to afford 123B as an amber oil (866.8 mg; 43% yield). $^1$H NMR (400 MHz, DMSO-d$_6$) δ 8.05 (d, J=2.6 Hz, 1H), 7.36-7.33 (m, 2H), 7.27-7.22 (m, 2H), 7.17-7.13 (m, 2H), 5.12-5.08 (m, 2H), 4.35 (s, 1H), 1.75 (s, 3H). $T_r$=2.39 min (Method C).

123C. (±)-5-Bromo-2,2-dimethyl-7-nitro-3-phenyl-2,3-dihydrobenzofuran

A mixture of 123B (729.8 mg, 2.1 mmol) in formic acid (5 ml, 130 mmol) was heated at reflux, under nitrogen atmosphere, for 3.5 h before being allowed to slowly cool to RT overnight. The mixture was partitioned between EtOAc and water. The layers were separated and the aqueous layer was extracted twice more with EtOAc. These organic extracts were combined with the original organic layer and were washed with water and then brine, before being dried (MgSO$_4$), filtered and concentrated in vacuo to afford a residue which was purified by Isco chromatography, using a RediSep normal phase silica flash column (40 g) and eluting from 0-100% EtOAc in hexane, to afford 123C as a yellow-brown solid (614.2 mg; 84% yield). $^1$H NMR (400 MHz, DMSO-d$_6$) δ 8.13-8.09 (m, 1H), 7.59-7.56 (m, 1H), 7.39-7.31 (m, 3H), 7.12-7.06 (m, 2H), 4.62 (s, 1H), 1.61 (s, 3H), 1.01 (s, 3H). $T_r$=2.22 min (Method C).

123D. (±)-5-Bromo-2,2-dimethyl-3-phenyl-2,3-dihydrobenzofuran-7-amine

To a homogeneous mixture of 123C (667.0 mg, 1.9 mmol) in EtOH (18 mL) and water (3 mL), at RT under nitrogen, was added ammonium chloride (2.05 g, 38.3 mmol). The mixture was stirred for 10 min before zinc (2.5 g, 38.3 mmol) was added in one portion. After stirring for 4.5 h, the mixture was diluted with DCM, then filtered through a pad of Celite. The pad was thoroughly rinsed with DCM before the combined filtrates were washed with water, dried (MgSO$_4$), filtered and concentrated in vacuo to afford an amber residue. The residue was consistent for the presence of starting material, by LC/MS, and was resubjected to the original conditions of the reaction. The residue was dissolved in EtOH (18 mL) and water (3 mL), then treated with ammonium chloride (2.05 g, 38.3 mmol). The mixture was stirred, at RT under nitrogen, for 10 min before zinc (2.5 g, 38.3 mmol) was added in one portion. After stirring for 4 h, the reaction was diluted with DCM, then filtered through a pad of Celite. The pad was thoroughly rinsed with DCM before the combined filtrates were washed with water, dried (MgSO$_4$), filtered and concentrated in vacuo to afford an amber residue which was purified by Isco chromatography, using a RediSep normal phase silica flash column (24 g) and eluting from 0-50% EtOAc in hexane, to afford 123D as an amber glass (310.4 mg; 51%). $^1$H NMR (400 MHz, DMSO-d$_6$) δ 7.35-7.30 (m, 2H), 7.29-7.23 (m, 1H), 7.07-7.02 (m, 2H), 6.68 (d, J=2.0 Hz, 1H), 6.30 (dd, J=2.0, 0.9 Hz, 1H), 4.98 (br. s, 2H), 4.33 (s, 1H), 1.50 (s, 3H), 0.89 (s, 3H). MS (ES): m/z=318/320 [M+H]$^+$. $T_r$=1.95 min (Method C).

123E. (±)-1-(5-Bromo-2,2-dimethyl-3-phenyl-2,3-dihydrobenzofuran-7-yl)-3-(p-tolyl)urea To a homogeneous mixture of 123D (53.4 mg, 0.17 mmol) in anhydrous THF (1 mL), at RT under nitrogen, was added p-tolyl isocyanate (36.0 µl, 0.29 mmol). The resulting mixture was heated at 55° C. under nitrogen for 3 h before being allowed to slowly cool to RT over 17 h. The reaction was quenched with water, then extracted twice with EtOAc and once with CHCl$_3$. The combined organic extracts were concentrated in vacuo to afford 123E as a pale yellow solid, which was used in the next step without further purification. MS (ES): m/z=451/453 [M+H]$^+$. $T_r$=2.38 min (Method C).

Example 123

Example 123 (3.1 mg; 7% yield) was prepared following a procedure analogous to that for the synthesis of Example 120, except that 123E (39 mg, 0.09 mmol) was used instead of 1-(5-bromo-2,2-dimethyl-2,3-dihydrobenzofuran-7-yl)-3-(p-tolyl)urea. $^1$H NMR (500 MHz, 1:1 CD$_3$OD/CDCl$_3$) δ 7.87 (d, J=1.5 Hz, 1H), 7.66 (dd, J=7.9, 1.0 Hz, 1H), 7.65-7.61 (m, 2H), 7.61-7.56 (m, 1H), 7.56-7.53 (m, 1H), 7.50-7.45 (m, 1H), 7.34 (d, J=8.4 Hz, 2H), 7.32-7.27 (m, 2H), 7.27-7.22 (m, 1H), 7.12 (d, J=8.4 Hz, 2H), 6.85 (d, J=6.9 Hz, 2H), 6.18 (d, J=1.0 Hz, 1H), 4.32 (s, 1H), 2.31 (s, 3H), 1.62 (s, 3H), 0.95 (s, 3H). MS (ES): m/z=517 [M+H]$^+$. $T_r$=2.11 min (Method B).

Example 124

(±)-2-(2,2-Dimethyl-3-phenyl-7-(3-(p-tolyl)ureido)-2,3-dihydrobenzofuran-5-yl) benzoic acid

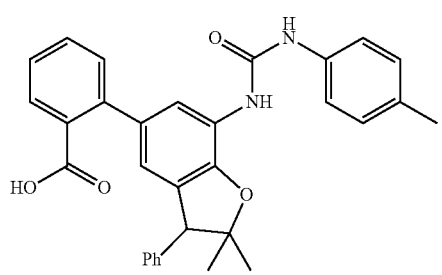 [SMILES: Cc1ccc(NC(=O)Nc2cc(-c3ccccc3C(=O)O)cc3c2OC(C)(C)C3c2ccccc2)cc1]

Example 124 (1.0 mg; 2% yield) was prepared following a procedure analogous to that for the synthesis of Example 123, except that 2-carboxybenzeneboronic acid (20.1 mg, 0.12 mmol) was used instead of (2-(1H-tetrazol-5-yl)phenyl)boronic acid. $^1$H NMR (500 MHz, 1:1 CD$_3$OD/CDCl$_3$) δ 7.99-7.96 (m, 1H), 7.73 (d, J=7.4 Hz, 1H), 7.63-7.62 (m, 2H), 7.49-7.44 (m, 1H), 7.44-7.41 (m, 1H), 7.35-7.29 (m, 5H), 7.29-7.24 (m, 1H), 7.17 (d, J=6.9 Hz, 2H), 7.10 (d, J=7.9 Hz, 2H), 6.73 (s, 1H), 4.48 (s, 1H), 2.30 (s, 3H), 1.67 (s, 3H), 1.01 (s, 3H). MS (ES): m/z=493 [M+H]$^+$. T$_r$=2.17 min (Method B).

Example 125

(±)-1-(5-(2-(1H-Tetrazol-5-yl)phenyl)-2,2-dimethyl-3-phenyl-2,3-dihydrobenzofuran-7-yl)-3-(2-fluorophenyl)urea

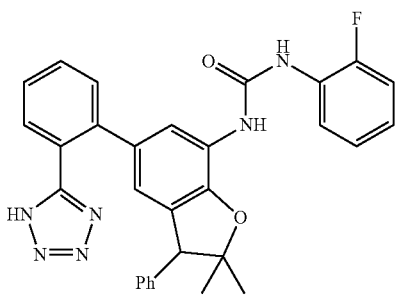 [SMILES: CC1(C)Oc2c(NC(=O)Nc3ccccc3F)cc(-c3ccccc3-c3nnn[nH]3)cc2C1c1ccccc1]

Example 125 (1.3 mg; 3% yield) was prepared following a procedure analogous to that for the synthesis of Example 123, except that 1-fluoro-2-isocyanatobenzene (0.03 mL, 0.29 mmol) was used instead of p-tolyl isocyanate in 123E. $^1$H NMR (500 MHz, 1:1 CD$_3$OD/CDCl$_3$) δ 8.17-8.09 (m, 1H), 7.98 (s, 1H), 7.88 (d, J=1.5 Hz, 1H), 7.68-7.65 (m, 1H), 7.64-7.64 (m, 1H), 7.62-7.54 (m, 2H), 7.50-7.45 (m, 1H), 7.33-7.28 (m, 2H), 7.28-7.22 (m, 1H), 7.15-7.07 (m, 2H), 7.05-6.98 (m, 1H), 6.86 (d, J=7.4 Hz, 2H), 6.21 (s, 1H), 4.33 (s, 1H), 1.63 (s, 3H), 0.96 (s, 3H). MS (ES): m/z=521 [M+H]$^+$. T$_r$=2.05 min (Method B).

Example 126

(±)-2-(7-(3-(2-Fluorophenyl)ureido)-2,2-dimethyl-3-phenyl-2,3-dihydrobenzofuran-5-yl)benzoic acid

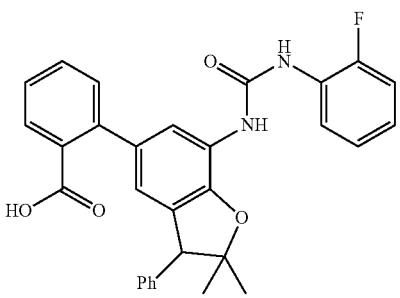 [SMILES: CC1(C)Oc2c(NC(=O)Nc3ccccc3F)cc(-c3ccccc3C(=O)O)cc2C1c1ccccc1]

Example 126 (2.4 mg; 6% yield) was prepared following a procedure analogous to that for the synthesis of Example 124, except that 1-fluoro-2-isocyanatobenzene (0.03 mL, 0.29 mmol) was used instead of p-tolyl isocyanate in 123E. $^1$H NMR (500 MHz, 1:1 CD$_3$OD/CDCl$_3$) δ 8.12-8.07 (m, 1H), 8.01-7.91 (m, 2H), 7.69-7.61 (m, 2H), 7.43-7.40 (m, 2H), 7.34-7.26 (m, 4H), 7.20-7.16 (m, 2H), 7.12-7.05 (m, 2H), 7.02-6.96 (m, 1H), 6.81 (s, 1H), 4.49 (s, 1H), 1.67 (s, 3H), 1.01 (s, 3H). MS (ES): m/z=497 [M+H]$^+$. T$_r$=2.13 min (Method B).

Example 127

(±)-1-(5-(2-(1H-Tetrazol-5-yl)phenyl)-2,2-dimethyl-3-phenyl-2,3-dihydrobenzofuran-7-yl)-3-(6-(trifluoromethyl)pyridin-3-yl)urea

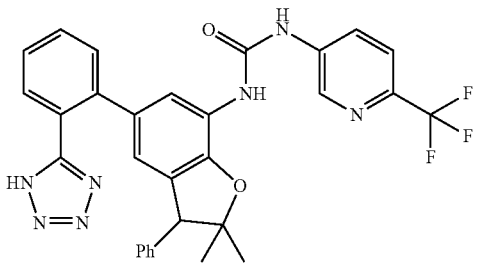 [SMILES: CC1(C)Oc2c(NC(=O)Nc3ccc(C(F)(F)F)nc3)cc(-c3ccccc3-c3nnn[nH]3)cc2C1c1ccccc1]

Example 127 (2.0 mg; 6% yield) was prepared following a procedure analogous to that for the synthesis of Example 123, except that 5-isocyanato-2-(trifluoromethyl)pyridine (0.5M solution in DMSO, 0.57 mL, 0.29 mmol) was used instead of p-tolyl isocyanate in 123E. The 5-isocyanato-2-(trifluoromethyl)pyridine solution was prepared by adding 1,1'-carbonyldiimidazole (1.14 g, 7 mmol) to a solution of 3-amino-6-(trifluoromethyl)pyridine (0.97 g, 6 mmol) in anhydrous DMSO (12 ml) and stirring at RT, under nitrogen, for 3 h. The resultant mixture was used, as a 0.5M solution in DMSO, without further purification. $^1$H NMR (500 MHz, 1:1 CD$_3$OD/CDCl$_3$) δ 8.68 (d, J=2.0 Hz, 1H), 8.28 (dd, J=8.9, 2.5 Hz, 1H), 7.84 (s, 1H), 7.69 (d, J=8.9 Hz, 1H), 7.67-7.63 (m, 1H), 7.63-7.57 (m, 2H), 7.57-7.51 (m, 2H), 7.46 (td, J=7.4, 1.5 Hz, 1H), 7.34-7.29 (m, 2H), 7.28-7.23 (m, 1H), 6.89 (d, J=6.9 Hz, 2H), 6.29 (s, 1H), 4.35 (s, 1H), 1.63 (s, 3H), 0.95 (s, 3H). MS (ES): m/z=572 [M+H]$^+$. T$_r$=2.03 min (Method B).

Example 128

(±)-2-(2,2-Dimethyl-3-phenyl-7-(3-(6-(trifluoromethyl)pyridin-3-yl)ureido)-2,3-dihydrobenzofuran-5-yl)benzoic acid

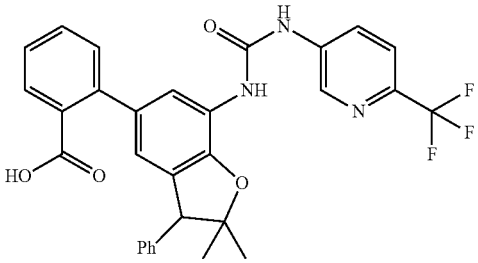 [SMILES: CC1(C)Oc2c(NC(=O)Nc3ccc(C(F)(F)F)nc3)cc(-c3ccccc3C(=O)O)cc2C1c1ccccc1]

Example 128 (6.8 mg; 22% yield) was prepared following a procedure analogous to that for the synthesis of Example 127, except that except that 2-carboxybenzeneboronic acid (13.2 mg, 0.08 mmol) was used instead of (2-(1H-tetrazol-5-yl)phenyl)boronic acid. $^1$H NMR (500 MHz, 1:1 CD$_3$OD/CDCl$_3$) δ 8.63 (d, J=2.5 Hz, 1H), 8.30 (dd, J=8.4, 2.5 Hz, 1H), 7.98 (s, 1H), 7.75 (dd, J=7.9, 1.0 Hz, 1H), 7.68 (d, J=8.4 Hz, 1H), 7.66-7.61 (m, 2H), 7.50-7.45 (m, 1H), 7.44-7.40 (m, 1H), 7.36-7.31 (m, 3H), 7.29-7.25 (m, 1H), 7.19-7.14 (m, 2H), 6.79 (s, 1H), 4.50 (s, 1H), 1.68 (s, 3H), 1.01 (s, 3H). MS (ES): m/z=548 [M+H]$^+$. T$_r$=2.13 min (Method B).

Example 129

1-((trans)-5-(2-(1H-tetrazol-5-yl)phenyl)-3-(3,3,3-trifluoropropyl)-2-vinyl-2,3-dihydrobenzofuran-7-yl)-3-(p-tolyl)urea (Enantiomer 1, Absolute Stereochemistry Unknown)

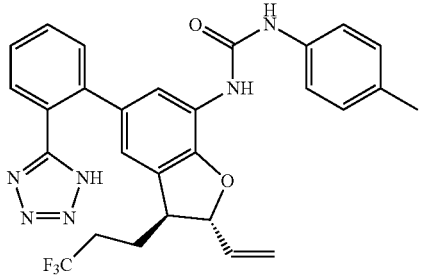

And

Example 130

1-((trans)-5-(2-(1H-tetrazol-5-yl)phenyl)-3-(3,3,3-trifluoropropyl)-2-vinyl-2,3-dihydrobenzofuran-7-yl)-3-(p-tolyl)urea (Enantiomer 2, Absolute Stereochemistry Unknown)

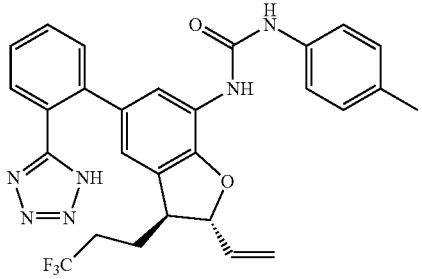 [SMILES: C=C[C@H]1Oc2c(NC(=O)Nc3ccc(C)cc3)cc(-c3ccccc3-c3nnn[nH]3)cc2[C@@H]1CCC(F)(F)F]

129A. 5-(2-((2R,3S)-7-nitro-3-(3,3,3-trifluoropropyl)-2-vinyl-2,3-dihydrobenzofuran-5-yl)phenyl)-1H-tetrazole A mixture of (2-(1H-tetrazol-5-yl)phenyl)boronic acid (0.226 g, 1.188 mmol), 7-bromo-9-nitro-5-(3,3,3-trifluoropropyl)-2,5-dihydrobenzo[b]oxepine (0.29 g, 0.792 mmol) (94D), and tetrakis(triphenylphosphine)palladium(0) (0.092 g, 0.079 mmol) was treated with aq. potassium carbonate (1.162 mL, 1.743 mmol) (bubbling). This mixture was taken up in degassed DMF (5 mL), placed under nitrogen, and heated at 92° C. for 1.5 h. The reaction was then cooled to RT, stirred overnight, then quenched by dropwise addition of glacial HOAc to pH ~5. The resulting solution was diluted with water, and this mixture was ext. twice with dichloromethane. The combined organic extract was dried (MgSO$_4$), stripped, and purified by flash chromatography (25-70% EtOAc-hexane, 0.5% HOAc). Concentration of the appropriate fractions afforded 129A (0.061 g, 17.9% yield) as a yellow glass. MS (ESI): m/z=432 [M+H]$^+$. T$_r$=0.94 (Method AA).

129B. (2R,3S)-5-(2-(1H-tetrazol-5-yl)phenyl)-2-ethyl-3-(3,3,3-trifluoropropyl)-2,3-dihydrobenzofuran-7-amine A solution of 129A (0.06 g, 0.139 mmol) in ethyl acetate (20 mL) was treated with palladium on carbon (0.030 g, 0.028 mmol) under nitrogen. This mixture was hydrogenated at 45 psi for 1 h. LCMS indicates complete olefin reduction but little reduction of the nitro group. The catalyst was removed by filtration, and the resulting solution was concentrated under a stream of nitrogen. The reaction was taken up in ~5 mL of 4:1 EtOH-THF and treated simultaneously with zinc (0.091 g, 1.391 mmol) and a solution of ammonium chloride (0.074 g, 1.391 mmol) in 0.5 mL of water. The resulting mixture was stirred 1 h at RT, diluted with water, and extracted with dichloromethane. The organic phase was dried (MgSO$_4$), concentrated, and chromatographed on silica gel to afford 129B (0.05 g, 89% yield) as an oil MS (ESI): m/z=404 [M+H]$^+$. T$_r$=0.82 (Method AA).

Examples 129 and 130

A solution of 129B (0.05 g, 0.124 mmol) in THF (1.5 mL) was treated with 1-isocyanato-4-methylbenzene (0.023 g, 0.174 mmol). The resulting brown solution was stirred 2 h at RT then purified by prep. HPLC. Concentration of the appropriate fractions afforded (+/−)-1-(5-(2-(1H-tetrazol-5-yl)phenyl)-2-ethyl-3-(3,3,3-trifluoropropyl)-2,3-dihydrobenzofuran-7-yl)-3-(p-tolyl)urea (0.053 g, 80% yield). Purification by chiral SCF (15% MeOH in CO$_2$, Chiral OX 250×30 mm column, 50 ml/min.) The peak 1 fraction was stripped to afford Example 129 (0.0175 g, 25.8% yield) as a colorless glass. MS (ESI): m/z=537 [M+H]$^+$. T$_r$=1.03 (Method AA). $^1$H NMR (400 MHz, chloroform-d) δ 8.04 (d, J=7.2 Hz, 1H), 7.82 (s, 1H), 7.50-7.60 (m, 2H), 7.43 (d, J=7.5 Hz, 1H), 7.24-7.32 (multiplicity, integral obscured by CHCl$_3$), 7.21 (d, J=8.1 Hz, 2H), 6.85 (s, 1H), 6.76 (s, 1H), 6.58 (s, 1H), 4.32-4.39 (m, 1H), 3.07-3.13 (m, 1H), 2.38 (s, 3H), 1.90-2.14 (m, 2H), 1.61-1.84 (m, integral obscured by water), 1.02 (t, J=7.3 Hz, 3H). The peak 2 fraction was stripped then lyophilized from benzene to afford Example 130 (0.017 g, 25.6% yield) as a white powder. MS (ESI): m/z=537 [M+H]$^+$. T$_r$=1.03 (Method AA). $^1$H NMR (400 MHz, chloroform-d) δ 8.04 (dd, J=7.3, 1.3 Hz, 1H), 7.83 (d, J=1.6 Hz, 1H), 7.52-7.60 (m, 2H), 7.43 (dd, J=8.8, 2.2 Hz, 1H), 7.24-7.32 (multiplicity, integral obscured by CHCl$_3$), 7.22 (d, J=8.3 Hz, 2H), 6.77 (s, 1H), 6.62 (s, 1H), 6.60 (s, 1H), 4.35-4.41 (m, 1H), 3.08-3.15 (m, 1H), 2.39 (s, 3H), 1.94-2.15 (m, 2H), 1.54-1.86 (m, integral obscured by water), 1.03 (t, J=7.3 Hz, 3H).

Example 131

3-(9-(4-Cyanophenylamino)-5-cyclopropyl-2,3,4,5-tetrahydrobenzo[b]oxepin-7-yl)-4-methoxybutanoic acid

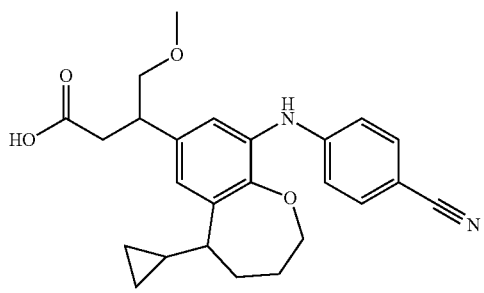 [SMILES: COCC(CC(=O)O)c1cc(Nc2ccc(C#N)cc2)c2c(c1)C(C1CC1)CCCO2]

131A. (E)-Methyl 3-cyclopropylacrylate

A 1000 mL single neck flask equipped with an additional funnel was charged with acetonitrile (400 mL) and lithium chloride (91 g, 2140 mmol). The reaction was then cooled to 0° C. Methyl 2-(dimethoxyphosphoryl)acetate (277 mL, 1712 mmol) and DBU (430 mL, 2853 mmol) were then added and stirring continued for 5 mins. Cyclopropanecarbaldehyde (100 g, 1427 mmol) was added via addition funnel over a period of 5 min. The reaction was allowed to come to room temperature and stirring was continued overnight. The reaction was quenched with water (1500 mL) and extracted with three portions of MTBE (3×1000 ml). The combined organic extracts were washed with brine. The organic layer was dried with sodium sulphate, filtered and evaporated to give the crude product (190 g pale yellow oil). The crude product was purified by silica gel chromatography using an ethyl acetate-petroleum ether gradient. Evaporation of the product containing fractions below 35° C. gave 131A (130 g). Ad NMR (300 MHz, CDCl$_3$) δ 6.42 (dd, 1H, J=15.3, 9.9 Hz), 5.88 (d, 1H, J=15.6 Hz), 3.72 (s, 3H), 1.53 (m, 1H), 0.95 (m, 2H), 0.63 (m, 2H).

131B. (E)-3-Cyclopropylprop-2-en-1-ol

To a −78° C. cooled solution of 131A (20 g, 159 mmol) in diethyl ether (200 mL) was added DIBAL-H in heptane (396 mL, 396 mmol) dropwise over a period of 25 min. After stirring for an hour, the reaction was warmed to RT. Stirring was continued for an additional hour. The reaction was then cooled to 0° C. and quenched with 20 ml of methanol. A saturated Rochelle salt solution (30 mL) was added and the reaction stirred overnight. The reaction was transferred to a separatory funnel and extracted with two additional portions of ether (2×100 mL). The combined organic layers were dried with sodium sulfate, filtered and evaporated to give 131B (14.8 g). This material was used without purification.

131C. (E)-4-Bromo-1-((3-cyclopropylallyl)oxy)-2-nitrobenzene

To an ice cold, stirred suspension of sodium hydride (238 mg, 5.94 mmol, 60% dispersion in oil) in dry THF (5.0 mL) under a nitrogen atmosphere was added 131B (350 mg, 3.57 mmol). Stirring was continued for 30 min when 4-bromo-1-fluoro-2-nitrobenzene (654 mg, 2.97 mmol) dissolved in THF (2.5 mL) was added. The reaction was stirred at RT for 2 h and then recooled to 0° C. The reaction was quenched with ice water and extracted with ethyl acetate (2×25 mL). The combined organic layers were dried over sodium sulfate, filtered and concentrated. The crude product was purified by silica gel chromatography using 0-10% ethyl acetate in petroleum ether as eluent. Evaporation of the product containing fractions gave 131C (750 mg, 2.52 mmol, 85% yield). $^1$H NMR (300 MHz, CDCl$_3$) δ 7.96 (d, 1H, J=2.7 Hz), 7.60 (dd, 1H, J=9.0, 2.4 Hz), 6.97 (d, 1H, J=9.0 Hz), 5.73 (dt, 1H), 5.38 (dd, 1H), 4.59 (d, 2H), 1.44 (m, 1H), 0.76 (m, 2H), 0.44 (m, 2H).

131D. 4-Bromo-2-(1-cyclopropylallyl)-6-nitrophenol

A stirred solution of 131C (8.0 g, 26.8 mmol) in diglyme (50 mL) was heated to 165° C. overnight. The cooled reaction was diluted with MTBE (200 mL) and washed successively with water (100 mL) and brine (100 mL). The organic layer was dried over sodium sulfate, filtered and concentrated to give a brown liquid. Purification was accomplished by flash silica gel chromatography using a 120 g Redicep column and eluting with 0-10% ethyl acetate in petroleum ether. Evaporation provided 131D (4.5 g, 15.09 mmol, 56%) as a light yellow liquid. LC-MS Anal. Calc'd for $C_{12}H_{12}BrNO_3$ 297.00, found [M+H] 298.0. T$_r$=3.55 min (Method U).

131E. 2-(Allyloxy)-5-bromo-1-(1-cyclopropylallyl)-3-nitrobenzene

A stirred solution of 131D (3.5 g, 11.74 mmol), in dry DMF (35.0 mL) was treated with potassium carbonate (4.87 g, 35.2 mmol) and 3-bromoprop-1-ene (1.562 g, 12.91 mmol). The reaction was then heated to 65° C. for 2 h. The cooled reaction was diluted with ethyl acetate (100 mL) and washed with water (2×50 mL). The aqueous layer was extracted with ethyl acetate (50 ml). The combined organic layers were dried over sodium sulfate, filtered and concentrated to give 131E (3.90 g, 11.53 mmol, 98% yield) as orange liquid. This material was of sufficient purity for the next reaction. $^1$H NMR (300 MHz, CDCl$_3$) δ 7.83 (d, 1H, J=2.4 Hz), 7.69 (d, 1H, J=2.7 Hz), 5.95 (m, 2H), 5.30 (m, 2H), 5.16 (m, 2H), 4.41 (m, 2H), 3.12 (t, 1H), 1.03 (m, 1H), 0.70 (m, 1H), 0.47 (m, 1H), 0.35 (m, 1H), 0.21 (m, 1H).

131F. 7-Bromo-5-cyclopropyl-9-nitro-2,5-dihydrobenzo[b]oxepine

A solution of 131E (230 mg, 0.680 mmol) in DCE (5 mL) was purged with argon for 15 min. The Grubbs II catalyst (28.9 mg, 0.034 mmol) was added and the reaction heated to 55° C. for 2 h. The solvent was evaporated and the residue purified by silica gel chromatography, eluting with a 3-5% gradient of ethyl acetate in petroleum ether. Evaporation provided 131F (170 mg, 0.548 mmol, 81%) as a light brown liquid. $^1$H NMR (300 MHz, CDCl$_3$) δ 7.80 (d, 1H, J=2.4 Hz), 7.60 (d, 1H, J=2.4 Hz), 5.85 (m, 1H), 5.50 (m, 1H), 4.76 (m, 2H), 2.84 (m, 1H), 1.27 (m, 1H), 0.70 (m, 1H), 0.63 (m, 1H), 0.38 (m, 1H), 0.15 (m, 1H).

131G. 7-Bromo-5-cyclopropyl-2,5-dihydrobenzo[b]oxepin-9-amine

A solution of 131F (1 g, 3.22 mmol) in ethanol (2 mL), THF (0.5 mL) and water (0.2 mL) was treated with ammonium chloride (450 mg, 8.41 mmol) and zinc (700 mg, 10.71 mmol). After stirring overnight, the reaction was filtered through a bed of celite. The celite was washed thoroughly with ethyl acetate. The liquid was washed with water and brine. The organic layer was dried with sodium sulfate, filtered and evaporated to give the crude product. Purification was accomplished by silica gel chromatography using a 2-4% gradient of ethyl acetate in petroleum ether. Evaporation of the product containing fractions gave 131G (580 mg) as a colorless liquid. $^1$H NMR (300 MHz, d$_6$-DMSO) δ 6.73 (d, 1H, J=2.4 Hz), 6.49 (d, 1H, J=2.4 Hz), 5.78 (m, 1H), 5.50 (m, 1H), 5.47 (d, 2H), 5.19 (bs, 2H), 4.46 (d, 1H), 4.28 (d, 1H), 1.21 (m, 1H), 0.51 (m, 1H), 0.40 (m, 1H), 0.27 (m, 1H), 0.11 (m, 1H), one resonance is likely obscured by the DMSO peak.

131H. tert-Butyl (7-bromo-5-cyclopropyl-2,5-dihydrobenzo[b]oxepin-9-yl)carbamate To a stirred solution of 131G (18 g, 64.2 mmol) in acetonitrile (360 mL) was added BOC$_2$O (44.8 mL, 193 mmol). The reaction was warmed to 80° C. and stirred overnight. The cooled reaction was concentrated an purified by silica gel chromatography using an ethyl acetate-petroleum ether gradient. Evaporation provided racemic 131H as a brown liquid (34 g). A portion of this material (26 g) was resolved by chiral SFC (Chiralpak AD-H using 0.2% DEA in methanol as cosolvent). Isolation of the separated material gave 131H enantiomer 1 (11 g) and 131H enantiomer 2 (10 g).

131H enantiomer 1: LC-MS Anal. Calc'd for C$_{18}$H$_{22}$BrNO$_3$ 379.08, found [M+H]380. T$_r$=4.17 min (Method U); Chiral SFC (Chiralpak AD-H, (250×4.6 mm, 5 u, 20% DEA in methanol cosolvent) T$_r$=3.01 min.

131H enantiomer 2: LC-MS Anal. Calc'd for C$_{18}$H$_{22}$BrNO$_3$ 379.08, found [M+H]380. T$_r$=4.03 min (Method U); Chiral SFC (Chiralpak AD-H, (250×4.6 mm, 5 u, 20% DEA in methanol col\solvent) T$_r$=4.01 min.

131I. tert-Butyl (7-bromo-5-cyclopropyl-2,3,4,5-tetrahydrobenzo[b]oxepin-9-yl)carbamate To a stirred solution of 131H enantiomer 1 (3.8 g, 9.99 mmol) in ethyl acetate (38 mL) was added 10% palladium on carbon (0.383 g, 0.360 mmol). The reaction mixture was stirred under H$_2$ bladder for 12 h at RT. The reaction was filtered through a pad of celite and the filtrate concentrated under reduced pressure to give crude 131I (3.7 g, 9.68 mmol, 97% yield). $^1$H NMR (300 MHz, d$_6$-DMSO) δ 8.24 (s, 1H), 7.86 (d, 1H, J=1.8 Hz), 7.10 (d, 1H J=1.8 Hz), 4.05 (m, 1H), 3.81 (m, 1H), 2.1 (m, 1H), 1.91 (m, 1H), 1.73 (m, 3H), 1.18 (m, 1H), 0.53 (m, 1H), 0.44 (m, 1H), 0.17 (m, 1H), 0.09 (m, 1H).

131 J. tert-Butyl (5-cyclopropyl-7-(5,5-dimethyl-1,3,2-dioxaborinan-2-yl)-2,3,4,5-tetrahydrobenzo[b]oxepin-9-yl)carbamate To a solution of 131I (500 mg, 1.308 mmol) in DMSO (7 mL) was added 5,5,5',5'-tetramethyl-2,2'-bi(1,3,2-dioxaborinane) (591 mg, 2.62 mmol) and potassium acetate (578 mg, 5.89 mmol). The reaction was degassed with nitrogen for 10 min and then PdCl$_2$(dppf)-CH$_2$Cl$_2$ (53.4 mg, 0.065 mmol) was added. The reaction was then heated to 80° C. for 5 h. The cooled reaction was diluted with ethyl acetate (50 mL) and washed with brine (10×50 mL). The organic layer was dried over sodium sulfate, filtered and concentrated under in vacuo to afford 131J (580 mg, 1.271 mmol, 97% yield) as brown solid.

131K. Methyl 3-(9-((tert-butoxycarbonyl)amino)-5-cyclopropyl-2,3,4,5-tetrahydrobenzo[b]oxepin-7-yl)-4-methoxybutanoate To a solution of 131J (1.6 g, 3.85 mmol) in dioxane (2 mL) was added (E)-methyl 4-methoxybut-2-enoate (1.504 g, 11.56 mmol), sodium hydroxide (3.47 mL, 3.47 mmol). The reaction mixture was purged with argon for 10 min then chloro(1,5-cyclooctadiene)rhodium(I) dimer (0.095 g, 0.193 mmol) was added. The reaction was heated at 50° C. overnight. The cooled reaction was diluted with ethyl acetate (50 mL) and washed with water (2×50 mL) and brine (2×50 mL). The organic layer was dried over sodium sulfate, filtered and concentrated to give the crude product. The material was purified by silica gel chromatography using 10% ethyl acetate in hexanes. Evaporation afforded 131K as a mixture of diastereomers. LC-MS Anal. Calc'd for C$_{24}$H$_{35}$NO$_6$ 433.25, found [M+NH3+H] 451. T$_r$=3.53 min (Method U).

131L. Methyl 3-(9-amino-5-cyclopropyl-2,3,4,5-tetrahydrobenzo[b]oxepin-7-yl)-4-methoxybutanoate To a solution of 131K (1.2 g, 2.77 mmol) in DCM (10 mL) was added TFA (5 ml, 64.9 mmol). Stirring was continued at RT for 2 h. The solvent was evaporated and the residue partitioned between ethyl acetate and sodium bicarbonate solution. The aqueous layer was further extracted with ethyl acetate. The combined organic layers were dries over sodium sulfate. Filtration and evaporation provided 131L (0.9 g, 2.213 mmol, 80% yield). LC-MS Anal. Calc'd for C$_{19}$H$_{27}$NO$_4$ 333.19, found [M+H] 334. T$_r$=2.4 min (Method U).

131M. Methyl 3-(9-((4-cyanophenyl)amino)-5-cyclopropyl-2,3,4,5 tetrahydrobenzo[b]oxepin-7-yl)-4-methoxybutanoate To a solution of 131L (0.1 g, 0.300 mmol) in 2-propanol (3 mL) was added 4-bromobenzonitrile (0.066 g, 0.360 mmol) and potassium acetate (0.088 g, 0.900 mmol). The reaction was degassed with nitrogen for 15 min and then 2-di-tert-butylphosphino-2',4',6'-triisopropylbiphenyl (0.025 g, 0.060 mmol) and Pd$_2$(dba)$_3$ (0.027 g, 0.030 mmol) were added. The reaction was then heated to 80° C. for 2 h. The cooled reaction was diluted with ethyl acetate (20 mL) and washed with water (2×15 mL) and brine (2×15 mL). The organic layer was dried over sodium sulfate and concentrated under reduced pressure to afford 131M (140 mg, 0.171 mmol, 56.9% yield) as a mixture of diastereomers. LC-MS Anal. Calc'd for C$_{26}$H$_{30}$N$_2$O$_4$ 434.22, found [M+H] 435. T$_r$=3.43 min (Method U).

Example 131

To a stirred solution of 131M (0.15 g, 0.345 mmol) in THF (3 mL) and MeOH (3 mL) was added LiOH—H$_2$O (0.145 g, 3.45 mmol). The reaction was stirred at RT overnight. The solvent was removed under reduced pressure. The residue was partitioned between ethyl acetate and citric acid solution The aqueous layer was further extracted with ethyl acetate. The combined organic layer was dried over sodium sulfate, filtered and concentrated under reduced pressure to give the crude product. The crude material was purified via preparative LC/MS with the following conditions: Column: Waters XBridge C18, 19×150 mm, 5-μm particles; Mobile Phase A: 0.1% trifluoroacetic acid; Mobile Phase B: acetonitrile; Gradient: 15-55% B over 25 min, then a 5-minute hold at 100% B; Flow: 15 mL/min. Fractions containing the desired product were combined and dried via centrifugal evaporation. This material was further purified by SFC (Chiralpak AS-H (250×4.6 mm, 5 u, 20% of 0.2% DEA in IP A) to afford Example 131 diastereomer 1 and diastereomer 2.

Example 131 diastereomer 1: LC-MS Anal. Calc'd for $C_{25}H_{28}N_2O_4$ 420.20, found [M+H] 421. $T_r$=1.72. min (Method O). Chiral SFC (Chiralpak AS-H, (250×4.6 mm, 5 u, 20% of 0.2% DEA in IPA cosolvent) $T_r$=5.16 min. $^1$H-NMR (400 MHz, DMSO-d6: δ 8.27 (s, 1H), 7.54 (d, J=8.80 Hz, 2H), 7.05 (d, J=8.40 Hz, 3H), 6.86 (d, J=1.60 Hz, 1H), 4.01-4.03 (m, 1H), 3.70 (t, J=9.60 Hz, 1H), 3.17-3.23 (m, 5H), 2.62-2.67 (m, 1H), 2.46-2.51 (m, 2H), 2.06-2.08 (m, 1H), 1.92-1.93 (m, 1H), 1.78-1.81 (m, 3H), 1.22-1.24 (m, 1H), 0.53-0.55 (m, 1H), 0.44-0.45 (m, 1H), 0.11-0.19 (m, 2H).

Example 131 diastereomer 2: LC-MS Anal. Calc'd for $C_{25}H_{28}N_2O_4$ 420.20, found [M+H] 421. $T_r$=1.72. min (Method O). Chiral SFC (Chiralpak AS-H, (250×4.6 mm, 5 u, 20% of 0.2% DEA in IPA cosolvent) $T_r$=8.3 min. $^1$H-NMR (400 MHz, DMSO-d6: δ 8.27 (s, 1H), 7.54 (d, J=8.80 Hz, 2H), 7.05 (d, J=8.80 Hz, 3H), 6.86 (s, 1H), 4.00-4.03 (m, 1H), 3.71 (t, J=9.60 Hz, 1H), 3.16-3.23 (m, 5H), 2.62-2.67 (m, 1H), 2.42-2.51 (m, 2H), 2.09-2.11 (m, 1H), 1.92-1.93 (m, 1H), 1.78-1.81 (m, 3H), 1.22-1.24 (m, 1H), 0.53-0.54 (m, 1H), 0.44-0.45 (m, 1H), 0.09-0.19 (m, 2H).

Example 132

(+/−)-1-(6-(2-(2H-tetrazol-5-yl)phenyl)-4-phenylchroman-8-yl)-3-(p-tolyl)urea

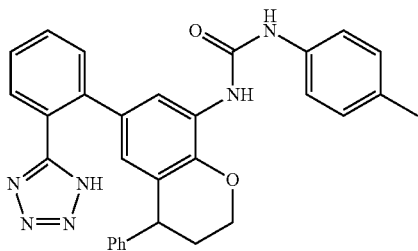 [SMILES: Cc1ccc(NC(=O)Nc2cc(-c3ccccc3-c3nnn[nH]3)cc3c2OCCC3c2ccccc2)cc1]

132A. (+/−)-(E)-ethyl 3-(5-bromo-2-hydroxy-3-nitrophenyl)acrylate 5-bromo-2-hydroxy-3-nitrobenzaldehyde (466 mg, 1.894 mmol) was dissolved in dry toluene (10 mL) under nitrogen. (Carbethoxymethylene)triphenylphosphorane (726 mg, 2.084 mmol) was added, and the reaction was warmed to 100° C. The reaction turns dark red upon addition of the ylide. The reaction was stirred for 3 h, cooled, and applied to an 80 g Isco silica gel column. The product was eluted with a gradient of 0 to 50% ethyl acetate in hexanes to afford, after concentration, 520 mg (85%) of 132A an orange oil. $^1$H NMR (400 MHz, CHLOROFORM-d) δ 11.18 (br.s, 1H), 8.83 (d, J=2.4 Hz, 1H), 8.18 (d, 1H, J=2.4 Hz), 7.86 (d, 1H, J=16.3 Hz), 6.86 (d, 1H, J=16.1 Hz), 4.23 (q, 2H, J=7.1 Hz), 1.28 (t, 3H, J=7.2 Hz).

132B. (+/−)-ethyl 3-(5-bromo-2-hydroxy-3-nitrophenyl)-3-phenylpropanoate

A reaction vial was charged with 132A (46 mg, 0.146 mmol), phenylboronic acid (53.2 mg, 0.437 mmol), and dioxane (7.5 mL). Sodium hydroxide (72.8 μl, 0.073 mmol) (1 M) was added, and nitrogen was bubbled through the mixture for 20 min. Chloro(1,5-cyclooctadiene)rhodium(I), dimer (3.59 mg, 7.28 μmol) was then added, and the vial was sealed and stirred overnight at 50° C. The reaction was quenched with acetic acid (4.17 μl, 0.073 mmol), applied to a 12 g Isco silica gel column, and eluted with a gradient of 0 to 50% ethyl acetate in hexanes. Concentration of the appropriate fractions afforded 39 mg (68%) of 132B an orange oil. $^1$H NMR (400 MHz, CHLOROFORM-d) δ 11.0 (s, 1H), 8.18 (s, 1H), 7.63 (s, 1H), 7.25-7.39 (m, 5H), 5.03 (t, 1H, J=8.0 Hz), 4.07-4.14 (m, 2H), 3.04-3.08 (m, 2H), 1.19 (t, 3H, J=7.2 Hz).

132C. (+/−)-6-bromo-8-nitro-4-phenylchroman 4-bromo-2-(3-hydroxy-1-phenylpropyl)-6-nitrophenol Compound 132B (39 mg, 0.099 mmol) was dissolved in dry THF (2.0 mL) and cooled in an ice bath. A solution of DIBAL-H (317 μl, 0.317 mmol) (1 M in hexanes) was added drop wise, and the reaction was stirred 1 h and treated with additional DIBAL-H (317 μl, 0.317 mmol). The reaction was stirred overnight, warming to RT, then quenched with 1 N hydrochloric acid. The resulting mixture was extracted with ethyl acetate, and the organic extract was washed with water then brine. The organic phase was then dried over magnesium sulfate, filtered, and stripped. The residue was applied to a 4 g Isco silica gel column and eluted with a gradient of 0 to 75% ethyl acetate in hexanes. Concentration of the appropriate fractions afforded 132C (22.7 mg, 0.064 mmol, 65.2% yield) as a yellow film. $^1$H NMR (500 MHz, CHLOROFORM-d) δ 7.92-7.81 (m, 1H), 7.41-7.36 (m, 2H), 7.35-7.30 (m, 1H), 7.21 (dd, J=2.4, 0.9 Hz, 1H), 7.15-7.11 (m, 2H), 4.39-4.35 (m, 2H), 4.23 (t, J=6.4 Hz, 1H), 2.42-2.34 (m, 1H), 2.24-2.16 (m, 1H). $^{13}$C NMR (126 MHz, CHLOROFORM-d) δ 148.3, 143.3, 139.7, 137.6, 130.0, 129.0, 128.4, 127.4, 126.9, 110.9, 65.2, 41.0, 30.2.

132D. 6-bromo-8-nitro-4-phenylchroman

Compound 132C (47 mg, 0.133 mmol) was dissolved in dry THF (1.0 mL) under nitrogen. Triphenylphosphine (52.5 mg, 0.200 mmol) was added followed by DIAD (44.1 μl, 0.227 mmol). The reaction was stirred overnight, applied to a flash silica gel column and eluted with a gradient of 15% to 25% ether-hexanes. Concentration of the appropriate fractions afforded 132D (32 mg, 0.096 mmol, 71.8% yield) as a pale rose oil. $^1$H NMR (500 MHz, CHLOROFORM-d) δ 7.92-7.81 (m, 1H), 7.41-7.36 (m, 2H), 7.35-7.30 (m, 1H), 7.21 (dd, J=2.4, 0.9 Hz, 1H), 7.15-7.11 (m, 2H), 4.39-4.35 (m, 2H), 4.23 (t, J=6.4 Hz, 1H), 2.42-2.34 (m, 1H), 2.24-2.16 (m, 1H). $^{13}$C NMR (126 MHz, CHLOROFORM-d) δ 148.3, 143.3, 139.7, 137.6, 130.0, 129.0, 128.4, 127.4, 126.9, 110.9, 65.2, 41.0, 30.2.

132E. (+/−)-1-(6-bromo-4-phenylchroman-8-yl)-3-(p-tolyl)urea

Compound 132D (32 mg, 0.096 mmol) was dissolved in ethanol (2.0 mL) and water (0.2 mL) under nitrogen. The resulting mixture was treated with ammonium chloride (51.2 mg, 0.958 mmol) followed by zinc (62.6 mg, 0.958 mmol). The reaction was stirred for an hour, diluted with methylene chloride, and filtered. The filtrate was washed with water then brine, dried over magnesium sulfate, filtered and evaporated. The residue was dissolved in THF (1.0 mL), treated with p-tolyl isocyanate (18.23 µl, 0.144 mmol), and stirred overnight. The reaction was then stripped, diluted with methanol, and filtered. The filtrate was stripped, redissolved in methanol and purified by RP-HPLC (methanol-water gradient +0.1% TFA). The appropriate fraction was brought to basic pH with half saturated sodium bicarbonate solution, partially concentrated, and extracted with methylene chloride. The organic phase was dried over magnesium sulfate, filtered and evaporated to afford 132E as a colorless solid. $^1$H NMR (500 MHz, THF) δ 8.45 (d, J=2.4 Hz, 1H), 8.42 (s, 1H), 7.73 (s, 1H), 7.41-7.36 (m, 2H), 7.31-7.26 (m, 2H), 7.22-7.17 (m, 1H), 7.15-7.12 (m, 2H), 7.04 (d, J=8.2 Hz, 2H), 6.53 (dd, J=2.4, 0.8 Hz, 1H), 4.29-4.21 (m, 2H), 4.18 (t, J=6.3 Hz, 1H), 2.41-2.27 (m, 1H), 2.26 (s, 3H), 2.08 (dtd, J=13.8, 6.7, 4.2 Hz, 1H). $^{13}$C NMR (126 MHz, THF) δ 152.9, 146.1, 143.2, 138.7, 132.0, 131.5, 130.0, 129.5, 129.5, 127.6, 126.7, 125.6, 120.2, 119.2, 113.6, 65.4, 41.8, 32.5, 21.0.

Example 132

A reaction vial was charged with 132E (6.6 mg, 0.015 mmol), (2-(2H-tetrazol-5-yl)phenyl)boronic acid (17.20 mg, 0.091 mmol), aq. potassium carbonate (121 µl, 0.181 mmol) (1.5 M solution), and DMF (0.6 mL). This mixture was degassed by three cycles of vacuum/nitrogen purge and treated with tetrakis(triphenylphosphine)palladium(0) (3.49 mg, 3.02 µmol). The degassing procedure was repeated, and the reaction was warmed to 90° C. and stirred overnight. Additional (2-(2H-tetrazol-5-yl)phenyl)boronic acid (17.20 mg, 0.091 mmol), aq. potassium carbonate (121 µl, 0.181 mmol) (1.5 M solution), and tetrakis(triphenylphosphine)palladium(0) (3.49 mg, 3.02 µmol) were added, and the degassing procedure was repeated. The reaction was heated at 90° C. for 2 h longer, cooled, and quenched with acetic acid (41.5 µl, 0.724 mmol). The quenched reaction was diluted with DMF (1.1 mL), filtered, and purified by prep. HPLC to afford Example 132 (0.9 mg, 12%). MS (ESI): m/z=503 [M+H]$^+$. $T_r$=2.07 (Method B). $^1$H NMR (400 MHz, DMSO-d$_6$) δ 9.25 (s, 1H), 8.22 (s, 1H), 7.96 (d, 1H, J=1.8 Hz), 7.85-7.64 (m, 2H), 7.54 (d, 1H, J=7.0 Hz), 7.48 (t, 1H, J=7.6 Hz), 7.41 (d, 1H, J=7.6 Hz), 7.32 (d, 2H, J=8.2 Hz), 7.28 (t, 2H, J=7.6 Hz), 7.20-7.23 (m, 1H), 7.09 (d, 2H, J=8.2 Hz), 6.99 (d, 2H, 7.3 Hz), 4.27-4.33 (m, 1H), 4.18-4.23 (m, 1H), 4.07 (t, 1H, J=6.1 Hz), 2.24 (s, 3H), 2.18-2.24 (m, 1H), 2.02-2.09 (m, 1H).

Evaluation of Biological Activity

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press, Cold Spring Harbor, NY (2001); and Ausubel et al., *Current Protocols in Molecular Biology*, Vols. 1-4, John Wiley and Sons, Inc. New York, NY (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, MO) unless specified otherwise. Groups of 1,000 human islets can be cultured for 24 h in 1 mL medium with cytokines, recovered by centrifugation for 5 min at 800×g and sonicated in 150 µL PBS containing a protease inhibitor cocktail (Set 2; Calbiochem, EMD Biosciences, San Diego, CA). The sonicate can be centrifuged for 10 min at 10,000×g, and the supernatant can be assayed in triplicate by incubating a 40 µl sample with an equal volume of 100 mmol/L potassium phosphate buffer, pH 6.5, containing 40 mmol/L ascorbic acid (neutralized to pH 7.0), 100 µmol/L methylene blue, 200 µg/mL catalase, and 400 µmol/1 L-Trp for 30 min at 37° C. The assay can be terminated by the addition of 16 µL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 µg/mL; 500-2,000 units/mL) and 1-a-methyl Trp (1-MT; 40 µmol/L) can be added to the incubation media as indicated. This assay can also form the basis of a cell-based assay, and may be quantified via LCMS/MS as an alternative to UV/Vis detection.

Immunohistochemical Detection of IDO.

Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 µm sections that were stained with antibodies raised against pancreatic duodenal homeobox 1 (PDX1) and IDO. Antigen retrieval can be performed in a water bath for 30 min in a buffer containing 10 mmol/1 Tris and 1 mmol/1 EDTA (pH 9.0) at 97° C. The sections can be blocked for 1 h with 5% normal goat serum in PBS. The tissues can then be reacted with mouse monoclonal anti-human IDO antibody (1:20; Chemicon) and goat polyclonal anti-human PDX1 antibody (1:2,000; which may be requested from Dr. Chris Wright, School of Medicine, Vanderbilt, TN) overnight at RT in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258 (Molecular Probes, Eugene, OR). Images can be acquired by Intelligent Imaging System software from an Olympus 1X81 inverted motorized microscope equipped with Olympus DSU (spinning disk confocal) and Hamamatsu ORCA HER monochromatic CCD camera.

Alternative means for evaluating the IDO inhibitors of the present invention are described in WO 2010/0233166 and are summarized hereafter.

Biochemical Assay. cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K. et al., *Prot. Exp. Purif.*, 19:22-29 (2000)). To screen for IDO inhibitory activity, compounds can be evaluated at a single concentration of, for example, 200 µM against 50 ng of IDO enzyme in 100 µL reaction volumes with tryptophan added at increasing concentrations at, for example, 0, 2, 20, and 200 µM. Kynurenine production can be measured at 1 hour.

Cell-based Assay. COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at $6 \times 10^4$ cells per well. The following day, the wells can be washed and new media (phenol red free) containing 20 µg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 µM. More extensive dose-escalation profiles can be collected for select compounds.

Exemplary compounds were tested for inhibition of IDO activity. Experimental procedures and results are provided below.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 µL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 µL) and 0.2% (w/v) Ehrlich reagent (4-dimethylaminobenzaldehyde, Sigma-Aldrich) in glacial acetic acid were mixed in a new clear bottom 384-well plate. This plate was then incubated at RT for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Assessment of inhibitor activity in HeLa cell-based indoleamine 2,3-dioxygenase (IDO) assay:

HeLa (ATCC® CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100U/mL penicillin, 100 µg/mL streptomycin (#SV30010, HyClone) and 10% fetal bovine serum (#SH30071.03 HyClone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 µL of culture medium. After a further 48 hour incubation, 170 µL of supernatant was transferred from each well to a fresh 96-well plate. 12.1 µL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 µL of the supernatant was transferred from each well to a fresh 96-well plate. 100 µl of 2% (w/v) p-dimethylaminobenzaldehyde (#15647-7, Sigma-Aldrich) in acetic acid (#A6283, Sigma-Aldrich) was added to each well mixed and incubated at RT for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Results of the IDO assays are shown in the table below.

| Example # | IDO1 HEK Human $IC_{50}$ (nM) | IDO1 HeLa $IC_{50}$ (nM) |
| --- | --- | --- |
| 1 | 18.7 | 13.9 |
| 2-1 | 98.2 | NA |
| 2-2 | 31.8 | NA |
| 2-3 | 21.4 | NA |
| 3 | 35.6 | NA |
| 4 | 70.2 | NA |
| 4 | 230.4 | NA |
| 5 | 232.3 | NA |
| 5 | 2,236 | NA |
| 6 | 70 | |
| 7 | 40.8 | NA |
| 8-1 | 27.2 | NA |
| 8-2 | 970.3 | NA |
| 9 (En. 1) | >6,000 | NA |
| 9 (En. 2) | 578.7 | NA |
| 9 (Rac.) | 1,035 | NA |
| 10 (En.2) | 41.4 | NA |
| 10 (En. 1) | 1,454 | NA |
| 12 | 1,067 | NA |
| 15 | 232 | |
| 17 | 53 | |
| 18 | 950.2 | NA |
| 21 | 177.1 | NA |
| 23 (En. 1) | 3,499 | NA |
| 23 (En. 2) | >6,000 | NA |
| 24 | 4.4 | NA |
| 24 (En. 1) | 0.98 | 28.9 |
| 24 (En. 2) | 6.3 | 161 |
| 25 (En. 1) | 28.6 | NA |
| 25 (En. 2) | 71.4 | NA |

-continued

| Example # | IDO1 HEK Human IC$_{50}$ (nM) | IDO1 HeLa IC$_{50}$ (nM) |
|---|---|---|
| 25 (Rac) | 29.9 | NA |
| 26 (En. 1) | 2,557 | NA |
| 26 (En. 2) | 423.7 | NA |
| 27 | 26.4 | NA |
| 28 | 2.6 | NA |
| 29 | 18 | NA |
| 30 (Dia. mix 1) | 77.6 | NA |
| 30 (Dia. mix 2) | 11.7 | NA |
| 30 (En. 1) | 4.1 | NA |
| 31 | 70.8 | NA |
| 32 | 419.4 | NA |
| 33-1 | 1.2 | |
| 33-2 | 8 | |
| 34-1 | 66 | |
| 34-2 | 5.1 | |
| 35 | 19.7 | NA |
| 36 | 7.6 | NA |
| 36 (En. 1) | 10.4 | 14.9 |
| 36 (En. 2) | 2.4 | 3.6 |
| 37 (En. 1) | 220.7 | NA |
| 37 (En. 2) | 30.8 | NA |
| 37 (Rac) | 117 | NA |
| 38 (En. 2) | 19.4 | NA |
| 38 (En. 1) | 223 | NA |
| 39 (En. 2) | 32.6 | NA |
| 39 (En. 1) | >6,000 | NA |
| 40 (En. 1) | 219.2 | NA |
| 40 (En. 2) | 58.6 | NA |
| 41 (En. 1) | 25.2 | NA |
| 41 (En. 2) | 93.8 | NA |
| 43 | 30.1 | NA |
| 44 | 1.7 | NA |
| 45 | 106.1 | NA |
| 45 | 287.6 | NA |
| 46 | 0.78 | NA |
| 47 | 282.3 | NA |
| 48 | 12.5 | NA |
| 50 | 0.69 | NA |
| 50 | 67.8 | NA |
| 51 | 3.8 | NA |
| 52 | 499 | NA |
| 53 | 4.2 | NA |
| 53 (En. 1) | 215.6 | NA |
| 53 (En. 2) | 1.3 | NA |
| 54 | 432.5 | NA |
| 55 (En. 2) | 77.6 | NA |
| 55 (Rac) | 154.7 | NA |
| 55 (En. 1) | 1,405 | NA |
| 56 | 68.8 | NA |
| 56 | 716.6 | NA |
| 57 (En. 2) | 188.7 | NA |
| 57 (En. 1) | 849.2 | NA |
| 58 | 1,361 | NA |
| 59 (En. 2) | 280.4 | NA |
| 60 (En. 1) | >6,000 | NA |
| 61 | 2,288 | NA |
| 62 (En. 2) | 44.9 | NA |
| 62 (En. 1) | 1,814 | NA |
| 63 (En. 1) | 539.4 | NA |
| 63 (En-2) | 11.6 | NA |
| 64 (En. 2) | 17 | NA |
| 64 (En. 1) | 421.5 | NA |
| 65 | 381.3 | NA |
| 66 | 327.2 | NA |
| 67 | 1.1 | 1 |
| 68 | 14.4 | NA |
| 69 | 14.6 | NA |
| 70 | 28.2 | NA |
| 71 | 3.1 | NA |
| 72 | 7.7 | NA |
| 72 | 30.4 | 24.2 |
| 74 | 7.7 | 5.1 |
| 75 | 18.5 | NA |
| 76 | 8.3 | NA |
| 78 | 8.5 | NA |
| 79 | 33.5 | NA |
| 81 | 2,512 | NA |
| 83 | 17.4 | NA |
| 84 (En. 2) | 25.8 | NA |
| 85 | 32 | |
| 86 | 12 | |
| 87 | NA | 10.9 |
| 88 | 105 | |
| 89 | 13 | |
| 90 | 18 | |
| 91 | 89 | |
| 92 | NA | 7.2 |
| 93 | 9.1 | |
| 94 | 19 | |
| 95 | 88 | |
| 96 | 26 | |
| 97 | 1800 | |
| 98 | 87 | |
| 99 | 5.6 | |
| 100 | 21 | |
| 101 | 7.1 | |
| 102 | 13 | |
| 103 | 11 | |
| 104 | 52 | |
| 105 | NA | 54.7 |
| 106 | NA | 30.1 |
| 107 | NA | 14.5 |
| 108 | NA | 164 |
| 109 | NA | 5.9 |
| 110 | 50.2 | 24.7 |
| 111 | 1400 | |
| 112 | 7900 | |
| 113 | 77 | |
| 114 | 1300 | |
| 115 | 28 | |
| 116 | 125 | |
| 117 | 2500 | |
| 118 | 23 | |
| 119 | 785 | |
| 120 | 460 | |
| 123 | 6.3 | |
| 124 | 77 | |
| 125 | 92 | |
| 126 | 310 | |
| 127 | 2100 | |
| 128 | 2300 | |
| 129 | 16 | |
| 130 | 40 | |
| 131 (dia. 1) | 25.6 | NA |
| 131 (dia. 2) | 2 | 2.1 |
| 132 | 21.2 | NA |

What is claimed:

1. A compound of formula (I):

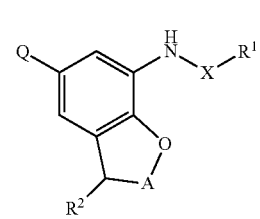

wherein:

A is —CR$^7$R$^8$—, —CR$^9$R$^{10}$CR$^{11}$R$^{12}$—, —CR$^{13}$R$^{14}$CR$^{15}$R$^{16}$CHR$^{17}$—, or —CR$^{14}$=CR$^{16}$CHR$^{17}$—;

Q is (C$_2$-C$_6$ alkyl substituted with (C(O)OH and R$^3$), (C$_3$-C$_6$ cycloalkyl substituted with W) or (phenyl substituted with W and R$^3$);

X is a bond, C(O), —C(O)CR⁴R⁵— or —C(O)NR⁶—;
W is selected from: C(O)OR$^a$, C(O)NH$_2$, —S(O)$_2$NHR$^b$,

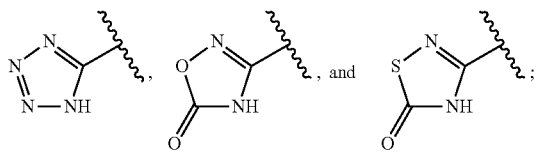 [SMILES: *c1nnn[nH]1 ; *c1noc(=O)[nH]1 ; *c1nsc(=O)[nH]1]

R¹ is selected from: C$_1$-C$_6$ alkyl, C$_3$-C$_6$ cycloalkyl, tetrahydro-2H-pyranyl, morpholinyl, phenyl, naphthalenyl, thiophenyl, thiazolyl, isoxazolyl, 1H-imidazolyl, pyrazolyl, 1,2,4-oxadiazolyl, 1,3,4-thiadiazolyl, 1H-tetrazolyl, pyridinyl, pyrimidinyl, pyridazinyl, pyrazinyl, benzo[b]thiophenyl, benzo[d]thiazolyl, benzo[d]oxazolyl, benzo[d]imidazolyl, pyrazolo[1,5-a]pyrimidinyl, [1,2,4]triazolo[4,3-b]pyridazinyl, 7H-pyrrolo[2,3-d]pyrimidinyl, and quinolin-2-yl; wherein each moiety is substituted with 0 to 2R$^c$;

R² is selected from: C$_1$-C$_6$ alkyl, C$_1$-C$_6$ haloalkyl, C$_3$-C$_6$ cycloalkyl, and (phenyl substituted with 0 to 2 Rd);

R³ is independently H, halo, C$_1$-C$_4$ alkyl, C$_1$-C$_4$ halolkyl, C$_1$-C$_4$ alkoxy or C$_1$-C$_4$ halolkoxy;

R⁴ and R⁵ are independently H, halo, or C$_1$-C$_4$ alkyl;

R⁶ is H or C-C$_4$ alkyl;

R⁷ is H, halo, C$_1$-C$_4$ alkyl, C$_2$-C$_4$ alkenyl, or cyclopropyl;

R⁸ is H, halo, or C$_1$-C$_4$ alkyl;

R⁹, R¹⁰, R¹¹ and R¹² are H, halo, or C$_1$-C$_4$ alkyl;

R¹³ and R¹⁵ are independently H, OH, halo or C$_1$-C$_4$ alkyl;

R¹⁴, R¹⁶ and R¹⁷ are independently H, halo or C$_1$-C$_4$ alkyl;

R$^a$ is H or C$_1$-C$_6$ alkyl;

R$^b$ is H, or C(O)(C$_1$-C$_4$ alkyl), or C(O)Ph;

R$^c$ is independently selected from: halo, CN, C$_1$-C$_6$ alkyl, C$_1$-C$_6$ halolkyl, C$_1$-C$_6$, alkoxy, C$_1$-C$_6$ halolkoxy, CH$_2$OH, C(O)OH, C(O)NH$_2$, —S(O)$_2$(C$_1$-C$_4$ alkyl), C$_3$-C$_6$ cycloalkyl, and (phenyl substituted with 0 to 2 R$^e$); and R$^d$ and R$^e$ are independently selected from halo, C$_1$-C$_4$ alkyl, C$_1$-C$_4$ halolkyl, C$_1$-C$_4$ alkoxy and C$_1$-C$_4$ halolkoxy;

or a pharmaceutically acceptable salt thereof.

2. The compound according to claim 1, wherein:
Q is C$_3$-C$_6$ alkyl substituted with (C(O)OH and R³; and
R³ is independently H, halo, C$_1$-C$_4$ alkyl, or C$_1$-C$_4$ alkoxy.

3. The compound according to claim 1, wherein:
Q is

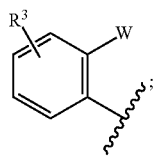

wherein:
W is selected from: C(O)OR$^a$, —S(O)$_2$NHR$^b$,

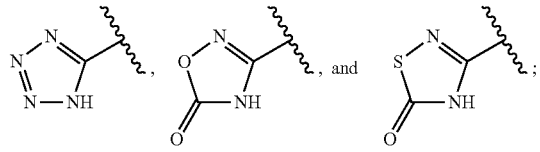 [SMILES: *c1nnn[nH]1 ; *c1noc(=O)[nH]1 ; *c1nsc(=O)[nH]1]

R$^a$ is H or C$_1$-C$_4$ alkyl.

4. The compound according to claim 1, wherein:
Q is

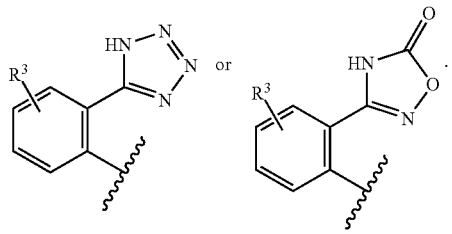

5. The compound according to claim 1, wherein: X is a bond, —C(O)CHR⁴—, or —C(O)NR⁶—.

6. The compound according to claim 1, wherein the compound is of formula (II):

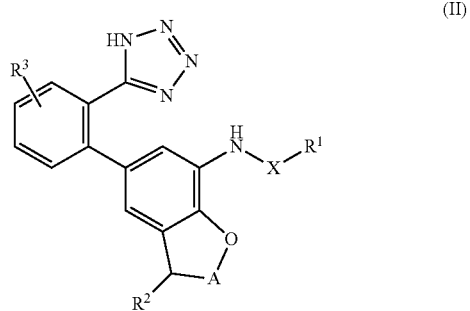

(II)

A is —CR⁷R⁸—, —CR⁹R¹⁰CR¹¹R¹²—, —CR¹³R¹⁴CR¹⁵R¹⁶CHR¹⁷—, or —CR¹³=CR¹⁵CHR¹⁷—;

X is a bond, —C(O)CH$_2$—, or —C(O)NH—;

R¹ is selected from: C$_3$-C$_6$ cycloalkyl, phenyl, thiazolyl, isoxazolyl, 1,2,4-oxadiazolyl, 1,3,4-thiadiazolyl, pyridinyl, pyrimidinyl, benzo[d]oxazolyl, benzo[d]thiazolyl, benzo[d]imidazolyl, pyrazolo[1,5-a]pyrimidinyl, and quinolinyl; wherein each moiety is substituted with 0 to 2 R$^c$;

R² is selected from: C$_1$-C$_6$ alkyl, C$_1$-C$_6$ haloalkyl, C$_3$-C$_6$ cycloalkyl, and (phenyl substituted with 0 to 1 halo);

R³ is H, halo, or C$_1$-C$_4$ alkyl;

R⁷ is H, halo, C$_1$-C$_4$ alkyl, C$_2$-C$_4$ alkenyl, or cyclopropyl;

R⁸ is H, halo, or C$_1$-C$_4$ alkyl;

R⁹, R¹⁰, R¹¹ and R¹² are H, halo, or C$_1$-C$_4$ alkyl;

R¹³ and R¹⁵ are independently H, OH, halo or C$_1$-C$_4$ alkyl;

R¹⁴, R¹⁶, and R¹⁷ are independently H, halo or C$_1$-C$_4$ alkyl; and

R$^c$ is independently selected from: halo, CN, C$_1$-C$_4$ alkyl, C$_1$-C$_4$ halolkyl, $C_1$-$C_4$ alkoxy, $C_1$-$C_4$ halolkoxy, cyclopropyl, and (phenyl is substituted with 0 to 1 $C_1$-$C_4$ alkyl);
or a pharmaceutically acceptable salt thereof.

7. The compound according to claim 1, wherein:
A is -$CR^{13}R^{14}CR^{15}R^{16}CHR^{17}$— or —$CR^{13}$=$C^{15}CHR^{17}$—;
$R^1$ is selected from: cyclopropyl, phenyl, thiazolyl, isoxazolyl, 1,2,4-oxadiazolyl, 1,3,4-thiadiazolyl, pyridinyl, pyrimidinyl, benzo[d]oxazolyl, benzo[d]thiazolyl, benzo[d]imidazolyl, pyrazolo[1,5-a]pyrimidinyl, and quinolinyl; wherein each moiety is substituted with 0 to 2 $R^c$;
$R^2$ is selected from: $C_1$-$C_6$ alkyl, $C_1$-$C_6$ haloalkyl, cyclopropyl, and (phenyl substituted with 0 to 1 F);
$R^3$ is H, F, or $CH_3$;
$R^{13}$ and $R^{15}$ are independently H, OH, F, Cl or $C_1$-$C_4$ alkyl;
$R^{14}$, $R^{16}$ and $R^{17}$ are independently H, F, Cl and $C_1$-$C_4$ alkyl; and
$R^c$ is independently selected from: halo, CN, $C_1$-$C_4$ alkyl, $C_1$-$C_4$ halolkyl, $C_1$-$C_4$ alkoxy, $C_1$-$C_4$ halolkoxy, cyclopropyl, and (phenyl is substituted with 0 to 1 $C_1$-$C_4$ alkyl).

8. The compound according to claim 1, wherein:
A is —$CR^7R^8$—;
$R^1$ is selected from: cyclopropyl, phenyl, thiazolyl, isoxazolyl, 1,2,4-oxadiazolyl, 1,3,4-thiadiazolyl, pyridinyl, pyrimidinyl, benzo[d]oxazolyl, benzo[d]thiazolyl, benzo[d]imidazolyl, pyrazolo[1,5-a]pyrimidinyl, and quinolinyl; wherein each moiety is substituted with 0 to 2 $R^c$;
$R^2$ is selected from: $C_1$-$C_6$ alkyl, $C_1$-$C_6$ haloalkyl, cyclopropyl, and (phenyl substituted with 0 to 1 F);
$R^3$ is H, F, or $CH_3$;
$R^7$ is H, F, Cl, $C_1$-$C_4$ alkyl, $C_2$-$C_4$ alkenyl, or cyclopropyl;
$R^8$ is H F Cl, or $C_1$-$C_4$ alkyl; and
$R^c$ is independently selected from: halo, CN, $C_1$-$C_4$ alkyl, $C_1$-$C_4$ halolkyl, $C_1$-$C_4$ alkoxy, $C_1$-$C_4$ halolkoxy, cyclopropyl, and (phenyl is substituted with 0 to 1 $C_1$-$C_4$ alkyl).

9. A pharmaceutical composition comprising a compound according to claim 1 and a pharmaceutically acceptable excipient.

10. The pharmaceutical composition of claim 9, further comprising ipilimumab, nivolumab, or pembroluzimab, or a combination thereof.

11. A method of treating cancer in a patient in need of such treatment comprising administering to the patient a therapeutically effective amount of a compound of claim 1;
wherein the cancer is selected from the group consisting of brain cancer, skin cancer, bladder cancer, ovarian cancer, breast cancer, gastric cancer, pancreatic cancer, prostate cancer, colon cancer, blood cancer, lung cancer and bone cancer.

\* \* \* \* \*

UNITED STATES PATENT AND TRADEMARK OFFICE
CERTIFICATE OF CORRECTION

| | |
|---|---|
| PATENT NO. | : 12,145,927 B2 |
| APPLICATION NO. | : 17/261968 |
| DATED | : November 19, 2024 |
| INVENTOR(S) | : James Aaron Balog et al. |

Page 1 of 3

It is certified that error appears in the above-identified patent and that said Letters Patent is hereby corrected as shown below:

On the Title Page

In Other Publications, item (56) Under Column no. 2, Line no. 3, Replace:
"Characerization"
With:
--Characterization--

In the Claims

Under Column no. 167, in Claim 1, Line no. 25, Replace:
"Rd);"
With:
--$R^d$);--

Under Column no. 167, in Claim 1, Line no. 26, Replace:
"halolkyl,"
With:
--haloalkyl,--

Under Column no. 167, in Claim 1, Line no. 27, Replace:
"halolkoxy;"
With:
--haloalkoxy;--

Under Column no. 167, in Claim 1, Line no. 30, Replace:
"C-$C_4$"
With:
--$C_1$-$C_4$--

Signed and Sealed this
Twenty-ninth Day of April, 2025

Coke Morgan Stewart
*Acting Director of the United States Patent and Trademark Office*

Under Column no. 167, in Claim 1, Line no. 43, Replace:
"halolkyl,"
With:
--haloalkyl,--

Under Column no. 167, in Claim 1, Line no. 43, Replace:
"halolkoxy,"
With:
--haloalkoxy,--

Under Column no. 167, in Claim 1, Line no. 49, Replace:
"halolkyl,"
With:
--haloalkyl,--

Under Column no. 167, in Claim 1, Line no. 50, Replace:
"halolkoxy;"
With:
--haloalkoxy;--

Under Column no. 168, in Claim 6, Line no. 67, Replace:
"halolkyl,"
With:
--haloalkyl,--

Under Column no. 169, in Claim 6, Line no. 1, Replace:
"halolkoxy,"
With:
--haloalkoxy,--

Under Column no. 169, in Claim 7, Line no. 5, Replace:
"is-$CR^{13}$"
With:
--is -$CR^{13}$--

Under Column no. 169, in Claim 7, Line no. 6, Replace:
"$C^{15}$"
With:
--$CR^{15}$--

Under Column no. 169, in Claim 7, Line no. 21, Replace:
"halolkyl,"
With:
--haloalkyl,--

CERTIFICATE OF CORRECTION (continued)
U.S. Pat. No. 12,145,927 B2

Under Column no. 169, in Claim 7, Line no. 22, Replace:
"halolkoxy,"
With:
--haloalkoxy,--

Under Column no. 170, in Claim 8, Line no. 8, Replace:
"H F"
With:
--H, F,--

Under Column no. 170, in Claim 8, Line no. 10, Replace:
"halolkyl,"
With:
--haloalkyl,--

Under Column no. 170, in Claim 8, Line no. 10, Replace:
"halolkoxy,"
With:
--haloalkoxy,--

Under Column no. 170, in Claim 10, Line no. 18, Replace:
"pembroluzimab,"
With:
--pembrolizumab,--